US007902196B2

(12) United States Patent
Myers et al.

(10) Patent No.: US 7,902,196 B2
(45) Date of Patent: Mar. 8, 2011

(54) SYNTHESIS OF AVRAINVILLAMIDE, STREPHACIDIN B, AND ANALOGUES THEREOF

(75) Inventors: Andrew G. Myers, Boston, MA (US);
Seth B. Herzon, New Haven, CT (US);
Jeremy Earle Wulff, Victoria (CA);
Romain Siegrist, Somerville, MA (US);
Jakub Svenda, Cambridge, MA (US);
Matthew Allen Zajac, Douglassville, PA (US)

(73) Assignee: President and Fellows of Harvard College, Cambridge, MA (US)

( * ) Notice: Subject to any disclaimer, the term of this patent is extended or adjusted under 35 U.S.C. 154(b) by 162 days.

(21) Appl. No.: 11/908,901

(22) PCT Filed: Mar. 17, 2006

(86) PCT No.: PCT/US2006/009749
§ 371 (c)(1),
(2), (4) Date: Nov. 18, 2008

(87) PCT Pub. No.: WO2006/102097
PCT Pub. Date: Sep. 28, 2006

(65) Prior Publication Data
US 2009/0143581 A1 Jun. 4, 2009

Related U.S. Application Data

(60) Provisional application No. 60/662,647, filed on Mar. 17, 2005.

(51) Int. Cl.
*A61K 31/4355* (2006.01)
*A61K 31/4985* (2006.01)
*A61K 31/424* (2006.01)
*A61K 31/403* (2006.01)
*A61K 31/407* (2006.01)
*C07D 221/18* (2006.01)
*C07D 241/00* (2006.01)
*C07D 498/22* (2006.01)
*C07D 209/58* (2006.01)
*C07D 487/04* (2006.01)

(52) U.S. Cl. ......... 514/249; 514/279; 514/375; 514/410; 514/411; 544/230; 546/35; 548/218; 548/421; 548/439; 548/448

(58) Field of Classification Search .................. None
See application file for complete search history.

(56) References Cited

U.S. PATENT DOCUMENTS
6,066,635 A   5/2000  Fenical et al.
6,291,461 B1  9/2001  Qian-Cutrone et al.

FOREIGN PATENT DOCUMENTS
EP      1571193 A1     9/2005
WO   WO 2004/053019 A1  6/2004
WO   WO 2006/102097 A2  9/2006

OTHER PUBLICATIONS

Myers et al. Journal of the American Chemical Society, 2003, 125 (40), pp. 12080-12081.*
Myers et al. J. Am. Chem. Soc., 125: 12080, 2003.*
Adams, et al., *Curr. Opin. Chem. Biol.*, 6:493, 2002.
Bain, et al., *J. Magn. Reson.*, 188a:21, 1996.
Banwell, et al., *Org. Lett.*, 5:2497, 2003.
Baran, et al., *Angew. Chem., Int. Ed. Engl.*, 44:606, 2004.
Barros, et al., *Chem. Eur. J.*, 6:3991, 2000.
Bassindale, et al., *J. Organomet. Chem.*, 271:C1, 1984.
Bella, et al., *Org. Biomol. Chem.*, 2:421, 2004.
Berge, et al., *J. Pharmaceutical Science*, 66:1-19, 1977.
Bloch, *Chem. Rev.*, 98:1407, 1998.
Bordwell, et al., J. Am. Chem. Soc., 118:8777, 1996.
Breuza, et al., *J. of Biological Chemistry*, 279:47242-47253, 2004.
Colonna, et al., *Gazz. Chim. Ital.*, 97:1569, 1967.
Corey, et al, *J. Am. Chem. Soc.*, 109:5551, 1987.
Corey, et al., *J. Am. Chem. Soc.*, 109:7925, 1987.
Corey, et al., *J. Angew. Chem., Int. Ed. Engl.*, 37:1986, 1998.
Cox, et al., *Tetrahedron Lett.*, 43:2149, 2002.
Cushing, et al., *J. Am. Chem. Soc.*, 118:557, 1996.
Dale, et al., *J. Am. Chem. Soc.*, 95:512, 1973.
Dess, et al., *J. Am. Chem. Soc.*, 113:7277, 1991.
Elomri, et al., *Heterocycles*, 34:799, 1992.
Farah, et al., *J. of Biological Chemistry*, 280:9439-9449, 2005.
Frigerio, et al., *J. Org. Chem.*, 64:4537, 1999.
Ghaffar, et al, *J. Mol. Catal. A.*, 160:249, 2000.
Ghaffar, et al., *Tetrahedron Lett.*, 36:8657, 1995. Gutsulyak, et al., *Chemistry of Heterocyclic Compounds*, 23:846-849, 1987 [abstract].
Herzon, et al., *J. Am. Chem. Soc.*, 127:5342-5344, 2005.
International Search Report, PCT/US06/09749, mailed on Nov. 27, 2006.
Ishiyama, et al., *J. Org. Chem.*, 60:7508, 1995.
Ito, et al., *J. Org. Chem.*, 43:1011, 1978.
Jackson, et al., *Chem. Commun.*, 2327, 2000.
Johnson, et al., *Tetrahedron Lett.*, 33:917, 1992.
Klopfenseein, et al., *EMBO J.*, 17:6168-6177, 1998.

(Continued)

*Primary Examiner* — Golam M. M. Shameem
*Assistant Examiner* — Alicia L Otton
(74) *Attorney, Agent, or Firm* — Wolf, Greenfield & Sacks, P.C.

(57) ABSTRACT

The syntheses of the natural products, avrainvillamide and stephacidin B, are provided. The α,β-unsaturated nitrone functionality of avrainvillamide and its 3-alkylidene-3H-indole 1-oxide core is shown to covalently and reversibly bond to heteroatom-based nucleophiles. This capability may allow these molecules to bind active site nucleophiles and may provide the basis for designing potent and selective enzyme inhibitors. Both avrainvillamide and its dimer stephacidin B have been reported to exhibit antiproliferative activity, and avrainvillamide has been reported to exhibit antimicrobial activity against multi-drug resistant bacteria. Avrainvillamide has been found to target cytoskeleton-linking membrane protein (CLIMP-63) thereby preventing cells from undergoing mitosis. The invention provides syntheses of these natural products as well as analogs of these natural products and their functional cores. The compounds of the invention may be used in the treatment of diseases such as cancer, autoimmune diseases, and bacterial infection.

69 Claims, 33 Drawing Sheets

OTHER PUBLICATIONS

Klopfenstein, et al., *J. of Cell Biology*, 153:1287-1299, 2001.
Knochel, et al., *Tetrahedron*, 49:29, 1993.
Kofron, et al., *J. Org. Chem.*, 41:1879, 1976.
Lau, et al., *J. Org. Chem.*, 43:1595, 1978.
Lecaille, et al., *Chem. Rev.*, 102:4459, 2002.
Lissel, et al., *Liebigs Ann. Chem.*, 263, 1987.
Lombardo, et al., *Synthesis*, 6:759, 2000.
Mundy, *Biochem. Soc. Trans.*, 23:572-576, 1995.
Mundy, et al., *J. Cell. Biol.*, 116:135-146, 1992.
Meyer, et al., *J. Org. Chem.*, 59:7549, 1994.
Myers, et al., *J. Am. Chem. Soc.*, 125:12080, 2003.
Nelson, et al., *Tetrahedron*, 47:3259, 1991.
Nicolaou, et al., *Angew. Chem., Int. Ed. Engl.*, 41:993, 2002.
Nussbaum, et al., *Angew. Chem. Int. Ed.*, 42:3068, 2002.
Ohtani, et al., *J. Am. Chem. Soc.*, 113:4092, 1991.
Oliveira, et al., *J. Org. Chem.*, 64:6646, 1999.
Page, et al, *J. Org. Chem.*, 67:7787, 2002.
Pangbom, et al., *Organometallics*, 15:1518, 1996.
Qian-Cutrone, et al., *J. Am. Chem. Soc.*, 124:14556, 2002.
Sanz-Cervera, et al., *J. Am. Chem. Soc.*, 124:2556, 2002.
Sapountzis, et al, *Angew. Chem., Int. Ed. Engl.*, 41:1610, 2002.
Schaefer, et al., *In the Chemistry of the Cyano Group, The Chemistry of Functional Groups, Wiley and Sons*: New York, 1970; pp. 239.
Schweizer, et al., *J. Cell. Sci.*, 104:671-683, 1993.
Schweizer, et al., *J. Cell. Sci.*, 104:685-694, 1993.
Schweizer, et al., *J. Cell. Sci.*, 108:2477-2485, 1995.
Schweizer, et al., *J. Cell. Sci.*, 126:25-39, 1994.
Spence, et al., *Chem. Rev.*, 70:231, 1970.
Still, et al, *J. Org. Chem.*, 43:2923, 1978.
Stocking, et al., *Angew. Chem., Int. Ed. Engl.*, 42:3078, 2003.
Stocking, et al., *J. Am. Chem. Soc.*, 122:1675, 2000.
Sugie, et al., *J. Antiobiot.*, 54:911, 2001.
Suginome, et al., *J. Chem. Soc., Perkin Trans.*, 1:917, 1991.
Sun, et al., *Synthesis*, 1249, 1997.
Tae, et al., *Can. J. Chem.*, 78:689, 2000.
Torri, et al., *Bull. Soc. Chem. Fr.*, 283, 1978.
Tosi, et al., *Montash. Chem.*, 118:369, 1987.
Utzinger, et al., *Helv. Chim. Acta.*, 37:1892, 1954.
Vedrenne, et al., *Mol. Biol. Cell.*, 16:1928-1937, 2005.
Williams, et al., *J. Am. Chem. Soc.*, 112:808, 1990.
Williams, et al., *J. Acc. Chem. Res.*, 36:127, 2003.
Williams, et al., *J. Am. Chem. Soc.*, 125:12172, 2003.
Wolfe, et al., *J. Am. Chem. Soc.*, 121:9550, 1999.
International Search Report and Written Opinion for PCT/US2006/009749 mailed Nov. 27, 2006.
International Preliminary Report on Patentability for PCT/US2006/009749 mailed Sep. 27, 2007.
Berger et al., Loss of the NPM1 gene in myeloid disorders with chromosome 5 rearrangements. Leukemia. Feb. 2006;20(2):319-21.
Bertwistle et al., Physical and functional interactions of the Arf tumor suppressor protein with nucleophosmin/B23. Mol Cell Biol. Feb. 2004;24(3):985-96.
Bradford, A rapid and sensitive method for the quantitation of microgram quantities of protein utilizing the principle of protein-dye binding. Anal Biochem. May 7, 1976;72:248-54.
Busch et al., Actinomycin D inhibition of monoclonal antibody binding to nucleolar phosphoprotein 37/5.2 (B23). Life Sci. Oct. 22, 1984;35(17):1777-85.
Cazzaniga et al., Nucleophosmin mutations in childhood acute myelogenous leukemia with normal karyotype. Blood. Aug. 15, 2005;106(4):1419-22. Epub May 3, 2005.
Chan, Characterization and cellular localization of nucleophosmin/B23 in HeLa cells treated with selected cytotoxic agents (studies of B23-translocation mechanism). Exp Cell Res. Nov. 1992;203(1):174-81.
Chan et al., Characterization of the cDNA encoding human nucleophosmin and studies of its role in normal and abnormal growth. Biochemistry. Feb. 7, 1989;28(3):1033-9.
Chan et al., Nucleolar protein B23 translocation after doxorubicin treatment in murine tumor cells. Cancer Res. Jul. 15, 1987;47(14):3798-801.
Chan et al., Nucleophosmin/B23-binding peptide inhibits tumor growth and up-regulates transcriptional activity of p53. Biochem Biophys Res Commun. Jul. 29, 2005;333(2):396-403.
Chen et al., Nucleophosmin gene mutations in acute myeloid leukemia. Arch Pathol Lab Med. Nov. 2006;130(11):1687-92.
Colombo et al., Nucleophosmin is required for DNA integrity and p19Arf protein stability. Mol Cell Biol. Oct. 2005;25(20):8874-86.
Colombo et al., Nucleophosmin regulates the stability and transcriptional activity of p53. Nat Cell Biol. Jul. 2002;4(7):529-33.
Coutts et al., The p53 response: emerging levels of co-factor complexity. Biochem Biophys Res Commun. Jun. 2005 10;331(3):778-85.
Dalenc et al., Increased expression of a COOH-truncated nucleophosmin resulting from alternative splicing is associated with cellular resistance to ionizing radiation in HeLa cells. Int J Cancer. Aug. 20, 2002;100(6):662-8.
Dhar et al., Specificity protein 1-dependent p53-mediated suppression of human manganese superoxide dismutase gene expression. J Biol Chem. Aug. 4, 2006;281(31):21698-709. Epub Jun. 1, 2006.
Duyster et al., Translocations involving anaplastic lymphoma kinase (ALK). Oncogene. Sep. 10, 2001;20(40):5623-37.
Falini et al., Acute myeloid leukemia carrying cytoplasmic/mutated nucleophosmin (NPMc+AML): biologic and clinical features. Blood. Feb. 1, 2007;109(3):874-85. Epub Sep. 28, 2006.
Falini et al., Cytoplasmic nucleophosmin in acute myelogenous leukemia with a normal karyotype. N Engl J Med. Jan. 20, 2005;352(3):254-66.
Frehlick et al., New insights into the nucleophosmin/nucleoplasmin family of nuclear chaperones. Bioessays. Jan. 2007;29(1):49-59.
Galkin et al., Identification of NVP-TAE684, a potent, selective, and efficacious inhibitor of NPM-ALK. Proc Natl Acad Sci U S A. Jan. 2, 2007;104(1):270-5. Epub Dec. 21, 2006.
Gjerset, DNA damage, p14ARF, nucleophosmin (NPM/B23), and cancer. J Mol Histol. Sep. 2006;37(5-7):239-51. Epub Jul. 20, 2006.
Grisendi et al., Nucleophosmin and cancer. Nat Rev Cancer. Jul. 2006;6(7):493-505.
Herrera et al., Sedimentation analyses of the salt- and divalent metal ion-induced oligomerization of nucleolar protein B23. Biochemistry. Feb. 27, 1996;35(8):2668-73.
Hingorani et al., Mapping the functional domains of nucleolar protein B23. J Biol Chem. Aug. 11, 2000;275(32):24451-7.
Hollstein et al., p53 mutations in human cancers. Science. Jul. 5, 1991;253(5015):49-53.
Kurki et al., Nucleolar protein NPM interacts with HDM2 and protects tumor suppressor protein p53 from HDM2-mediated degradation. Cancer Cell. May 2004;5(5):465-75.
Kurki et al., Nucleophosmin, HDM2 and p53: players in UV damage incited nucleolar stress response. Cell Cycle. Aug. 2004;3(8):976-9. Epub Aug. 8, 2004.
Lambert et al., Characterisation of the interface between nucleophosmin (NPM) and p53: potential role in p53 stabilisation. FEBS Lett. Jan. 9, 2006;580(1):345-50. Epub Dec. 19, 2005.
Latonen et al., Cellular UV damage responses—functions of tumor suppressor p53. Biochim Biophys Acta. Jul 25, 2005;1755(2):71-89.
Lee et al., Crystal structure of human nucleophosmin-core reveals plasticity of the pentamer-pentamer interface. Proteins. Nov. 15, 2007;69(3):672-8.
Lee et al., Release of nucleophosmin from the nucleus: Involvement in aloe-emodin-induced human lung non small carcinoma cell apoptosis. Int J Cancer. Mar. 1, 2005;113(6):971-6.
Li et al., Hypoxia-induced nucleophosmin protects cell death through inhibition of p53. J Biol Chem. Oct. 1, 2004;279(40):41275-9. Epub Aug. 13, 2004.
Li et al., Negative regulation of p53 by nucleophosmin antagonizes stress-induced apoptosis in human normal and malignant hematopoietic cells. Leuk Res. Dec. 2005;29(12):1415-23. Epub Jun. 17, 2005.
Li et al., Nucleophosmin suppresses oncogene-induced apoptosis and senescence and enhances oncogenic cooperation in cells with genomic instability. Carcinogenesis. Jun. 2007;28(6):1163-70. Epub Feb. 2, 2007.
Lim et al., Nucleophosmin and human cancer. Cancer Detect Prev. 2006;30(6):481-90. Epub Nov. 17, 2006.

Liu et al., Synthesis of biaryls and polyaryls by ligand-free Suzuki reaction in aqueous phase. J Org Chem. May 12, 2006;71(10):3994-7.

Maiguel et al., Nucleophosmin sets a threshold for p53 response to UV radiation. Mol Cell Biol. May 2004;24(9):3703-11.

Maya et al., Synthesis of Fluorinated Oligomers toward Physical Vapor Deposition Molecular Electronics Candidates. Chem Mater. 2005;17:1331-45.

Moore et al., Culture of normal human leukocytes. JAMA. Feb. 20, 1967;199(8):519-24.

Namboodiri et al., The structure and function of Xenopus NO38-core, a histone chaperone in the nucleolus. Structure. Dec. 2004;12(12):2149-60.

Naoe et al., Nucleophosmin: a versatile molecule associated with hematological malignancies. Cancer Sci. Oct. 2006;97(10):963-9.

Nicolini et al., Biomolecular markers of breast cancer. Front Biosci. May 1, 2006;11:1818-43.

Okuda et al., The role of nucleophosmin in centrosome duplication. Oncogene. Sep. 9, 2002;21(40):6170-4.

Peng, Current status of gendicine in China: recombinant human Ad-p53 agent for treatment of cancers. Hum Gene Ther. Sep. 2005;16(9):1016-27.

Redner et al., The t(5;17) variant of acute promyelocytic leukemia expresses a nucleophosmin-retinoic acid receptor fusion. Blood. Feb. 1, 1996;87(3):882-6.

Seko et al., A convenient copper-catalyzed direct amination of nitroarenes with O-alkylhydroxylamines. J Chem Soc., Perkin Trans 1. 1999:1437-44.

Strausberg et al., Generation and initial analysis of more than 15,000 full-length human and mouse cDNA sequences. Proc Natl Acad Sci U S A. Dec. 24, 2002;99(26):16899-903. Epub Dec. 11, 2002.

Szebeni et al., Interaction of nucleolar protein B23 with peptides related to nuclear localization signals. Biochemistry. Jun. 27, 1995;34(25):8037-42.

Townsend et al., A glutathione S-transferase pi-activated prodrug causes kinase activation concurrent with S-glutathionylation of proteins. Mol Pharmacol. Feb. 2006;69(2):501-8. Epub Nov. 15, 2005.

Turner et al., What have we learnt from mouse models of NPM-ALK-induced lymphomagenesis? Leukemia. Jul. 2005;19(7):1128-34.

Vassilev et al., In vivo activation of the p53 pathway by small-molecule antagonists of MDM2. Science. Feb. 6, 2004;303(5659):844-8. Epub Jan. 2, 2004.

Ventura et al., Restoration of p53 function leads to tumour regression in vivo. Nature. Feb. 8, 2007;445(7128):661-5. Epub Jan. 24, 2007.

Wulff et al., Evidence for the rapid conversion of stephacidin B into the electrophilic monomer avrainvillamide in cell culture. J Am Chem Soc. Apr. 25, 2007;129(16):4898-9. Epub Mar. 31, 2007.

Wulff et al., The natural product avrainvillamide binds to the oncoprotein nucleophosmin. J Am.Chem Soc. Nov. 21, 2007;129(46):14444-51. Epub Oct. 25, 2007. Author Manuscript.

Ye, Nucleophosmin/B23, a multifunctional protein that can regulate apoptosis. Cancer Biol Ther. Sep. 2005;4(9):918-23. Epub Sep. 1, 2005.

Yoneda-Kato et al., The t(3;5)(q25.1;q34) of myelodysplastic syndrome and acute myeloid leukemia produces a novel fusion gene, NPM-MLF1. Oncogene. Jan. 18, 1996;12(2):265-75.

You et al., Decrease in nucleophosmin/B23 mRNA and telomerase activity during indomethacin-induced apoptosis of gastric KATO-III cancer cells. Naunyn Schmiedebergs Arch Pharmacol. Dec. 1999;360(6):683-90.

Yung et al., Effects of luzopeptins on protein B23 translocation and ribosomal RNA synthesis in HeLa cells. Cancer Res. Feb. 1986;46(2):922-5.

Zou et al., Polyamine depletion increases cytoplasmic levels of RNA-binding protein HuR leading to stabilization of nucleophosmin and p53 mRNAs. J Biol Chem. Jul. 14, 2006;281(28):19387-94 Epub May 10, 2006.

Zou et al., Polyamine depletion induces nucleophosmin modulating stability and transcriptional activity of p53 in intestinal epithelial cells. Am J Physiol Cell Physiol. Sep. 2005;289(3):C686-96 Epub May 4, 2005.

\* cited by examiner

Figure 1. Capped-stick and space-filling models of 5 from X-ray data.

Figure 2. $^1$H NMR spectra at 23 °C (500 MHz, 1:1 DMSO-$d_6$–CD$_3$CN) of (a) synthetic "avrainvillamide" (2), (b) synthetic stephacidin B (1), (c) stephacidin B from a fungal source $^1$H (500 MHz) and $^{13}$C (100 MHz) NMR Spectra of Synthetic Avrainvillamide (2) (CDCl$_3$)

Authentic stephacidin B (500 MHz, 50% $d_6$-DMSO-CD$_3$CN)

Synthetic stephacidin B (500 MHz, 50% $d_6$-DMSO-CD$_3$CN)

Synthetic stephacidin B (500 MHz, 50% $d_6$-DMSO-CD$_3$CN;

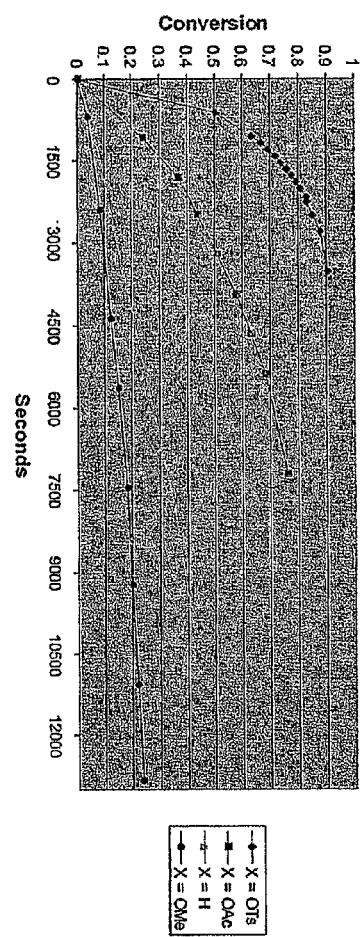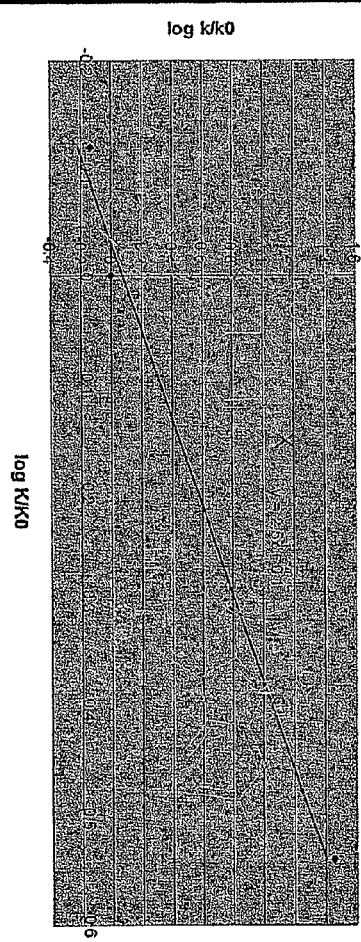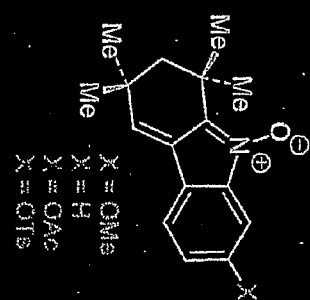
Fig. 5

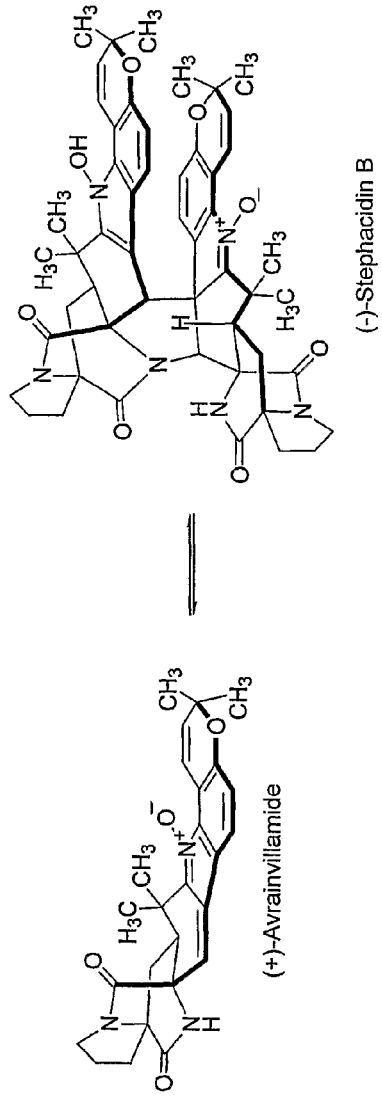

GI50 Data for Avrainvillamide & Stephacidin B: "Method A"

| | "Natural" Enantiomer | | "Unnatural" Enantiomer | | Literature Value | |
|---|---|---|---|---|---|---|
| | (+)-Avrainvillamide | (–)-Stephacidin B | (–)-Avrainvillamide | (+)-Stephacidin B | Avrainvillamide | Stephacidin B |
| BT-549 | 621 nM (531 nM – 710 nM) | 346 nM (315 nM – 377 nM) | 786 nM (703 nM – 869 nM) | 550 nM (475 nM – 624 nM) | 34 nM | not reported |
| T-47D | 205 nM (88 nM – 321 nM) | 91 nM (16 nM – 165 nM) | 1485 nM (1267 nM – 1703 nM) | 942 nM (508 nM – 1376 nM) | 72 nM | not reported |
| MALME-3M | 406 nM (160 nM – 653 nM) | 289 nM (67 nM – 511 nM) | 1854 nM (1729 nM – 1978 nM) | 987 nM (673 nM – 1301 nM) | 53 nM | not reported |
| LnCAP | 241 nM (140 nM – 342 nM) | 135 nM (18 nM – 253 nM) | 1514 nM (1186 nM – 1843 nM) | 952 nM (572 nM – 1332 nM) | not reported | 60 nM | values in parentheses represent 95% confidence intervals

Fig. 12

GI50 Data for Avrainvillamide Analogues: "Method C"

| GI50 values: | LnCAP | T-47D |
|---|---|---|
| (+)-Avrainvillamide : 445.52 g/mol | 0.3 µM | 0.4 µM |
| (−)-Avrainvillamide : 445.52 g/mol | 2.7 µM | 1.9 µM |
| SH-02 : 454.51 g/mol | > 20 µM | > 20 µM |
| Stephacidin-amine | > 20 µM | > 20 µM |
| Avrain-methylenedioxy: 407.43 g/mol | 9.9 µM | 7.4 µM |
| Avrain-phenol : 379.42 g/mol | > 20 µM | > 20 µM |
| JS-II-303-2: 415.44 g/mol | > 20 µM | > 20 µM |
| Avrain-sulfone | 10 µM | 5.9 µM |
| Avrain-nitrile | > 20 µM | > 20 µM |
| Avrain-H : 363.42 g/mol | 10 µM | 8.1 µM |
| Avrain-Amide : 451.51 g/mol | > 20 µM | > 20 µM | values are based on at least four duplicate analyses (ie: 8 assays in total) over a minimum of two weeks

Fig. 13A

GI50 Data for Tetramethyl-Substituted Analogues: "Method C"

| GI50 values: | LnCAP | T-47D |
|---|---|---|
| Me₄-O₂Me : 285.35 g/mol | 6.1 μM | 1.7 μM |
| Me₄-OMe : 271.36 g/mol | 7.3 μM | 7.1 μM |
| Me₄-H : 241.34 g/mol | 4.2 μM | 1.4 μM |
| Me₄-CO₂Me : 299.37 g/mol | 4.0 μM | 4.6 μM |
| SH-03 : 454.51 g/mol | 5.2 μM* | 4.0 μM* |
| JW4-161 : 363.50 g/mol | 7.6 μM | 4.6 μM |
| JS-I-190 : 670.90 g/mol | > 20 μM | 7.5 μM |
| Me₄-OAc : 299.37 g/mol | 11 μM* | 4.4 μM* |
| JS-II-316-1 : 235.24 g/mol | > 20 μM | > 20 μM |
| PBN : 241.34 g/mol | > 20 μM | > 20 μM | values are based on at least four duplicate analyses (ie: 8 assays in total) over a minimum of two weeks

* these (mostly inactive) compounds have not been re-run in the three-day assay

Fig. 16A

GI50 Data for Tetramethyl-Substituted Analogues Continued: "Method C"
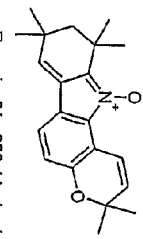
Romain_01 : 323.44 g/mol
5.2 μM
8.4 μM
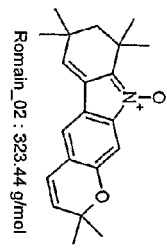
Romain_02 : 323.44 g/mol
2.2 μM
2.3 μM
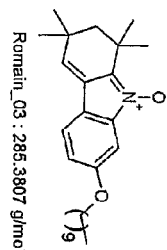
Romain_03 : 285.3807 g/mol
not run
8.2 μM
values are based on at least four duplicate analyses (ie: 8 assays in total) over a minimum of two weeks
Fig. 16B

IC50 & GI50 Data for Probe Compounds: "Method B"
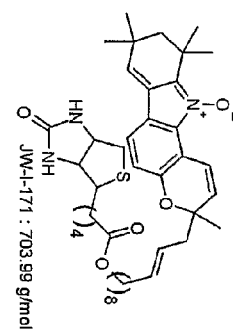
JW-I-171 : 703.99 g/mol
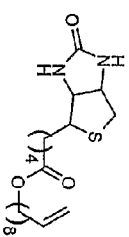
JW-I-159 : 382.99 g/mol
> 20 μM
> 20 μM
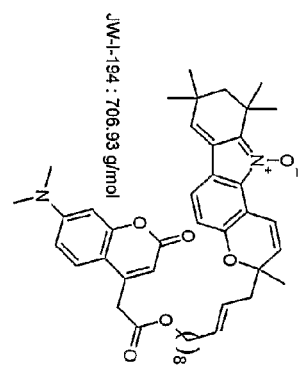
JW-I-194 : 706.93 g/mol
> 20 μM
16 μM
JW-I-191 : 385.51 g/mol
> 20 μM
> 20 μM
GI50 values:
LnCAP    5.6 μM
T-47D    7.0 μM
values are based on at least four duplicate analyses (ie: 8 assays in total) over a minimum of two weeks
Fig. 17

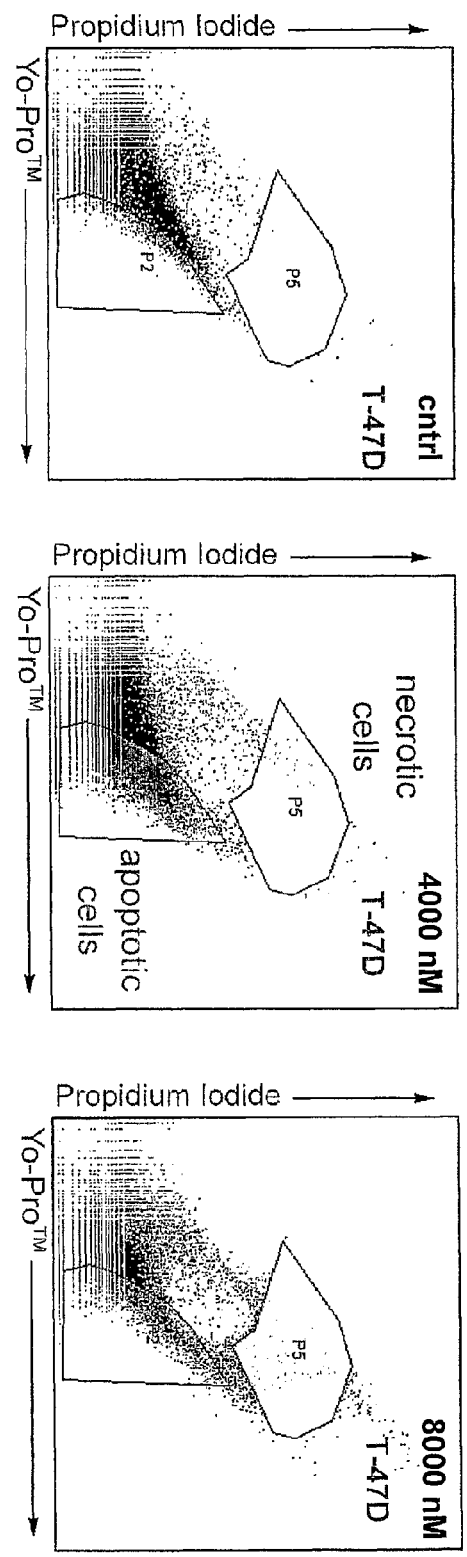
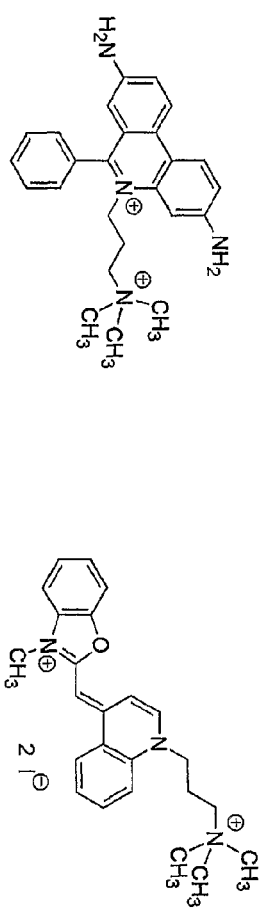
Fig. 20

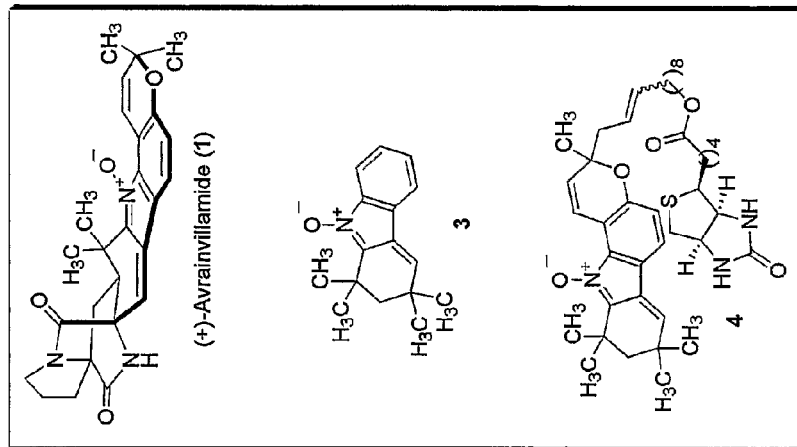
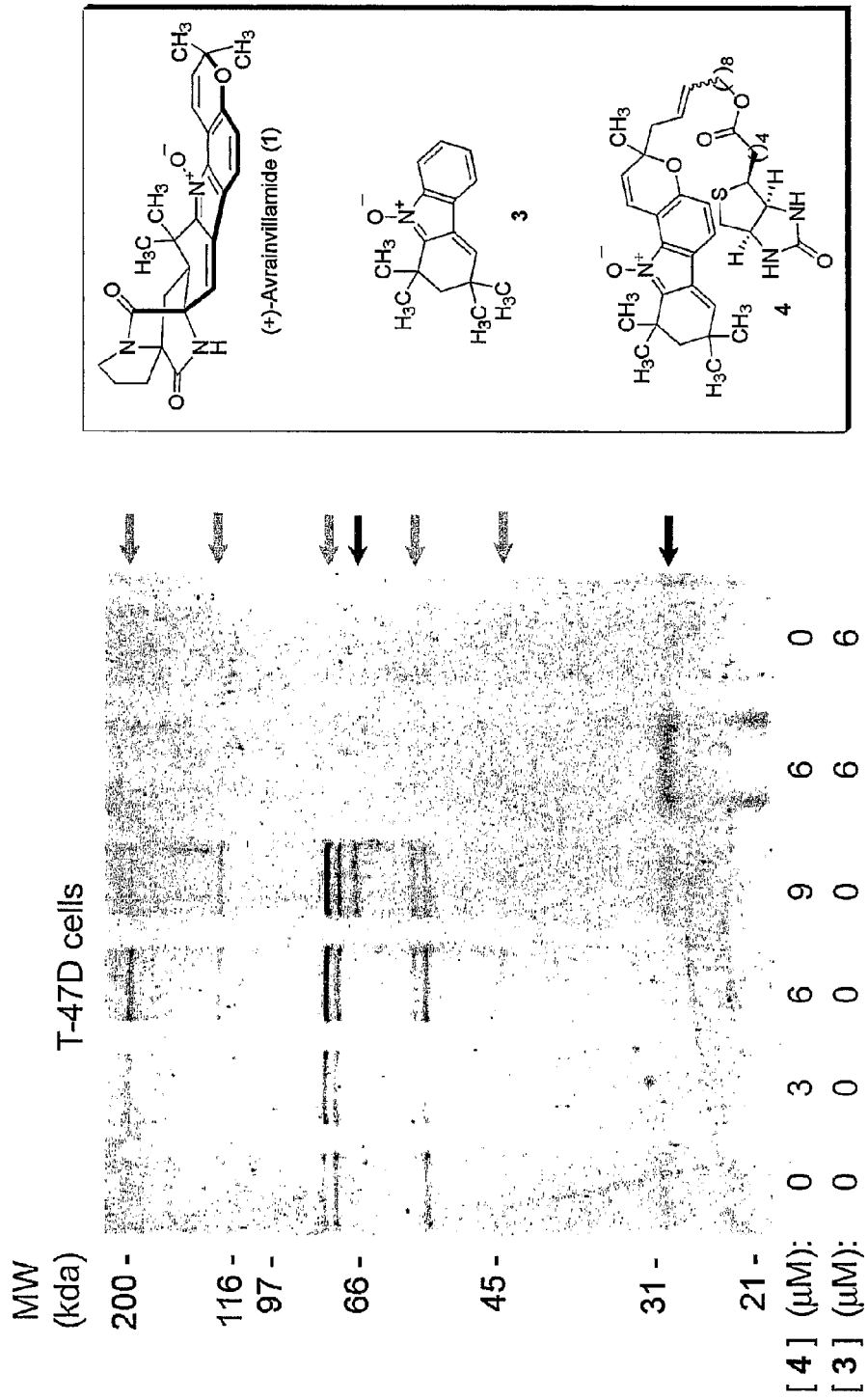
Fig. 22

MS/MS identified CLIMP-63

CLIMP-63 → MPSAKQRGSK GGHGAASPSE KGAHPSGGAD DVAKKPPPAP QQPPPPAPH PQQHPQQHPQ
NQAHGKGGHR GGGGGGGKSS SSSSASAAAA AAAASSSASC SRRLGRALNF LFYLALVAAA
AFSGWCVHHV LEEVQQVRRS HQDFSRQREE LGQGLQGVEQ KVQSLQATFG TFESILRSSQ
HKQDLITEKAV KQGESEVSRI SEVLQKLQNE ILKDLSDGIH VVKDARERDF TSLENTVEER
LTELTKSIND NIAFTEVQK RSQKEINDMK AKVASLEESE GNKQDLKALK EAVKEIQTSA
KSREWDMEAL RSTLQTMESD IYTEVRELVS LKQEEQQAFKE AADTERLALQ ALTEKLLRSE
ESVSRLPEEI RRLEEELRQL KSDSHGPKED GGFRHSEAFE ALQQKSQGLD SRLQHVEDGV
LSMQVASARQ TESLESLLSK SQEHEQRLAA LQGRLEGLGS SEADQDGLAS TVRSLGETQL
VLYGDVEELK RSVGELPSTV ESLQKVQEQV HTLLSQDQAQ AARLPPQDFL DRLSSLDNLK
ASVSQVEADL KMLRTAVDSL VAYSVKIETN ENNLESAKGL LDDIRNDLDR LFVKVEKIHE KV

Fig. 25

Preparation of the biotin portion of the probe:
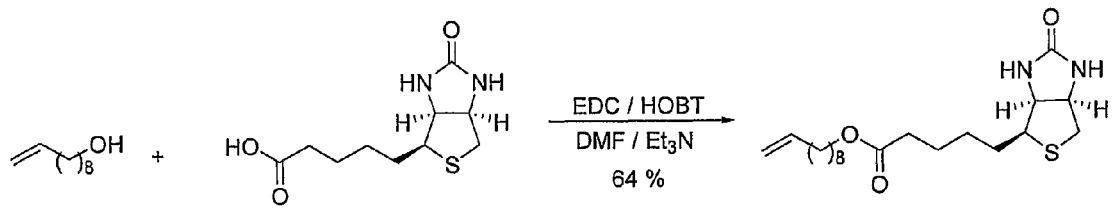
Preparation of the "left half" of the probe and several analogues:
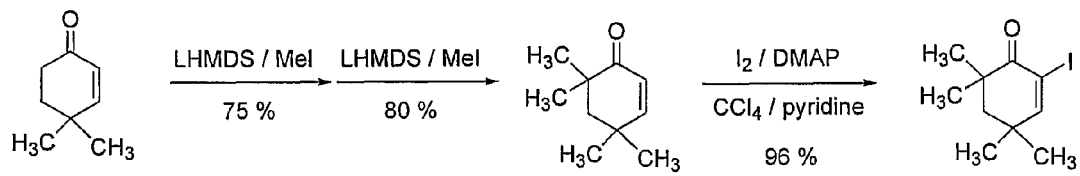
Preparation of the "right half" of the natural product and several analogues:
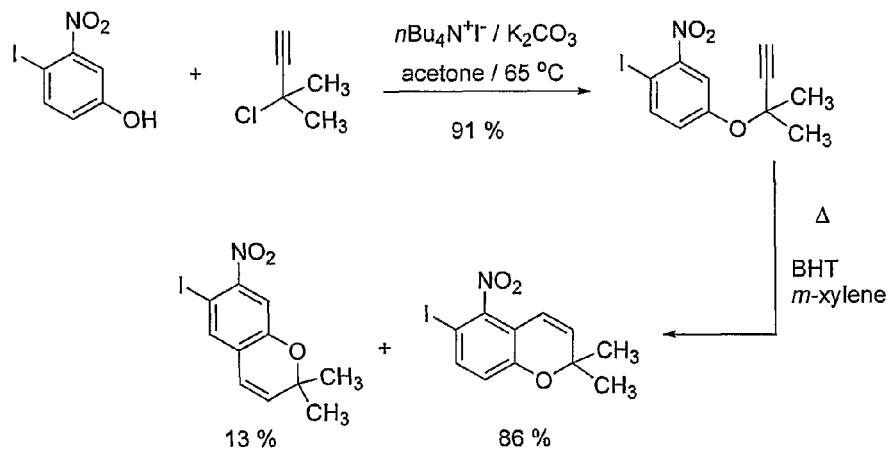
Fig. 26B

SYNTHESIS OF AVRAINVILLAMIDE, STREPHACIDIN B, AND ANALOGUES THEREOF

RELATED APPLICATIONS

The present application is a national stage filing under 35 U.S.C. §371 of international PCT application, PCT/US2006/009749, filed Mar. 17, 2006, which claims priority under 35 U.S.C. §119(e) to U.S. provisional patent application, U.S. Ser. No. 60/662,647, filed Mar. 17, 2005, each of which is incorporated herein by reference in its entirety.

GOVERNMENT SUPPORT

This invention was made with Government support under the National Institutes of Health award CA047148. The Government has certain rights in the invention.

BACKGROUND OF THE INVENTION

Many pharmaceutical agents work by covalently binding to nucleophiles found on their molecular targets in vivo. For example, enzyme inhibitors are frequently designed to target and covalently bind to nucleophiles (e.g., thiols of cysteines, hydroxyl groups of serine, threonine, or tyrosine) in the active site of the enzyme. Functional groups that bond covalently to active site nucleophiles, therefore, frequently form the basis for the design of potent and selective enzyme inhibitors. Those functional groups that form covalent bonds reversibly (e.g., carbonyl groups, boronic esters) are especially valuable in pharmaceutical development (for leading references, please see Adams, *J. Curr. Opin. Chem. Biol.* 6:493, 2002, Lecaille et al. *Chem. Rev.* 102:4459, 2002; each of which is incorporated herein by reference).

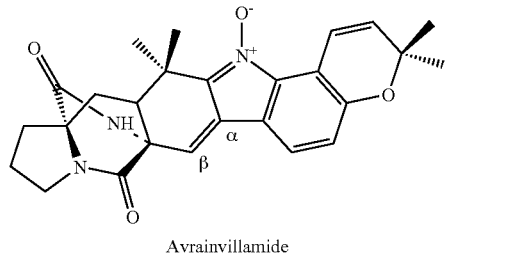

Avrainvillamide

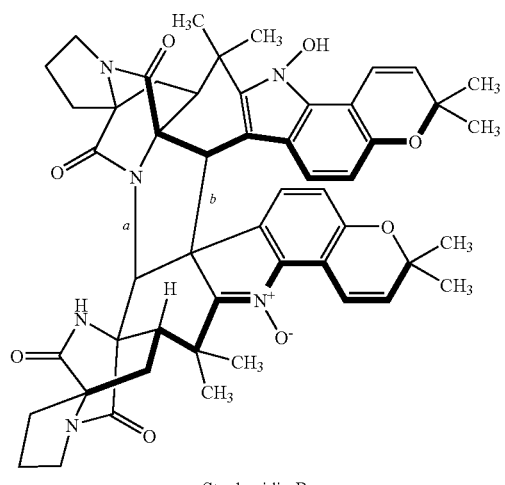

Stephacidin B

Avrainvillamide and stephacidin B, formally a dimer of avrainvillamide, have recently been identified and have been shown to include a 3-alkylidene-3H-indole 1-oxide group, which is capable of reversible covalent modification of a heteroatom-based nucleophile. Both of these compounds have been separately identified in culture media from various strains of *Aspergillus* (for the isolation of avrainvillamide, see Fenical et al. U.S. Pat. No. 6,066,635, issued May 23, 2000; Sugie et al. *J. Antibiot.* 54:911, 2001; each of which is incorporated herein by reference; for the isolation of stephacidins A and B, see Qian-Cutrone et al. *J. Am. Chem. Soc.* 124: 14556, 2002; Qian-Cutrone et al., U.S. Pat. No. 6,291,461, 2003; each of which is incorporated herein by reference). Both compounds exhibit anti-proliferative activity ($IC_{50}$ values ~50-100 nM), and avrainvillamide has been reported to exhibit anti-microbial activity against multidrug-resistant bacteria. These compounds are apparently the first natural product with a 3-alkylidene-3H-indole 1-oxide functional group.

Crystallization and x-ray analysis has been used to establish the structure of stephacidin B. It has now been recognized that stephacidin B is formed by the dimerization of avrainvillamide. A mechanism for the putative dimerization reaction was advanced that involved the protonation of avrainvillamide followed by formation of bonds b and a, in that order, via cationic intermediates (Qian-Cutrone et al. *J. Am. Chem. Soc.* 124:14556, 2002; incorporated herein by reference).

Given the biological activity of these newly isolated natural products, a synthetic route for preparing these compounds and analogs of these compounds would be useful in designing new therapeutics and investigating the structure-activity relationship of these compounds.

SUMMARY OF THE INVENTION

The present invention provides syntheses of avrainvillamide, stephacidin B, and analogues thereof. The compounds of the invention typically include the electrophilic α,β-unsaturated nitrone group of avrainvillamide. In certain embodiments, the compounds include the novel electrophilic group, 3-alkylidene-3H-indole 1 oxide, which includes an α,β-unsaturated nitrone group. These compounds may be used as pharmaceutical agents themselves or may be used as lead compounds in designing new pharmaceutical agents. Particularly, useful compounds are those which exhibit antiproliferative activity or antimicrobial activity. Pharmaceutical compositions and methods of using these compounds to treat diseases such as cancer, inflammatory diseases, or infectious diseases are also provided. The present invention also includes intermediates and synthetic methods useful in preparing avrainvillamide, stephacidin B, and analogues thereof. Furthermore, the invention includes the use of biological targets of avrainvillamide (e.g., cytoskeleton-linking membrane protein (CLIMP-63) in screening for other compounds useful in treating proliferative diseases or infectious diseases.

In one aspect of the invention, the compounds include an α,β-unsaturated nitrone functional group and are of the formula:

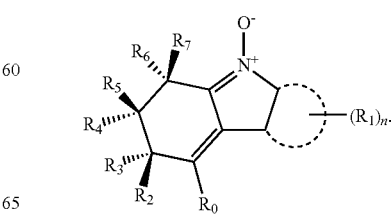

In certain embodiments, the

represents a monocyclic, bicyclic, tricyclic, or polycyclic ring system, preferably a substituted or unsubstituted phenyl ring as shown in the formula below:

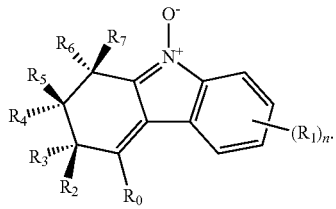

These electrophilic compounds are useful in covalently modifying the nucleophiles of biomolecules such as proteins or polynucleotides. In certain embodiments, the compounds covalently modify CLIMP-63 (e.g., Cys100). Oxygen- and sulfur-based nucleophiles have been shown to add to the β-position of the α,β-unsaturated nitrone. This property makes these compounds useful in the design of pharmaceutical agents as well as research tools in probing biological pathways. Compounds resulting from the 1,5-addition of a nucleophile to the α,β-unsaturated nitrone are of the formula:

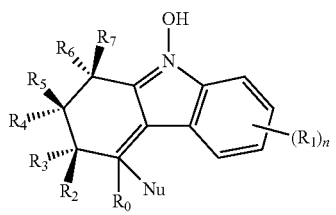

wherein Nu is a nucleophile, preferably an oxygen- or sulfur-containing nucleophile. The nucleophile may be part of a protein (e.g., serine, threonine, or cysteine), peptide, polynucleotide, or other biomolecule. In certain embodiments, Nu is Cys100 of CLIMP-63. In other embodiments, Nu is another nucleophilic amino acid of CLIMP-63 (e.g., a cysteine, serine, threonine, tyrosine).

The invention also provides analogs of avrainvillamide with the formula:

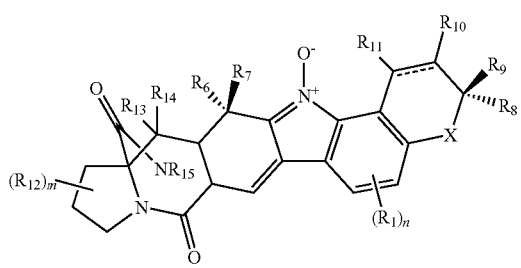

or with the stereochemistry defined as in formula:

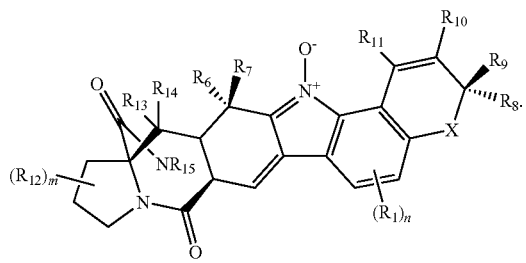

Analogs resulting from the 1,5-addition of a nucleophile to avrainvillamide are also within the scope of the invention. Such compounds are typically of the formula:

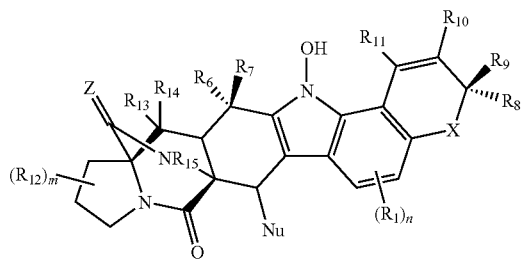

wherein Nu is a nucleophile.

Analogs of stephacidin B are also provided as in the formula

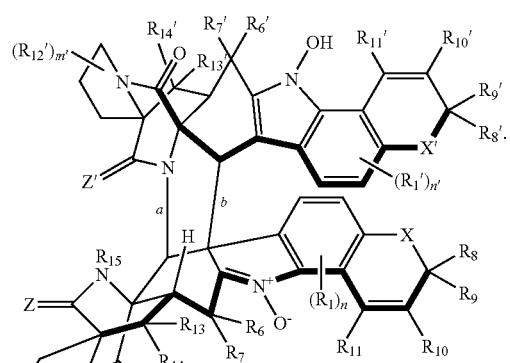

In certain embodiments, analogs of avrainvillamide and stephacidin B have anti-proliferative or anti-microbial activity and are useful in treating diseases such as cancer or infection.

The invention also provides pharmaceutical compositions of these compounds for use in treating human and veterinary disease. The compounds of the invention are combined with a pharmaceutical excipient to form a pharmaceutical composition for administration to a subject. Methods of treating a disease such as cancer or infection are also provided wherein a therapeutically effective amount of an inventive compound is administered to a subject.

In another aspect, synthetic methods useful in preparing avrainvillamide, stephacidin B, or analogues thereof are provided. Such methods include the Suzuki coupling, Stille coupling, or Ulmann coupling of an α-iodoenone with an arylboronic acid, aryl stannane, or aryl iodide, respectively, to produce a nitroarene coupling product. The nitroarene coupling product is then reduced in the presence of a metal such as zinc powder to form the nitrone. Other steps in the synthesis of the inventive compounds are also included within the invention.

The invention also provides a method of identifying other compounds that target CLIMP-63. Compounds that target CLIMP-63 are useful in the treatment of various proliferative diseases and infectious diseases. The method involved contacting a test compound with CLIMP-63 to determine if the compound has any effect on CLIMP-63. In certain instances, the compound may alkylate CLIMP-63, prevent the acylation of CLIMP-63, prevent the phosphorylation of CLIMP-63, or prevent the binding of CLIMP-63 to microtubules. Since these compounds typically covalently modify their target, a labeled derivative of the compound may be used to identify the biological target. Identification of compounds in this manner may then be used to refine and develop a lead compounds for the treatment of diseases or for probing biological pathways.

Therefore, the syntheses of avrainvillamide, stephacidin B, and the 3-alkylidene-3H-indole 1-oxide core provide methods for the preparation of these compounds as well as other compounds which may be useful in treating diseases such as cancer and infection. The use of the compounds in pharmaceutical composition and treatment regimens are also provided. The identification of CLIMP-63 as a biological target of avrainvillamide provides for the identification of antagonists, agonists, or compounds which bind or modulate the activity of CLIMP-63. The identified compounds are also considered part of the invention.

DEFINITIONS

Definitions of specific functional groups and chemical terms are described in more detail below. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in "Organic Chemistry," Thomas Sorrell, University Science Books, Sausalito: 1999, the entire contents of which are incorporated herein by reference.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

One of ordinary skill in the art will appreciate that the synthetic methods, as described herein, utilize a variety of protecting groups. By the term "protecting group", as used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group should be selectively removable in good yield by readily available, preferably non-toxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen, and carbon protecting groups may be utilized. Hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl, (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio)ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napthtyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate. Amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten) carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), diallyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide. Exemplary protecting groups are detailed herein. However, it will be appreciated that the present invention is not intended to be limited to these protecting groups; rather, a variety of additional equivalent protecting groups can be readily identified using the above criteria and utilized in the method of the present invention. Additionally, a variety of protecting groups are described in *Protective Groups in Organic Synthesis*, Third Ed. Greene, T. W. and Wuts, P. G., Eds., John Wiley & Sons, New York: 1999, the entire contents of which are hereby incorporated by reference.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example, of infectious diseases or proliferative disorders. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term "aliphatic", as used herein, includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "lower alkyl" is used to indicate those alkyl groups (cyclic, acyclic, substituted, unsubstituted, branched or unbranched) having 1-6 carbon atoms.

In certain embodiments, the alkyl, alkenyl, and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the allyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, cyclopropyl, —$CH_2$-cyclopropyl, vinyl, allyl, n-butyl, sec-butyl, isobutyl, tert-butyl, cyclobutyl, —$CH_2$-cyclobutyl, n-pentyl, sec-pentyl, isopentyl, tert-pentyl, cyclopentyl, —$CH_2$-cyclopentyl, n-hexyl, sec-hexyl, cyclohexyl, —$CH_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

The term "alkoxy", or "thioalkyl" as used herein refers to an alkyl group, as previously defined, attached to the parent molecule through an oxygen atom or through a sulfur atom. In certain embodiments, the alkyl, alkenyl, and alkynyl groups contain 1-20 alipahtic carbon atoms. In certain other embodiments, the alkyl, alkenyl, and alkynyl groups contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups contain 1-6 aliphatic carbon atoms. In yet other embodiments, the alkyl, alkenyl, and alkynyl groups contain 1-4 aliphatic carbon atoms. Examples of alkoxy, include but are not limited to, methoxy, ethoxy, propoxy, isopropoxy, n-butoxy, tert-butoxy, neopentoxy, and n-hexoxy. Examples of thioalkyl include, but are not limited to, methylthio, ethylthio, propylthio, isopropylthio, n-butylthio, and the like.

The term "alkylamino" refers to a group having the structure —NHR', wherein R' is aliphatic, as defined herein. In certain embodiments, the aliphatic group contains 1-20 aliphatic carbon atoms. In certain other embodiments, the aliphatic group contains 1-10 aliphatic carbon atoms. In yet other embodiments, the aliphatic group employed in the invention contain 1-8 aliphatic carbon atoms. In still other embodiments, the aliphatic group contains 1-6 aliphatic carbon atoms. In yet other embodiments, the aliphatic group contains 1-4 aliphatic carbon atoms. Examples of alkylamino groups include, but are not limited to, methylamino, ethylamino, n-propylamino, iso-propylamino, cyclopropylamino, n-butylamino, tert-butylamino, neopentylamino, n-pentylamino, hexylamino, cyclohexylamino, and the like.

The term "dialkylamino" refers to a group having the structure —NRR', wherein R and R' are each an aliphatic group, as defined herein. R and R' may be the same or different in an dialkyamino moiety. In certain embodiments, the aliphatic groups contains 1-20 aliphatic carbon atoms. In certain other embodiments, the aliphatic groups contains 1-10 aliphatic carbon atoms. In yet other embodiments, the aliphatic groups employed in the invention contain 1-8 aliphatic carbon atoms. In still other embodiments, the aliphatic groups contains 1-6 aliphatic carbon atoms. In yet other embodiments, the aliphatic groups contains 1-4 aliphatic carbon atoms. Examples of dialkylamino groups include, but are not limited to, dimethylamino, methyl ethylamino, diethylamino, methylpropylamino, di(n-propyl)amino, di(iso-propyl)amino, di(cyclopropyl)amino, di(n-butyl)amino, di(tert-butyl)amino, di(neopentyl)amino, di(n-pentyl)amino, di(hexyl)amino, di(cyclohexyl)amino, and the like. In certain embodiments, R and R' are linked to form a cyclic structure. The resulting cyclic structure may be aromatic or non-aromatic. Examples of cyclic diaminoalkyl groups include, but are not limited to, aziridinyl, pyrrolidinyl, piperidinyl, morpholinyl, pyrrolyl, imidazolyl, 1,3,4-trianolyl, and tetrazolyl.

Some examples of substituents of the above-described aliphatic (and other) moieties of compounds of the invention include, but are not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

In general, the terms "aryl" and "heteroaryl", as used herein, refer to stable mono- or polycyclic, heterocyclic, polycyclic, and polyheterocyclic unsaturated moieties having preferably 3-14 carbon atoms, each of which may be substituted or unsubstituted. Substituents include, but are not limited to, any of the previously mentioned substitutents, i.e., the substituents recited for aliphatic moieties, or for other moieties as disclosed herein, resulting in the formation of a stable compound. In certain embodiments of the present invention, "aryl" refers to a mono- or bicyclic carbocyclic ring system having one or two aromatic rings including, but not limited to, phenyl, naphthyl, tetrahydronaphthyl, indanyl, indenyl, and the like. In certain embodiments of the present invention, the term "heteroaryl", as used herein, refers to a cyclic aromatic radical having from five to ten ring atoms of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups can be unsubstituted or substituted, wherein substitution includes replacement of one, two, three, or more of the hydrogen atoms thereon independently with any one or more of the following moieties including, but not limited to: aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

The term "cycloalkyl", as used herein, refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of other aliphatic, heteroaliphatic, or heterocyclic moieties, may optionally be substituted with substituents including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

The term "heteroaliphatic", as used herein, refers to aliphatic moieties that contain one or more oxygen, sulfur, nitrogen, phosphorus, or silicon atoms, e.g., in place of carbon atoms. Heteroaliphatic moieties may be branched, unbranched, cyclic or acyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of $R_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

The terms "halo" and "halogen" as used herein refer to an atom selected from fluorine, chlorine, bromine, and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "heterocycloalkyl" or "heterocycle", as used herein, refers to a non-aromatic 5-, 6-, or 7-membered ring or a polycyclic group, including, but not limited to a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may be optionally be oxidized, (iii) the nitrogen heteroatom may optionally be quaternized, and (iv) any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. In certain embodiments, a "substituted heterocycloalkyl or heterocycle" group is utilized and as used herein, refers to a heterocycloalkyl or heterocycle group, as defined above, substituted by the independent replacement of one, two or three of the hydrogen atoms thereon with but are not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of $R_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples which are described herein.

"Carbocycle": The term "carbocycle", as used herein, refers to an aromatic or non-aromatic ring in which each atom of the ring is a carbon atom.

"Independently selected": The term "independently selected" is used herein to indicate that the R groups can be identical or different.

"Labeled": As used herein, the term "labeled" is intended to mean that a compound has at least one element, isotope, or chemical compound attached to enable the detection of the compound. In general, labels typically fall into three classes: a) isotopic labels, which may be radioactive or heavy isotopes, including, but not limited to, $^2$H, $^3$H, $^{13}$C, $^{14}$C, $^{15}$N, $^{31}$P, $^{32}$P, $^{35}$S, $^{67}$Ga, $^{99m}$Tc (Tc-99m), $^{111}$In, $^{123}$I, $^{125}$I, $^{169}$Yb, and $^{186}$Re; b) immune labels, which may be antibodies or antigens, which may be bound to enzymes (such as horseradish peroxidase) that produce detectable agents; and c) colored, luminescent, phosphorescent, or fluorescent dyes. It will be appreciated that the labels may be incorporated into the compound at any position that does not interfere with the biological activity or characteristic of the compound that is being detected. In certain embodiments, hydrogen atoms in the compound are replaced with deuterium atoms ($^2$H) to slow the degradation of compound in vivo. Due to isotope effects, enzymatic degradation of the deuterated compounds may be slowed thereby increasing the half-life of the compound in vivo. In other embodiments such as in the identification of the biological target of a natural product or derivative thereof, the compound is labeled with a radioactive isotope, preferably an isotope which emits detectable particles, such as β particles. In certain other embodiments of the invention, photoaffinity labeling is utilized for the direct elucidation of intermolecular interactions in biological systems. A variety of known photophores can be employed, most relying on photoconversion of diazo compounds, azides, or diazirines to nitrenes or carbenes (See, Bayley, H., Photogenerated Reagents in Biochemistry and Molecular Biology (1983), Elsevier, Amsterdam.), the entire contents of which are hereby incorporated by reference. In certain embodiments of the invention, the photoaffinity labels employed are o-, m- and p-azidobenzoyls, substituted with one or more halogen moieties, including, but not limited to 4-azido-2,3,5,6-tetrafluorobenzoic acid. In other embodiments, biotin labeling is utilized.

"Tautomers": As used herein, the term "tautomers" are particular isomers of a compound in which a hydrogen and double bond have changed position with respect to the other atoms of the molecule. For a pair of tautomers to exist there must be a mechanism for interconversion. Examples of tautomers include keto-enol forms, imine-enamine forms, amide-imino alcohol forms, amidine-aminidine forms, nitroso-oxime forms, thio ketone-enethiol forms, N-nitroso-hydroxyazo forms, nitro-aci-nitro forms, and pyridione-hydroxypyridine forms.

Definitions of non-chemical terms used throughout the specification include:

"Animal": The term animal, as used herein, refers to humans as well as non-human animals, including, for example, mammals, birds, reptiles, amphibians, and fish. Preferably, the non-human animal is a mammal (e.g., a rodent, a mouse, a rat, a rabbit, a monkey, a dog, a cat, a primate, or a pig). A non-human animal may be a transgenic animal.

"Associated with": When two entities are "associated with" one another as described herein, they are linked by a direct or indirect covalent or non-covalent interaction. Preferably, the association is covalent. Desirable non-covalent interactions include hydrogen bonding, van der Waals interactions, hydrophobic interactions, magnetic interactions, electrostatic interactions, etc.

"CLIMP-63": The term "CLIMP-63" or "cytoskeleton-linking membrane protein" or "p63" or "CKAP4 protein" refers to CLIMP-63 polypeptides, proteins, peptides, fragments, variants, and mutants thereof as well as to nucleic acids that encode CLIMP-63 polypeptides, proteins, peptides, fragments, variants, or mutants thereof. CLIMP-63 has been found to be a biological target of avrainvillamide. CLIMP-63 is an integral membrane protein that links the endoplasmic reticulum (ER) to the microtubule cytoskeleton.

CLIMP-63 may be derived from any species. In certain embodiments, mammalian or human CLIMP-63 is referred to.

"Effective amount": In general, the "effective amount" of an active agent or the microparticles refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the patient. For example, the effective amount of a compound with anti-proliferative activity is the amount that results in a sufficient concentration at the site of the tumor to kill or inhibit the growth of tumor cells. The effective amount of a compound used to treat infection is the amount needed to kill or prevent the growth of the organism(s) responsible for the infection.

"Polynucleotide" or "oligonucleotide" refers to a polymer of nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, C5-bromouridine, C5-fluorouridine, C5-iodouridine, 7-deazaadenosine, 7-deazaguanosine, 8-oxoadenosine, 8-oxoguanosine, O(6)-methylguanine, 4-acetylcytidine, 5-(carboxyhydroxymethyl)uridine, dihydrouridine, methylpseudouridine, 1-methyl adenosine, 1-methyl guanosine, N6-methyl adenosine, and 2-thiocytidine), chemically modified bases, biologically modified bases (e.g., methylated bases), intercalated bases, modified sugars (e.g., 2'-fluororibose, ribose, 2'-deoxyribose, 2'-O-methylcytidine, arabinose, and hexose), or modified phosphate groups (e.g., phosphorothioates and 5'-N-phosphoramidite linkages).

A "protein" or "peptide" comprises a polymer of amino acid residues linked together by peptide bonds. The term, as used herein, refers to proteins, polypeptides, and peptide of any size, structure, or function. Typically, a protein will be at least three amino acids long. A protein may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive protein may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein may also be a single molecule or may be a multi-molecular complex. A protein may be just a fragment of a naturally occurring protein or peptide. A protein may be naturally occurring, recombinant, or synthetic, or any combination of these.

BRIEF DESCRIPTION OF THE DRAWING

FIG. 5 shows the addition of methanol to the α,β-unsaturated nitrone funationality of avrainvillamide.

FIG. 12 shows GI50 data for avrainvillamide and stepacidin B for four difference cell lines.

FIG. 16 shows GI50 data for tetramethyl-substitute analogues of avrainvillamide.

FIG. 17 shows IC$_{50}$ and GI50 data for certain probe compounds used to identify the biological target of avrainvillamide.

FIG. 20 induces apoptosis at 1-4 µM and necrosis at 8 µM.

FIG. 22 shows the results of a the pull down experiment in T-47D cells with controls. CLIMP-63 can be shown pulled down in the lane with 9 µM probe (Compound 4).

FIG. 25 includes the amino acid sequence of CLIMP-63 (SEQ ID NO:XX).

DETAILED DESCRIPTION OF CERTAIN EMBODIMENTS OF THE INVENTION

Figure 1:
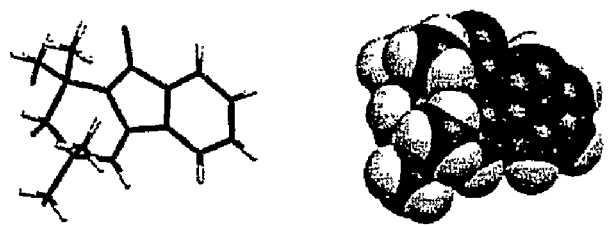
FIG. 1 shows the capped-stick and space-filling models of the 3-alkylidene-3H-indole 1-oxide function of avrainvillamide from X-ray data.

The syntheses of the 3-alkylidene-3H-indole 1-oxide function of avrainvillamide, avrainvillamide, and stephacidin B are provided herein. The 3-alkylidene-3H-indole 1-oxide function is capable of undergoing reversible covalent bond formation with nucleophiles. Such functionality is thought to account for the biological activity of avrainvillamide and its dimer, stephacidin B. The syntheses of these compounds provides for not only these compounds but other related compounds which may be used as pharmaceutical agents in the treatment of proliferative diseases such as cancer, inflammatory diseases, diabetic retinopathy, etc.

Compounds

In one aspect, the present invention provides compounds of the formula:

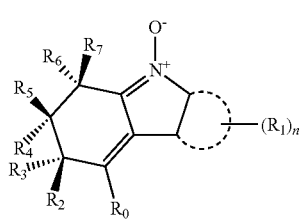

(III)

wherein $R_0$, $R_1$, $R_2$, $R_3$, $R_4$, $R_5$, $R_6$, and $R_7$ are independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_G$; —$C(=O)R_G$; —$CO_2R_G$; —CN; —SCN; —$SR_G$; —$SOR_G$; —$SO_2R_G$; —$NO_2$; —$N_3$; —$N(R_G)_2$; —$NHC(=O)R_G$; —$NR_GC(=O)N(R_G)_2$; —$OC(=O)OR_G$; —$OC(=O)R_G$; —$OC(=O)N(R_G)_2$; —$NR_GC(=O)OR_G$; or —$C(R_G)_3$; wherein each occurrence of $R_G$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

wherein two or more substituents may form substituted or unsubstituted, cyclic, heterocyclic, aryl, or heteroaryl structures;

wherein $R_2$ and $R_3$, $R_4$ and $R_5$, or $R_6$ and $R_7$ may form together =O, =$NR_G$, or =$C(R_G)_2$, wherein each occurrence of $R_G$ is defined as above;

represents a substituted or unsubstituted, cyclic, heterocyclic, aryl, or heteroaryl ring system; and n is an integer between 0 and 4.

In certain embodiments,

is a monocyclic, bicyclic, tricyclic, or polycyclic ring system, preferably

is a monocyclic, bicyclic, or tricyclic ring system. The ring system may be carbocyclic or heterocyclic, aromatic or non-aromatic, substituted or unsubstituted. The ring may include fused rings, bridged rings, spiro-linked rings, or a combination thereof. In certain embodiments,

is a monocyclic ring system, preferably a 4-, 5-, 6-, or 7-membered monocyclic ring system, more preferably a 5- or 6-membered ring system, optionally including one, two, or three heteroatoms such as oxygen, nitrogen, or sulfur. In certain embodiments,

represents a phenyl ring. In other embodiments,

represents a six-member heteroaromatic ring. In other embodiments,

represents a five-member heteroaromatic ring. In yet other embodiments,

represents a six-membered non-aromatic ring. In still other embodiments, represents a five-membered non-aromatic ring. Examples of particular monocyclic ring systems include:
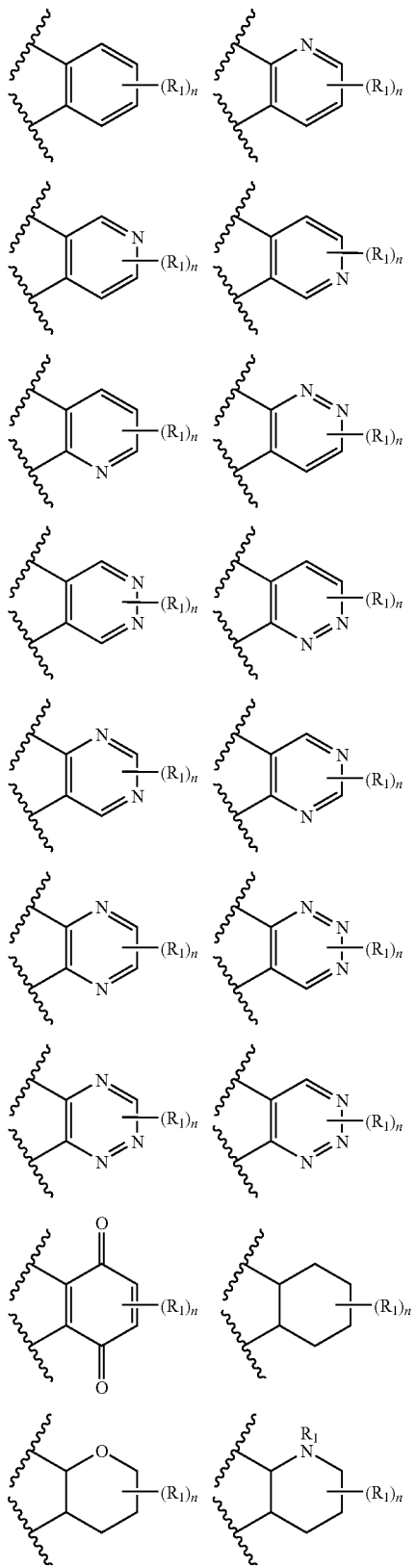
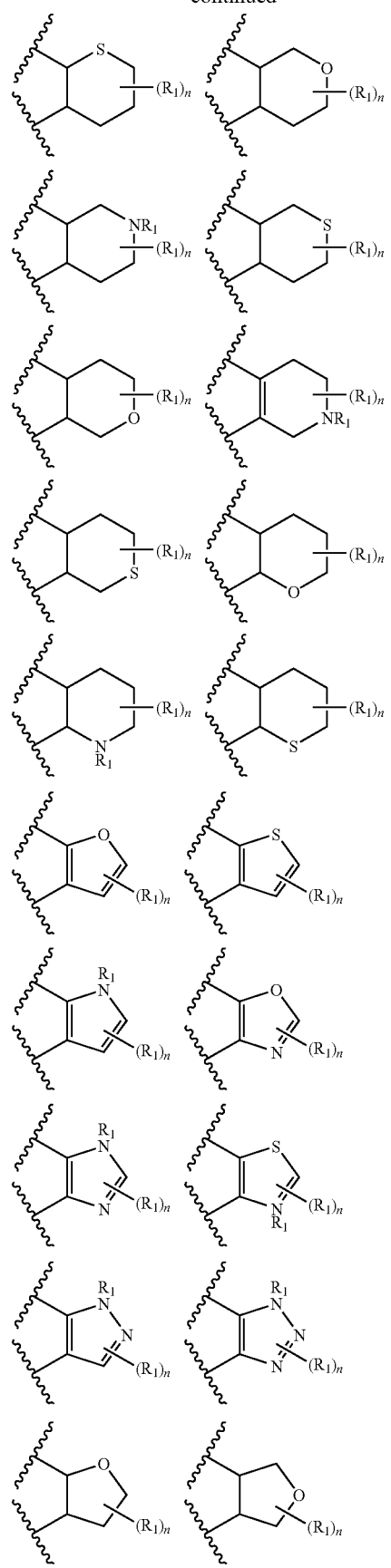
-continued -continued

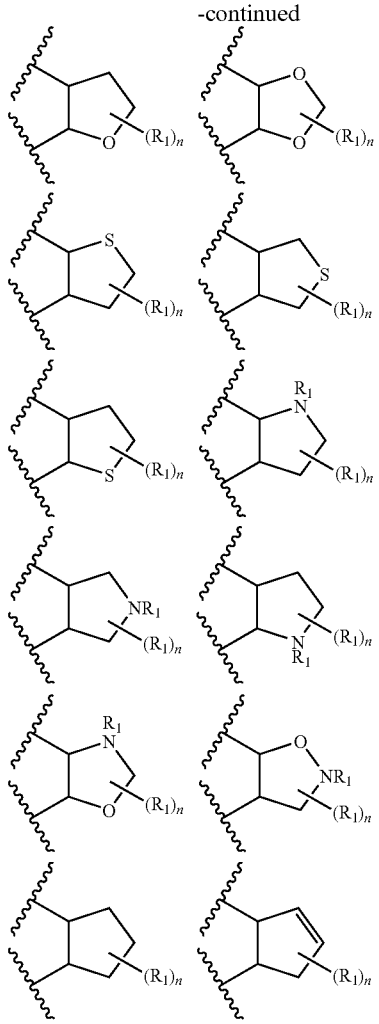

In certain embodiments,

is a phenyl ring with one, two, three, or four substituents, preferably one, two, or three substituents, more preferably one or two substituents. For example,

may be

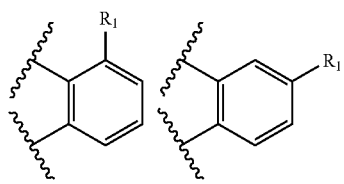

-continued

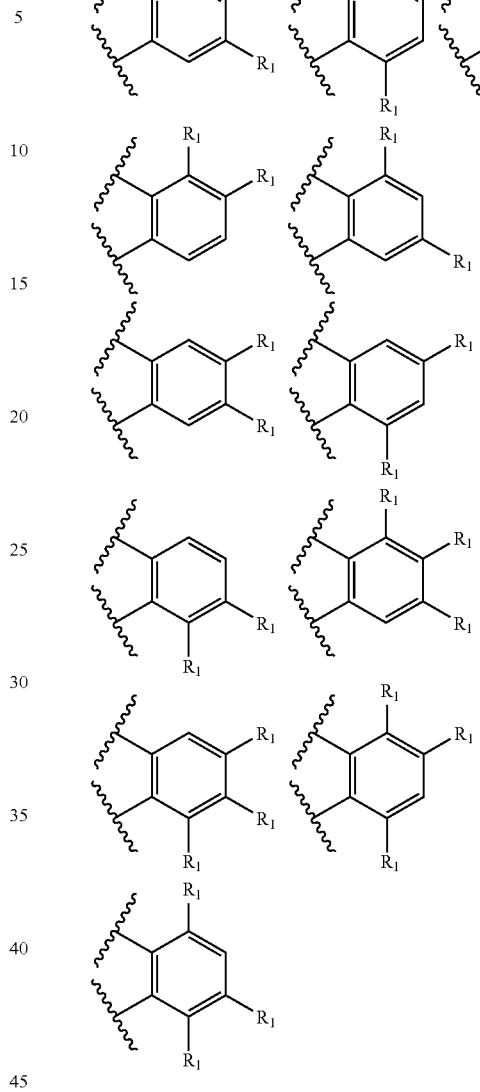

In certain preferred embodiments,

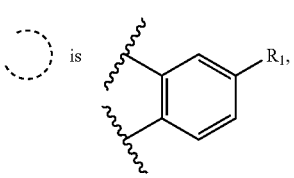

wherein $R_1$ is $-C(R_G)_3$, $-OR_G$, $-N(R_G)_2$, or $-SR_G$, wherein each occurrence of $R_G$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety; preferably $R_1$ is alkoxy, more preferably methoxy, ethoxy, propoxy, or butoxy. In certain embodiments, $R_G$ is an unsubstituted alkyl, alkenyl, or alkynyl group. In certain embodiments, $R_G$ is $C_1$-$C_{20}$ alkyl. In other embodiments, $R_G$ is $C_1$-$C_{16}$ alkyl. In yet other embodiments, $R_G$ is $C_1$-$C_{12}$ alkyl. In still other embodiments, $R_G$ is $C_1$-$C_6$ alkyl. In certain embodiments, $R_G$ is $C_1$-$C_{20}$ alkenyl. In other embodiments, $R_G$ is $C_1$-$C_{16}$ alkenyl. In yet other embodiments, $R_G$ is $C_1$-$C_{12}$ alkenyl. In still other embodiments, $R_G$ is $C_1$-$C_6$ alkenyl. In certain embodiments, $R_G$ is —$(CH_2CH_2O)_n$—$CH_2CH_2OR_g'$, wherein n is an integer between 0 and 10, and $R_G'$ is hydrogen or $C_1$-$C_6$ alkyl (e.g., methyl, ethyl).

In other embodiments,

represents a bicyclic ring system, preferably a 8-, 9-, 10-, 11-, or 12-membered bicyclic ring system, optionally substituted with one or more heteroatom such as oxygen, nitrogen, or sulfur. The ring system may optionally contain an aromatic ring. In certain embodiments, the bicyclic ring system is a phenyl ring fused with a 4-, 5-, 6-, or 7-membered ring, preferably a 5- or 6-membered ring. In certain embodiments, the bicyclic ring system is a six-membered heteroaromatic ring fused with a 4-, 5-, 6-, or 7-membered ring, preferably a 5- or 6-membered ring. Examples of bicyclic systems include:

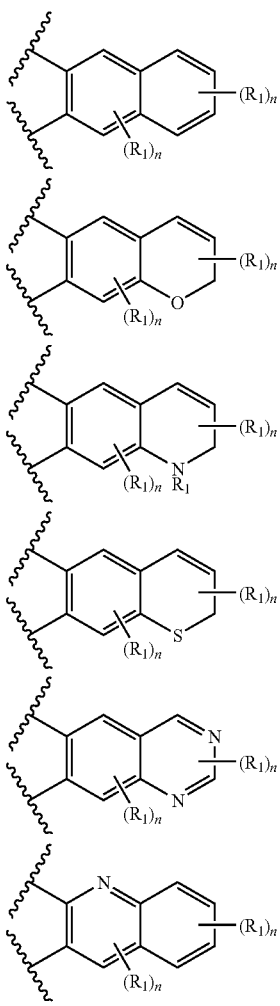

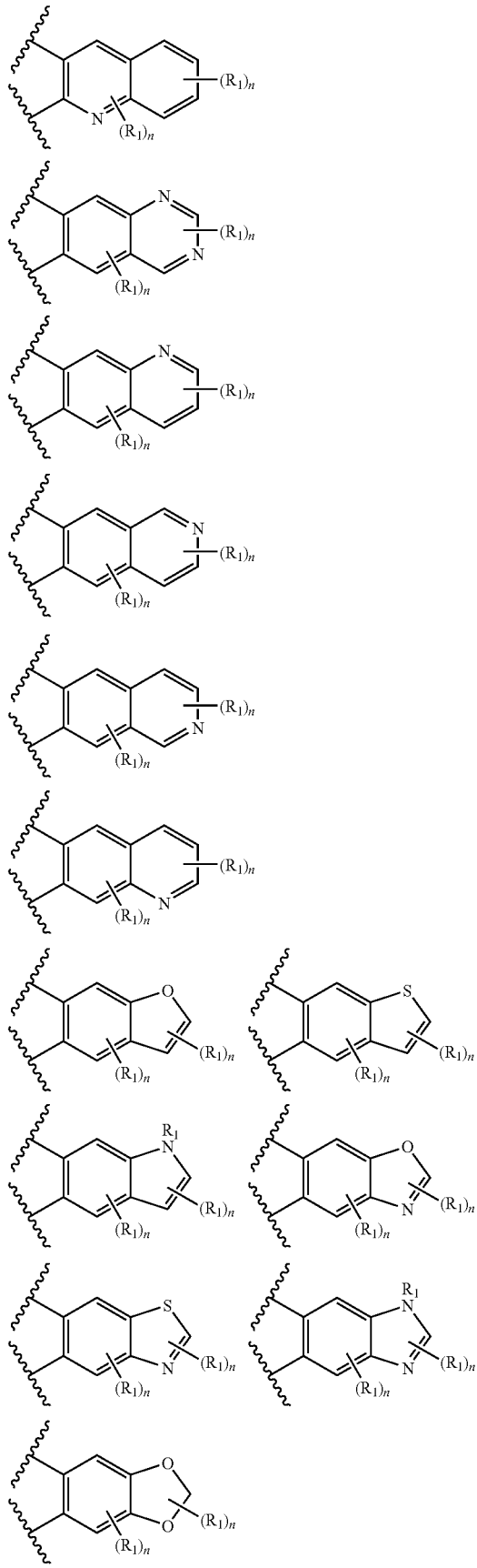

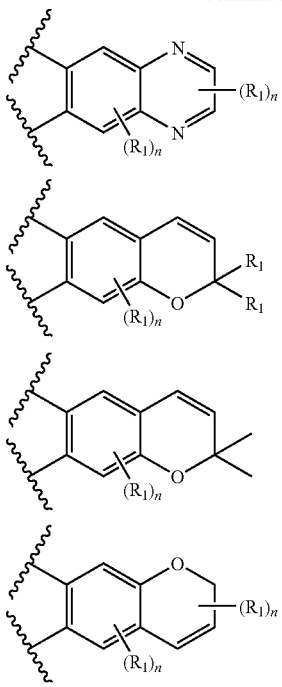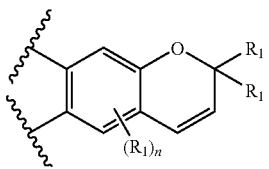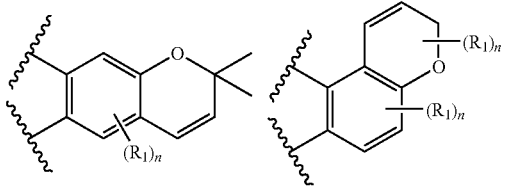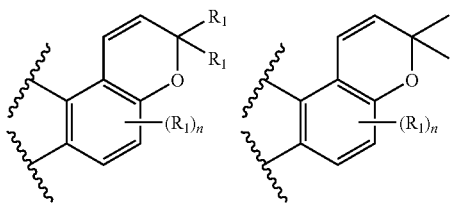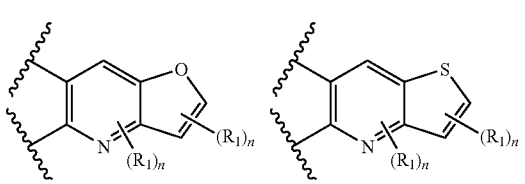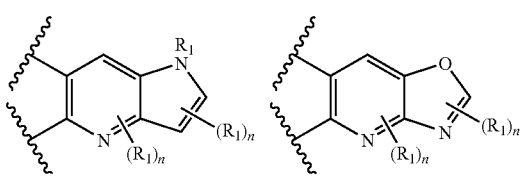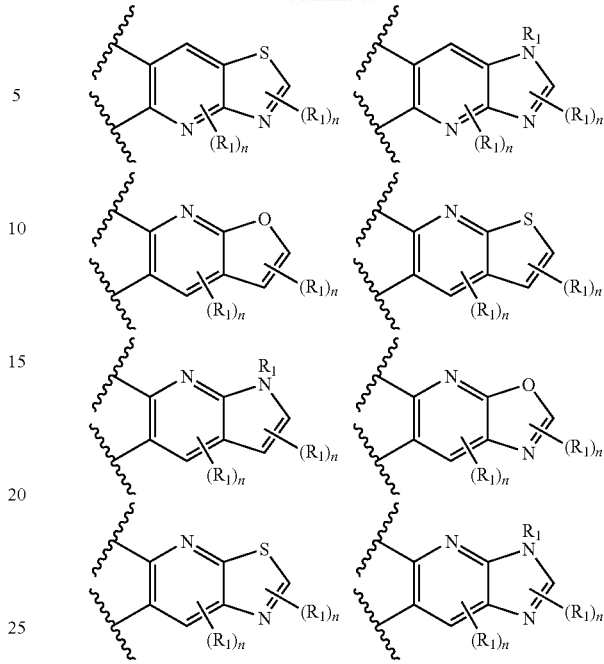

In certain embodiments, $R_0$ is hydrogen. In certain embodiments, $R_0$ is halogen. In other embodiments, $R_0$ is aliphatic. In yet other embodiments, $R_0$ is $C_1$-$C_6$ alkyl. In certain embodiments, $R_0$ is selected from the group consisting of hydrogen, methyl, ethyl, n-propyl, iso-propyl, n-butyl, iso-butyl, and tert-butyl. In certain embodiments, $R_0$ is heteroaliphatic.

In certain embodiments, $R_1$ is hydrogen; halogen; substituted or unsubstituted aliphatic; substituted or unsubstituted heteroaliphatic; alkoxy; alkylthioxy; acyl; cyano; nitro; amino; alkylamino; or dialkylamino. In certain embodiments, $R_1$ is hydrogen; halogen; substituted or unsubstituted aliphatic; alkoxy; alkylthioxy; amino; alkylamino; or dialkylamino. In certain embodiments, $R_1$ is hydrogen, alkoxy, acetoxy, or tosyloxy. In certain embodiments, $R_1$ is hydrogen or methoxy. In certain embodiments, $R_1$ is an unsubstituted alkyl, alkenyl, or alkynyl group. In certain embodiments, $R_1$ is $C_1$-$C_{20}$ alkyl. In other embodiments, $R_1$ is $C_1$-$C_{16}$ alkyl. In yet other embodiments, $R_1$ is $C_1$-$C_{12}$ alkyl. In still other embodiments, $R_1$ is $C_1$-$C_6$ alkyl. In certain embodiments, $R_1$ is methyl. In certain embodiments, $R_1$ is $C_1$-$C_{20}$ alkenyl. In other embodiments, $R_1$ is $C_1$-$C_{16}$ alkenyl. In yet other embodiments, $R_1$ is $C_1$-$C_{12}$ alkenyl. In still other embodiments, $R_1$ is $C_1$-$C_6$ alkenyl. In certain embodiments, $R_1$ is $-(CH_2CH_2O)_k-CH_2CH_2OR_1'$, wherein k is an integer between 0 and 10, and $R_1'$ is hydrogen or $C_1$-$C_6$ alkyl (e.g., methyl, ethyl). In certain embodiments, $R_1$ is $-OR_G$, $-N(R_G)_2$, or $-SR_G$, wherein each occurrence of $R_G$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety. In certain embodiments, $R_1$ is alkoxy (e.g., methoxy, ethoxy, propoxy, butoxy, etc.). In certain embodiments, $R_G$ is an unsubstituted alkyl, alkenyl, or alkynyl group. In certain embodiments, $R_G$ is $C_1$-$C_{20}$ alkyl. In other embodiments, $R_G$ is $C_1$-$C_{16}$ alkyl. In yet other embodiments, $R_G$ is $C_1$-$C_{12}$ alkyl. In still other embodiments, $R_G$ is $C_1$-$C_6$ alkyl. In certain embodiments, $R_G$ is $C_1$-$C_{20}$ alkenyl. In other embodiments, $R_G$ is $C_1$-$C_{16}$ alkenyl. In yet other embodiments, $R_G$ is $C_1$-$C_{12}$ alkenyl. In still other embodiments, $R_G$ is $C_1$-$C_6$ alkenyl. In certain embodiments, $R_G$ is —$(CH_2CH_2O)_n$—$CH_2CH_2OR_G'$, wherein n is an integer between 0 and 10, and $R_G'$ is hydrogen or $C_1$-$C_6$ alkyl (e.g., methyl, ethyl).

In certain embodiments, n is 0. In other embodiments, n is 1. In yet other embodiments n is 2. In still other embodiments, n is 3, 4, or 5. As would be appreciated by one of skill in this art, as the ring system grows larger, n may be larger as the number of possible positions for substitutions grows. When n is at least 2, any two $R_1$ groups may form a cyclic structure. The cyclic structure may be carbocyclic or heterocyclic, aromatic or non-aromatic. The cyclic ring system formed may be a fused ring system, spiro-linked ring system, or a bridged ring system depending on the placement of the $R_1$ groups.

In certain embodiments, each of $R_2$, $R_3$, $R_4$, $R_5$, $R_6$, and $R_7$ is independently a hydrogen, or cyclic or acyclic, substituted or unsubstituted, branched or unbranched aliphatic or heteroaliphatic. In certain embodiments, at least one, two, three, four, five, or all six of $R_2$, $R_3$, $R_4$, $R_5$, $R_6$, and $R_7$ are hydrogen. In other embodiments, at least one, two, three, four, five, or all six of $R_2$, $R_3$, $R_4$, $R_5$, $R_6$, and $R_7$ are hydrogen or $C_1$-$C_{20}$ alkyl, preferably hydrogen, methyl, ethyl, n-propyl, iso-propyl, n-butyl, iso-butyl, or tert-butyl. In certain embodiments, all six of $R_2$, $R_3$, $R_4$, $R_5$, $R_6$, and $R_7$ are hydrogen or methyl. In other embodiments, at least one of $R_2$, $R_3$, $R_4$, $R_5$, $R_6$, and $R_7$ is substituted or unsubstituted, branched or unbranched acyl. In yet other embodiments, at least one of $R_2$, $R_3$, $R_4$, $R_5$, $R_6$, and $R_7$ is substituted or unsubstituted, aryl or heteroaryl. In certain embodiments, at least one of $R_2$, $R_3$, $R_4$, $R_5$, $R_6$, and $R_7$ is an unsubstituted alkyl, alkenyl, or alkynyl group. In certain embodiments, at least one of $R_2$, $R_3$, $R_4$, $R_5$, $R_6$, and $R_7$ is $C_1$-$C_{20}$ alkyl. In other embodiments, at least one of $R_2$, $R_3$, $R_4$, $R_5$, $R_6$, and $R_7$ is $C_1$-$C_{16}$ alkyl. In yet other embodiments, at least one of $R_2$, $R_3$, $R_4$, $R_5$, $R_6$, and $R_7$ is $C_1$-$C_{12}$ alkyl. In still other embodiments, at least one of $R_2$, $R_3$, $R_4$, $R_5$, $R_6$, and $R_7$ is $C_1$-$C_6$ alkyl. In certain embodiments, at least one of $R_2$, $R_3$, $R_4$, $R_5$, $R_6$, and $R_7$ is methyl. In certain embodiments, at least one of $R_2$, $R_3$, $R_4$, $R_5$, $R_6$, and $R_7$ is $C_1$-$C_{20}$ alkenyl. In other embodiments, at least one of $R_2$, $R_3$, $R_4$, $R_5$, $R_6$, and $R_7$ is $C_1$-$C_{16}$ alkenyl. In yet other embodiments, at least one of $R_2$, $R_3$, $R_4$, $R_5$, $R_6$, and $R_7$ is $C_1$-$C_{12}$ alkenyl. In still other embodiments, at least one of $R_2$, $R_3$, $R_4$, $R_5$, $R_6$, and $R_7$ is $C_1$-$C_6$ alkenyl. In certain embodiments, at least one of $R_2$, $R_3$, $R_4$, $R_5$, $R_6$, and $R_7$ is —$(CH_2CH_2O)_k$—$CH_2CH_2OR_B'$, wherein k is an integer between 0 and 10, and $R_B'$ hydrogen or $C_1$-$C_6$ alkyl (e.g., methyl, ethyl).

In certain embodiments, $R_1$, $R_2$, $R_3$, $R_4$, $R_5$, $R_6$, or $R_7$ comprises a label such as a radiolabel, biotin, peptide epitope, colored, phosphorescent, luminescent, or fluorescent tag. The radiolabel may include an isotope of hydrogen, carbon, nitrogen, phosphorus, sulfur, or iodine, e.g. $^3H$, $^{14}C$, $^{31}P$, $^{32}P$, $^{35}S$, and $^{125}I$. The radiolabel may emit alpha particles, beta particles, or gamma particles, preferably beta particles. The fluorescent tag may be fluoroscein or a fluoroscein derivative. The label may also include a protein or peptide. The protein or peptide may contain an epitope recognized by an antibody or antibody fragment. The peptide or protein may be fluorescent, e.g., green fluorescent protein (GFP). In certain embodiments, $R_1$ comprises a biotin label. In certain embodiments, the labelled compound is of formula:

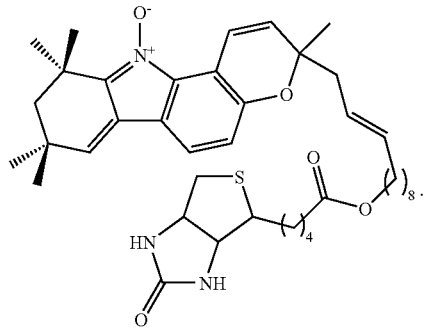

In certain embodiments, one or both of $R_2$ and $R_3$ is hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; —$OR_G$; —$SR_G$; —C(=O)$R_G$; —$CO_2R_G$; —CN; —$N_3$; —$N(R_G)_2$; —NH(C=O)$R_G$; —OC(=O)$R_G$; wherein each occurrence of $R_G$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety. In certain embodiments, one or both of $R_2$ and $R_3$ is —$OR_G$; —$SR_G$; —(C=O) $R_G$; —CN; —$CO_2R_G$; —$CO_2H$; —C(=O)N($R_G)_2$; —C(=O)$NH_2$; or —N($R_G)_2$; wherein $R_G$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety. In certain embodiments, $R_2$ and/or $R_3$ is —C(=O)$R_G$ or —NH($R_G$), wherein $R_G$ is as defined above. In other embodiments, $R_2$ and/or $R_3$ is —C(=O)$R_G$ or —NH($R_G$), wherein $R_G$ is an amino acid or peptide. In certain particular embodiments, $R_2$ is —C(=O)$R_G$, wherein $R_G$ is an amino acid or peptide; and $R_3$ is —NH($R_G$), wherein $R_G$ is an amino acid or peptide. In certain embodiments, $R_2$ and $R_3$ are taken together to form =O. In other embodiments, $R_2$ and $R_3$ are taken together to form a cyclic acetal group.

In certain embodiments, $R_6$ and $R_7$ are both hydrogen or $C_1$-$C_6$ alkyl, preferably both are methyl. In certain embodiments, $R_4$ and $R_5$ are both hydrogen or $C_1$-$C_6$ alkyl, preferably both are hydrogen. In yet other embodiments, $R_4$ and $R_5$ are both hydrogen, and $R_6$ and $R_7$ are both methyl.

These functional cores of avrainvillamide may be modified by the 1,5-addition of a nucleophile as described in Example 1. Compounds of the formula III having undergone such nucleophilic attack are of the formula:

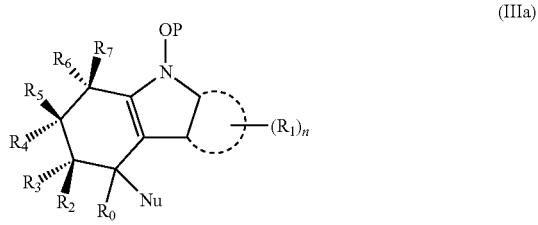

(IIIa)

wherein $R_0$, $R_1$, $R_2$, $R_3$, $R_4$, $R_5$, $R_6$, and $R_7$ are independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_G$; —C(=O)R$_G$; —CO$_2$R$_G$; —CN; —SCN; —SR$_G$; —SOR$_G$; —SO$_2$R$_G$; —NO$_2$; —N$_3$; —N(R$_G$)$_2$; —NHC(=O)R$_G$; —NR$_G$C(=O)N(R$_G$)$_2$; —OC(=O)OR$_G$; —OC(=O)R$_G$; —OC(=O)N(R$_G$)$_2$; —NR$_G$C(=O)OR$_G$; or —C(R$_G$)$_3$; wherein each occurrence of R$_G$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

wherein two or more substituents may form substituted or unsubstituted, cyclic, heterocyclic, aryl, or heteroaryl structures;

wherein R$_2$ and R$_3$, R$_4$ and R$_5$, or R$_6$ and R$_7$ may form together =O, =NR$_G$, or =C(R$_G$)$_2$, wherein each occurrence of R$_G$ is defined as above;

P is an oxygen protecting group or hydrogen;

Nu is hydrogen, —OR$_{Nu}$, —SR$_{Nu}$, —C(R$_{Nu}$)$_3$, or —N(R$_{Nu}$)$_2$, wherein each occurrence of R$_{Nu}$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

represents a substituted or unsubstituted, cyclic, heterocyclic, aryl, or heteroaryl ring system; and n is an integer between 0 and 4. In certain preferred embodiments, P is hydrogen. In other embodiments, P is C$_1$-C$_6$ allyl. In yet other embodiments, P is an oxygen-protecting group. In certain embodiments, P is acetyl. In certain embodiments, Nu is a sulfur-based nucleophile of the formula —SR$_{Nu}$. In other embodiments, Nu is an oxygen-based nucleophile of the formula —OR$_{Nu}$ (e.g., —OMe, —OEt, etc.). In other embodiments, Nu is a nitrogen-based nucleophile of the formula —N(R$_{Nu}$)$_2$. In certain embodiments, the nucleophile is an amino acid (e.g., the side chain of serine, threonine, cysteine, lysine, histidine, glutamine, asparagine, arginine, tyrosine; preferably, serine, threonine, or cysteine). In certain particular embodiments the nucleophile is cysteine. In other embodiments, the nucleophile is an amino acid which is part of a peptide or protein. In other embodiments, the nucleophile is glutathione. These nucleophilic adducts) may be useful in delivering the drug. For example, these adducts may serve to temporarily protect the α,β-unsaturated nitrone functionality of the molecule. In certain embodiments, the adduct may be a hydrate of the molecule. In certain embodiments, the adduct is a reduced form, wherein Nu is hydrogen.

In certain embodiments, compounds of the invention are of the formula:

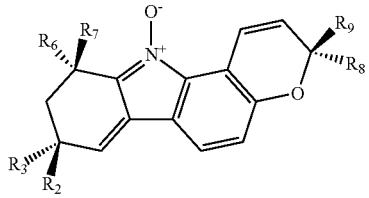

wherein
R$_2$, R$_3$, R$_6$, and R$_7$ are defined as above; and
each of R$_8$ and R$_9$ are independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_G$; —C(=O)R$_G$; —CO$_2$R$_G$; —CN; —SCN; —SR$_G$; —SOR$_G$; —SO$_2$R$_G$; —NO$_2$; —N$_3$; —N(R$_G$)$_2$; —NHC(=O)R$_G$; —NR$_G$C(=O)N(R$_G$)$_2$; —OC(=O)OR$_G$; —OC(=O)R$_G$; —OC(=O)N(R$_G$)$_2$; —NR$_G$C(=O)OR$_G$; or —C(R$_G$)$_3$; wherein each occurrence of R$_G$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety.

In certain embodiments, at least one of R$_2$, R$_3$, R$_6$, R$_7$, R$_8$, and R$_9$ is C$_1$-C$_{20}$ alkyl. In certain embodiments, at least two of R$_2$, R$_3$, R$_6$, R$_7$, R$_8$, and R$_9$ are C$_1$-C$_{20}$ alkyl. In certain embodiments, at least three of R$_2$, R$_3$, R$_6$, R$_7$, R$_8$, and R$_9$ are C$_1$-C$_{20}$ alkyl. In certain embodiments, at least four of R$_2$, R$_3$, R$_6$, R$_7$, R$_8$, and R$_9$ are C$_1$-C$_{20}$ alkyl. In certain embodiments, at least five of R$_2$, R$_3$, R$_6$, R$_7$, R$_8$, and R$_9$ are C$_1$-C$_{20}$ alkyl. In certain embodiments, at least one of R$_2$, R$_3$, R$_6$, R$_7$, R$_8$, and R$_9$ is C$_1$-C$_{10}$ alkyl. In certain embodiments, at least two of R$_2$, R$_3$, R$_6$, R$_7$, R$_8$, and R$_9$ are C$_1$-C$_{10}$ alkyl. In certain embodiments, at least three of R$_2$, R$_3$, R$_6$, R$_7$, R$_8$, and R$_9$ are C$_1$-C$_{10}$ alkyl. In certain embodiments, at least four of R$_2$, R$_3$, R$_6$, R$_7$, R$_8$, and R$_9$ are C$_1$-C$_{10}$ alkyl. In certain embodiments, at least five of R$_2$, R$_3$, R$_6$, R$_7$, R$_8$, and R$_9$ are C$_1$-C$_{10}$ alkyl. In certain embodiments, at least one of R$_2$, R$_3$, R$_6$, R$_7$, R$_8$, and R$_9$ is C$_1$-C$_6$ alkyl. In certain embodiments, at least two of R$_2$, R$_3$, R$_6$, R$_7$, R$_8$, and R$_9$ are C$_1$-C$_6$ alkyl. In certain embodiments, at least three of R$_2$, R$_3$, R$_6$, R$_7$, R$_8$, and R$_9$ are C$_1$-C$_6$ alkyl. In certain embodiments, at least four of R$_2$, R$_3$, R$_6$, R$_7$, R$_8$, and R$_9$ are C$_1$-C$_6$ alkyl. In certain embodiments, at least five of R$_2$, R$_3$, R$_6$, R$_7$, R$_8$, and R$_9$ are C$_1$-C$_6$ alkyl. In certain embodiments, at least one of R$_2$, R$_3$, R$_6$, R$_7$, R$_8$, and R$_9$ is methyl. In certain embodiments, at least two of R$_2$, R$_3$, R$_6$, R$_7$, R$_8$, and R$_9$ are methyl. In certain embodiments, at least three of R$_2$, R$_3$, R$_6$, R$_7$, R$_8$, and R$_9$ are methyl. In certain embodiments, at least four of R$_2$, R$_3$, R$_6$, R$_7$, R$_8$, and R$_9$ are methyl. In certain embodiments, at least five of R$_2$, R$_3$, R$_6$, R$_7$, R$_8$, and R$_9$ are methyl.

In certain embodiments, R$_2$ is hydrogen. In certain embodiments, R$_2$ is substituted or unsubstituted, branched or unbranched aliphatic. In certain embodiments, R$_2$ is substituted or unsubstituted, branched or unbranched heteroaliphatic. In certain embodiments, R$_2$ is alkyl. In certain embodiments, R$_2$ is C$_1$-C$_{20}$ alkyl. In other embodiments, R$_2$ is C$_1$-C$_{15}$ alkyl. In yet other embodiments, R$_2$ is C$_1$-C$_{12}$ alkyl. In still other embodiments, $R_2$ is $C_1$-$C_6$ alkyl. In still further embodiments, $R_2$ is $C_1$-$C_3$ alkyl. In certain embodiments, $R_2$ is methyl. In certain embodiments, $R_2$ is alkenyl. In certain embodiments, $R_2$ is $C_2$-$C_{20}$ alkenyl. In other embodiments, $R_2$ is $C_2$-$C_{15}$ alkenyl. In yet other embodiments, $R_2$ is $C_2$-$C_{12}$ alkenyl. In still other embodiments, $R_2$ is $C_2$-$C_6$ alkenyl. In certain embodiments, $R_2$ is vinyl. In certain embodiments, $R_2$ is alkoxy. In certain embodiments, $R_2$ is $C_{1-20}$ alkoxy. In other embodiments, $R_2$ is $C_1$-$C_{15}$ alkoxy. In yet other embodiments, $R_2$ is $C_1$-$C_{10}$ alkoxy. In still other embodiments, $R_2$ is $C_1$-$C_6$ alkoxy. In certain embodiments, $R_2$ is alkylthioxy. In certain embodiments, $R_2$ is $C_1$-$C_{20}$ alkylthioxy. In other embodiments, $R_2$ is $C_1$-$C_{15}$ alkylthioxy. In yet other embodiments, $R_2$ is $C_1$-$C_{10}$ alkylthioxy. In still other embodiments, $R_2$ is $C_1$-$C_6$ alkylthioxy. In other embodiments, $R_2$ is acyl. In certain embodiments, $R_2$ is —(CO)R', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_2$ is —(CO)OR', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_2$ is —(CO)NHR', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_2$ is —O(CO)R', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_2$ is —NH(CO)R', wherein R' is substituted or unsubstituted, branched or unbranched aliphatic or heteroaliphatic (e.g., $C_1$-$C_{20}$ alkyl, $C_1$-$C_{20}$ alkenyl, etc.).

In certain embodiments, $R_3$ is hydrogen. In certain embodiments, $R_3$ is substituted or unsubstituted, branched or unbranched aliphatic. In certain embodiments, $R_3$ is substituted or unsubstituted, branched or unbranched heteroaliphatic. In certain embodiments, $R_3$ is alkyl. In certain embodiments, $R_3$ is $C_1$-$C_{20}$ alkyl. In other embodiments, $R_3$ is $C_1$-$C_{15}$ alkyl. In yet other embodiments, $R_3$ is $C_1$-$C_{12}$ alkyl. In still other embodiments, $R_3$ is $C_1$-$C_6$ alkyl. In still further embodiments, $R_3$ is $C_1$-$C_3$ alkyl. In certain embodiments, $R_3$ is methyl. In certain embodiments, $R_3$ is alkenyl. In certain embodiments, $R_3$ is $C_2$-$C_{20}$ alkenyl. In other embodiments, $R_3$ is $C_2$-$C_{15}$ alkenyl. In yet other embodiments, $R_3$ is $C_2$-$C_{12}$ alkenyl. In still other embodiments, $R_3$ is $C_2$-$C_6$ alkenyl. In certain embodiments, $R_3$ is vinyl. In certain embodiments, $R_3$ is alkoxy. In certain embodiments, $R_3$ is $C_{1-20}$ alkoxy. In other embodiments, $R_3$ is $C_1$-$C_{15}$ alkoxy. In yet other embodiments, $R_3$ is $C_1$-$C_{10}$ alkoxy. In still other embodiments, $R_3$ is $C_1$-$C_6$ alkoxy. In certain embodiments, $R_3$ is alkylthioxy. In certain embodiments, $R_3$ is $C_1$-$C_{20}$ alkylthioxy. In other embodiments, $R_3$ is $C_1$-$C_{15}$ alkylthioxy. In yet other embodiments, $R_3$ is $C_1$-$C_{10}$ alkylthioxy. In still other embodiments, $R_3$ is $C_1$-$C_6$ alkylthioxy. In other embodiments, $R_3$ is acyl. In certain embodiments, $R_3$ is —(CO)R', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_3$ is —(CO)OR', wherein R' is substituted or unsubstituted, branched or unbranched aliphatic or heteroaliphatic (e.g., $C_1$-$C_{20}$ allyl, $C_1$-$C_{20}$ alkenyl, etc.). In certain embodiments, $R_3$ is —(CO)NHR', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_3$ is —O(CO)R', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_3$ is —NH(CO)R', wherein R' is substituted or unsubstituted, branched or unbranched aliphatic or heteroaliphatic (e.g., $C_1$-$C_{20}$ alkyl, $C_1$-$C_{20}$ alkenyl, etc.).

In certain embodiments, one or both of $R_2$ and $R_3$ is hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; —$OR_G$; —$SR_G$; —C(=O)$R_G$; —$CO_2R_G$; —CN; —$N_3$; —$N(R_G)_2$; —NH(C=O)$R_G$; —OC(=O)$R_G$; wherein each occurrence of $R_G$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety. In certain embodiments, one or both of $R_2$ and $R_3$ is —$OR_G$; —$SR_G$; —C(=O)$R_G$; —CN; —$CO_2R_G$; —$CO_2H$; —C(=O)N($R_G$)$_2$; —C(=O)NH$_2$; or —N($R_G$)$_2$; wherein $R_G$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety. In certain embodiments, $R_2$ and/or $R_3$ is —C(=O)$R_G$ or —NH($R_G$), wherein $R_G$ is as defined above. In other embodiments, $R_2$ and/or $R_3$ is —C(=O)$R_G$ or —NH($R_G$), wherein $R_G$ is an amino acid or peptide. In certain particular embodiments, $R_2$ is —C(=O)$R_G$, wherein $R_G$ is an amino acid or peptide; and $R_3$ is —NH($R_G$), wherein $R_G$ is an amino acid or peptide. In certain embodiments, $R_2$ and $R_3$ are taken together to form =O. In other embodiments, $R_2$ and $R_3$ are taken together to form a cyclic acetal group.

In certain embodiments, $R_6$ is hydrogen. In certain embodiments, $R_6$ is substituted or unsubstituted, branched or unbranched aliphatic. In certain embodiments, $R_6$ is substituted or unsubstituted, branched or unbranched heteroaliphatic. In certain embodiments, $R_6$ is alkyl. In certain embodiments, $R_6$ is $C_1$-$C_{20}$ alkyl. In other embodiments, $R_6$ is $C_1$-$C_{15}$ alkyl. In yet other embodiments, $R_6$ is $C_1$-$C_{12}$ alkyl. In still other embodiments, $R_6$ is $C_1$-$C_6$ alkyl. In still further embodiments, $R_6$ is $C_1$-$C_3$ alkyl. In certain embodiments, $R_6$ is methyl. In certain embodiments, $R_6$ is alkenyl. In certain embodiments, $R_6$ is $C_2$-$C_{20}$ alkenyl. In other embodiments, $R_6$ is $C_2$-$C_{15}$ alkenyl. In yet other embodiments, $R_6$ is $C_2$-$C_{12}$ alkenyl. In still other embodiments, $R_6$ is $C_2$-$C_6$ alkenyl. In certain embodiments, $R_6$ is vinyl. In certain embodiments, $R_6$ is alkoxy. In certain embodiments, $R_6$ is $C_{1-20}$ alkoxy. In other embodiments, $R_6$ is $C_1$-$C_{15}$ alkoxy. In yet other embodiments, $R_6$ is $C_1$-$C_{10}$ alkoxy. In still other embodiments, $R_6$ is $C_1$-$C_6$ alkoxy. In certain embodiments, $R_6$ is alkylthioxy. In certain embodiments, $R_6$ is $C_1$-$C_{20}$ alkylthioxy. In other embodiments, $R_6$ is $C_1$-$C_{15}$ alkylthioxy. In yet other embodiments, $R_6$ is $C_1$-$C_{10}$ alkylthioxy. In still other embodiments, $R_6$ is $C_1$-$C_6$ alkylthioxy. In other embodiments, $R_6$ is acyl. In certain embodiments, $R_6$ is —(CO)R', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_6$ is —(CO)OR', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_6$ is —(CO)NHR', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_6$ is —O(CO)R', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_6$ is —NH(CO)R', wherein R' is substituted or unsubstituted, branched or unbranched aliphatic or heteroaliphatic (e.g., $C_1$-$C_{20}$ alkyl, $C_1$-$C_{20}$ alkenyl, etc.).

In certain embodiments, $R_7$ is hydrogen. In certain embodiments, $R_7$ is substituted or unsubstituted, branched or unbranched aliphatic. In certain embodiments, $R_7$ is substituted or unsubstituted, branched or unbranched heteroaliphatic. In certain embodiments, $R_7$ is alkyl. In certain embodiments, $R_7$ is $C_1$-$C_{20}$ alkyl. In other embodiments, $R_7$ is $C_1$-$C_{15}$ alkyl. In yet other embodiments, $R_7$ is $C_1$-$C_{12}$ alkyl. In still other embodiments, $R_7$ is $C_1$-$C_6$ alkyl. In still further embodiments, $R_7$ is $C_1$-$C_3$ alkyl. In certain embodiments, $R_7$ is methyl. In certain embodiments, $R_7$ is alkenyl. In certain embodiments, $R_7$ is $C_2$-$C_{20}$ alkenyl. In other embodiments, $R_7$ is $C_2$-$C_{15}$ alkenyl. In yet other embodiments, $R_7$ is $C_2$-$C_{12}$ alkenyl. In still other embodiments, $R_7$ is $C_2$-$C_6$ alkenyl. In certain embodiments, $R_7$ is vinyl. In certain embodiments, $R_7$ is alkoxy. In certain embodiments, $R_7$ is $C_{1-20}$ alkoxy. In other embodiments, $R_7$ is $C_1$-$C_{15}$ alkoxy. In yet other embodiments, $R_7$ is $C_1$-$C_{10}$ alkoxy. In still other embodiments, $R_7$ is $C_1$-$C_6$ alkoxy. In certain embodiments, $R_7$ is alkylthioxy. In certain embodiments, $R_7$ is $C_1$-$C_{20}$ alkylthioxy. In other embodiments, $R_7$ is $C_1$-$C_{15}$ alkylthioxy. In yet other embodiments, $R_7$ is $C_1$-$C_{10}$ alkylthioxy. In still other embodiments, $R_7$ is $C_1$-$C_6$ alkylthioxy. In other embodiments, $R_7$ is acyl. In certain embodiments, $R_7$ is —(CO)R', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_7$ is —(CO)OR', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_7$ is —(CO)NHR', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_7$ is —O(CO)R', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_7$ is —NH(CO)R', wherein R' is substituted or unsubstituted, branched or unbranched aliphatic or heteroaliphatic (e.g., $C_1$-$C_{20}$ alkyl, $C_1$-$C_{20}$ alkenyl, etc.).

In certain embodiments, $R_8$ is hydrogen. In certain embodiments, $R_8$ is substituted or unsubstituted, branched or unbranched aliphatic. In certain embodiments, $R_8$ is substituted or unsubstituted, branched or unbranched heteroaliphatic. In certain embodiments, $R_8$ is alkyl. In certain embodiments, $R_8$ is $C_1$-$C_{20}$ alkyl. In other embodiments, $R_8$ is $C_1$-$C_{15}$ alkyl. In yet other embodiments, $R_8$ is $C_1$-$C_{12}$ alkyl. In still other embodiments, $R_8$ is $C_1$-$C_6$ alkyl. In still further embodiments, $R_8$ is $C_1$-$C_3$ alkyl. In certain embodiments, $R_8$ is methyl. In certain embodiments, $R_8$ is alkenyl. In certain embodiments, $R_8$ is $C_2$-$C_{20}$ alkenyl. In other embodiments, $R_8$ is $C_2$-$C_{15}$ alkenyl. In yet other embodiments, $R_8$ is $C_2$-$C_{12}$ alkenyl. In still other embodiments, $R_8$ is $C_2$-$C_6$ alkenyl. In certain embodiments, $R_8$ is vinyl. In certain embodiments, $R_8$ is alkoxy. In certain embodiments, $R_8$ is $C_{1-20}$ alkoxy. In other embodiments, $R_8$ is $C_1$-$C_{15}$ alkoxy. In yet other embodiments, $R_8$ is $C_1$-$C_{10}$ alkoxy. In still other embodiments, $R_8$ is $C_1$-$C_6$ alkoxy. In certain embodiments, $R_8$ is alkylthioxy. In certain embodiments, $R_8$ is $C_1$-$C_{20}$ alkylthioxy. In other embodiments, $R_8$ is $C_1$-$C_{15}$ alkylthioxy. In yet other embodiments, $R_8$ is $C_1$-$C_{10}$ alkylthioxy. In still other embodiments, $R_8$ is $C_1$-$C_6$ alkylthioxy. In other embodiments, $R_8$ is acyl. In certain embodiments, $R_8$ is —(CO)R', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_8$ is —(CO)OR', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_8$ is —(CO)NHR', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_8$ is —O(CO)R', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_8$ is —NH(CO)R', wherein R' is substituted or unsubstituted, branched or unbranched aliphatic or heteroaliphatic (e.g., $C_1$-$C_{20}$ alkyl, $C_1$-$C_{20}$ alkenyl, etc.).

In certain embodiments, $R_9$ is hydrogen. In certain embodiments, $R_9$ is substituted or unsubstituted, branched or unbranched aliphatic. In certain embodiments, $R_9$ is substituted or unsubstituted, branched or unbranched heteroaliphatic. In certain embodiments, $R_9$ is alkyl. In certain embodiments, $R_9$ is $C_1$-$C_{20}$ alkyl. In other embodiments, $R_9$ is $C_1$-$C_{15}$ alkyl. In yet other embodiments, $R_9$ is $C_1$-$C_{12}$ alkyl. In still other embodiments, $R_9$ is $C_1$-$C_6$ alkyl. In still further embodiments, $R_9$ is $C_1$-$C_3$ alkyl. In certain embodiments, $R_9$ is methyl. In certain embodiments, $R_9$ is alkenyl. In certain embodiments, $R_9$ is $C_2$-$C_{20}$ alkenyl. In other embodiments, $R_9$ is $C_2$-$C_{15}$ alkenyl. In yet other embodiments, $R_9$ is $C_2$-$C_{12}$ alkenyl. In still other embodiments, $R_9$ is $C_2$-$C_6$ alkenyl. In certain embodiments, $R_9$ is vinyl. In certain embodiments, $R_9$ is alkoxy. In certain embodiments, $R_9$ is $C_{1-20}$ alkoxy. In other embodiments, $R_9$ is $C_1$-$C_{15}$ alkoxy. In yet other embodiments, $R_9$ is $C_1$-$C_{10}$ alkoxy. In still other embodiments, $R_9$ is $C_1$-$C_6$ alkoxy. In certain embodiments, $R_9$ is alkylthioxy. In certain embodiments, $R_9$ is $C_1$-$C_{20}$ alkylthioxy. In other embodiments, $R_9$ is $C_1$-$C_{15}$ alkylthioxy. In yet other embodiments, $R_9$ is $C_1$-$C_{10}$ alkylthioxy. In still other embodiments, $R_9$ is $C_1$-$C_6$ alkylthioxy. In other embodiments, $R_9$ is acyl. In certain embodiments, $R_9$ is —(CO)R', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_9$ is —(CO)OR', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_9$ is —(CO)NHR', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_9$ is —O(CO)R', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_9$ is —NH(CO)R', wherein R' is substituted or unsubstituted, branched or unbranched aliphatic or heteroaliphatic (e.g., $C_1$-$C_{20}$ alkyl, $C_1$-$C_{20}$ alkenyl, etc.).

In certain embodiments, the compound is of the formula:

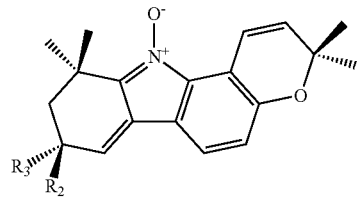

wherein $R_2$ and $R_3$ are defined as above.

In certain embodiments, the compound is of the formula:

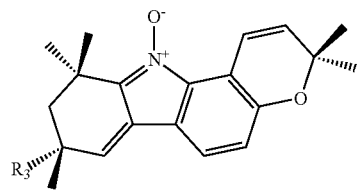

wherein $R_2$ and $R_3$ are defined as above.

In certain embodiments, the compound is of the formula:

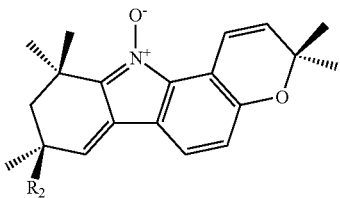

wherein $R_2$ and $R_3$ are defined as above.

In other embodiments, the compound is of the formula:

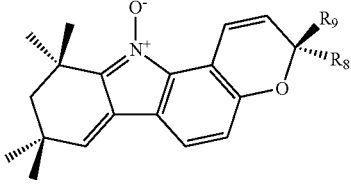

wherein $R_8$ and $R_9$ are defined as above.

In other embodiments, the compound is of the formula:

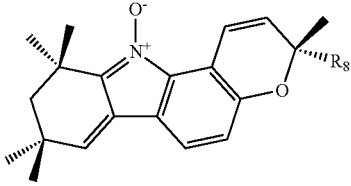

wherein $R_8$ and $R_9$ are defined as above.

In other embodiments, the compound is of the formula:

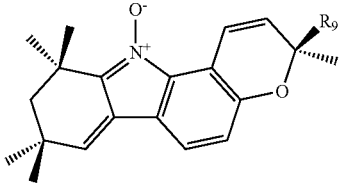

wherein $R_8$ and $R_9$ are defined as above.

In other embodiments, the compound is of the formula:

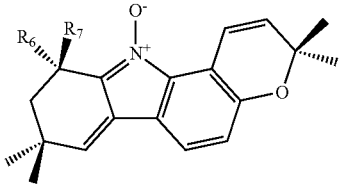

wherein $R_6$ and $R_7$ are defined as above.

In other embodiments, the compound is of the formula:

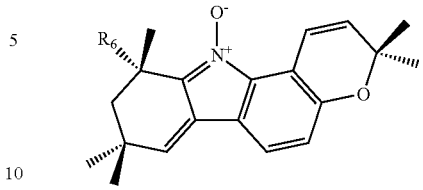

wherein $R_6$ and $R_7$ are defined as above.

In other embodiments, the compound is of the formula:

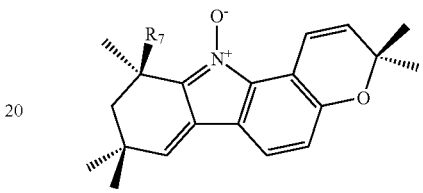

wherein $R_6$ and $R_7$ are defined as above.

In certain embodiments, compounds of the invention are of the formula:

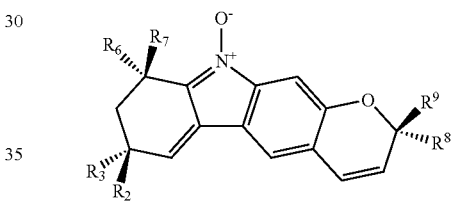

wherein $R_2$, $R_3$, $R_6$, $R_7$, $R_8$, and $R_9$ are defined as above. In certain embodiments, at least one of $R_2$, $R_3$, $R_6$, $R_7$, $R_8$, and $R_9$ is methyl. In certain embodiments, at least two of $R_2$, $R_3$, $R_6$, $R_7$, $R_8$, and $R_9$ are methyl. In certain embodiments, at least three of $R_2$, $R_3$, $R_6$, $R_7$, $R_8$, and $R_9$ are methyl. In certain embodiments, at least four of $R_2$, $R_3$, $R_6$, $R_7$, $R_8$, and $R_9$ are methyl. In certain embodiments, at least five of $R_2$, $R_3$, $R_6$, $R_7$, $R_8$, and $R_9$ are methyl.

In certain embodiments, $R_2$ is hydrogen. In certain embodiments, $R_2$ is substituted or unsubstituted, branched or unbranched aliphatic. In certain embodiments, $R_2$ is substituted or unsubstituted, branched or unbranched heteroaliphatic. In certain embodiments, $R_2$ is alkyl. In certain embodiments, $R_2$ is $C_1$-$C_{20}$ alkyl. In other embodiments, $R_2$ is $C_1$-$C_{15}$ alkyl. In yet other embodiments, $R_2$ is $C_1$-$C_{12}$ alkyl. In still other embodiments, $R_2$ is $C_1$-$C_6$ alkyl. In still further embodiments, $R_2$ is $C_1$-$C_3$ alkyl. In certain embodiments, $R_2$ is methyl. In certain embodiments, $R_2$ is alkenyl. In certain embodiments, $R_2$ is $C_2$-$C_{20}$ alkenyl. In other embodiments, $R_2$ is $C_2$-$C_{15}$ alkenyl. In yet other embodiments, $R_2$ is $C_2$-$C_{12}$ alkenyl. In still other embodiments, $R_2$ is $C_2$-$C_6$ alkenyl. In certain embodiments, $R_2$ is vinyl. In certain embodiments, $R_2$ is alkoxy. In certain embodiments, $R_2$ is $C_{1-20}$ alkoxy. In other embodiments, $R_2$ is $C_1$-$C_{15}$ alkoxy. In yet other embodiments, $R_2$ is $C_1$-$C_{10}$ alkoxy. In still other embodiments, $R_2$ is $C_1$-$C_6$ alkoxy. In certain embodiments, $R_2$ is alkylthioxy. In certain embodiments, $R_2$ is $C_1$-$C_{20}$ alkylthioxy. In other embodiments, $R_2$ is $C_1$-$C_{15}$ alkylthioxy. In yet other embodiments, $R_2$ is $C_1$-$C_{10}$ alkylthioxy. In still other embodiments, $R_2$ is $C_1$-$C_6$ alkylthioxy. In other embodiments, $R_2$ is acyl. In certain embodiments, $R_2$ is —(CO)R', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_2$ is —(CO)OR', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_2$ is —(CO)NHR', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_2$ is —O(CO)R', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_2$ is —NH(CO)R', wherein R' is substituted or unsubstituted, branched or unbranched aliphatic or heteroaliphatic (e.g., $C_1$-$C_{20}$ alkyl, $C_1$-$C_{20}$ alkenyl, etc.).

In certain embodiments, $R_3$ is hydrogen. In certain embodiments, $R_3$ is substituted or unsubstituted, branched or unbranched aliphatic. In certain embodiments, $R_3$ is substituted or unsubstituted, branched or unbranched heteroaliphatic. In certain embodiments, $R_3$ is alkyl. In certain embodiments, $R_3$ is $C_1$-$C_{20}$ alkyl. In other embodiments, $R_3$ is $C_1$-$C_{15}$ alkyl. In yet other embodiments, $R_3$ is $C_1$-$C_{12}$ alkyl. In still other embodiments, $R_3$ is $C_1$-$C_6$ alkyl. In still further embodiments, $R_3$ is $C_1$-$C_3$ alkyl. In certain embodiments, $R_3$ is methyl. In certain embodiments, $R_3$ is alkenyl. In certain embodiments, $R_3$ is $C_2$-$C_{20}$ alkenyl. In other embodiments, $R_3$ is $C_2$-$C_{15}$ alkenyl. In yet other embodiments, $R_3$ is $C_2$-$C_{12}$ alkenyl. In still other embodiments, $R_3$ is $C_2$-$C_6$ alkenyl. In certain embodiments, $R_3$ is vinyl. In certain embodiments, $R_3$ is alkoxy. In certain embodiments, $R_3$ is $C_{1-20}$ alkoxy. In other embodiments, $R_3$ is $C_1$-$C_{15}$ alkoxy. In yet other embodiments, $R_3$ is $C_1$-$C_{10}$ alkoxy. In still other embodiments, $R_3$ is $C_1$-$C_6$ alkoxy. In certain embodiments, $R_3$ is alkylthioxy. In certain embodiments, $R_3$ is $C_1$-$C_{20}$ alkylthioxy. In other embodiments, $R_3$ is $C_1$-$C_{15}$ alkylthioxy. In yet other embodiments, $R_3$ is $C_1$-$C_{10}$ alkylthioxy. In still other embodiments, $R_3$ is $C_1$-$C_6$ alkylthioxy. In other embodiments, $R_3$ is acyl. In certain embodiments, $R_3$ is —(CO)R', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_3$ is —(CO)OR', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_3$ is —(CO)NHR', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_3$ is —O(CO)R', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_3$ is —NH(CO)R', wherein R' is substituted or unsubstituted, branched or unbranched aliphatic or heteroaliphatic (e.g., $C_1$-$C_{20}$ alkyl, $C_1$-$C_{20}$ alkenyl, etc.).

In certain embodiments, $R_6$ is hydrogen. In certain embodiments, $R_6$ is substituted or unsubstituted, branched or unbranched aliphatic. In certain embodiments, $R_6$ is substituted or unsubstituted, branched or unbranched heteroaliphatic. In certain embodiments, $R_6$ is alkyl. In certain embodiments, $R_6$ is $C_1$-$C_{20}$ alkyl. In other embodiments, $R_6$ is $C_1$-$C_{15}$ alkyl. In yet other embodiments, $R_6$ is $C_1$-$C_{12}$ alkyl. In still other embodiments, $R_6$ is $C_1$-$C_6$ alkyl. In still further embodiments, $R_6$ is $C_1$-$C_3$ alkyl. In certain embodiments, $R_6$ is methyl. In certain embodiments, $R_6$ is alkenyl. In certain embodiments, $R_6$ is $C_2$-$C_{20}$ alkenyl. In other embodiments, $R_6$ is $C_2$-$C_{15}$ alkenyl. In yet other embodiments, $R_6$ is $C_2$-$C_{12}$ alkenyl. In still other embodiments, $R_6$ is $C_2$-$C_6$ alkenyl. In certain embodiments, $R_6$ is vinyl. In certain embodiments, $R_6$ is alkoxy. In certain embodiments, $R_6$ is $C_{1-20}$ alkoxy. In other embodiments, $R_6$ is $C_1$-$C_{15}$ alkoxy. In yet other embodiments, $R_6$ is $C_1$-$C_{10}$ alkoxy. In still other embodiments, $R_6$ is $C_1$-$C_6$ alkoxy. In certain embodiments, $R_6$ is alkylthioxy. In certain embodiments, $R_6$ is $C_1$-$C_{20}$ alkylthioxy. In other embodiments, $R_6$ is $C_1$-$C_{15}$ alkylthioxy. In yet other embodiments, $R_6$ is $C_1$-$C_{10}$ alkylthioxy. In still other embodiments, $R_6$ is $C_1$-$C_6$ alkylthioxy. In other embodiments, $R_6$ is acyl. In certain embodiments, $R_6$ is —(CO)R', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_6$ is —(CO)OR', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_6$ is —(CO)NHR', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_6$ is —O(CO)R', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_6$ is —NH(CO)R', wherein R' is substituted or unsubstituted, branched or unbranched aliphatic or heteroaliphatic (e.g., $C_1$-$C_{20}$ alkyl, $C_1$-$C_{20}$ alkenyl, etc.).

In certain embodiments, $R_7$ is hydrogen. In certain embodiments, $R_7$ is substituted or unsubstituted, branched or unbranched aliphatic. In certain embodiments, $R_7$ is substituted or unsubstituted, branched or unbranched heteroaliphatic. In certain embodiments, $R_7$ is alkyl. In certain embodiments, $R_7$ is $C_1$-$C_{20}$ alkyl. In other embodiments, $R_7$ is $C_1$-$C_{15}$ alkyl. In yet other embodiments, $R_7$ is $C_1$-$C_{12}$ alkyl. In still other embodiments, $R_7$ is $C_1$-$C_6$ alkyl. In still further embodiments, $R_7$ is $C_1$-$C_3$ alkyl. In certain embodiments, $R_7$ is methyl. In certain embodiments, $R_7$ is alkenyl. In certain embodiments, $R_7$ is $C_2$-$C_{20}$ alkenyl. In other embodiments, $R_7$ is $C_2$-$C_{15}$ alkenyl. In yet other embodiments, $R_7$ is $C_2$-$C_{12}$ alkenyl. In still other embodiments, $R_7$ is $C_2$-$C_6$ alkenyl. In certain embodiments, $R_7$ is vinyl. In certain embodiments, $R_7$ is alkoxy. In certain embodiments, $R_7$ is $C_{1-20}$ alkoxy. In other embodiments, $R_7$ is $C_1$-$C_{15}$ alkoxy. In yet other embodiments, $R_7$ is $C_1$-$C_{10}$ alkoxy. In still other embodiments, $R_7$ is $C_1$-$C_6$ alkoxy. In certain embodiments, $R_7$ is alkylthioxy. In certain embodiments, $R_7$ is $C_1$-$C_{20}$ alkylthioxy. In other embodiments, $R_7$ is $C_1$-$C_{15}$ alkylthioxy. In yet other embodiments, $R_7$ is $C_1$-$C_{10}$ alkylthioxy. In still other embodiments, $R_7$ is $C_1$-$C_6$ alkylthioxy. In other embodiments, $R_7$ is acyl. In certain embodiments, $R_7$ is —(CO)R', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_7$ is —(CO)OR', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_7$ is —(CO)NHR', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_7$ is —O(CO)R', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_7$ is —NH(CO)R', wherein R' is substituted or unsubstituted, branched or unbranched aliphatic or heteroaliphatic (e.g., $C_1$-$C_{20}$ alkyl, $C_1$-$C_{20}$ alkenyl, etc.).

In certain embodiments, $R_8$ is hydrogen. In certain embodiments, $R_8$ is substituted or unsubstituted, branched or unbranched aliphatic. In certain embodiments, $R_8$ is substituted or unsubstituted, branched or unbranched heteroaliphatic. In certain embodiments, $R_8$ is alkyl. In certain embodiments, $R_8$ is $C_1$-$C_{20}$ allyl. In other embodiments, $R_8$ is $C_1$-$C_{15}$ alkyl. In yet other embodiments, $R_8$ is $C_1$-$C_{12}$ alkyl. In still other embodiments, $R_8$ is $C_1$-$C_6$ alkyl. In still further embodiments, $R_8$ is $C_1$-$C_3$ alkyl. In certain embodiments, $R_8$ is methyl. In certain embodiments, $R_8$ is alkenyl. In certain embodiments, $R_8$ is $C_2$-$C_{20}$ alkenyl. In other embodiments, $R_8$ is $C_2$-$C_{15}$ alkenyl. In yet other embodiments, $R_8$ is $C_2$-$C_{12}$ alkenyl. In still other embodiments, $R_8$ is $C_2$-$C_6$ alkenyl. In certain embodiments, $R_8$ is vinyl. In certain embodiments, $R_8$ is alkoxy. In certain embodiments, $R_8$ is $C_{1-20}$ alkoxy. In other embodiments, $R_8$ is $C_1$-$C_{15}$ alkoxy. In yet other embodiments, $R_8$ is $C_1$-$C_{10}$ alkoxy. In still other embodiments, $R_8$ is $C_1$-$C_6$ alkoxy. In certain embodiments, $R_8$ is alkylthioxy. In certain embodiments, $R_8$ is $C_1$-$C_{20}$ alkylthioxy. In other embodiments, $R_8$ is $C_1$-$C_{15}$ alkylthioxy. In yet other embodiments, $R_8$ is $C_1$-$C_{10}$ alkylthioxy. In still other embodiments, $R_8$ is $C_1$-$C_6$ alkylthioxy. In other embodiments, $R_8$ is acyl. In certain embodiments, $R_8$ is —(CO)R', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_8$ is —(CO)OR', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_8$ is —(CO)NHR', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_8$ is —O(CO)R', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_8$ is —NH(CO)R', wherein R' is substituted or unsubstituted, branched or unbranched aliphatic or hetetroaliphatic (e.g., $C_1$-$C_{20}$ alkenyl, etc.).

In certain embodiments, $R_9$ is hydrogen. In certain embodiments, $R_9$ is substituted or unsubstituted, branched or unbranched aliphatic. In certain embodiments, $R_9$ is substituted or unsubstituted, branched or unbranched heteroaliphatic. In certain embodiments, $R_9$ is alkyl. In certain embodiments, $R_9$ is $C_1$-$C_{20}$ alkyl. In other embodiments, $R_9$ is $C_1$-$C_{15}$ alkyl. In yet other embodiments, $R_9$ is $C_1$-$C_{12}$ alkyl. In still other embodiments, $R_9$ is $C_1$-$C_6$ alkyl. In still further embodiments, $R_9$ is $C_1$-$C_3$ alkyl. In certain embodiments, $R_9$ is methyl. In certain embodiments, $R_9$ is alkenyl. In certain embodiments, $R_9$ is $C_2$-$C_{20}$ alkenyl. In other embodiments, $R_9$ is $C_2$-$C_{15}$ alkenyl. In yet other embodiments, $R_9$ is $C_2$-$C_{12}$ alkenyl. In still other embodiments, $R_9$ is $C_2$-$C_6$ alkenyl. In certain embodiments, $R_9$ is vinyl. In certain embodiments, $R_9$ is alkoxy. In certain embodiments, $R_9$ is $C_{1-20}$ alkoxy. In other embodiments, $R_9$ is $C_1$-$C_{15}$ alkoxy. In yet other embodiments, $R_9$ is $C_1$-$C_{10}$ alkoxy. In still other embodiments, $R_9$ is $C_1$-$C_6$ alkoxy. In certain embodiments, $R_9$ is alkylthioxy. In certain embodiments, $R_9$ is $C_1$-$C_{20}$ alkylthioxy. In other embodiments, $R_9$ is $C_1$-$C_{15}$ alkylthioxy. In yet other embodiments, $R_9$ is $C_1$-$C_{10}$ alkylthioxy. In still other embodiments, $R_9$ is $C_1$-$C_6$ alkylthioxy. In other embodiments, $R_9$ is acyl. In certain embodiments, $R_9$ is —(CO)R', wherein R' is substituted or unbranched aliphatic or heteroaliphatic (e.g., $C_1$-$C_{20}$ alkyl, $C_1$-$C_{20}$ alkenyl, etc.). In certain embodiments, $R_9$ is —(CO)OR', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_9$ is —(CO)NHR', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_9$ is —O(CO)R', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_9$ is —NH(CO)R', wherein R' is substituted or unsubstituted, branched or unbranched aliphatic or heteroaliphatic (e.g., $C_1$-$C_{20}$ alkyl, $C_1$-$C_{20}$ alkenyl, etc.).

In certain embodiments, the compound is of the formula:

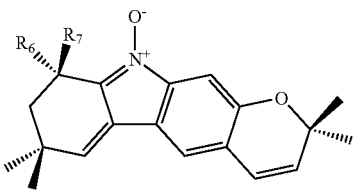

wherein $R_6$ and $R_7$ are defined as above.

In certain embodiments, the compound is of the formula:

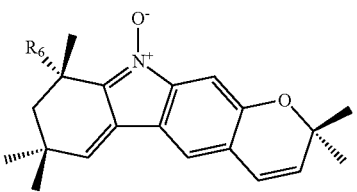

wherein $R_6$ and $R_7$ are defined as above.

In certain embodiments, the compound is of the formula:

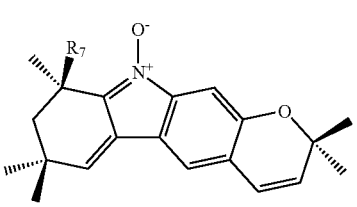

wherein $R_6$ and $R_7$ are defined as above.

In other embodiments, the compound is of the formula:

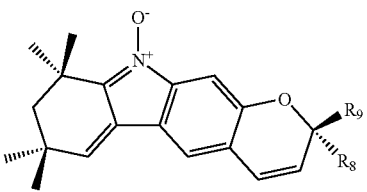

wherein $R_8$ and $R_9$ are defined as above.

In other embodiments, the compound is of the formula:

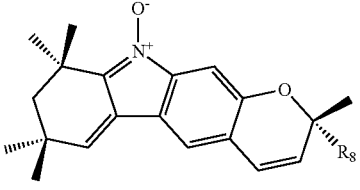

wherein $R_8$ and $R_9$ are defined as above.

In other embodiments, the compound is of the formula:

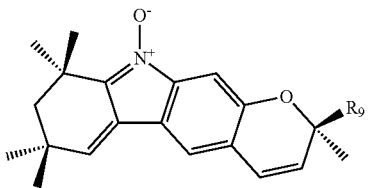

wherein $R_8$ and $R_9$ are defined as above.

In other embodiments, the compound is of the formula:

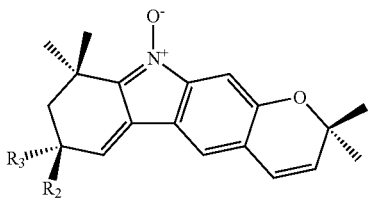

wherein $R_2$ and $R_3$ are defined as above.

In other embodiments, the compound is of the formula:

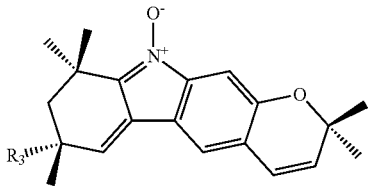

wherein $R_2$ and $R_3$ are defined as above.

In other embodiments, the compound is of the formula:

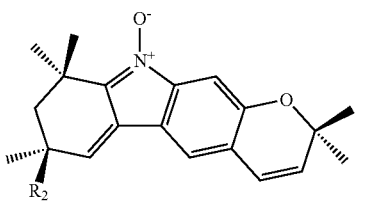

wherein $R_2$ and $R_3$ are defined as above.

In certain embodiments, compounds of the invention are of the formula:

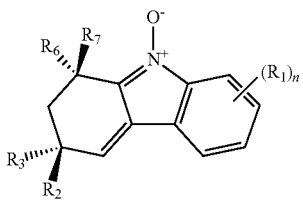

wherein $R_1$, $R_2$, $R_3$, $R_6$, $R_7$, and n are defined as above. In certain embodiments, at least one of $R_2$, $R_3$, $R_6$, and $R_7$ is methyl. In certain embodiments, at least two of $R_2$, $R_3$, $R_6$, and $R_7$ are methyl. In certain embodiments, at least three of $R_2$, $R_3$, $R_6$, and $R_7$ are methyl. In certain embodiments, all four of $R_2$, $R_3$, $R_6$, and $R_7$ are methyl.

In certain embodiments, n is 1. In other embodiments, n is 2. In yet other embodiments, n is 3. In still other embodiments, n is 4.

In certain embodiments, $R_1$ is hydrogen. In certain embodiments, $R_1$ is substituted or unsubstituted, branched or unbranched aliphatic. In certain embodiments, $R_1$ is substituted or unsubstituted, branched or unbranched heteroaliphatic. In certain embodiments, $R_1$ is alkyl. In certain embodiments, $R_1$ is $C_1$-$C_{20}$ alkyl. In other embodiments, $R_1$ is $C_1$-$C_{15}$ alkyl. In yet other embodiments, $R_1$ is $C_1$-$C_{12}$ alkyl. In still other embodiments, $R_1$ is $C_1$-$C_6$ alkyl. In still further embodiments, $R_1$ is $C_1$-$C_3$ alkyl. In certain embodiments, $R_1$ is methyl. In certain embodiments, $R_1$ is alkenyl. In certain embodiments, $R_1$ is $C_2$-$C_{20}$ alkenyl. In other embodiments, $R_1$ is $C_2$-$C_{15}$ alkenyl. In yet other embodiments, $R_1$ is $C_2$-$C_{12}$ alkenyl. In still other embodiments, $R_1$ is $C_2$-$C_6$ alkenyl. In certain embodiments, $R_1$ is vinyl. In certain embodiments, $R_1$ is alkoxy. In certain embodiments, $R_1$ is $C_{1-20}$ alkoxy. In other embodiments, $R_1$ is $C_1$-$C_{15}$ alkoxy. In yet other embodiments, $R_1$ is $C_1$-$C_{10}$ alkoxy. In still other embodiments, $R_1$ is $C_1$-$C_6$ alkoxy. In certain embodiments, $R_1$ is alkylthioxy. In certain embodiments, $R_1$ is $C_1$-$C_{20}$ alkylthioxy. In other embodiments, $R_1$ is $C_1$-$C_{15}$ alkylthioxy. In yet other embodiments, $R_1$ is $C_1$-$C_{10}$ alkylthioxy. In still other embodiments, $R_1$ is $C_1$-$C_6$ alkylthioxy. In other embodiments, $R_1$ is acyl. In certain embodiments, $R_1$ is —(CO)R', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_1$ is —(CO)OR', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_1$ is —(CO)NHR', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_1$ is —O(CO)R', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_1$ is —NH(CO)R', wherein R' is substituted or unsubstituted, branched or unbranched aliphatic or heteroaliphatic (e.g., $C_1$-$C_{20}$ alkyl, $C_1$-$C_{20}$ alkenyl, etc.).

In certain embodiments, $R_2$ is hydrogen. In certain embodiments, $R_2$ is substituted or unsubstituted, branched or unbranched aliphatic. In certain embodiments, $R_2$ is substituted or unsubstituted, branched or unbranched heteroaliphatic. In certain embodiments, $R_2$ is alkyl. In certain embodiments, $R_2$ is $C_1$-$C_{20}$ allyl. In other embodiments, $R_2$ is $C_1$-$C_{15}$ alkyl. In yet other embodiments, $R_2$ is $C_1$-$C_{12}$ alkyl. In still other embodiments, $R_2$ is $C_1$-$C_6$ alkyl. In still further embodiments, $R_2$ is $C_1$-$C_3$ alkyl. In certain embodiments, $R_2$ is methyl. In certain embodiments, $R_2$ is alkenyl. In certain embodiments, $R_2$ is $C_2$-$C_{20}$ alkenyl. In other embodiments, $R_2$ is $C_2$-$C_{15}$ alkenyl. In yet other embodiments, $R_2$ is $C_2$-$C_{12}$ alkenyl. In still other embodiments, $R_2$ is $C_2$-$C_6$ alkenyl. In certain embodiments, $R_2$ is vinyl. In certain embodiments, $R_2$ is alkoxy. In certain embodiments, $R_2$ is $C_{1-20}$ alkoxy. In other embodiments, $R_2$ is $C_1$-$C_{15}$ alkoxy. In yet other embodiments, $R_2$ is $C_1$-$C_{10}$ alkoxy. In still other embodiments, $R_2$ is $C_1$-$C_6$ alkoxy. In certain embodiments, $R_2$ is alkylthioxy. In certain embodiments, $R_2$ is $C_1$-$C_{20}$ alkylthioxy. In other embodiments, $R_2$ is $C_1$-$C_{15}$ alkylthioxy. In yet other embodiments, $R_2$ is $C_1$-$C_{10}$ alkylthioxy. In still other embodiments, $R_2$ is $C_1$-$C_6$ alkylthioxy. In other embodiments, $R_2$ is acyl. In certain embodiments, $R_2$ is —(CO)R', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_2$ is —(CO)OR', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_2$ is —(CO)NHR', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_2$ is —O(CO)R', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_2$ is —NH(CO)R', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_2$ is —NHAc.

In certain embodiments, $R_3$ is hydrogen. In certain embodiments, $R_3$ is substituted or unsubstituted, branched or unbranched aliphatic. In certain embodiments, $R_3$ is substituted or unsubstituted, branched or unbranched heteroaliphatic. In certain embodiments, $R_3$ is alkyl. In certain embodiments, $R_3$ is $C_1$-$C_{20}$ alkyl. In other embodiments, $R_3$ is $C_1$-$C_{15}$ alkyl. In yet other embodiments, $R_3$ is $C_1$-$C_{12}$ alkyl. In still other embodiments, $R_3$ is $C_1$-$C_6$ alkyl. In still further embodiments, $R_3$ is $C_1$-$C_3$ alkyl. In certain embodiments, $R_3$ is methyl. In certain embodiments, $R_3$ is alkenyl. In certain embodiments, $R_3$ is $C_2$-$C_{20}$ alkenyl. In other embodiments, $R_3$ is $C_2$-$C_{15}$ alkenyl. In yet other embodiments, $R_3$ is $C_2$-$C_{12}$ alkenyl. In still other embodiments, $R_3$ is $C_2$-$C_6$ alkenyl. In certain embodiments, $R_3$ is vinyl. In certain embodiments, $R_3$ is alkoxy. In certain embodiments, $R_3$ is $C_{1-20}$ alkoxy. In other embodiments, $R_3$ is $C_1$-$C_{15}$ alkoxy. In yet other embodiments, $R_3$ is $C_1$-$C_{10}$ alkoxy. In still other embodiments, $R_3$ is $C_1$-$C_6$ alkoxy. In certain embodiments, $R_3$ is alkylthioxy. In certain embodiments, $R_3$ is $C_1$-$C_{20}$ alkylthioxy. In other embodiments, $R_3$ is $C_1$-$C_{15}$ alkylthioxy. In yet other embodiments, $R_3$ is $C_1$-$C_{10}$ alkylthioxy. In still other embodiments, $R_3$ is $C_1$-$C_6$ alkylthioxy. In other embodiments, $R_3$ is acyl. In certain embodiments, $R_3$ is —(CO)R', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_3$ is —(CO)OR', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_3$ is —(CO)NHR', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_3$ is —O(CO)R', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_3$ is —NH(CO)R', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_3$ is —$CO_2Me$.

In certain embodiments, $R_2$ and $R_3$ taken together form a cyclic structure. In certain embodiments $R_2$ and $R_3$ taken together form a carbocyclic structure. In other embodiments, $R_2$ and $R_3$ taken together form a heterocyclic structure. In certain embodiments, $R_2$ and $R_3$ taken together form a structure of the structure. In certain embodiments, $R_2$ and $R_3$ taken together form a structure of the formula:

In other embodiments, $R_2$ and $R_3$ taken together form a structure of the formula:

In certain embodiments, $R_6$ is hydrogen. In certain embodiments, $R_6$ is substituted or unsubstituted, branched or unbranched aliphatic. In certain embodiments, $R_6$ is substituted or unsubstituted, branched or unbranched heteroaliphatic. In certain embodiments, $R_6$ is alkyl. In certain embodiments, $R_6$ is $C_1$-$C_{20}$ alkyl. In other embodiments, $R_6$ is $C_1$-$C_{15}$ alkyl. In yet other embodiments, $R_6$ is $C_1$-$C_{12}$ alkyl. In still other embodiments, $R_6$ is $C_1$-$C_6$ alkyl. In still further embodiments, $R_6$ is $C_1$-$C_3$ alkyl. In certain embodiments, $R_6$ is methyl. In certain embodiments, $R_6$ is alkenyl. In certain embodiments, $R_6$ is $C_2$-$C_{20}$ alkenyl. In other embodiments, $R_6$ is $C_2$-$C_{15}$ alkenyl. In yet other embodiments, $R_6$ is $C_2$-$C_{12}$ alkenyl. In still other embodiments, $R_6$ is $C_2$-$C_6$ alkenyl. In certain embodiments, $R_6$ is vinyl. In certain embodiments, $R_6$ is alkoxy. In certain embodiments, $R_6$ is $C_{1-20}$ alkoxy. In other embodiments, $R_6$ is $C_1$-$C_{15}$ alkoxy. In yet other embodiments, $R_6$ is $C_1$-$C_{10}$ alkoxy. In still other embodiments, $R_6$ is $C_1$-$C_6$ alkoxy. In certain embodiments, $R_6$ is alkylthioxy. In certain embodiments, $R_6$ is $C_1$-$C_{20}$ alkylthioxy. In other embodiments, $R_6$ is $C_1$-$C_{15}$ alkylthioxy. In yet other embodiments, $R_6$ is $C_1$-$C_{10}$ alkylthioxy. In still other embodiments, $R_6$ is $C_1$-$C_6$ alkylthioxy. In other embodiments, $R_6$ is acyl. In certain embodiments, $R_6$ is —(CO)R', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_6$ is —(CO)OR', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_6$ is —(CO)NHR', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_6$ is —O(CO)R', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_6$ is —NH(CO)R', wherein R' is substituted or unsubstituted, branched or unbranched aliphatic or heteroaliphatic (e.g., $C_1$-$C_{20}$ alkyl, $C_1$-$C_{20}$ alkenyl, etc.).

In certain embodiments, $R_7$ is hydrogen. In certain embodiments, $R_7$ is substituted or unsubstituted, branched or unbranched aliphatic. In certain embodiments, $R_7$ is substituted or unsubstituted, branched or unbranched heteroaliphatic. In certain embodiments, $R_7$ is alkyl. In certain embodiments, $R_7$ is $C_1$-$C_{20}$ alkyl. In other embodiments, $R_7$ is $C_1$-$C_{15}$ alkyl. In yet other embodiments, $R_7$ is $C_1$-$C_{12}$ alkyl. In still other embodiments, $R_7$ is $C_1$-$C_6$ alkyl. In still further embodiments, $R_7$ is $C_1$-$C_3$ alkyl. In certain embodiments, $R_7$ is methyl. In certain embodiments, $R_7$ is alkenyl. In certain embodiments, $R_7$ is $C_2$-$C_{20}$ alkenyl. In other embodiments, $R_7$ is $C_2$-$C_{15}$ alkenyl. In yet other embodiments, $R_7$ is $C_2$-$C_{12}$ alkenyl. In still other embodiments, $R_7$ is $C_2$-$C_6$ alkenyl. In certain embodiments, $R_7$ is vinyl. In certain embodiments, $R_7$ is alkoxy. In certain embodiments, $R_7$ is $C_{1-20}$ alkoxy. In other embodiments, $R_7$ is $C_1$-$C_{15}$ alkoxy. In yet other embodiments, $R_7$ is $C_1$-$C_{10}$ alkoxy. In still other embodiments, $R_7$ is $C_1$-$C_6$ alkoxy. In certain embodiments, $R_7$ is alkylthioxy. In certain embodiments, $R_7$ is $C_1$-$C_{20}$ alkylthioxy. In other embodiments, $R_7$ is $C_1$-$C_{15}$ alkylthioxy. In yet other embodiments, $R_7$ is $C_1$-$C_{10}$ alkylthioxy. In still other embodiments, $R_7$ is $C_1$-$C_6$ alkylthioxy. In other embodiments, $R_7$ is acyl. In certain embodiments, $R_7$ is —(CO)R', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_7$ is —(CO)OR', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_7$ is —(CO)NHR', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_7$ is —O(CO)R', wherein R' is substituted or unsubstituted, branched or unbranched aliphatic or heteroaliphatic (e.g., $C_1$-$C_{20}$ alkyl, $C_1$-$C_{20}$ alkenyl, etc.). In certain embodiments, $R_7$ is —NH(CO)R', wherein R' is substituted or unsubstituted, branched or unbranched aliphatic or heteroaliphatic (e.g., $C_1$-$C_{20}$ alkyl, $C_1$-$C_{20}$ alkenyl, etc.).

In certain embodiments, the compound is of the formula:

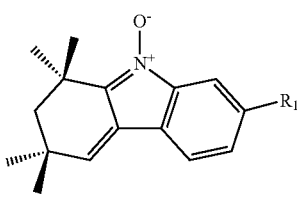

wherein $R_1$ is defined as above.

In certain embodiments, the compound is of the formula:

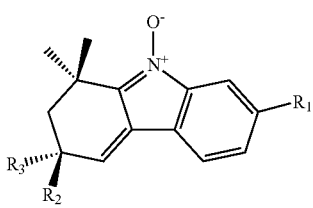

wherein $R_2$ and $R_3$ are defined as above.

In certain embodiments, the compound is of the formula:

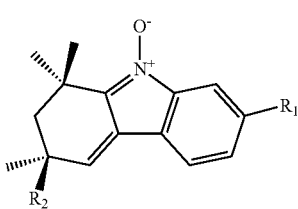

wherein $R_2$ and $R_3$ are defined as above.

In certain embodiments, the compound is of the formula:

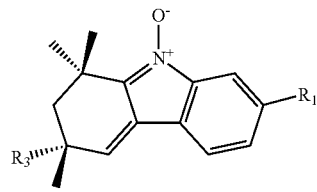

wherein $R_2$ and $R_3$ are defined as above.

In certain embodiments, the compound is of the formula:

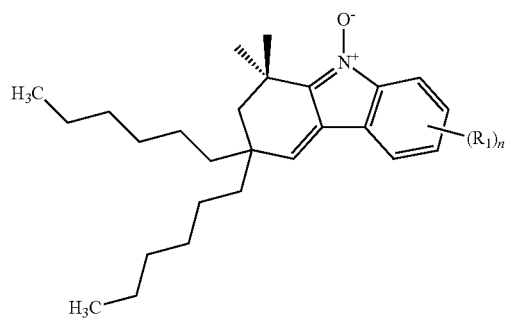

wherein $R_1$ and n are defined as above.

In certain embodiments, the compound is of the formula:

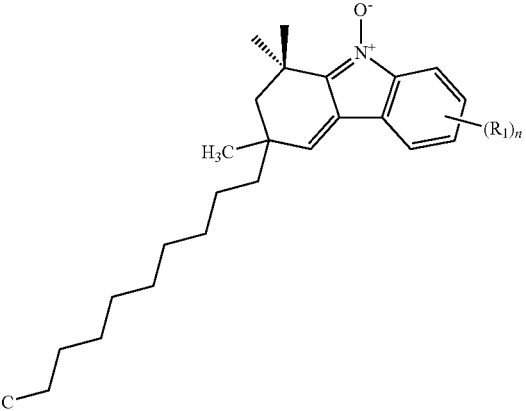

wherein $R_1$ and n are defined as above.

Compounds related to the natural product avrainvillamide are also provided. The synthesis of avrainvillamide detailed below in Example 2 allows for the preparation of avrainvillamide and analogues of avrainvillamide. The total synthesis of avrainvillamide provides access to a variety of analogues which are not able to be prepared by fermentation or semi-synthesis. These compounds are of the generic formula:

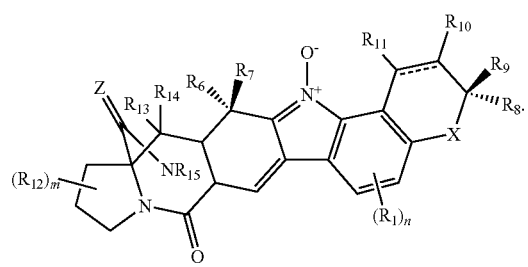

wherein each occurrence of $R_1$ is independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_A$; —$C(=O)R_A$; —$CO_2R_A$; —CN; —SCN; —$SR_A$; —$SOR_A$; —$SO_2R_A$; —$NO_2$; —$N_3$; —$N(R_A)_2$; —$NHC(=O)R_A$; —$NR_AC(=O)N(R_A)_2$; —$OC(=O)OR_A$; —$OC(=O)R_A$; —$OC(=O)N(R_A)_2$; —$NR_AC(=O)OR_A$; or —$C(R_A)_3$; wherein each occurrence of $R_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_6$ is selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_F$; —$C(=O)R_F$; —$CO_2R_F$; —CN; —SCN; —$SR_F$; —$SOR_F$; —$SO_2R_F$; —$NO_2$; —$N_3$; —$N(R_F)_2$; —$NHC(=O)R_F$; —$NR_FC(=O)N(R_F)_2$; —$OC(=O)OR_F$; —$OC(=O)R_F$; —$OC(=O)N(R_F)_2$; —$NR_FC(=O)OR_F$; or —$C(R_F)_3$; wherein each occurrence of $R_F$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_7$ is selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_G$; —$C(=O)R_G$; —$CO_2R_G$; —CN; —SCN; —$SR_G$; —$SOR_G$; —$SO_2R_G$; —$NO_2$; —$N_3$; —$N(R_G)_2$; —$NHC(=O)R_G$; —$NR_GC(=O)N(R_G)_2$; —$OC(=O)OR_G$; —$OC(=O)R_G$; —$OC(=O)N(R_G)_2$; —$NR_GC(=O)OR_G$; or —$C(R_G)_3$; wherein each occurrence of $R_G$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_8$ and $R_9$ are independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_H$; —$C(=O)R_H$; —$CO_2R_H$; —CN; —SCN; —$SR_H$; —$SOR_H$; —$SO_2R_H$; —$NO_2$; —$N_3$; —$N(R_H)_2$; —$NHC(=O)R_H$; —$NR_HC(=O)N(R_H)_2$; —$OC(=O)OR_H$; —$OC(=O)R_H$; —$OC(=O)N(R_H)_2$; —$NR_HC(=O)OR_H$; or —$C(R_H)_3$; wherein each occurrence of $R_H$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_{10}$ and $R_{11}$ are independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_J$; —$C(=O)R_J$; —$CO_2R_J$; —CN; —SCN; —$SR_J$; —$SOR_J$; —$SO_2R_J$; —$NO_2$; —$N_3$; —$N(R_J)_2$; —$NHC(=O)R_J$; —$NR_JC(=O)N(R_J)_2$; —$OC(=O)OR_J$; —$OC(=O)R_J$; —$OC(=O)N(R_J)_2$; —$NR_JC(=O)OR_J$; or —$C(R_J)_3$; wherein each occurrence of $R_J$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_{12}$ is selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_L$; —$C(=O)R_L$; —$CO_2R_L$; —CN; —SCN; —$SR_L$; —$SOR_L$; —$SO_2R_L$; —$NO_2$; —$N_3$; —$N(R_L)_2$; —$NHC(=O)R_L$; —$NR_LC(=O)N(R_L)_2$; —$OC(=O)OR_L$; —$OC(=O)R_L$; —$OC(=O)N(R_L)_2$; —$NR_LC(=O)OR_L$; or —$C(R_L)_3$; wherein each occurrence of $R_L$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_{13}$ and $R_{14}$ are independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_M$; —$C(=O)R_M$; —$CO_2R_M$; —CN; —SCN; —$SR_M$; —$SOR_M$; —$SO_2R_M$; —$NO_2$; —$N_3$; —$N(R_M)_2$; —$NHC(=O)R_M$; —$NR_MC(=O)N(R_M)_2$; —$OC(=O)OR_M$; —$OC(=O)R_M$; —$OC(=O)N(R_M)_2$; —$NR_MC(=O)OR_M$; or —$C(R_M)_3$; wherein each occurrence of $R_M$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_{15}$ is selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_P$; —$C(=O)R_P$; —$CO_2R_P$; —CN; —SCN; —$SR_P$; —$SOR_P$;

—SO$_2$R$_P$; —NO$_2$; —N$_3$; —N(R$_P$)$_2$; —NHC(=O)R$_P$; —NR$_P$C(=O)N(R$_P$)$_2$; —OC(=O)OR$_P$; —OC(=O)R$_P$; —OC(=O)N(R$_P$)$_2$; —NR$_P$C(=O)OR$_P$; or —C(R$_P$)$_3$; wherein each occurrence of R$_P$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

wherein two or more substituents may form substituted or unsubstituted, cyclic, heterocyclic, aryl, or heteroaryl structures;

wherein R$_6$ and R$_7$, R$_8$ and R$_9$, R$_{13}$ and R$_{14}$, and one R$_{12}$ and another R$_{12}$ may form together =O, =NR$_G$, or =C(R$_G$)$_2$, wherein each occurrence of R$_G$ is defined as above;

X is O, S, C(R$_X$)$_2$, or NR$_X$, wherein R$_X$ is hydrogen, a protecting group, an aliphatic, heteroaliphatic, aryl, heteroaryl, alkylaryl, or alkylheteroaryl moiety, Z is O, S, or NR$_Z$, wherein R$_Z$ is hydrogen, a protecting group, an aliphatic, heteroaliphatic, aryl, heteroaryl, alkylaryl, or alkylheteroaryl moiety, or OR$_{Z'}$, wherein R$_{Z'}$ is hydrogen, a protecting group, an aliphatic, heteroaliphatic, aryl, heteroaryl, alkylaryl, or alkylheteroaryl moiety;

the dashed line represents the presence or absence of a bond;

m is an integer between 0 and 6, inclusive; and n is an integer between 0 and 2, inclusive.

In certain embodiments, when R$_{10}$, R$_{11}$, R$_{12}$, R$_{13}$, and R$_{14}$ are hydrogen, X is O, Z is O, and the dashed line represent a bond, then R$_6$, R$_7$, R$_8$, R$_9$, and R$_{15}$ are not hydrogen, alkyl, aminoalkyl, or perfluoroalkyl. In certain embodiments, when R$_{10}$, R$_{11}$, R$_{12}$, R$_{13}$, and R$_{14}$ are hydrogen, X is O, Z is O, and the dashed line represent a bond, then all of R$_6$, R$_7$, R$_8$, and R$_9$ are not methyl, or R$_{15}$ is not hydrogen.

In certain embodiments, the compounds have the stereochemistry as shown in the formula:

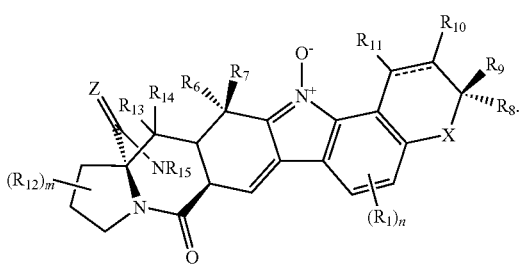

In certain embodiments, X is O, S, or NR$_X$, wherein R$_X$ is defined as above. In certain embodiments, X is O. In other embodiments, X is S. In yet other embodiments, X is NR$_X$, preferably NH. In certain embodiments, X is C(R$_X$)$_2$, preferably CH$_2$. In other embodiments, X is C(=O), C(=S), or C(=NR$_X$).

In certain embodiments, Z is O. In other embodiments, Z is S. In yet other embodiments, Z is NR$_Z$, wherein R$_Z$ is as defined above. In certain embodiments, R$_Z$ is hydrogen; a protecting group; C$_1$-C$_6$ alkyl; or acyl.

In certain embodiments, R$_1$ is hydrogen; halogen; substituted or unsubstituted aliphatic; substituted or unsubstituted heteroaliphatic; alkoxy; alkylthioxy; acyl; cyano; nitro; amino; alkylamino; or dialkylamino. In certain embodiments, R$_1$ is hydrogen; halogen; substituted or unsubstituted aliphatic; alkoxy; alkylthioxy; amino; alkylamino; or dialkylamino. In certain embodiments, R$_1$ is hydrogen, alkoxy, acetoxy, or tosyloxy. In certain embodiments, R$_1$ is hydrogen or methoxy.

In certain embodiments, n is 0. In other embodiments, n is 1. In yet other embodiments, n is 2.

In certain embodiments, R$_6$ and R$_7$ are independently a hydrogen, or cyclic or acyclic, substituted or unsubstituted, branched or unbranched aliphatic or heteroaliphatic. In other embodiments, R$_6$ and R$_7$ are hydrogen or C$_1$-C$_6$ alkyl, preferably hydrogen, methyl, ethyl, n-propyl, iso-propyl, n-butyl, iso-butyl, or tert-butyl. In other embodiments, at least one of R$_6$ and R$_7$ is substituted or unsubstituted, branched or unbranched acyl. In yet other embodiments, at least one of R$_6$ and R$_7$ is substituted or unsubstituted, aryl or heteroaryl. In certain embodiments, R$_6$ and R$_7$ are both hydrogen or C$_1$-C$_6$ alkyl, preferably both are methyl.

In certain embodiments, R$_8$ and R$_9$ are hydrogen; cyclic or acyclic, substituted or unsubstituted, branched or unbranched aliphatic; cyclic or acyclic, substituted or unsubstituted, branched or unbranched aliphatic; alkoxy; acyl; amino; alkylamino; or dialkylamino. In certain embodiments, R$_8$ and R$_9$ are hydrogen or cyclic or acyclic, substituted or unsubstituted, branched or unbranched aliphatic. In certain embodiments, R$_8$ and R$_9$ are hydrogen or C$_1$-C$_6$ alkyl. In certain embodiments, R$_5$ and R$_9$ are both methyl.

In certain embodiments, R$_{10}$ and R$_{11}$ are hydrogen; halogen; substituted or unsubstituted aliphatic; substituted or unsubstituted heteroaliphatic; alkoxy; alkylthioxy; acyl; cyano; nitro; amino; alkylamino; or dialkylamino. In certain embodiments, R$_{10}$ and R$_{11}$ are hydrogen; halogen; substituted or unsubstituted aliphatic; alkoxy; alkylthioxy; amino; alkylamino; or dialkylamino. In certain embodiments, R$_{10}$ and R$_{11}$ are hydrogen, alkoxy, acetoxy, or tosyloxy. In certain embodiments, R$_{10}$ and R$_{11}$ are hydrogen or methoxy.

In certain embodiments, R$_{12}$ is hydrogen; halogen; substituted or unsubstituted aliphatic; substituted or unsubstituted heteroaliphatic; alkoxy; alkylthioxy; acyl; cyano; nitro; amino; alkylamino; or dialkylamino. In certain embodiments, R$_{12}$ is hydrogen; halogen; substituted or unsubstituted aliphatic; alkoxy; alkylthioxy; amino; alkylamino; or dialkylamino. In certain embodiments, R$_{12}$ is hydrogen, alkoxy, acetoxy, or tosyloxy. In certain embodiments, R$_{12}$ is hydrogen or methoxy.

In certain embodiments, R$_1$, R$_6$, R$_7$, R$_8$, R$_9$, R$_{10}$, R$_{11}$, R$_{12}$, R$_{13}$, R$_{14}$, or R$_{15}$ comprises a label such as a radiolabel, biotin, or fluorescent tag. The radiolabel may include a isotope of hydrogen, carbon, phosphorus, sulfur, or iodine, e.g., $^3$H, $^{14}$c, $^{31}$P, $^{32}$P, $^{35}$S, and $^{125}$I. The radiolabel may emit alpha particles, beta particles, or gamma particles, preferably beta particles. The fluorescent tag may be fluoroscein or a fluoroscein derivative. The label may also include a protein or peptide. The protein or peptide may contain an epitope recognized by an antibody or antibody fragment. The peptide or protein may be fluorescent, e.g., green fluorescent protein (GFP).

In certain embodiments, m is 0. In other embodiments, m is 1. In other embodiments, m is 2. In yet other embodiments, m is 3.

In certain embodiments R$_{13}$ and R$_{14}$ are hydrogen; cyclic or acyclic, substituted or unsubstituted, branched or unbranched aliphatic; cyclic or acyclic, substituted or unsubstituted, branched or unbranched aliphatic; alkoxy; acyl; amino; alkylamino; or dialkylamino. In certain embodiments, R$_{13}$ and R$_{14}$ are hydrogen or cyclic or acyclic, substituted or unsubstituted, branched or unbranched aliphatic. In certain embodiments, R$_{13}$ and R$_{14}$ are hydrogen or C$_1$-C$_6$ alkyl. In certain embodiments, R$_{13}$ and R$_{14}$ are both hydrogen.

In certain embodiments, $R_{15}$ is hydrogen, a nitrogen-protecting group, or aliphatic. In other embodiments, $R_{15}$ is hydrogen. In certain embodiments, $R_{15}$ is a nitrogen protecting groups. In other embodiments, $R_{15}$ is an aliphatic group, preferably $C_1$-$C_6$ alkyl.

In certain embodiments, the compound is of the formula:

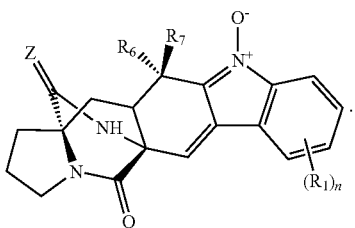

wherein $R_1$, $R_6$, $R_7$, and n are defined as above. In certain embodiments, n is 1. In other embodiments, n is 2. When n is greater than 1, the two or more $R_1$ group may form a cyclic structure. In certain embodiments, $R_1$ is aliphatic preferably $C_1$-$C_{20}$ aliphatic. In particular embodiments, $R_1$ is alkyl, preferably $C_1$-$C_{20}$ alkyl. In particular embodiments, $R_1$ is alkenyl, preferably $C_1$-$C_{20}$ alkenyl. In particular embodiments, $R_1$ is alkynyl, preferably $C_1$-$C_{20}$ alkynyl. In certain embodiments, $R_1$ is —OH. In certain embodiments, $R_1$ is alkoxy. In certain embodiments, $R_1$ is acyl, preferably —CO(CH$_2$)$_x$CH$_3$, wherein x is an integer between 0 and 20 inclusive. In other embodiments, $R_1$ is —SH. In yet other embodiments, $R_1$ is —CN. In other embodiments, $R_1$ is —SO$_2$Me.

The α,β-unsaturated nitrone group of avrainvillamide and derivatives of avrainvillamide are subject to 1,5-addition by nucleophile resulting in a compound of the formula:

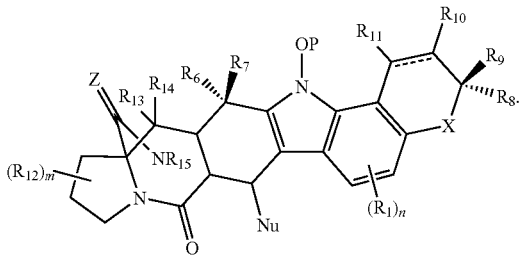

wherein
each occurrence of $R_1$ is independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_A$; —C(=O)R$_A$; —CO$_2$R$_A$; —CN; —SCN; —SR$_A$; —SOR$_A$; —SO$_2$R$_A$; —NO$_2$; —N$_3$; —N(R$_A$)$_2$; —NHC(=O)R$_A$; —NR$_A$C(=O)N(R$_A$)$_2$; —OC(=O)OR$_A$; —OC(=O)R$_A$; —OC(=O)N(R$_A$)$_2$; —NR$_A$C(=O)OR$_A$; or —C(R$_A$)$_3$; wherein each occurrence of R$_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_6$ is selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substitute or unsubstituted, branched or unbranched aryl; substituted or unsubstituted, branched or unbranched heteroaryl; —OR$_F$; —C(=O)R$_F$; —CO$_2$R$_F$; —CN; —SCN; —SR$_F$; —SOR$_F$; —SO$_2$R$_F$; —NO$_2$; —N$_3$; —N(R$_F$)$_2$; —NHC(=O)R$_F$; —NR$_F$C(=O)N(R$_F$)$_2$; —OC(=O)OR$_F$; —OC(=O)R$_F$; —OC(=O)N(R$_F$)$_2$; —NR$_F$C(=O)OR$_F$; or —C(R$_F$)$_3$; wherein each occurrence of R$_F$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_7$ is selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_G$; —C(=O)R$_G$; —CO$_2$R$_G$; —CN; —SCN; —SR$_G$; —SOR$_G$; —SO$_2$R$_G$; —NO$_2$; —N$_3$; —N(R$_G$)$_2$; —NHC(=O)R$_G$; —NR$_G$C(=O)N(R$_G$)$_2$; —OC(=O)OR$_G$; —OC(=O)R$_G$; —OC(=O)N(R$_G$)$_2$; —NR$_G$C(=O)OR$_G$; or —C(R$_G$)$_3$; wherein each occurrence of R$_G$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_8$ and $R_9$ are independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_H$; —C(=O)R$_H$; —CO$_2$R$_H$; —CN; —SCN; —SR$_H$; —SOR$_H$; —SO$_2$R$_H$; —NO$_2$; —N$_3$; —N(R$_H$)$_2$; —NHC(=O)R$_H$; —NR$_H$C(=O)N(R$_H$)$_2$; —OC(=O)OR$_H$; —OC(=O)R$_H$; —OC(=O)N(R$_H$)$_2$; —NR$_H$C(=O)OR$_H$; or —C(R$_H$)$_3$; wherein each occurrence of R$_H$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_{10}$ and $R_{11}$ are independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_J$; —C(=O)R$_J$; —CO$_2$R$_J$; —CN; —SCN; —SR$_J$; —SOR$_J$; —SO$_2$R$_J$; —NO$_2$; —N$_3$; —N(R$_J$)$_2$; —NHC(=O)R$_J$; —NR$_J$C(=O)N(R$_J$)$_2$; —OC(=O)OR$_J$; —OC(=O)R$_J$; —OC(=O)N(R$_J$)$_2$; —NR$_J$C(=O)OR$_J$; or —C(R$_J$)$_3$; wherein each occurrence of $R_J$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_{12}$ is selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_L$; —C(=O)$R_L$; —$CO_2R_L$; —CN; —SCN; —$SR_L$; —$SOR_L$; —$SO_2R_L$; —$NO_2$; —$N_3$; —$N(R_L)_2$; —NHC(=O)$R_L$; —$NR_LC$(=O)N($R_L$)$_2$; —OC(=O)$OR_L$; —OC(=O)$R_L$; —OC(=O)N($R_L$)$_2$; —$NR_LC$(=O)$OR_L$; or —C($R_L$)$_3$; wherein each occurrence of $R_L$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_{13}$ and $R_{14}$ are independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_M$; —C(=O)$R_M$; —$CO_2R_M$; —CN; —SCN; —$SR_M$; —$SOR_M$; —$SO_2R_M$; —$NO_2$; —$N_3$; —$N(R_M)_2$; —NHC(=O)$R_M$; —$NR_MC$(=O)N($R_M$)$_2$; —OC(=O)$OR_M$; —OC(=O)$R_M$; —OC(=O)N($R_M$)$_2$; —$NR_MC$(=O)$OR_M$; or —C($R_M$)$_3$; wherein each occurrence of $R_M$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_{15}$ is selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_P$; —C(=O)$R_P$; —$CO_2R_P$; —CN; —SCN; —$SR_P$; —$SOR_P$; —$SO_2R_P$; —$NO_2$; —$N_3$; —$N(R_P)_2$; —NHC(=O)$R_P$; —$NR_PC$(=O)N($R_P$)$_2$; —OC(=O)$OR_P$; —OC(=O)$R_P$; —OC(=O)N($R_P$)$_2$; —$NR_PC$(=O)$OR_P$; or —C($R_P$)$_3$; wherein each occurrence of $R_P$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

wherein two or more substituents may form substituted or unsubstituted, cyclic, heterocyclic, aryl, or heteroaryl structures;

wherein $R_6$ and $R_7$, $R_8$ and $R_9$, $R_{13}$ and $R_{14}$, and one $R_{12}$ and another $R_{12}$ may form together =O, =$NR_G$, or =C($R_G$)$_2$, wherein each occurrence of $R_G$ is defined as above;

X is O, S, C($R_X$)$_2$, or $NR_X$, wherein $R_X$ is hydrogen, a protecting group, an aliphatic, heteroaliphatic, aryl, heteroaryl, alkylaryl, or alkylheteroaryl moiety, Z is O, S, or $NR_Z$, wherein $R_Z$ is hydrogen, a protecting group, an aliphatic, heteroaliphatic, aryl, heteroaryl, alkylaryl, or alkylheteroaryl moiety, or $OR_{Z'}$, wherein $R_{Z'}$ is hydrogen, a protecting group, an aliphatic, heteroaliphatic, aryl, heteroaryl, alkylaryl, or alkylheteroaryl moiety;

P is an oxygen-protecting group or hydrogen;

Nu is hydrogen, —$OR_{Nu}$, —$SR_{Nu}$, —C($R_{Nu}$)$_3$, or —N($R_{Nu}$)$_2$, wherein each occurrence of $R_{Nu}$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

the dashed line represents the presence or absence of a bond;

m is an integer between 0 and 6, inclusive; and n is an integer between 0 and 2, inclusive. In certain preferred embodiments, P is hydrogen. In other embodiments, P is $C_1$-$C_6$ allyl. In yet other embodiments, P is an oxygen-protecting group. In certain embodiments, P is acetyl. In certain embodiments, Nu is a sulfur-based nucleophile of the formula —$SR_{Nu}$. In other embodiments, Nu is an oxygen-based nucleophile of the formula —$OR_{Nu}$, for example —OH, —OMe, —OEt, etc. In other embodiments, Nu is a nitrogen-based nucleophile of the formula —N($R_{Nu}$)$_2$. In certain embodiments, the nucleophile is an amino acid (e.g., the side chain of serine, threonine, cysteine, lysine, histidine, glutamine, asparagine, arginine, or tyrosine; preferably, serine, threonine, or cysteine). In certain embodiments, the nucleophile is cysteine. In other embodiments, the nucleophile is an amino acid which is part of a peptide or protein. In certain particular embodiments, the nucleophile is glutathione. In certain embodiments, the nucleophile is a reducing agent such as hydride. These nucleophilic adducts of avrainvillamide and derivatives (including the homodimerization product stephacidin B) may be useful in delivering the drug. For example, these adducts may serve to temporarily protect the α,β-unsaturated nitrone functionality of the molecule. In certain embodiments, the adduct may be a hydrate of avrainvillamide or a derivative thereof.

Exemplary compounds of the invention include compounds of the formulae:

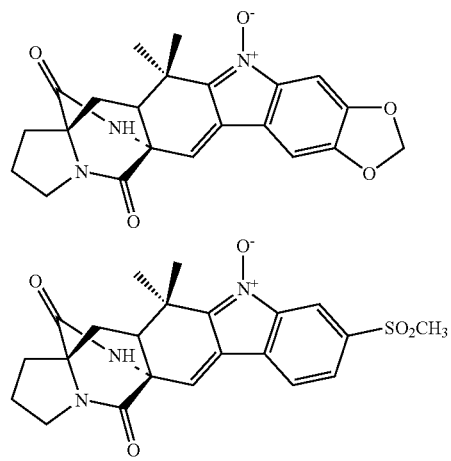

55
-continued
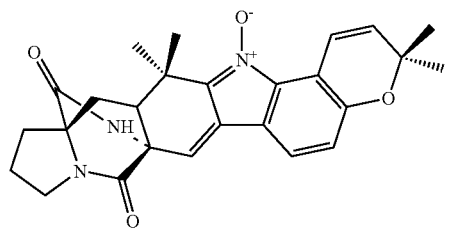
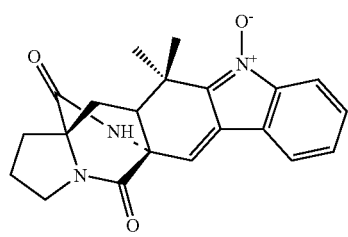
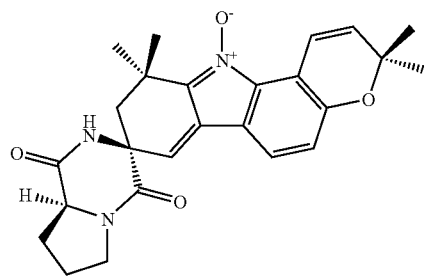
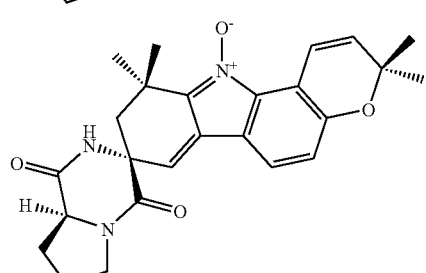
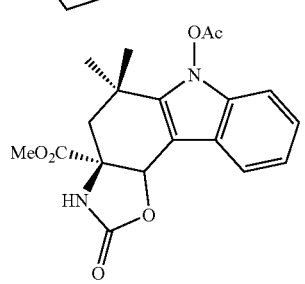
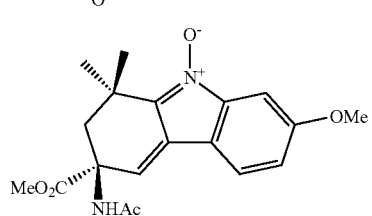
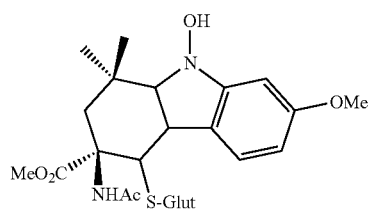
56
-continued
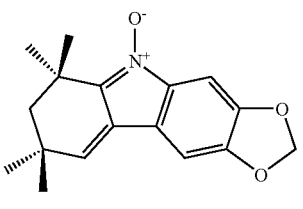
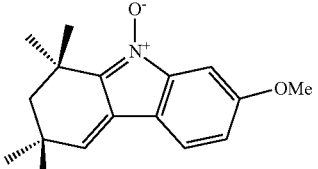
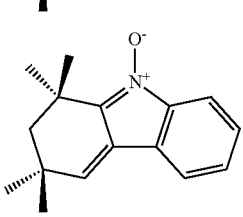
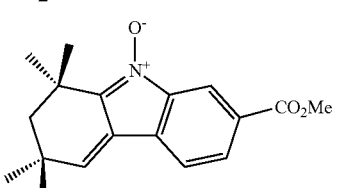
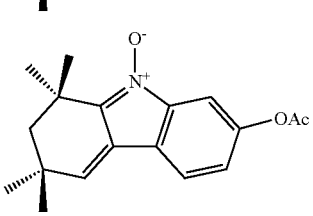
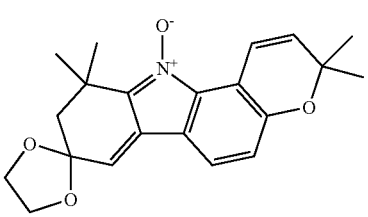
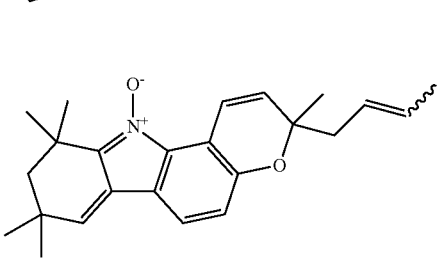
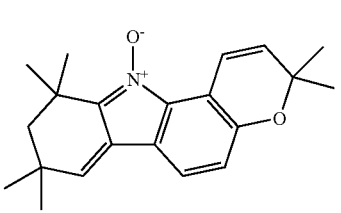

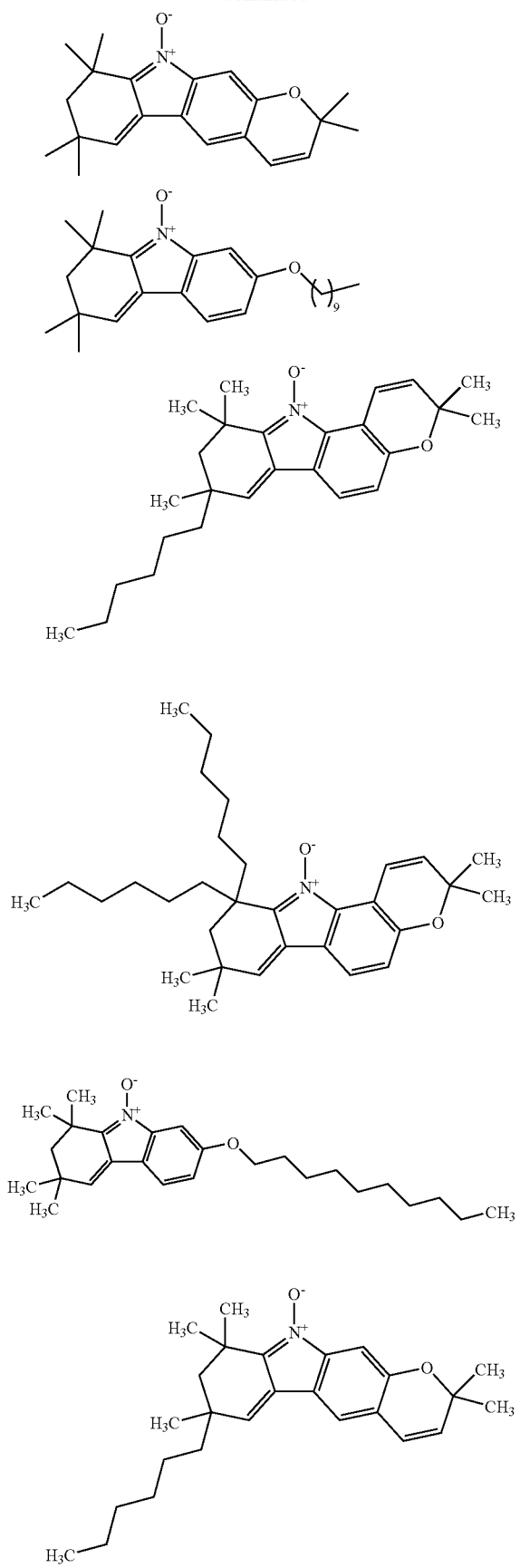
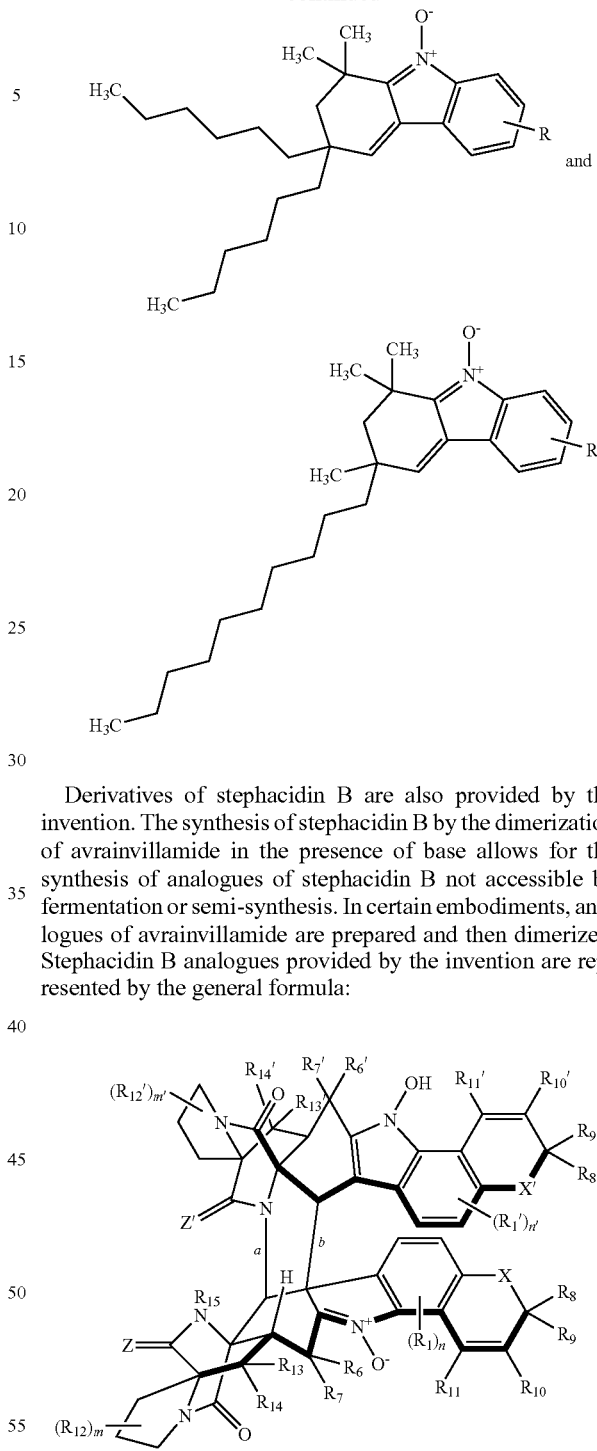

Derivatives of stephacidin B are also provided by the invention. The synthesis of stephacidin B by the dimerization of avrainvillamide in the presence of base allows for the synthesis of analogues of stephacidin B not accessible by fermentation or semi-synthesis. In certain embodiments, analogues of avrainvillamide are prepared and then dimerized. Stephacidin B analogues provided by the invention are represented by the general formula:

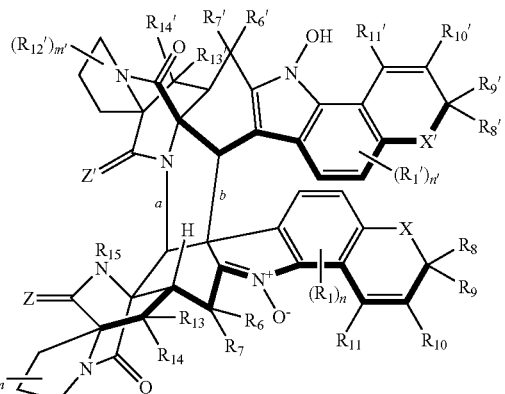

wherein each occurrence of $R_1$ and $R_1'$, is independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_A$; —C(=O)$R_A$; —$CO_2R_A$; —CN; —SCN; —$SR_A$; —$SOR_A$;

—SO$_2$R$_A$; —NO$_2$; —N$_3$; —N(R$_A$)$_2$; —NHC(═O)R$_A$; —NR$_A$C(═O)N(R$_A$)$_2$; —OC(═O)OR$_A$; —OC(═O)R$_A$; —OC(═O)N(R$_A$)$_2$; —NR$_A$C(═O)OR$_A$; or —C(R$_A$)$_3$; wherein each occurrence of R$_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

R$_6$ and R$_6$' are independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_F$; —C(═O)R$_F$; —CO$_2$R$_F$; —CN; —SCN; —SR$_F$; —SOR$_F$; —SO$_2$R$_F$; —NO$_2$; —N$_3$; —N(R$_F$)$_2$; —NHC(═O)R$_F$; —NR$_F$C(═O)N(R$_F$)$_2$; —OC(═O)OR$_F$; —OC(═O)R$_F$; —OC(═O)N(R$_F$)$_2$; —NR$_F$C(═O)OR$_F$; or —C(R$_F$)$_3$; wherein each occurrence of R$_F$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

R$_7$ and R$_7$' are independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_G$; —C(═O)R$_G$; —CO$_2$R$_G$; —CN; —SCN; —SR$_G$; —SOR$_G$; —SO$_2$R$_G$; —NO$_2$; —N$_3$; —N(R$_G$)$_2$; —NHC(═O)R$_G$; —NR$_G$C(═O)N(R$_G$)$_2$; —OC(═O)OR$_G$; —OC(═O)R$_G$; —OC(═O)N(R$_G$)$_2$; —NR$_G$C(═O)OR$_G$; or —C(R$_G$)$_3$; wherein each occurrence of R$_G$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

R$_8$, R$_9$, R$_8$', and R$_9$' are independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_H$; —C(═O)R$_H$; —CO$_2$R$_H$; —CN; —SCN; —SR$_H$; —SOR$_H$; —SO$_2$R$_H$; —NO$_2$; —N$_3$; —N(R$_H$)$_2$; —NHC(═O)R$_H$; —NR$_H$C(═O)N(R$_H$)$_2$; —OC(═O)OR$_H$; —OC(═O)R$_H$; —OC(═O)N(R$_H$)$_2$; —NR$_H$C(═O)OR$_H$; or —C(R$_H$)$_3$; wherein each occurrence of R$_H$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

R$_{10}$, R$_{11}$, R$_{10}$', and R$_{11}$' are independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_J$; —C(═O)R$_J$; —CO$_2$R$_J$; —CN; —SCN; —SR$_J$; —SOR$_J$; —SO$_2$R$_J$; —NO$_2$; —N$_3$; —N(R$_J$)$_2$; —NHC(═O)R$_J$; —NR$_J$C(═O)N(R$_J$)$_2$; —OC(═O)OR$_J$; —OC(═O)R$_J$; —OC(═O)N(R$_J$)$_2$; —NR$_J$C(═O)OR$_J$; or —C(R$_J$)$_3$; wherein each occurrence of R$_J$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

R$_{12}$ and R$_{12}$' are independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_L$; —C(═O)R$_L$; —CO$_2$R$_L$; —CN; —SCN; —SR$_L$; —SOR$_L$; —SO$_2$R$_L$; —NO$_2$; —N$_3$; —N(R$_L$)$_2$; —NHC(═O)R$_L$; —NR$_L$C(═O)N(R$_L$)$_2$; —OC(═O)OR$_L$; —OC(═O)R$_L$; —OC(═O)N(R$_L$)$_2$; —NR$_L$C(═O)OR$_L$; or —C(R$_L$)$_3$; wherein each occurrence of R$_L$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

R$_{13}$, R$_{14}$, R$_{13}$', and R$_{14}$' are independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_M$; —C(═O)R$_M$; —CO$_2$R$_M$; —CN; —SCN; —SR$_M$; —SOR$_M$; —SO$_2$R$_M$; —NO$_2$; —N$_3$; —N(R$_M$)$_2$; —NHC(═O)R$_M$; —NR$_M$C(═O)N(R$_M$)$_2$; —OC(═O)OR$_M$; —OC(═O)R$_M$; —OC(═O)N(R$_M$)$_2$; —NR$_M$C(═O)OR$_M$; or —C(R$_M$)$_3$; wherein each occurrence of R$_M$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

R$_{15}$ and R$_{15}$' are selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_P$; —C(═O)R$_P$; —CO$_2$R$_P$; —CN; —SCN; —SR$_P$; —SOR$_P$; —SO$_2$R$_P$; —NO$_2$; —N$_3$; —N(R$_P$)$_2$; —NHC(═O)R$_P$; —NR$_P$C(═O)N(R$_P$)$_2$; —OC(═O)OR$_P$; —OC(═O)R$_P$; —OC(═O)N(R$_P$)$_2$; —NR$_P$C(═O)OR$_P$; or —C(R$_P$)$_3$; wherein each occurrence of R$_P$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

wherein two or more substituents may form substituted or unsubstituted, cyclic, heterocyclic, aryl, or heteroaryl structures;

wherein $R_6$ and $R_7$, $R_6'$ and $R_7'$, $R_8$ and $R_9$, $R_8'$ and $R_9'$, $R_{13}$ and $R_{14}$, $R_{13}'$ and $R_{14}'$, one $R_{12}$ and another $R_{12}'$, and one $R_{12}$ and another $R_{12}$ may form together $=O$, $=NR_G$, or $=C(R_G)_2$, wherein each occurrence of $R_G$ is defined as above;

X and X' are independently O, S, $C(R_X)_2$, or $NR_X$, wherein $R_X$ is hydrogen, a protecting group, an aliphatic, heteroaliphatic, aryl, heteroaryl, alkylaryl, or alkylheteroaryl moiety, Z and Z' are independently O, S, or $NR_Z$, wherein $R_Z$ is hydrogen, a protecting group, an aliphatic, heteroaliphatic, aryl, heteroaryl, alkylaryl, or alkylheteroaryl moiety, or $OR_{Z'}$, wherein $R_{Z'}$ is hydrogen, a protecting group, an aliphatic, heteroaliphatic, aryl, heteroaryl, alkylaryl, or alkylheteroaryl moiety;

m and m' are independently an integer between 0 and 6, inclusive; and n and n' are independently an integer between 0 and 2, inclusive.

In certain embodiments, as when the stephacidin B analogue is prepared by the dimerization of the same avrainvillamide analogues, $R_1$ and $R_1'$ as well as the other R groups and their analogous R' groups are the same. In other embodiments, the stephacidin B analogues may be prepared by the dimerization of two different avrainvillamide analogues (e.g., a heterodimer). In this case, R groups and their corresponding R' groups may be the same or different. In certain embodiments, the R groups and R' groups may be the same at some positions and different at other positions.

In certain embodiments, X and X' are independently O, S, or $NR_X$, wherein $R_X$ is defined as above. In certain embodiments, X and X' are both O. In other embodiments, X and X' are both S. In yet other embodiments, X and X' are both $NR_X$, preferably NH. In certain embodiments, X and X' are both $C(R_X)_2$, preferably $CH_2$. In other embodiments, X and X' are both $C(=O)$, $C(=S)$, or $C(=NR_X)$.

In certain embodiments, Z and Z' are both O. In other embodiments, Z and Z' are both S. In yet other embodiments, Z and Z' are both $NR_Z$, wherein $R_Z$ is as defined above. In certain embodiments, $R_Z$ is hydrogen; a protecting group; $C_1$-$C_6$ alkyl; or acyl.

In certain embodiments, $R_1$ and $R_1'$ are independently hydrogen; halogen; substituted or unsubstituted aliphatic; substituted or unsubstituted heteroaliphatic; alkoxy; alkylthioxy; acyl; cyano; nitro; amino; alkylamino; or dialkylamino. In certain embodiments, $R_1$ and $R_1'$ are independently hydrogen; halogen; substituted or unsubstituted aliphatic; alkoxy; alkylthioxy; amino; alkylamino; or dialkylamino. In certain embodiments, $R_1$ and $R_1'$ are independently hydrogen, alkoxy, acetoxy, or tosyloxy. In certain embodiments, $R_1$ and $R_1'$ are independently hydrogen or methoxy. In certain embodiments, $R_1$ and $R_1'$ are both hydrogen.

In certain embodiments, n and n' are both 0. In other embodiments, n and n' are both 1. In yet other embodiments, n and n' are both 2. In certain embodiments, n and n' are either 1 or 0.

In certain embodiments, $R_6$, $R_6'$, $R_7$, and $R_7'$ are independently a hydrogen, or cyclic or acyclic, substituted or unsubstituted, branched or unbranched aliphatic or heteroaliphatic. In other embodiments, $R_6$, $R_6'$, $R_7$, and $R_7'$ are hydrogen or $C_1$-$C_6$ alkyl, preferably hydrogen, methyl, ethyl, n-propyl, iso-propyl, n-butyl, iso-butyl, or tert-butyl. In other embodiments, at least one of $R_6$, $R_6'$, $R_7$, and $R_7'$ is substituted or unsubstituted, branched or unbranched acyl. In yet other embodiments, at least one of $R_6$, $R_6'$, $R_7$, and $R_7'$ is substituted or unsubstituted, aryl or heteroaryl. In certain embodiments, $R_6$, $R_6'$, $R_7$, and $R_7'$ are both hydrogen or $C_1$-$C_6$ alkyl, preferably both are methyl.

In certain embodiments, $R_8$, $R_8'$, $R_9$, and $R_9'$ are independently hydrogen; cyclic or acyclic, substituted or unsubstituted, branched or unbranched aliphatic; cyclic or acyclic, substituted or unsubstituted, branched or unbranched aliphatic; alkoxy; acyl; amino; alkylamino; or dialkylamino. In certain embodiments, $R_8$, $R_8'$, $R_9$, and $R_9'$ are independently hydrogen or cyclic or acyclic, substituted or unsubstituted, branched or unbranched aliphatic. In certain embodiments, $R_8$, $R_8'$, $R_9$, and $R_9'$ are independently hydrogen or $C_1$-$C_6$ alkyl. In certain embodiments, $R_8$, $R_8'$, $R_9$, and $R_9'$ are all $C_1$-$C_6$ alkyl. In certain embodiments, $R_8$, $R_8'$, $R_9$, and $R_9'$ are independently are all methyl.

In certain embodiments, $R_{10}$, $R_{10}'$, $R_{11}$, and $R_{11}'$ are independently hydrogen; halogen; substituted or unsubstituted aliphatic; substituted or unsubstituted heteroaliphatic; alkoxy; alkylthioxy; acyl; cyano; nitro; amino; alkylamino; or dialkylamino. In certain embodiments, $R_{10}$, $R_{10}'$, $R_{11}$ and $R_{11}'$ are independently hydrogen; halogen; substituted or unsubstituted aliphatic; alkoxy; alkylthioxy; amino; alkylamino; or dialkylamino. In certain embodiments, $R_{10}$, $R_{10}'$, $R_{11}$, and $R_{11}'$ are independently hydrogen, alkoxy, acetoxy, or tosyloxy. In certain embodiments, $R_{10}$, $R_{10}'$, $R_{11}$, and $R_{11}'$ are independently hydrogen or methoxy.

In certain embodiments, $R_{12}$ and $R_{12}'$ are independently hydrogen; halogen; substituted or unsubstituted aliphatic; substituted or unsubstituted heteroaliphatic; alkoxy; alkylthioxy; acyl; cyano; nitro; amino; alkylamino; or dialkylamino. In certain embodiments, $R_{12}$ and $R_{12}'$ are independently hydrogen; halogen; substituted or unsubstituted aliphatic; alkoxy; alkylthioxy; amino; alkylamino; or dialkylamino. In certain embodiments, $R_{12}$ and $R_{12}'$ are independently hydrogen or aliphatic. In certain embodiments, $R_{12}$ and $R_{12}'$ are all hydrogen.

In certain embodiments, m and m' are independently 0, 1, 2, or 3. In certain embodiments, m and m' are 0. In other embodiments, m and m' are 1. In other embodiments, m and m' are 2. In yet other embodiments, m and m' are 3.

In certain embodiments, $R_{13}$, $R_{13}'$, $R_{14}$, and $R_{14}'$ are independently hydrogen; cyclic or acyclic, substituted or unsubstituted, branched or unbranched aliphatic; cyclic or acyclic, substituted or unsubstituted, branched or unbranched aliphatic; alkoxy; acyl; amino; alkylamino; or dialkylamino. In certain embodiments, $R_{13}$, $R_{13}'$, $R_{14}$, and $R_{14}'$ are independently hydrogen or cyclic or acyclic, substituted or unsubstituted, branched or unbranched aliphatic. In certain embodiments, $R_{13}$, $R_{13}'$, $R_{14}$, and $R_{14}'$ are independently hydrogen or $C_1$-$C_6$ alkyl. In certain embodiments, $R_{13}$, $R_{13}'$, $R_{14}$, and $R_{14}'$ are all hydrogen.

In certain embodiments, $R_{15}$ and $R_{15}'$ are independently hydrogen, a nitrogen-protecting group, or aliphatic. In other embodiments, $R_{15}$ and $R_{15}'$ are both hydrogen. In certain embodiments, $R_{15}$ and $R_{15}'$ are both nitrogen protecting groups. In other embodiments, $R_{15}$ and $R_{15}'$ are both aliphatic groups, preferably $C_1$-$C_6$ alkyl.

In certain embodiments, $R_1$, $R_1'$, $R_6$, $R_6'$, $R_7$, $R_7'$, $R_8$, $R_8'$, $R_9$, $R_9'$, $R_{10}$, $R_{10}'$, $R_{11}$, $R_{11}'$ $R_{12}$, $R_{12}'$, $R_{13}$, $R_{13}'$, $R_{14}$, $R_{14}'$, $R_{15}$, or $R_{15}'$ comprises a label such as a radiolabel, biotin, or fluorescent tag. The radiolabel may include a isotope of hydrogen, carbon, phosphorus, sulfur, or iodine, e.g., $^3H$, $^{14}C$, ³¹P, ³²P, ³⁵S, and ¹²⁵I. The radiolabel may emit alpha particles, beta particles, or gamma particles, preferably beta particles. The fluorescent tag may be fluoroscein or a fluoroscein derivative. The label may also include a protein or peptide. The protein or peptide may contain an epitope recognized by an antibody or antibody fragment. The peptide or protein may be fluorescent, e.g., green fluorescent protein (GFP). In certain embodiments, the label is biotin.

As will be appreciated by one of skill in this art, compounds of invention include derivatives, labeled forms, salts, pro-drugs, isomers, and tautomers thereof. Derivatives include protected forms. Salts include any pharmaceutically acceptable salts including HCl, HBr, HI, acetate, sulfonate (e.g., besylate, p-toluenesulfonate, mesylate, etc.) and fatty acid (e.g., lactate, citrate, myristoleate, oleate, valerate) salts.

As will be appreciated by one of skill in this art, the invention includes compositions in which the compounds are at least 90%, 95%, 98%, 99%, or 99.9% pure. In certain embodiments, a preparation of avrainvillamide or stephacidin B is provided of at least 90%, 95%, 98%, 99%, or 99.9% purity, preferably at least 95% or 98% purity. In other embodiments, a preparation of a compound of the formula:

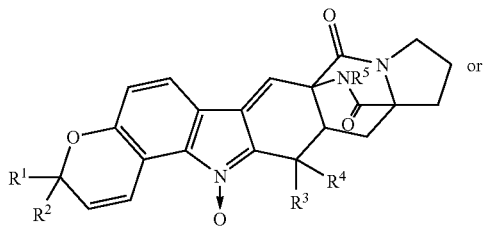

or

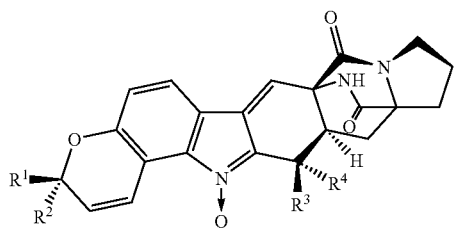

wherein, $R^1$, $R^2$, $R^3$, $R^4$ and $R^5$ are independently selected from H, alkyl, aminoalkyl, perfluoroalkyl, is provided of at least 90%, 95%, 98%, 99%, or 99.9% purity, preferably at least 95% or 98% purity. The synthetic methods described herein allow for the preparation of compositions of such purity. However, achieving these levels of purity by isolating compounds such as avrainvillamide or stephacidin B from a natural source may be difficult or impossible due to their instability. This level of purity is even more of a challenge when large quantities of these compounds are needed. Sufficiently pure preparations of these compounds are particularly useful in formulating pharmaceutical compositions for administration to humans or other animals.

Methods of Synthesis

An exemplary synthesis of avrainvillamide is shown in the scheme below. As will be appreciated by one of skill in this art, various modification can be made to the starting materials and reagents used in the scheme to provide the compounds of the invention.

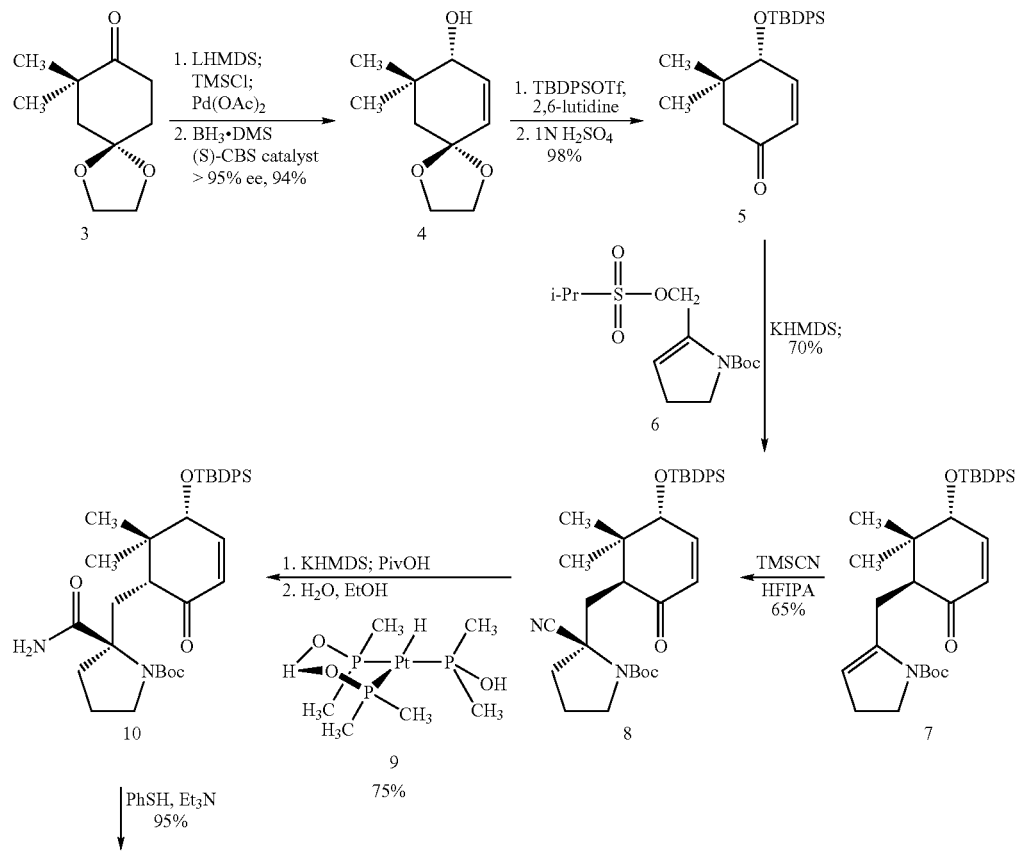

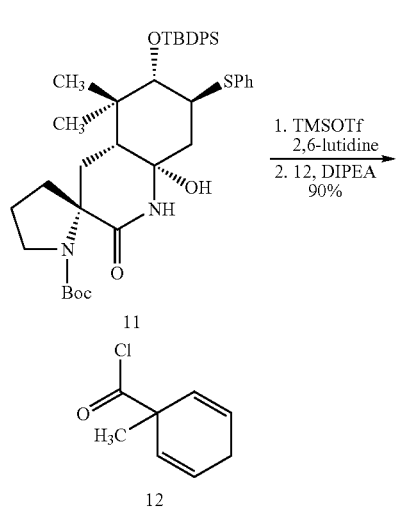
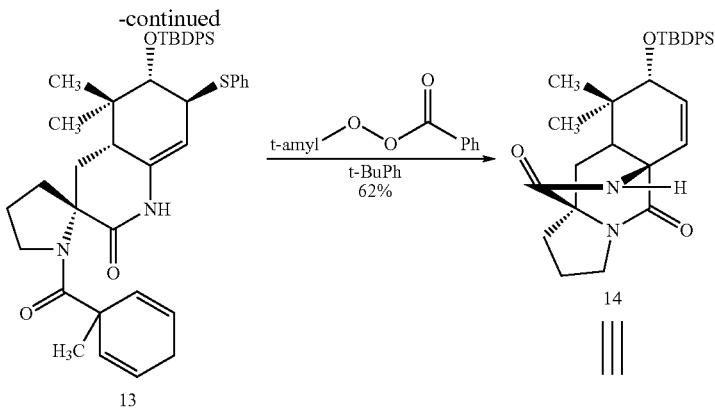
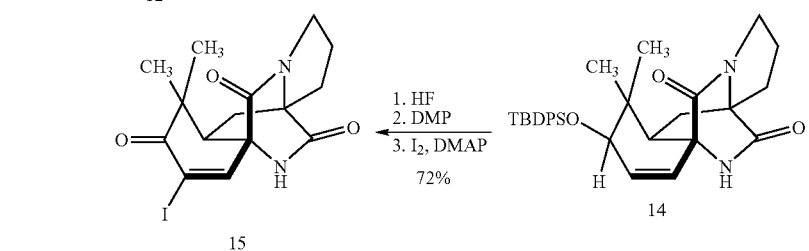
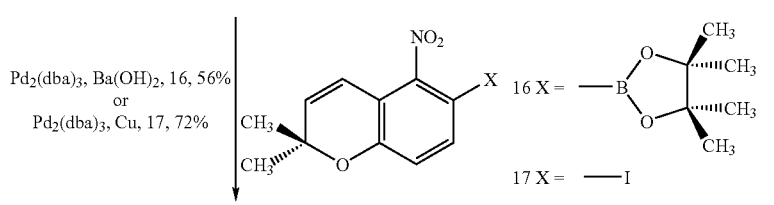
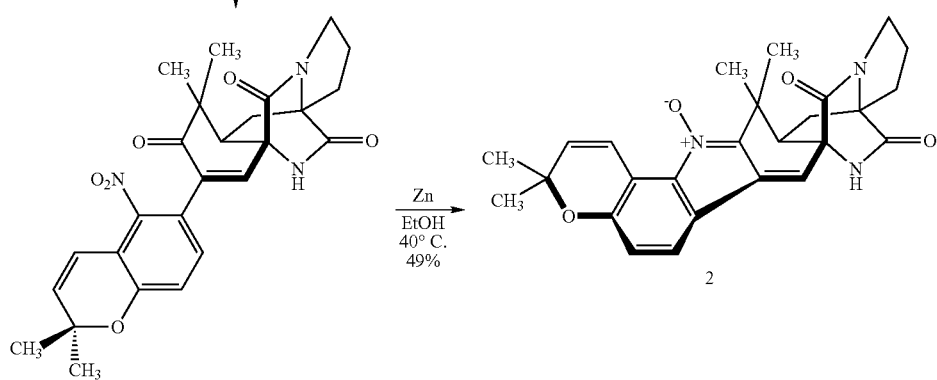

The synthesis of avrainvillamide begins with the achiral cyclohexanone derivative 3; however, other chiral or achiral cyclohexanone derivatives may also be used as the starting material. The cyclohexanone derivative is transformed via its protected enol ether into the corresponding α,β-unsaturated ketone. This oxidation reaction can be accomplished by palladium-mediated oxidation as shown. Other oxidation methods which may be used include the oxidation with 2-iodoxybenzoic acid in the presence of 4-methoxypyridine N-oxide. As will be appreciated by one of skill in this art, other oxidation may also be used to effect this transformation.

The resulting α,β-unsaturated ketone is reduced enantioselectively. In one embodiment, the Corey-Bakshi-Shibata catalyst is used in the reduction. Either the (S)-CBS catalyst or the (R)-CBS catalyst may be used in the reduction reaction to achieve either enantiomer. The (S)-CBS catalyst was used for the (R)-allylic alcohol. In other embodiments, another enantioselective catalyst is utilized. In certain embodiments, the α,β-unsaturated ketone is reduced to give a mixture of enantiomers or diastereomers, and the desired isomer is purified. In the synthesis shown above, the stereochemistry introduced by the CBS reduction is subsequently relayed to all other stereocenters in avrainvillamide and stephacidin B.

The resulting allylic alcohol is protected (e.g., as the silyl ether), and the ketal group is hydrolysed to yield the α,β-unsaturated ketone 5. The ketone 5 is deprotonated at the α-position using a base (e.g., potassium hexamethyldisilazide (KHMDS), LDA), and the resulting enolate is reacted with electrophile 6, which can be prepared from N-(tert-butoxycarbonyl)-2,3-dihydropyrrole by a sequence involving α-lithiation, formylation, reduction (e.g., borohydride), and iso-propylsulfonylation. The resulting trans-coupling product 7 is formed as a single diastereomer. The alkylation product 7 underwent Strecker-like addition of hydrogen cyanide in hexyluoroisopropanol (HFIPA) forming the N-Boc amino nitrile 8. To establish the stereorelationships required for the synthesis of stephacidin B, the α-carbon of the ketone 8 was epimerized (e.g., by deprotonation with base (e.g., KHDMS) followed by quenching with pivalic acid). The platinum catalyst 9 was then used to transform the nitrile group of the epimerized product into the corresponding primary amide. Treatment of the resulting primary amide 10 with thiophenol and triethylamine led to conjugate addition of thiophenol as well as cyclic hemiaminal formation, giving the tricyclic product 11. Dehydration of the cyclic hemiaminal 11 in the presence of trimethylsilyl triflate and 2,6-lutidine was accompanied by cleavage of the N-Boc protective group. Amide 13 was then formed by the acylation of the pyrrolidinyl amine group that was liberated with 1-methyl-2,5-cyclohexadiene-1-carbonyl chloride. Heating of rigorously deoxygenated solutions of 13 and t-amyl peroxybenzoate in t-butyl benzene as solvent produced the bridged diketopiperazine core of avrainvillamide.

The tetracylic product 14 was then transformed into the α-iodoenone 15 in a three-step sequence as shown. The α-iodoenone 15 was coupled in a Suzuki reaction with the arylboronic acid derivative 16 or by Ullmann-like coupling with the aryl iodide 17. The nitroarene coupling product was reduced in the presence of activated zinc powder, forming the heptacyclic unsaturated nitrone 2.

(−)-2 ("Avrainvillamide") can be transformed into stephacidin B in the presence of base. For example, (−)-2 was transformed into stephacidin B in the presence of triethylamine at 23° C.

One particularly useful aspect of the synthesis of avrainvillamide which is also useful in preparing derivative of the 3-alkylidene-3H-indole 1-oxide is the coupling of an α-iodoenone to an arylboronic acid derivative or aryl iodide. The product of such coupling reaction can then be reduced used a metal such as activated zinc powder to form the α,β-unsaturated nitrone.

In one embodiment, an α-iodoenone of the formula:

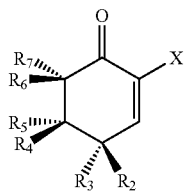

wherein $R_2$, $R_3$, $R_4$, $R_5$, $R_6$, and $R_7$ are independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_G$; —C(=O)$R_G$; —$CO_2R_G$; —CN; —SCN; —$SR_G$; —$SOR_G$; —$SO_2R_G$; —$NO_2$; —$N_3$; —N($R_G$)$_2$; —NHC(=O)$R_G$; —$NR_GC(=O)N(R_G)_2$; —OC(=O)$OR_G$; —OC(=O)$R_G$; —OC(=O)N($R_G$)$_2$; —$NR_GC(=O)OR_G$; or —C($R_G$)$_3$;
wherein each occurrence of $R_G$ is independently a hydrogen, a protecting group, an aliphatic moiety, a heteroaliphatic moiety, an acyl moiety, an aryl moiety; a heteroaryl moiety; alkoxy; aryloxy; alkylthio; arylthio; amino, alkylamino, dialkylamino, heteroaryloxy; or heteroarylthio moiety;
wherein two or more substituents may form substituted or unsubstituted, cyclic, heterocyclic, aryl, or heteroaryl structures;
wherein $R_2$ and $R_3$, $R_4$ and $R_5$, or $R_6$ and $R_7$ may form together =O, =$NR_G$, or =C($R_G$)$_2$, wherein each occurrence of $R_G$ is defined as above; and
X is a halogen;
is reacted in the presence of a transition metal catalyst with arylboronic acid derivative or aryl iodide of formula:

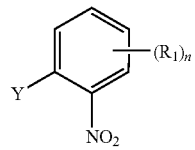

wherein each occurrence of $R_1$ is independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_G$; —C(=O)$R_G$; —$CO_2R_G$; —CN; —SCN; —$SR_G$; —$SOR_G$; —$SO_2R_G$; —$NO_2$; —$N_3$; —N($R_G$)$_2$; —NHC(=O)$R_G$; —$NR_GC(=O)N(R_G)_2$; —OC(=O)$OR_G$; —OC(=O)$R_G$; —OC(=O)N($R_G$)$_2$; —$NR_GC(=O)OR_G$; or —C($R_G$)$_3$;
wherein each occurrence of $R_G$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;
wherein two or more substituents may form substituted or unsubstituted, cyclic, heterocyclic, aryl, or heteroaryl structures; and
n is an integer between 0 and 4; and
Y is a halogen, boronic acid (—B(OH)$_2$), boronic ester, or organoborane to form a product of formula:

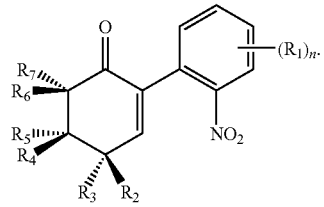

In certain embodiments, either $R_4$ or $R_5$ is not hydrogen. In another embodiment, at least one of $R_2$, $R_3$, $R_6$, and $R_7$ is not methyl. In yet another embodiment, at least one occurrence of $R_1$ is not hydrogen. In certain embodiments, the transition metal catalyst is a palladium catalyst. The palladium catalyst is Pd(OAc)$_2$ or Pd$_2$dba$_3$. In certain particular embodiments, the catalyst is Pd$_2$(dba)$_3$ and Ba(OH)$_2$. In other embodiments, the catalyst is Pd$_2$(dba)$_3$ and Cu. In certain embodiments, X is I or Br.

In other embodiments, Y is —B(OH)$_2$ or a boronic ester (e.g.,

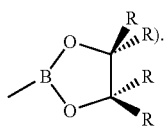

In certain embodiments, the arylboronic acid derivative or aryl iodide is a bicyclic, tricyclic, or polycyclic ring system as shown in the formulae below:

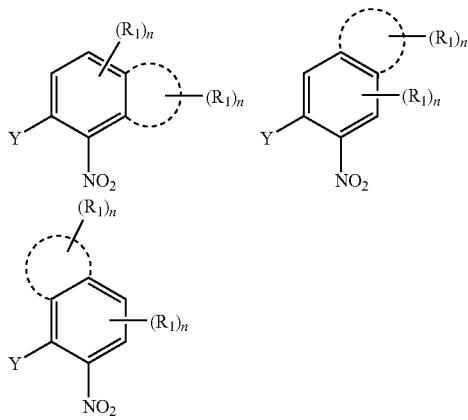

wherein R$_1$, n, and Y are as defined above, and

represents a substituted or unsubstituted, cyclic, heterocyclic, aryl, or heteroaryl ring system. In certain embodiments,

is a monocyclic ring system, preferably a 5- or 6-membered ring. In other embodiments,

is bicyclic ring system, preferably an 8-, 9-, 10-, 11- or 12-membered bicyclic ring system. In yet other embodiments,

is a tricyclic ring system. Two or more substituents R$_1$ may together from an additional cyclic structure, which may be carbocyclic or heterocyclic, substituted or unsubstituted, or aromatic or non-aromatic. In certain embodiments, the arylboronic acid derivative or aryl iodide is of the formula:

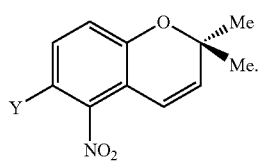

The nitroarene coupling product is then reduced to form the polycyclic unsaturated nitrone. In certain embodiments, a nitroarene compound of formula:

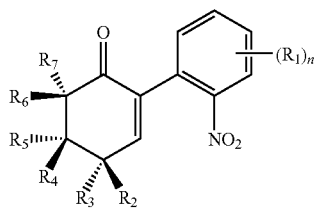

wherein R$_1$, R$_2$, R$_3$, R$_4$, R$_5$, R$_6$, and R$_7$ are independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_G$; —C(=O)R$_G$; —CO$_2$R$_G$; —CN; —SCN; —SR$_G$; SOR$_G$; —SO$_2$R$_G$; —NO$_2$; —N$_3$; —N(R$_G$)$_2$; —NHC(=O)R$_G$; —NR$_G$C(=O)N(R$_G$)$_2$; —OC(=O)OR$_G$; —OC(=O)R$_G$; —OC(=O)N(R$_G$)$_2$; —NR$_G$C(=O)OR$_G$; or —C(R$_G$)$_3$; wherein each occurrence of R$_G$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;
    wherein two or more substituents may form substituted or unsubstituted, cyclic, heterocyclic, aryl, or heteroaryl structures;
    wherein R$_2$ and R$_3$, R$_4$ and R$_5$, or R$_6$ and R$_7$ may form together =O, =NR$_G$, or =C(R$_G$)$_2$, wherein each occurrence of R$_G$ is defined as above; and
    n is an integer between 0 and 4;
is reduced to form the nitrone:

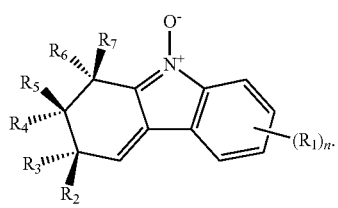

In certain embodiments, the reducing agent is a metal. In certain particular embodiments, the metal is activated zinc powder.

Avrainvillamide or avrainvillamide derivative may be dimerized to form stephacidin B or analogs of stephacidin B. In certain embodiments, two molecules of an avrainvillamide derivative of the formula:

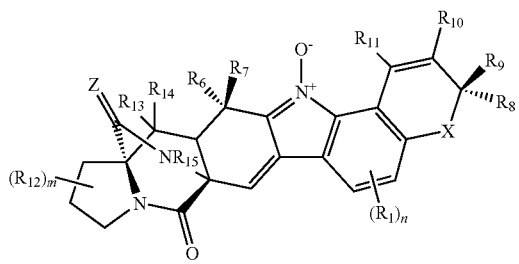

are reacted together in the presence of base to form a stephacidin B analog of the formula:

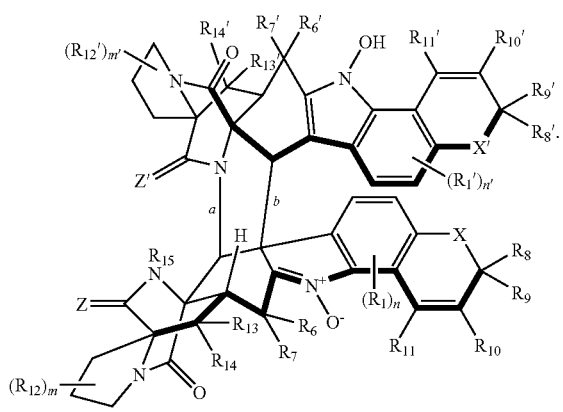

In certain embodiments, the two avrainvillamide molecules are the same. In other embodiments, the two avrainvillamide molecules are different. In certain embodiments, the base is an amine such as ammonia, alkyl amine (e.g., methylamine, ethylamine, etc.), dialkylamine (e.g. dimethylamine, diethylamine, methylethylamine, etc.), or trialkylamine (e.g., trimethylamine, triethylamine, etc.). In certain embodiments, the reaction is carried out in the presence of a large excess of triethylamine in acetonitrile at approximately room temperature.

Pharmaceutical Compositions

This invention also provides a pharmaceutical preparation comprising at least one of the compounds as described above and herein, or a pharmaceutically acceptable derivative thereof, which compounds inhibit the growth of or kill tumor cells. In other embodiments, the compounds show cytostatic or cytotoxic activity against neoplastic cells such as cancer cells. In yet other embodiments, the compounds inhibit the growth of or kill rapidly dividing cells such as stimulated inflammatory cells. In certain other embodiments, the compounds are anti-microbial compound.

As discussed above, the present invention provides novel compounds having antimicrobial and/or antiproliferative activity, and thus the inventive compounds are useful for the treatment of a variety of medical conditions including infectious diseases, cancer, autoimmune diseases, inflammatory diseases, and diabetic retinopathy. Accordingly, in another aspect of the present invention, pharmaceutical compositions are provided, wherein these compositions comprise any one of the compounds as described herein, and optionally comprise a pharmaceutically acceptable carrier. In certain embodiments, these compositions optionally further comprise one or more additional therapeutic agents, e.g., another anti-microbial agent or another anti-proliferative agent. In other embodiments, these compositions further comprise an anti-inflammatory agent such as aspirin, ibuprofen, acetaminophen, etc., pain reliever, or anti-pyretic. In other embodiments, these compositions further comprise an anti-emetic agent, a pain reliever, a multi-vitamin, etc.

It will also be appreciated that certain of the compounds of the present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof, e.g., a prodrug.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences*, 66: 1-19, 1977; incorporated herein by reference. The salts can be prepared in situ during the final isolation and purification of the compounds of the invention, or separately by reacting the free base functionality with a suitable organic or inorganic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid, or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate, and aryl sulfonate.

Additionally, as used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates. In certain embodiments, the esters are cleaved by enzymes such as esterases.

Furthermore, the term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

As described above, the pharmaceutical compositions of the present invention additionally comprise a pharmaceutically acceptable carrier, which, as used herein, includes any and all solvents, diluents, or other liquid vehicles, dispersion or suspension aids, surface active agents, isotonic agents, thickening or emulsifying agents, preservatives, solid binders, lubricants and the like, as suited to the particular dosage form desired. Remington's *Pharmaceutical Sciences*, Fifteenth Edition, E. W. Martin (Mack Publishing Co., Easton, Pa., 1975) discloses various carriers used in formulating pharmaceutical compositions and known techniques for the preparation thereof. Except insofar as any conventional carrier medium is incompatible with the anti-cancer compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; Cremophor; Solutol; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutical Compositions

The invention further provides a method of treating infections and inhibiting tumor growth. The method involves the administration of a therapeutically effective amount of the compound or a pharmaceutically acceptable derivative thereof to a subject (including, but not limited to a human or animal) in need of it.

The compounds and pharmaceutical compositions of the present invention may be used in treating or preventing any disease or conditions including infections (e.g., skin infections, GI infection, urinary tract infections, genito-urinary infections, systemic infections), proliferative diseases (e.g., cancer), and autoimmune diseases (e.g., rheumatoid arthritis, lupus). The compounds and pharmaceutical compositions may be administered to animals, preferably mammals (e.g., domesticated animals, cats, dogs, mice, rats), and more preferably humans. Any method of administration may be used to deliver the compound of pharmaceutical compositions to the animal. In certain embodiments, the compound or pharmaceutical composition is administered orally. In other embodiments, the compound or pharmaceutical composition is administered parenterally.

The exact amount required will vary from subject to subject, depending on the species, age, and general condition of the subject, the particular compound, its mode of administration, its mode of activity, and the like. The compounds of the invention are preferably formulated in dosage unit form for ease of administration and uniformity of dosage. It will be understood, however, that the total daily usage of the compounds and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

Furthermore, after formulation with an appropriate pharmaceutically acceptable carrier in a desired dosage, the pharmaceutical compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations).

Liquid dosage forms for oral and parenteral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents. In certain embodiments for parenteral administration, the compounds of the invention are mixed with solubilizing agents such an Cremophor, alcohols, oils, modified oils, glycols, polysorbates, cyclodextrins, polymers, and combinations thereof.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

It will also be appreciated that the compounds and pharmaceutical compositions of the present invention can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anticancer agent), or they may achieve different effects (e.g., control of any adverse effects).

In still another aspect, the present invention also provides a pharmaceutical pack or kit comprising one or more containers filled with one or more of the ingredients of the pharmaceutical compositions of the invention, and in certain embodiments, includes an additional approved therapeutic agent for use as a combination therapy. Optionally associated with such container(s) can be a notice in the form prescribed by a governmental agency regulating the manufacture, use or sale of pharmaceutical products, which notice reflects approval by the agency of manufacture, use or sale for human administration.

Biological Target

Figure 21:
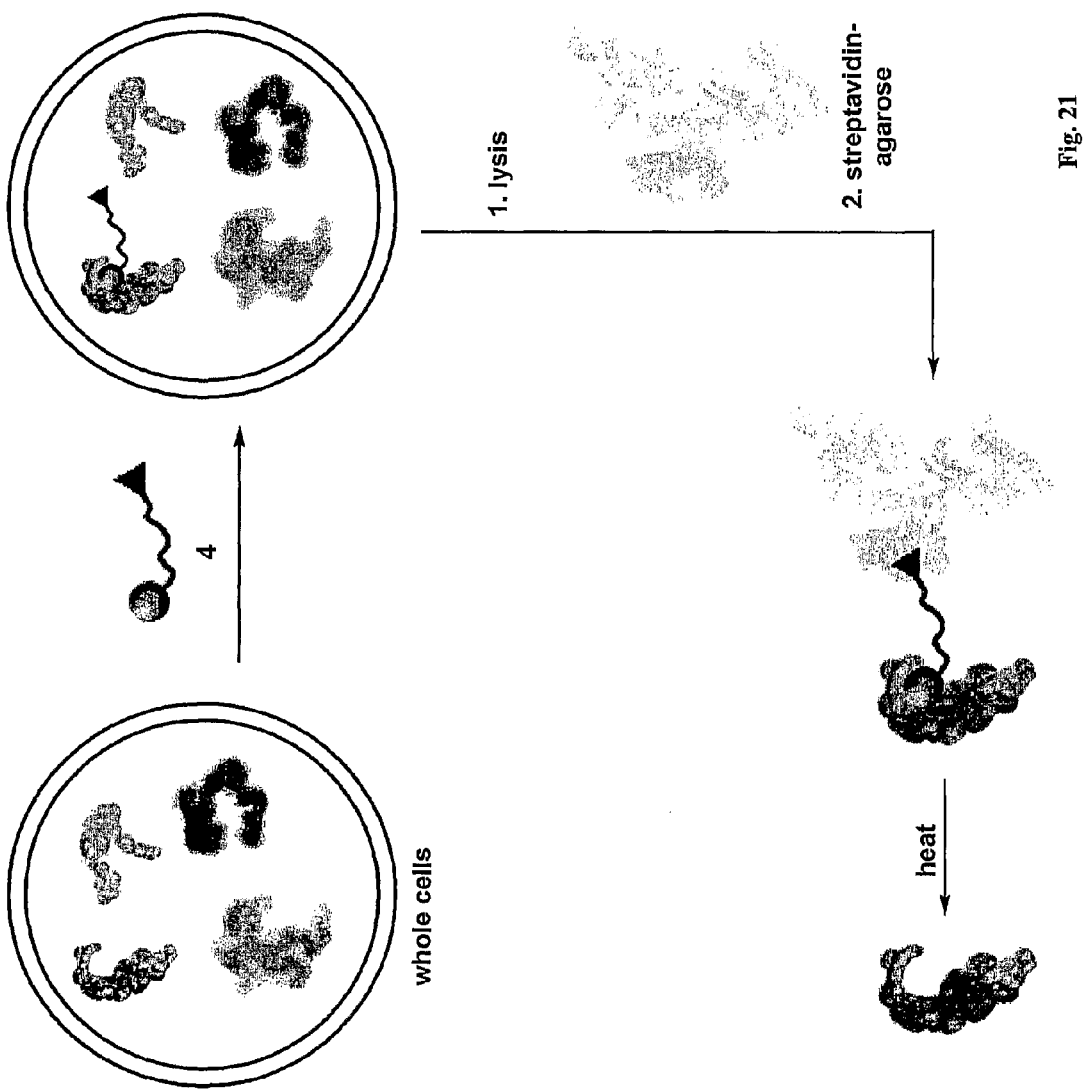
FIG. 21 is a schematic of the in cellulo affinity based probe (pulldown) experiments used to identify CLIMP-63 as a biological target of avrainvillamide. The experiment uses a avrainvillamide analog linked to biotin (shown on the right) as the probe.
Figure 23:
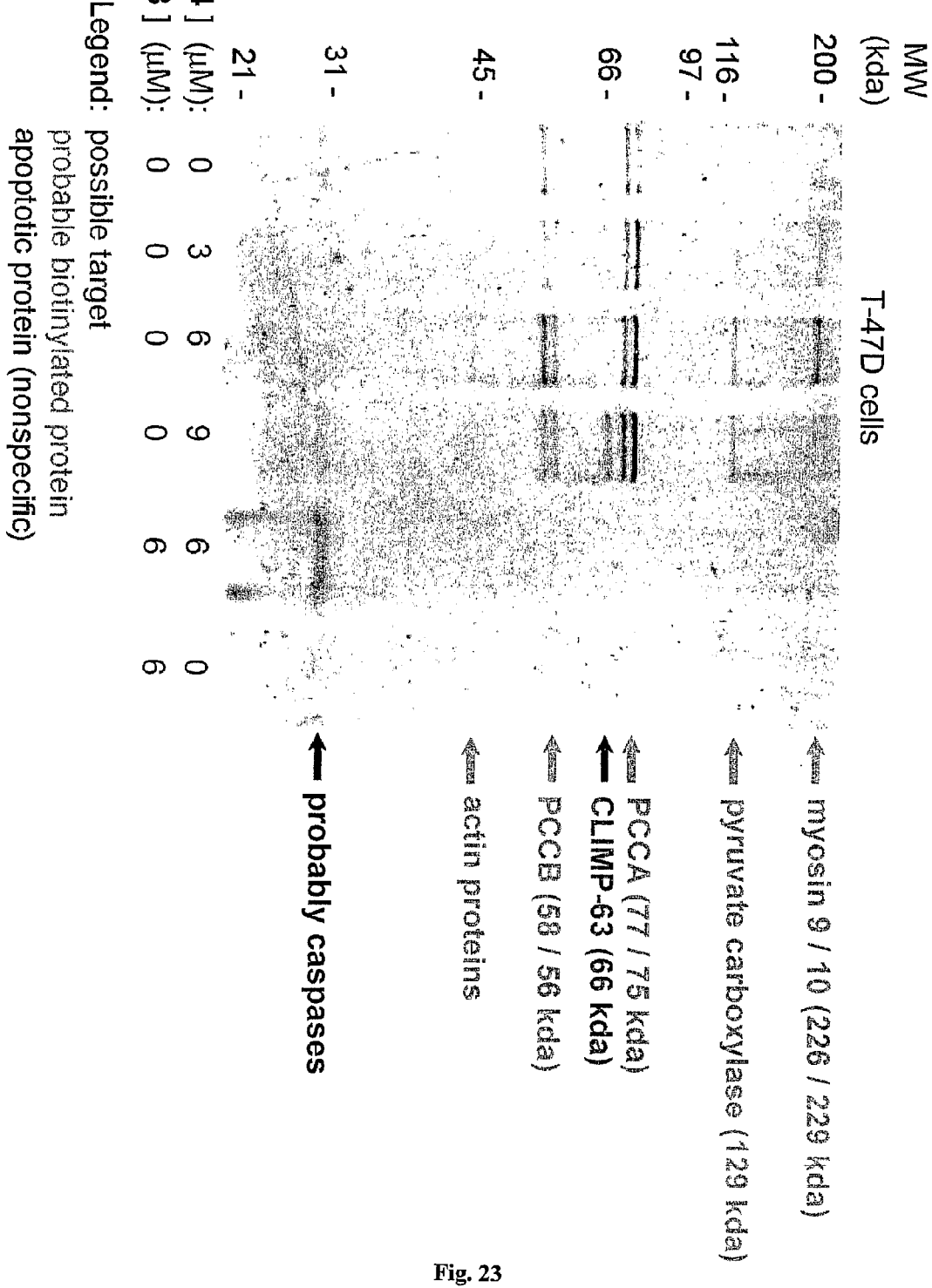
FIG. 23 shows the same gel from FIG. 20 with the various bands identified.

At least one biological target of avrainvillamide and stephacidin B has been identified as CLIMP-63 (cytoskeleton-linking membrane protein; formerly, p63 or CKAP4 protein) by in vivo affinity based pull-down experiments using biotin-labelled avrainvillamide. Whole cells were incubated with the biotin-labelled avrainvillamide. The cells were then lysed, and the resulting cell lysate was incubated with streptavidin-agarose resin that binds biotin (FIG. 21). The resin with bound protein was collected by centrifugation. Bound proteins isolated in this manner were released from the column matrix by heating, and the proteins were identified by mass spectrometry. CLIMP-63 was identified as one of the bound protein and therefore is thought to be a biological target of arainvillamide. CLIMP-63 has subsequently been confirmed through other experimentation to be a target. The pull-down of CLIMP-63 by biotin-labelled avrainvillamide has been shown to be dose-dependent. The identity of CLIMP-63 has been confirmed by Western blot using an antibody specific for CLIMP-63. The present invention includes the use of CLIMP-63 (cytoskeleton-linking membrane protein; formerly, p63) in assays for screening compounds that target it. Identification of CLIMP-63 allows for the screening of other compounds, besides avrainvillamide, that bind to, inhibit, interfere with, modulate, or activate this target. These identified compounds are also within the scope of the invention. CLIMP-63 is also a validated target for identifying anti-proliferative and/or cytotoxic compounds useful in the treatment of such proliferative diseases as cancer, benign tumors, inflammatory diseases, diabetic retinopathy, infectious diseases, etc. The identified compounds are particularly useful in the treatment of cancer.

CLIMP-63 is a 63 kDa non-glycosylated type II integral endoplasmic reticulum membrane protein (Schweizer et al. *J. Cell Sci.* 104:671-83, 1993; incorporated herein by reference). The protein is found in the rough endoplasmic reticulum but not in the nuclear envelope. The protein has an extracytoplasmic domain of 474 amino acids, and an N-terminal domain of 106 amino acids (Schweizer et al., *J. Cell Sci.* 104:671-83, 1993; Schweizer et al., *J. Cell Sci.* 104:685-94, 1993; Schweizer et al. *J. Cell Sci.* 126:25-39, 1994; Schweizer et al., *J. Cell Sci.* 108:2477-85, 1995; each of which is incorporated herein by reference). The N-terminal cytosolic domain is known to bind to microtubules (Klopfenstein et al. *EMBO J.* 17:6168-6177, 1998; incorporated herein by reference). The protein is thought to anchor the endoplasmic reticulum to the microtubule cytoskeleton. Cysteine-100 of the N-terminal domain is reversibly palmitoylated prior to entry of the cell into mitosis (Mundy et al. *J. Cell Biol.* 116:135-146, 1992; Schweizer et al., *J. Cell Sci.* 104:671-683, 1993; Mundy, *Biochem. Soc. Trans.* 23:572-576, 1995; each of which is incorporated herein by reference). This palmitoylation event is thought to disrupt the interaction between CLIMP-63 and the microtubules, thereby releasing the ER from the microtubules of the cytoskeleton prior to mitosis. It has also been observed that CLIMP-63 undergoes increased phosphorylated during mitosis (Vedrenne et al. *Mol. Biol. Cell* 16:1928-37, April 2005; incorporated herein by reference). Without wishing to be bound by any particular theory, it is thought that the reversible alkylation of CLIMP-63 by avrainvillamide prevents the palmitoylation of this protein, thereby preventing the release of the ER from the microtubule cytoskeleton prior to or during mitosis.

Screening for Compounds that Target CLIMP-63

The identification of a biological target of avrainvillamide makes possible an assay for use in identifying other compounds that inhibit, activate, bind to, or modify CLIMP-63. The compounds identified using the inventive screen are useful in the treatment of proliferative diseases such as cancer. In certain embodiments, the identified compounds inhibit the palmitoylation of CLIMP-63. The compounds may also effect the phosphorylation status of CLIMP-63. In other embodiments, the identified compounds modulate the binding of CLIMP-63 to the microtubules. The compounds identified using the inventive assay are considered part of the present invention. These compounds may or may not have structural similarity to avrainvillamide, stephacidin B, or the $\alpha,\beta$-unsaturated nitrone-containing core of these molecules. In certain embodiments, the compounds are described herein and include the $\alpha,\beta$-unsaturated nitrone-containing core of avrainvillamide.

The inventive assay includes (1) contacting at least one test compound with CLIMP-63, and (2) detecting an effect on CLIMP-63 or an effect mediated by CLIMP-63. The assay may be adapted for high-throughput screening of test compounds. For example, multi-well plates, fluid-handling robots, plate readers, software, computers, etc. may be used to perform the assay on a plurality of test compounds in parallel.

In the inventive assay, a test compound is incubated with CLIMP-63. The assay may use any form of CLIMP-63. In certain embodiments, purified CLIMP-63 is used. In other embodiments, partially purified or unpurified CLIMP-63 is used. For example, cell lysates containing CLIMP-63 may be used. The CLIMP-63 protein used in the inventive assays may be derived from any species. In certain embodiments, mammlian CLIMP-63, preferably human CLIMP-63, is used. CLIMP-63 may be obtained from natural sources such as a cell line known to express CLIMP-63, or CLIMP-63 may be obtained from recombinant sources such as bacteria, yeast, fungi, mammalian cells, or human cells made to overexpress CLIMP-63.

In certain embodiments, rather than using purified or partially purified CLIMP-63, cells expressing CLIMP-63 are used. Preferably, the cells are whole cells which are intact when incubated with the test compound. The cells may be any type of cell including cancer cell lines, mammalian cells, human cells, bacterial cells, yeast cells, etc. The cells may normally express CLIMP-63. In certain embodiments, the cells may overexpress CLIMP-63. In certain embodiments, the expression of CLIMP-63 in the cells may be altered (e.g., increased or decreased) using any technique known in the art (see, for example, Sambrook et al., Molecular Cloning, second edition, Cold Spring Harbor Laboratory, Plainview, N.Y.; (1989), or Ausubel et al., Current Protocols in Molecular Biology, Current Protocols (1989), and DNA Cloning: A Practical Approach, Volumes I and II (ed. D. N. Glover) IREL Press, Oxford, (1985); each of which is incorporated herein by reference). For example, the expression of CLIMP-63 may be increased by transfecting a cell line with a vector which constitutively or upon induction (e.g., addition of an inducing agent) expresses CLIMP-63. In other embodiments, the expression of CLIMP-63 in the cell may be knocked down by siRNA. Wild type CLIMP-63 protein may be used, or a mutant form of CLIMP-63 may be used in the inventive assay. In certain embodiments, the cytoplasmic domain of CLIMP-63 is used in the assay. In other embodiments, the lumenal domain of CLIMP-63 is used in the assay. In certain embodiments, certain amino acid of CLIMP-63 may be mutated or deleted. In other embodiments, amino acids may be added to the wild type CLIMP-63 sequence (e.g., green fluorescent protein, a poly-histidine tag, an epitope, etc.).

The CLIMP-63 and the test compound are contacted under any test conditions; however, conditions close to physiological conditions are preferred. For example, the test compound and CLIMP-63 are contacted with each other at approximately 30-40° C., preferably at approximately 37° C. The pH may range from 6.5-7.5, preferably pH 7.4. Various salts, metal ions, co-factors, proteins, peptides, polynucleotides, etc. may be added to the incubation mixture.

After CLIMP-63 has been incubated for a certain time with the test compound, it is then determined if the test compounds has had an effect on CLIMP-63 or the cells expressing CLIMP-63. For example, the CLIMP-63 protein may be assayed for palmitoyation, binding to microtubules, alkylation, conformational changes, phosphorlation, etc. In certain embodiments, CLIMP-63 is assayed for palmitoylation via immunoassay, radioactive assay using labeled palmitate, mass spectroscopy, etc. These same techniques may be used to determine the phosphorylation status of CLIMP-63. In other embodiments, covalent modification of CLIMP-63 protein by the test compound is assayed for in the inventive assay. In certain embodiments, the compound is labeled with a radioactive isotope for detection. In other embodiments, the covalent modification of CLIMP-63 may be detected via mass spectrometry. The binding of CLIMP-63 for microtubules may also be determined (e.g., by capillary electrophoresis). The effect of the test compound may also be assessed by determining the effect on the cell expressing CLIMP-63. For example, the proliferation or inhibition of growth of the cells may be determined. In other embodiments, another phenotype of the cells may be determined for example, morphology of the ER, morphology of the cell, size of the cell, size of nucleus, DNA content, etc.

Any type of compound may be tested using the inventive assay including small molecules, peptides, proteins, polynucleotides, biomolecules, etc. In certain embodiments, the test compounds are small molecules. In certain embodiments, the small molecules have molecular weights less than 1000 g/mol. In other embodiments, the small molecules have molecular weights less than 500 g/mol. In other embodiments, the test compounds are peptides or proteins. In yet other embodiments, the test compounds are polynucleotides. In certain embodiments, the test compounds are biomolecules. In other embodiments, the test compounds are not biomolecules. The compounds to be tested in the inventive assay may be purchased, obtained from natural sources (i.e., natural products), obtained by semi-synthesis, or obtained by total synthesis. In certain embodiments, the test compounds are obtained from collections of small molecules such as the historical compound collections from the pharmaceutical industry. In certain embodiments, the test compounds are prepared using combinatorial chemistry. In other embodiments, the test compounds are prepared by traditional one-by-one chemical synthesis.

Once a compounds is identified as targeting CLIMP-63, it may be optionally further modified to obtain a compounds with greater activity and/or specificity for CLIMP-63. The compound may also be modified to obtain a compound with better pharmacological properties for use in administration to a subject (e.g., human).

Methods of Treating Proliferative Diseases Based on Targeting CLIMP-63

The identification of CLIMP-63 as the biological target of avrainvillamide is the first demonstration of CLIMP-63 as a target in the treatment of proliferative diseases. Compounds that inferere with CLIMP-63, and specifically is interaction with the microtubule cytoskeleton, are particularly useful in the treatment of proliferative diseases. Proliferative disorders include, but are not limited to, cancer, inflammatory diseases, graft-vs.-host disease, diabetic retinopathy, and benign tumors. In certain embodiments, compounds that target CLIMP-63 may also be useful in the treatment of infectious diseases. Compounds that target CLIMP-63 are administered in therapeutically effective doses to a subject suffering from a proliferative disease. In certain embodiments, the subject suffers from cancer. In certain embodiments, the subject suffers from an inflammatory disease (e.g., autoimmune diseases, rheumatoid arthritis, allergies, etc.). In certain embodiments, the subject suffers from an infectious disease (e.g., bacterial infection, fungal infection, protazoal infection, etc.).

A therapeutically effective amount of a compound that targets CLIMP-63 is administered to a subject. In certain embodiments, 0.01-10 mg/kg of the compound is administered per day. In other embodiments, 0.01-5 mg/kg of the compound is administered per day. In yet other embodiments, 0.01-1 mg/kg of the compound is administered per day. The daily dose may be divided into several dosages taken within a twenty four hour period (e.g., twice a day, three times a day, four times a day, or more). The compound may be administered to the subject using any route known in the art as described above. In certain embodiments, the compound is administered orally. In other embodiments, the compound is administered parenterally. In yet other embodiments, the compound is administered intravenously.

These and other aspects of the present invention will be further appreciated upon consideration of the following Examples, which are intended to illustrate certain particular embodiments of the invention but are not intended to limit its scope, as defined by the claims.

EXAMPLES

Example 1

Identification of a Novel Michael Acceptor Group for the Reversible Addition of Nucleophiles. Synthesis and Reactivity of the 3-Alkylidene-3H-Indole 1-Oxide Function of Avrainvillamide In studies directed toward the synthesis of the alkaloids avrainvillamide (1) and stephacidin B (2), the 3-alkylidene-3H-indole 1-oxide group has been identified as a new function that is capable of reversible covalent bond formation with heteroatom-based nucleophiles.

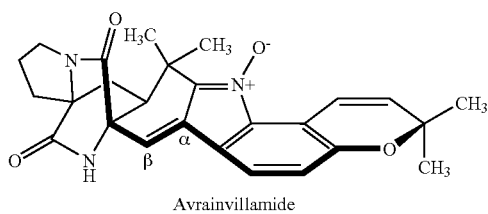

Avrainvillamide (1)

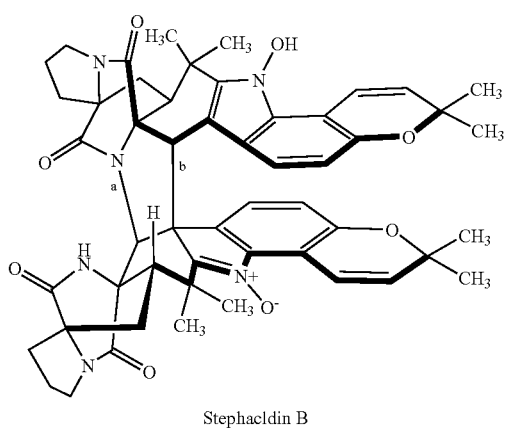

Stephacidin B (2)

Avrainvillamide and stephacidin B, formally a dimer of 1 (vide infra), have been separately identified in culture media from various strains of *Aspergillus*. Both compounds exhibit antiproliferative activity, and 1 is reported to exhibit antimicrobial activity against multidrug-resistant bacteria (isolation of avrainvillamide: (a) Fenical et al. Avrainvillamide, a Cytotoxic Marine Natural Product, and the Derivatives thereof. U.S. Pat. No. 6,066,635, 2000; incorporated herein by reference. (b) Sugie et al. *J. Antibiot.* 2001, 54, 911. Isolation of stephacidins A and B; incorporated herein by reference (c) Qian-Cutrone et al. *J. Am. Chem. Soc.* 2002, 124, 14556; incorporated herein by reference; (d) An alternative sequence of formation of bonds a and b was recently proposed for the biosynthesis of 2 from 1, contemporaneous with and independent of the present work: Nussbaum, *Angew. Chem. Int. Ed.* 2003, 42, 3068; each of which is incorporated herein by reference). Avrainvillamide is apparently the first natural product with a 3-alkylidene-3H-indole 1-oxide function; synthetic efforts were therefore initially directed toward the development of a viable strategy to introduce this group. A process that forms the nitrogen heterocycle with C—C bond formation between carbon 3 (a in structure 1) and the arene ring was recognized to be especially convergent in the context of targets 1 and 2. A two-step organometallic coupling-reductive condensation sequence was envisioned (Scheme 1) (for prior syntheses of this function see: Colonna et al. *Gazz. Chim. Ital.* 1967, 97, 1569; Tosi et al. *Monatsh. Chem.* 1987, 118, 369; each of which is incorporated herein by reference).

To implement the proposed two-step process, the model substrate 3 was prepared by iodination (Johnson et al. *Tetrahedron Lett.* 1992, 33, 917; Barros et al. *Chem. Eur J.* 2000, 6, 3991; each of which is incorporated herein by reference) of 4,4,6,6-tetramethylcyclohex-2-en-1-one (Lissel et al. *Liebigs Ann. Chem.* 1987, 263; incorporated herein by reference) (96%, Scheme 1). A Suzuki coupling of 3 with 2-nitrophenylboronic acid then afforded the α-arylated ketone 4 in 73% yield (Scheme 1) (Ishiyama et al. *J. Org. Chem.* 1995, 60, 7508; Wolfe et al. *J. Am. Chem. Soc.* 1999, 121, 9550; each of which is incorporated herein by reference). Alternatively, 4 could be formed from 3 in 70% yield by using 2-iodo-nitrobenzene as the coupling partner in the presence of Pd$_2$(dba)$_3$ and copper powder (Banwell et al. *Org. Lett.*, 2003, 5, 2497; incorporated herein by reference). Reductive condensation of 4 was accomplished in the presence of activated zinc powder (Knochel et al. *Tetrahedron* 1993, 49, 29; incorporated herein by reference), providing the 3-alkylidene-3H-indole 1-oxide 5 in 48% yield, as well as the (separable) by-products 6 (9%), and 7 (7%). Spectroscopic data supported the assignment of the major product as 5; this assignment was confirmed by single-crystal X-ray analysis (FIG. 1).

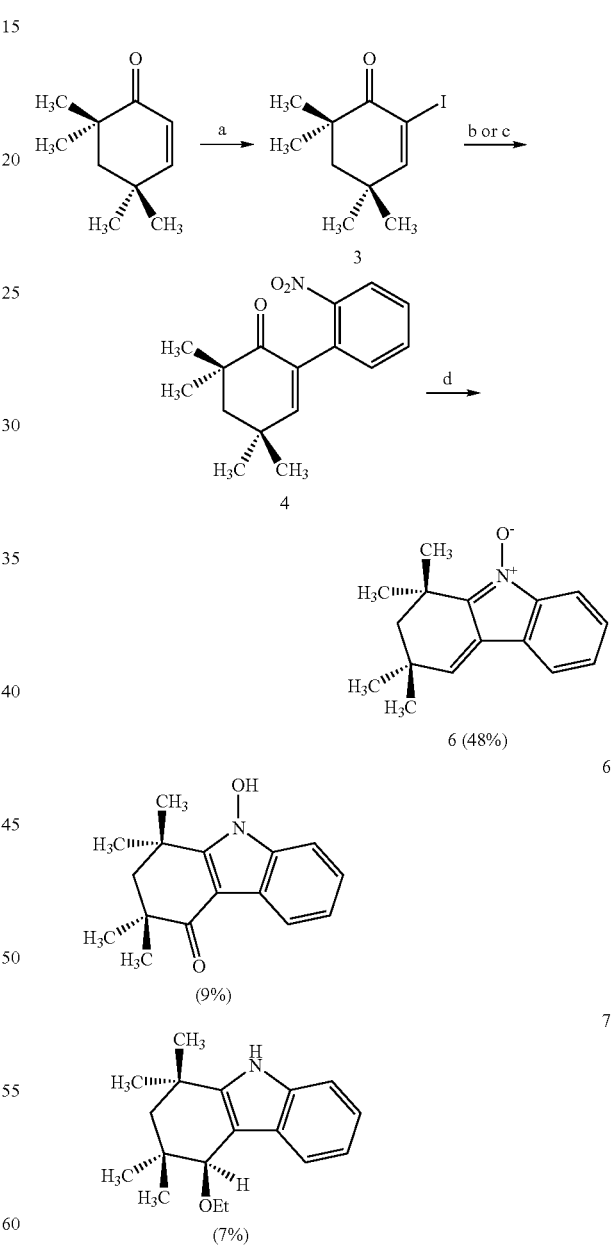

Reaction conditions: (a) I$_2$ (3 equiv), DMAP (0.2 equiv), CCl$_4$-pyridine, 49° C., 96%. (b) Pd$_2$(dba)$_3$ (0.05 equiv), 2-nitrophenylboronic acid (1 equiv), 2-(di-t-butylphosphino)biphenyl (0.20 equiv), Ba(OH)$_2$.8H$_2$O (3.0 equiv), THF—H$_2$O, 38° C., 73%. (c) 2-iodonitrobenzene (2 equiv), Pd$_2$(dba)$_3$ (0.025 equiv), Cu (powder, 5 equiv), DMSO, 70° C., 70%. (d) Zn (dust, 2.7 equiv), 1M NH$_4$Cl (2.2 equiv), EtOH, 48° C., 64%.

Deuterium-labeling experiments (see Experimentals below) established that product 5 had been formed with the expected connectivity, that is, with nitrogen bonding to the carbonyl carbon (this was also shown for 4→7), but interestingly, in the formation of the N-hydroxy indole by-product 6, nitrogen was shown to bond to the β-carbon of enone 4 (potentially a 5-endo-trig closure). Control experiments demonstrated that the (unstable) by-product 7 was formed slowly from 5 under the reaction conditions, however the yield was low (10%) and paths connecting 4 and 7 not involving 5 are readily envisioned. In practice, by-products 6 and 7 were minor and 5 was easily purified chromatographically.

Solutions of 5 in benzene or chloroform were found to be quite stable when protected from light (vide infra), however in methanol a surprisingly facile, reversible 1,5-addition of solvent to the α,β-unsaturated nitrone group occurred (eq 1) (For discussion of 1,3-addition of nucleophiles to nitrones, see: Bloch, R. *Chem. Rev.* 1998, 98, 1407; Lombardo, M.; Trombini, C. *Synthesis* 2000, 6, 759; each of which is incorporated herein by reference). At 23° C. in pure methanol-d$_4$ the half-life for the conversion of 5 to 8 (Nu=OCD$_3$) was approximately 5 h. The equilibrium between 5 and 8 was significantly temperature dependent. At equilibrium, the ratio of 8 (Nu=OCD$_3$) to 5 was 2:1 at 23° C. and 10:1 at -20° C. (7 d to achieve). Warming a cold (-20° C.) solution of 8 and 5 at equilibrium quickly re-established equilibrium at the higher temperature (23° C.), now from the product side (8→5). Removal of methanol in vacuo led to complete and clean reversal of adduct formation (8→5). Addition of methanol to 5 was found to be catalyzed by both base (NaOCH$_3$, 10 mol %, equilibrium <10 min, 23° C.) and acid (CH$_3$CCO$_2$H, 10 mol %, t$_{1/2}$≈1 h, 23° C.; Cl$_3$CCO$_2$H, 10 mol %, equilibrium <10 min, 23° C.). As expected, small amounts (≦10 mol %) of catalyst did not perturb the equilibrium between 5 and 8, however stoichiometric quantities of sodium methoxide did (8:5=100:1 at equilibrium, 10 equiv NaOCH$_3$).

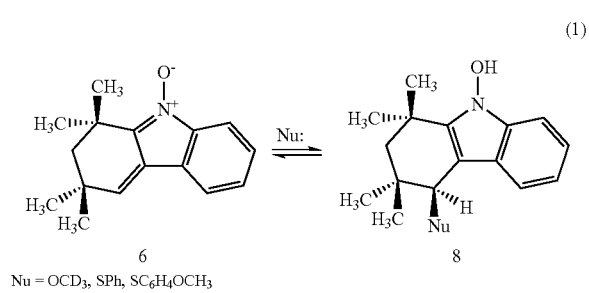

(1)

Nu = OCD$_3$, SPh, SC$_6$H$_4$OCH$_3$

Thiols were also found to add cleanly and reversibly to 5 in the presence of a base, but not without. For example, addition of 4-methoxybenzenethiol (1.2 equiv) to 5 in the presence of triethylamine-d$_{15}$ (0.2 equiv) in CD$_2$Cl$_2$ at 23° C. afforded the 1,5-adduct (8, Nu=SC$_6$H$_4$OCH$_3$) quickly (<15 min) and quantitatively ($^1$H NMR analysis). Under similar conditions, addition of thiophenol (8, Nu=SC$_6$H$_5$) proceeded to afford a 9:1 ratio of adduct to starting material, whereas the ratio was >98:2 at -40° C. ($^1$H NMR analysis, k$_{8\to5}$=0.25±0.15 s$^{-1}$ M$^{-1}$ at -40° C.) (rate determined by inversion-transfer, analyzed with the CIFIT program: Bain et al. *J. Magn. Reson.* 1996, 118a, 21; incorporated herein by reference). Neither addition was significantly affected by the presence (or absence) of oxygen. The 1,5-adducts were highly labile toward silica gel, to the extent that they could not be purified chromatographically without inducing complete reversal (8→5).

Other transformations of 5 of note include its reduction with NaBH$_4$ in methanol (8, Nu=H, 89%) and its photochemical rearrangement under ambient light or, more rapidly, upon direct irradiation (200 W Hg lamp) to form the lactam 9 (eq 2, 67%) (1-D NOESY experiments confirmed the stereochemistry of the exocyclic double bond to be that shown). The latter transformation may involve an intermediate oxaziridine, as is frequently proposed in the photochemistry of nitrones (Spence et al. *Chem. Rev.* 1970, 70, 231; incorporated herein by reference. Similar fragmentations have been reported, see Suginome et al. *J. Chem. Soc., Perkin Trans.* 1 1991, 917; Page et al. *J. Org. Chem.* 2002, 67, 7787; each of which is incorporated herein by reference).

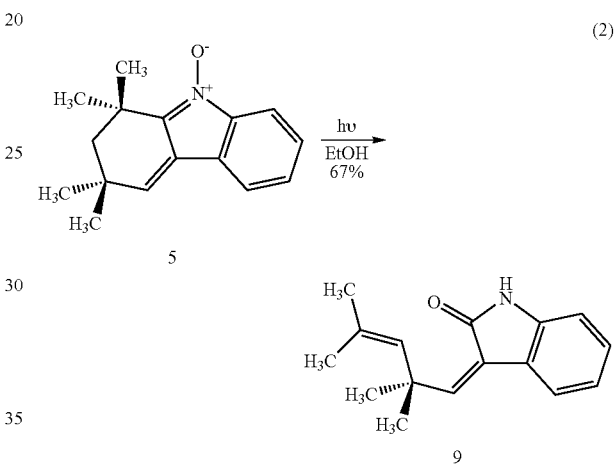

(2)

In contrast to the facile addition of oxygen- and sulfur-based nucleophiles that was observed, all potential nitrogen-based nucleophiles examined to date (e.g., n-propyl amine, formamide, 2-pyrrolidinone, 2-hydroxypyridine, 2-trimethyl-silyloxypyrroline) have failed to produce detectable levels of adducts in reactions with 5. Given the steric hindrance about the β-position of 5 (see FIG. 1), it is remarkable that any nucleophilic addition occurs at all. The failure of amides to add to 5 is of interest given the proposed dimerization of 1 to form 2, however the differences between our model system and 1 caution against over-interpretation of this result. In particular, analysis of X-ray data for 2 suggests that there is a stabilizing hydrogen bond between the secondary lactam NH group and the carbonyl oxygen of the adjacent amide; this would be replaced by a repulsive interaction with a methyl group in our model system.

In an effort to explore the potentially greater generality of nucleophilic additions to α,β-unsaturated nitrones, the nitrones derived from the condensation of N-phenyl-hydroxylamine with (E)-cinnamaldehyde (Utzinger et al. *Helv. Chim. Acta* 1954, 37, 1892; incorporated herein by reference) and (E)-4,4-dimethyl-2-pentenal were prepared and subjected to conditions leading to adduct formation with 5 described above. However, in neither case was nucleophilic addition observed. By and large, the acyclic α,β-unsaturated nitrones were found to be unreactive. These observations might point towards the importance of the formation of the aromatic indole structure in 5→8, a driving force that would be lacking in acyclic α,β-unsaturated nitrones. Thus far, our studies have identified the 3-alkylidene-3H-indole 1-oxide group as both necessary and sufficient to function as a novel Michael acceptor group for oxygen- and sulfur-based nucleophiles.

Experimentals:

General Experimental Procedures. All reactions were performed in single-neck, flame-dried, round-bottom flasks fitted with a rubber septum under a positive pressure of argon, unless otherwise noted. Air- and moisture-sensitive liquids were transferred via syringe or stainless steel cannula. Organic solutions were concentrated at ambient temperature by rotary evaporation at 40 Torr (house vacuum). Analytical thin-layer chromatography was performed using glass plates pre-coated with a 0.25-mm layer of silica gel impregnated with a fluorescent indicator (254 nm). Thin-layer chromatography plates were visualized under ultraviolet light (UV), then were stained using one of the following solutions: ceric ammonium molybdate (CAM), acidic p-anisaldehyde (anis), or phosphomolybdic acid (PMA), followed by development on a hot plate. Flash-column chromatography was performed as described by Still et al. (*J. Org. Chem.* 1978, 43, 2923; incorporated herein by reference), employing silica gel (60 Å, standard grade) purchased from Sorbent Technologies.

Materials. Commercial solvents and reagents were used as received with the following exceptions. Methylene chloride, tetrahydrofuran, methanol, and pyridine were purified by the method of Pangborn et al. (*Organometallics* 1996, 15, 1518; incorporated herein by reference). Trimethylsilyl chloride was distilled from calcium hydride at 760 torr under an atmosphere of dinitrogen immediately before use. Methanol-$d_4$ was distilled from calcium hydride at 760 torr and stored over 3-Å molecular sieves under an argon atmosphere.

Instrumentation. Proton magnetic resonance spectra were recorded at 400 or 500 MHz at 23° C., unless otherwise noted. Chemical shifts are expressed in parts per million (ppm, δ scale) downfield from tetramethylsilane and are referenced to the residual proton in the NMR solvent (CHCl$_3$, δ 7.26; CHD$_2$OD, δ 3.30; CHDCl$_2$, δ 5.33; (CHD$_2$)S(O)CD$_3$, δ 2.49, (CHD$_2$)C(O)CD$_3$, δ 2.05). Data are represented as follows: chemical shift, multiplicity (s=singlet, d=doublet, t=triplet, m=multiplet, br=broad), integration, coupling constant in Hertz. Carbon nuclear magnetic resonance spectra were recorded at 100 MHz at 23° C., unless otherwise noted. Chemical shifts are reported in parts per million downfield from tetramethylsilane and are referenced to the carbon resonances of the solvent (CDCl$_3$, δ 77.0; CHD$_2$OD, δ 49.0; CHDCl$_2$, δ 52.5; (CHD$_2$)S(O)CD$_3$, δ 39.5). Infrared (IR) spectra were obtained using a Perkin-Elmer FT-IR spectrometer referenced to a polystyrene standard. Data are represented as follows: frequency of absorption (cm$^{-1}$), intensity of absorption (vs=very strong, s=strong, m=medium, w=weak, br=broad). High-resolution mass spectra were obtained at the Harvard University Mass Spectrometry Facility. The X-ray crystal structure of 5 was solved by Andrew Haidle (Myers' laboratory, Harvard University).

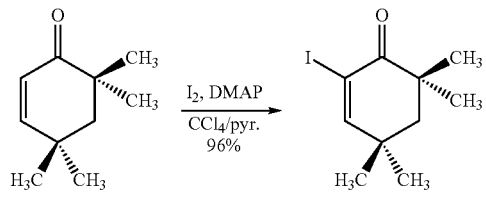

2-Iodo-4,4,6,6-tetramethyl-cyclohex-2-en-1-one (3). Note: Although iodide 3 has not been determined to be light-sensitive, all procedures involving its preparation, purification, and handling were carried out in the dark. A solution of 4,4,6,6-tetramethyl-cyclohex-2-en-1-one (1.86 g, 12.2 mmol, 1 equiv), iodine (9.3 g, 36 mmol, 3.0 equiv), and 4-(dimethylamino)pyridine (300 mg, 2.44 mmol, 0.2 equiv) in carbon tetrachloride (15 mL) and pyridine (15 mL) was stirred under an argon atmosphere, in the dark, heated at 49° C. The progress of the reaction was monitored by thin-layer chromatography (14% ethyl acetate-hexanes, R$_f$=0.42, 0.32 for product and starting material, respectively; UV, CAM). After 2 h, the reaction mixture was allowed to cool to 22° C., and then was diluted with ethyl acetate (100 mL). The resulting solution was washed with saturated aqueous sodium thiosulfate solution (2×50 mL). The aqueous layers were isolated, combined, and extracted with dichloromethane (2×100 mL). The combined organic extracts were washed with brine (50 mL) and dried over sodium sulfate. Following filtration of solids, volatiles were removed in vacuo and the concentrate was purified by flash-column chromatography (5% tetrahydrofuran-hexanes, 10-cm column) to furnish 2-iodo-4,4,6,6-tetramethyl-cyclohex-2-en-1-one (3, 3.25 g, 96%) as a clear oil which solidified upon standing (mp 41-42° C.).

$^1$H NMR (400 MHz, CDCl$_3$), δ 7.35 (s, 1H, CH), 1.84 (s, 2H, CH$_2$), 1.20 (s, 12H, CH$_3$). $^{13}$C NMR (125 MHz, CDCl$_3$), δ 197.6, 165.9, 101.0, 49.1, 41.9, 38.3, 30.4, 28.1. IR (NaCl, thin film), cm$^{-1}$ 2963 (m), 2921 (w), 2869 (w), 1684 (s). HRMS (CI) m/z calcd for C$_{10}$H$_{16}$IO [M+H]$^+$: 279.0251, found 279.0246.

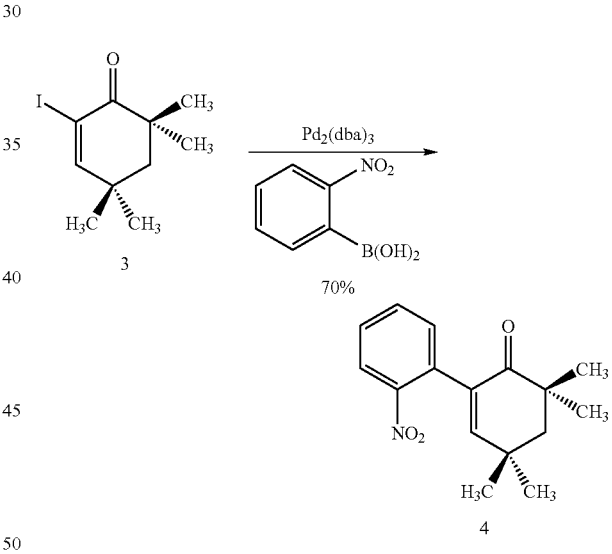

4,4,6,6-Tetramethyl-2-(o-nitrophenyl)-cyclohex-2-en-1-one (4). A 250-mL modified Schlenk-type flask was charged with 2-iodo-4,4,6,6-tetramethyl-cyclohex-2-en-1-one (3, 1.06 g, 3.96 mmol, 1 equiv), 2-nitrophenyl boronic acid (661 mg, 3.95 mmol, 1.0 equiv), Pd$_2$(dba)$_3$ (181 mg, 0.198 mmol, 0.05 equiv), 2-(di-t-butylphosphino)-biphenyl (236 mg, 0.791 mmol, 0.20 equiv), and barium hydroxide octahydrate (3.73 g, 11.8 mmol, 3.0 equiv). Tetrahydrofuran (64 mL) and distilled water (13 mL) were added sequentially to the flask, and the resulting red, heterogeneous mixture was heated to 38° C. The progress of the reaction was monitored by thin-layer chromatography (20% ethyl acetate-hexanes, R$_f$=0.37, 0.61 for product, starting material, respectively; UV, CAM). After 1.5 h, the reaction was allowed to cool to 23° C., then was quenched by the addition of saturated aqueous ammonium chloride solution (30 mL). The layers were separated, and the aqueous layer was extracted with ethyl acetate (2×30 mL). The combined organic layers were washed with brine (20 mL), and then were dried over sodium sulfate. Filtration and concentration of the dried organic layers afforded a brown oil which was purified by flash column chromatography (10% ethyl acetate-hexanes), to afford 4,4,6,6-tetramethyl-2-(o-nitrophenyl)-cyclohex-2-en-1-one (4, 755 mg, 70%) as a white solid. 4,4,6,6-Tetramethyl-2-(o-nitrophenyl)-cyclohex-2-en-1-one (4) could be further purified by re-crystallization from hot 10% ethyl acetate-hexanes solution (white crystals, mp 101-102° C.).

$^1$H NMR (400 MHz, CDCl$_3$), δ 7.98 (dd, 1H, J=7.8, 1.2 Hz, ArH), 7.57 (dt, 1H, J=7.6, 1.6 Hz, ArH), 7.44 (dt, 1H, J=7.2, 1.6 Hz, ArH), 7.24 (dd, 1H, J=7.6, 1.6 Hz, ArH), 6.62 (s, 1H, CH), 1.89 (s, 2H, CH$_2$), 1.30 (s, 6H, CH$_3$), 1.25 (s, 6H, CH$_3$). $^{13}$C NMR (100 MHz, CDCl$_3$), δ 201.4, 154.5, 149.1, 135.0, 133.3, 132.7, 132.5, 128.9, 124.3, 49.3, 41.4, 33.3, 30.1, 27.4. IR (NaCl, thin film), cm$^{-1}$ 2921 (w), 1679 (s, C=O), 1527 (s, NO$_2$), 1348 (s, NO$_2$). HRMS (CI) m/z calcd for C$_{16}$H$_{20}$NO$_3$ [M+H]$^+$: 274.1443, found 274.1432.

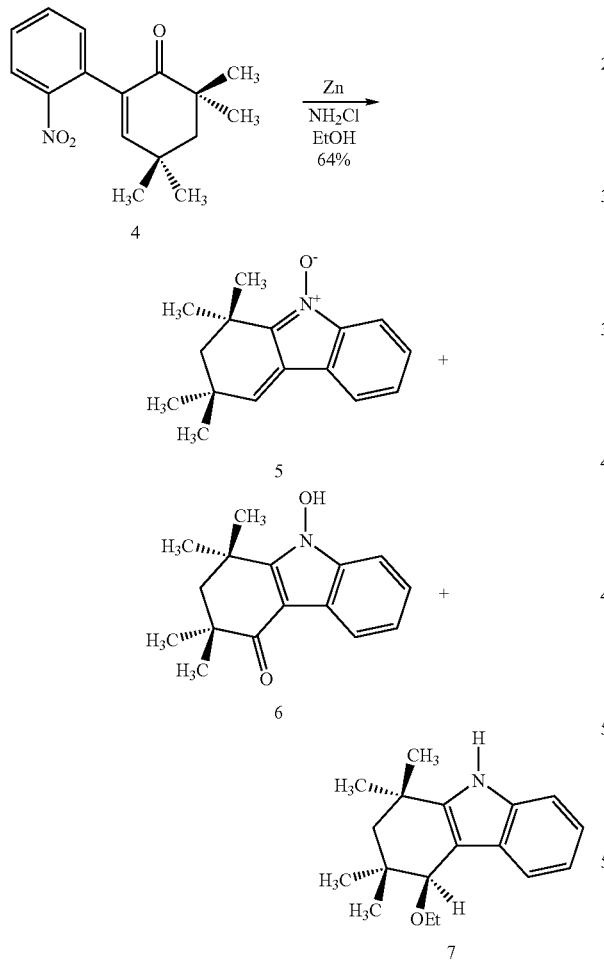

4

5

6

7

Reductive Condensation of 4,4,6,6-Tetramethyl-2-(o-nitrophenyl)-cyclohex-2-en-1-one (4). A mixture of zinc powder (133.1 mg, 2.036 mmol) and 1,2-dibromoethane (11.7 μL, 0.135 mmol, 0.067 equiv based on zinc) in tetrahydrofuran (2 mL) was heated to a vigorous boil (70° C.), then was allowed to cool to room temperature (22° C.). After repeating this process three additional times, trimethylsilyl chloride (10.3 μL, 0.0814 mmol, 0.04 equiv based on zinc) was injected and the resulting grey suspension was stirred for 10 min at 22° C. A separate 10-mL flask was charged sequentially with 4,4,6,6-tetramethyl-2-(o-nitrophenyl)-cyclohex-2-en-1-one (4, 113 mg, 0.414 mmol, 1 equiv), absolute ethanol (4 mL), and aqueous ammonium chloride solution (1.0 M, 911 μL, 0.911 mmol, 2.2 equiv). The resulting yellow solution was heated to 48° C. in an oil bath. Using a cannula, the zinc suspension was transferred portion-wise to the reaction vessel (approximately 200 μL for each addition) at 20-30 min intervals. Upon addition of zinc, the solution became lime-green. The progress of the reaction was monitored by thin-layer chromatography (30% ethyl acetate-hexanes, R$_f$=0.11, 0.27, 0.43, and 0.60, for the 3-alkylidene-3H-indole 1-oxide 5, N-hydroxy indole 6, 4,4,6,6-tetramethyl-2-(o-nitrophenyl)-cyclohex-2-en-1-one (4), and the indole 7, respectively; UV, CAM). After 2.25 h, the reaction vessel was allowed to cool to 22° C., and then was diluted with ethyl acetate (10 mL). The resulting solution was filtered through a Celite plug, eluting with ethyl acetate. The filtrate was washed with brine (1 mL), then was dried over sodium sulfate. Removal of the volatiles in vacuo furnished a yellow oil which was purified by flash-column chromatography (100% methylene chloride initially, grading to 15% ethyl acetate-methylene chloride), affording separately 3-alkylidene-3H-indole 1-oxide 5 (48.3 mg, 48%, mp 173-174° C.), the N-hydroxy indole 6 (9.6 mg, 9%, clear oil), and the indole 7 (8.4 mg, 7.5%, clear oil). By weighing the residual zinc from the reaction flask, it was determined that 2.7 equiv had been consumed. The color of alkylidene-3H-indole 1-oxide 5 varied from bright yellow to light brown, in all cases it was isolated as a semi-crystalline solid. Dissolution of 5 in a minimal amount of warm ethyl acetate followed by gradual cooling to 23° C. furnished light brown crystals which were suitable for X-ray analysis (see ORTEP below; CIF file submitted).

3-Alkylidene-3H-indole 1-Oxide 5: $^1$H NMR (500 MHz, CDCl$_3$), δ 7.73 (d, 1H, J=7.5 Hz, ArH), 7.57 (d, 1H, J=7.5 Hz, ArH), 7.46 (td, 1H, J=8.0, 1.0 Hz, ArH), 7.39 (dt, 1H, J=7.5, 1.0 Hz, ArH), 6.74 (s, 1H, CH), 1.76 (s, 2H, CH$_2$), 1.61 (s, 6H, CH$_3$), 1.28 (s, 6H, CH$_3$). $^{13}$C NMR (100 MHz, CDCl$_3$), δ 146.6, 145.3, 141.8, 128.8, 128.1, 127.9, 125.2, 119.5, 113.8, 52.2, 35.7, 33.0, 31.0, 26.1. IR (NaCl, thin film), cm$^1$ 2953 (s), 2912 (s), 1702 (m), 1456 (s,), 1251 (m). HRMS (CI) m/z calcd for C$_{16}$H$_{20}$NO [M+H]$^+$: 242.1545, found 242.1544.

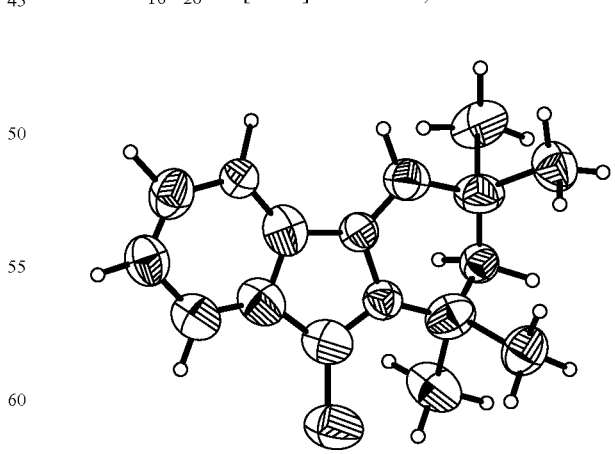

N-Hydroxy Indole 6: $^1$H NMR (500 MHz, CD$_3$OD), δ 8.12 (dt, 1H, J=9.5, 1.0 Hz, ArH), 7.43 (dt, 1H, J=10.0, 1.0 Hz, ArH), 7.26 (td, 1H, J=9.5, 1.5 Hz, ArH), 7.20 (td, 1H, J=9.25, 1.5 Hz, ArH), 2.02 (s, 2H, CH$_2$), 1.63 (s, 6H, CH$_3$), 1.26 (s, 6H, CH₃). ¹³C NMR (100 MHz, CD₃OD), δ 200.5, 152.9, 135.9, 123.1, 122.5, 121.5, 120.9, 108.3, 103.9, 53.0, 42.2, 32.4, 27.8, 26.8. IR (NaCl, thin film), cm⁻¹ 3128 (m), 2964 (m), 2923 (m), 1605 (s), 1476 (s), 1451 (vs), 1317 (m). HRMS (CI) m/z calcd for $C_{16}H_{20}NO_2$ [M+H]⁺: 258.1494, found 258.1504.

Indole 7: ¹H NMR (500 MHz, CDCl₃), δ 7.86 (br, 1H, NH), 7.61 (d, 1H, J=8.0 Hz, ArH), 7.32 (d, 1H, J=8.0 Hz, ArH), 7.12 (m, 2H, 2 (ArH)), 4.17 (s, 1H, OCH), 3.66 (m, 2H, OCH₂), 2.10 (d, 1H, J=13.5 Hz, CH₂), 1.39 (d, 1H, J=13.5 Hz, CH₂), 1.35 (s, 3H, CH₃), 1.34 (s, 3H, CH₃), 1.16 (m, 6H, OCH₂CH₃, CH₃), 0.93 (s, 3H, CH₃). ¹³C NMR (100 MHz, CDCl₃), δ142.6, 136.2, 128.6, 121.3, 119.7, 118.8, 110.8, 110.3, 78.1, 65.5, 47.4, 36.9, 33.2, 31.5, 30.0, 27.7, 27.4, 15.9. IR (NaCl, thin film), cm⁻¹ 3405 (m), 3312 (w), 1953 (vs), 2861 (m), 1456 (s). HRMS (CI) m/z calcd for $C_{18}H_{20}NO$ [M−C₂H₅O]⁺: 226.1595, found 226.1593.

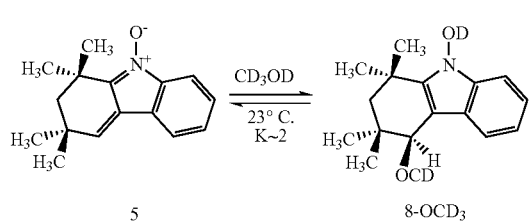

Reaction of 3-Alkylidene-3H-indole 1-Oxide 5 with Methanol-d₄. A solution of 3-alkylidene-3H-indole 1-oxide 5 (0.01 M) in methanol-d₄ was prepared at 23° C. and monitored by ¹H NMR spectroscopy. After 11.5 h at 23° C., the relative amounts of 5 and 8-OCD₃ did not change (ratio 5:8≈1:2). After 50 h the spectra reported below were recorded.

¹H NMR (500 MHz, CD₃OD, * denotes 8-OCD₃), δ 7.81 (d, 1H, J=8 Hz, ArH), 7.66 (d, 1H, J=7 Hz, ArH), 7.55 (m, 1H+1H*, ArH, ArH*), 7.50 (t, 1H, J=7 Hz, ArH), 7.35 (d, 1H*, J=8 Hz, ArH*), 7.25 (s, 1H, CH), 7.12 (t, 1H*, J=8 Hz, ArH*), 7.03 (t, 1H*, J=7 Hz, ArH*), 4.12 (s, 1H*, OH*), 2.09 (d, 1H*, J=13.5 Hz, CH*), 1.84 (s, 2H, CH₂), 1.62 (s, 6H, CH₃), 1.51 (s, 3H*, CH₃*), 1.48 (s, 3H*, CH₃*), 1.38 (d, 1H*, J=14.5 Hz, CH₂*), 1.33 (s, 6H, CH₃), 1.15 (s, 3H*, CH₃*), 0.97 (s, 3H*, CH₃*). ¹³C NMR (100 MHz, CD₃OD, * denotes 11), δ 148.4, 147.0, 145.7, 139.8*, 134.9*, 128.8, 128.3, 127.3, 125.0, 123.6*, 121.4*, 120.7*, 120.1, 119.0*, 117.7*, 112.9, 107.6*, 103.9*, 80.0*, 51.4, 36.4*, 35.5, 33.0, 32.0*, 30.3*, 29.6, 28.8*, 26.9*, 26.4*, 25.2 (OCD₃ not observed). IR (NaCl, thin film), cm⁻¹ 2912 (m), 1702 (w), 1451 (m). HRMS (CI) m/z calcd for $C_{16}H_{20}NO$ [M−CD₄O₂+H]⁺: 242.1545, found 242.1548.

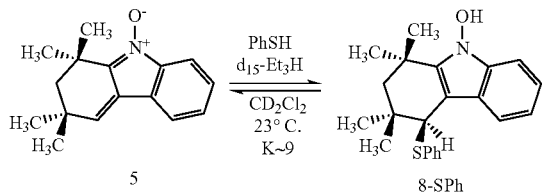

Reaction of 3-Alkylidene-3H-indole 1-Oxide 5 with Thiophenol. 3-Alkylidene-3H-indole 1-oxide 5 (4.95 mg, 0.0205 mmol, 1.0 equiv), triethyl-d₁₅-amine (1 μL, 0.007 mmol, 0.36 equiv), and thiophenol (2.4 μL, 0.024 mmol, 1.15 equiv) were added in sequence to methylene-d₂ chloride (0.8 mL). The reaction was monitored with ¹H NMR spectroscopy (5:8≈1:9 at 23° C.; 5:8≦2:98 at −40° C.).

¹H NMR (500 MHz, CD₂Cl₂, −20° C.), δ 7.54 (d, 1H, J=7 Hz, ArH), 7.50 (d, 2H, J=7.5 Hz, SPh), 7.30 (t, 2H, J=7.5 Hz, SPh), 7.23 (m, 2H, ArH, SPh), 7.10 (t, 1H, J=7.5 Hz, ArH), 7.02 (t, 1H, J=7 Hz, ArH), 4.50 (s, 1H, SCH), 2.12 (d, 1H, J=13.5 Hz, CH₂), 1.44 (s, 3H, CH₂), 1.37 (s, 3H, CH₃), 1.34 (d, 1H, J=14.5 Hz, CH₃), 1.07 (s, 6H, CH₃). ¹³C NMR (100 MHz, CD₂Cl₂, −35° C.) δ 139.4, 138.8, 134.4, 131.3, 128.7, 126.1, 121.1, 120.5, 118.1, 117.7, 107.7, 102.8, 54.4, 48.6, 37.8, 31.7, 30.8, 29.8, 27.9, 26.7. IR (NaCl, thin film), cm⁻¹ 2943 (s) 1574 (m), 1466 (s). HRMS (CI) m/z calcd for $C_{16}H_{20}NO$ [M−C₆H₅S]⁺: 242.1545, found 242.1547.

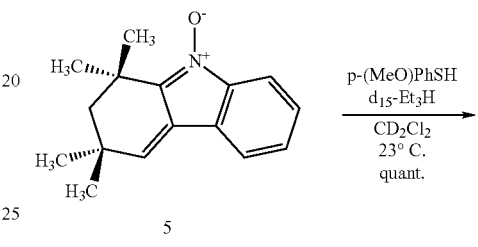

Reaction of 3-Alkylidene-3H-indole 1-Oxide 5 with p-Methoxybenzenethiol. 4-Methoxybenzenethiol (6.2 μL, 0.050 mmol, 1.0 equiv) was added to a solution of 3-alkylidene-3H-indole 1-oxide 5 (12.0 mg, 0.0497 mmol, 1 equiv) and triethyl-d₁₅-amine (1.4 μL, 0.010 mmol, 0.20 equiv) in CD₂Cl₂ (0.75 mL) at 23° C. After stirring 5 min, the reaction was transferred to an NMR tube via cannula and the spectra reported below were obtained.

¹H NMR (500 MHz, CD₂Cl₂), δ 7.47 (d, 1H, J=8.0 Hz, ArH), 7.33 (d, 2H, J=8.5 Hz, SArH), 7.29 (d, 1H, J=8.0 Hz, ArH), 7.13 (t, 1H, J=7.5 Hz, ArH), 7.00 (t, 1H, J=8.0 Hz ArH), 6.76 (d, 2H, J=9.0 Hz, SArH), 4.27 (s, 1H, SCH), 3.78 (s, 3H, OCH₃), 2.11 (d, 1H, J=14 Hz, CH₂), 1.49 (s, 3H, CH₃), 1.33 (m, 4H, CH₃, CH₂), 1.20 (s, 3H, CH₃), 1.08 (s, 3H, CH₃). ¹³C NMR (100 MHz, CD₂Cl₂), δ 158.8, 139.4, 135.3, 134.6, 131.9, 128.1, 120.9, 118.6, 117.9, 114.5, 114.0, 107.7, 56.0, 55.2, 48.8, 37.7, 31.7, 30.8, 30.1, 28.3, 26.9. IR (NaCl, thin film), cm⁻¹ 3302 (w), 2953 (m), 1584 (m), 1487 (s), 1241 (vs). HRMS (CI) m/z calcd for $C_{16}H_{20}NO$ [M−C₇H₇—OS]⁺: 242.1545, found 242.1541

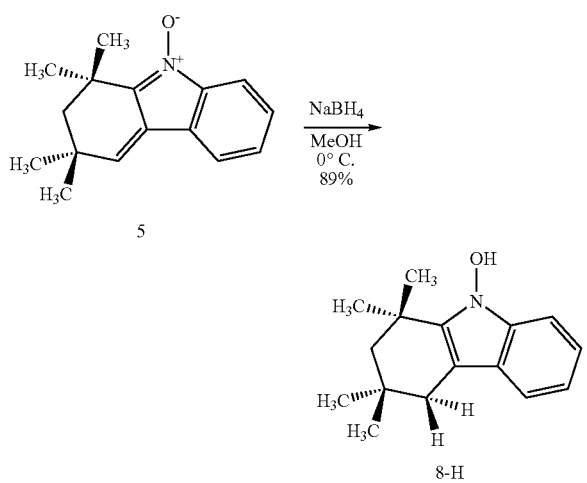

Reduction of 3-Alkylidene-3H-indole 1-Oxide 5 with Sodium Borohydride. Sodium borohydride (48.5 mg, 1.28 mmol, 15.0 equiv) was added to a solution of 3-alkylidene-3H-indole 1-oxide 5 (20.6 mg, 0.0855 mmol, 1 equiv) in methanol (1.7 mL) at 0° C. After 10 min, the reaction mixture was allowed to warm to room temperature, then was stirred for 60 min. The progress of the reaction was monitored by thin-layer chromatography (30% ethyl acetate-hexanes, $R_f$=0.25, 0.49, 3-alkylidene-3H-indole 1-oxide 5, product 8-H, respectively; UV, CAM). Excess borohydride was quenched by the addition of saturated aqueous ammonium chloride solution (2 mL), then the reaction mixture was diluted with ethyl acetate (6 mL) and distilled water (1 mL). The aqueous layer was extracted with three 4-mL portions of ethyl acetate. The combined organic extracts were washed with brine (1 mL) and dried over sodium sulfate. After concentration, flash-column chromatography (10% ethyl acetate-hexanes) furnished 8-H (18.4 mg, 89%) as a clear oil.

$^1$H NMR (400 MHz, CD$_3$OD), δ 7.33 (d, 1H, J=8.0 Hz, ArH), 7.27 (d, 1H, J=8.0 Hz, ArH), 7.05 (t, 1H, J=7.6 Hz, ArH), 6.92 (t, 1H, J=7.6 Hz, ArH), 2.45 (s, 2H, CH$_2$), 1.63 (s, 2H, CH$_2$), 1.47 (s, 6H, CH$_3$), 1.07 (s, 6H, CH$_3$). $^{13}$C NMR (100 MHz, CD$_3$OD), δ138.3, 135.6, 123.1, 120.5, 118.2, 117.3, 107.4, 103.3, 54.2, 35.4, 32.1, 31.5, 29.1, 28.7. IR (NaCl, thin film), cm$^{-1}$ 3394 (s), 2953 (vs), 2892 (s), 1456 (m). HRMS (CI) m/z calcd for C$_{16}$H$_{22}$NO [M+H]$^+$ 244.1701, found 244.1698.

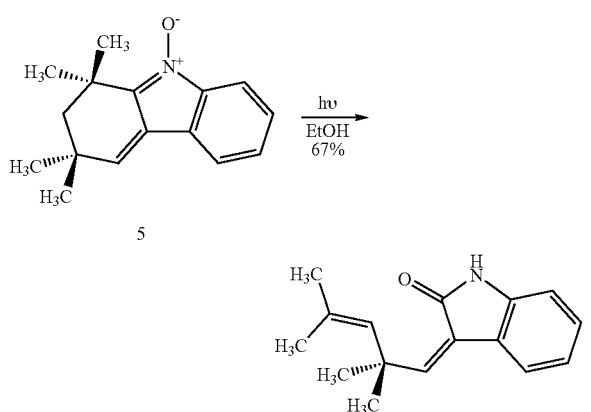

Photochemical Isomerization of 3-Alkylidene-3H-indole 1-Oxide 5. A solution of 3-alkylidene-3H-indole 1-oxide 5 (30.1 mg, 0.125 mmol, 1 equiv) in absolute ethanol (50 mL) in a 100 mL Pyrex pear-shaped flask was positioned within 1 cm of a mercury lamp (Ace Glass, 200 W) and irradiated for 15 m. The progress of the reaction was monitored by thin-layer chromatography (30% ethyl acetate-hexanes, $R_f$=0.21, 0.41, 3-alkylidene-3H-indole 1-oxide 5, lactam 9, respectively; UV, CAM). The product was isolated by concentration and then flash-column chromatography (20% ethyl acetate-hexanes), providing the lactam 9 (20.2 mg, 67%) as a green solid (mp 124-126° C.).

$^1$H NMR (500 MHz, acetone-d$_6$), δ 9.33 (br, 1H, NH), 7.52 (d, 1H, J=7.5 Hz, ArH), 7.26 (s, 1H, (CH$_3$)$_2$CCHC(CH$_3$)$_2$CH), 7.17 (t, 1H, J=7.5 Hz, ArH), 6.94 (t, 1H J=7.5 Hz ArH), 6.85 (d, 1H, J=8 Hz, ArH), 5.59 (s, 1H, (CH$_3$)$_2$CCHC(CH$_3$)$_2$CH), 1.63 (s, 3H, (CH$_3$)$_2$CCHC(CH$_3$)$_2$CH), 1.56 (s, 3H, (CH$_3$)$_2$CCHC(CH$_3$)$_2$CH), 1.49 (s, 6H, (CH$_3$)$_2$CCHC(CH$_3$)$_2$CH). $^{13}$C NMR (100 MHz, CD$_2$Cl$_2$), δ 165.7, 151.6, 138.9, 134.4, 128.8, 127.3, 125.0, 124.1, 120.4, 117.9, 108.3, 36.3, 28.1, 24.9, 19.5. IR (NaCl, thin film), cm$^{-1}$ 3195 (w), 2960 (w), 1700 (vs), 1469 (m). HRMS (CI) m/z calcd for C$_{16}$H$_{20}$NO [M+H]$^+$: 242.1545, found 242.1543.

Preparation of Isotopically Labeled Derivatives.

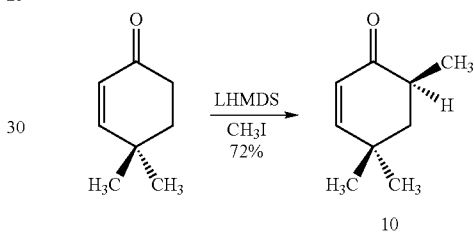

4,4,6-Trimethylcyclohex-2-en-1-one. A solution of 4,4-dimethyl-cyclohex-2-en-1-one (5.00 g, 40.3 mmol, 1 equiv) in tetrahydrofuran (130 mL) was added to a solution of LHMDS (1 M in tetrahydrofuran, 58.4 mL, 58.4 mmol, 1.45 equiv) in tetrahydrofuran (60 mL) at −78° C. After stirring for 1 h, iodomethane (5.02 mL, 80.6 mmol, 2.0 equiv) was added dropwise to the flask. The cooling bath was immediately removed and the reaction mixture was allowed to warm to room temperature (23° C.). After stirring 11 h, saturated aqueous ammonium chloride solution (50 mL) and distilled water (10 mL) were added to the flask. The layers were separated and the aqueous layer was extracted with three 50-mL portions of ether. The combined organic layers were washed once with brine (10 mL) and dried over sodium sulfate (15 min). Following filtration, volatiles were removed in vacuo, leaving a brown residue which was distilled at 22 torr furnishing 4,4,6-trimethyl-cyclohex-2-en-1-one (10, 3.93 g, 72%) as a clear oil, bp 82-86° C. (Torri, J.; Azzaro, M. *Bull. Soc. Chem. Fr.* 1978, 283; incorporated herein by reference).

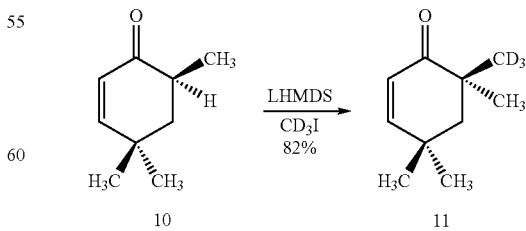

6-(Trideuteriomethyl)-4,4,6-trimethyl-cyclohex-2-en-1-one (11). A solution of n-butyllithium (2.57 M in tetrahydrofuran, 7.39 mL, 19.0 mmol, 1.20 equiv) was added to a solution of hexamethyldisilazane (4.28 mL, 19.0 mmol, 1.20 equiv) in tetrahydrofuran (50 mL) at −78° C. The reaction mixture was stirred for 10 min, then was warmed to 0° C. After an additional 10 min of stirring at 0° C., the solution was cooled to −78° C. and 4,4,6-trimethyl-cyclohex-2-en-1-one (2.15 g, 15.8 mmol, 1 equiv) in tetrahydrofuran (50 mL) was transferred to the flask via cannula over 5 min. The clear solution was stirred at −78° C. for 1 h and then iodomethane-$d_3$ (5.0 g, 35.2 mmol, 2.2 equiv) was injected into the flask. The reaction was allowed to warm to room temperature (23° C.) and then stirred an additional 12 h. Saturated aqueous ammonium chloride solution (25 mL) was added and the resulting bi-phasic mixture was extracted with three 50-mL portions of ether. The combined organic layers were washed once with brine (20 mL), then were dried over sodium sulfate. Following filtration, volatiles were removed in vacuo and the brown oily residue was distilled at 10 torr to furnish 6-(trideuteriomethyl)-4,6,6-trimethyl-cyclohex-2-en-1-one (11, 2.00 g, 82%) as a clear oil, bp=73° C.

$^1$H NMR (500 MHz, CDCl$_3$), δ 6.56 (d, 1H, J=10 Hz, CH), 5.75 (d, 1H, J=10 Hz, CH), 1.77 (s, 2H, CH$_2$), 1.78 (s, 6H, CH$_3$), 1.55 (s, 3H, CH$_3$). $^{13}$C NMR (100 MHz, CDCl$_3$), δ 205.1, 157.6, 125.2, 49.4, 41.1, 33.4, 30.7, 27.5 (CD$_3$ not observed). IR (NaCl, thin film), cm$^{-1}$ 2953 (m), 1671 (s). HRMS (EI) m/z calcd for C$_{10}$H$_{13}$D$_3$O [M]$^+$ 155.1386, found 155.1384.

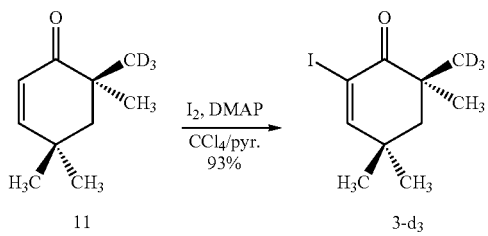

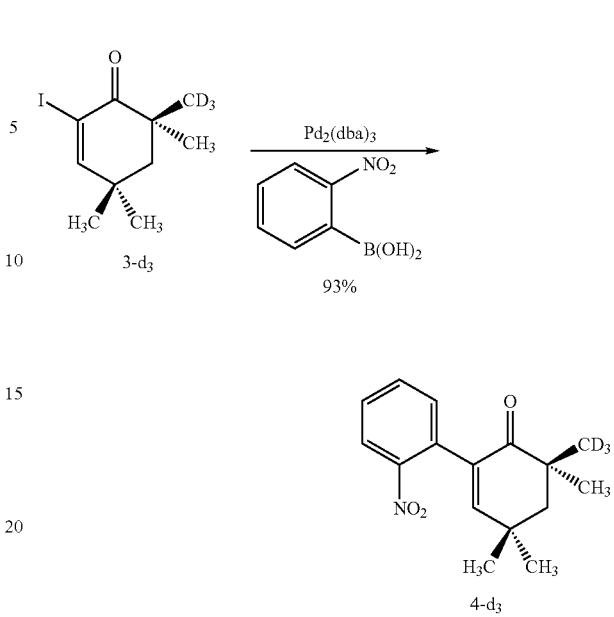

2-Iodo-6-(trideuteriomethyl)-4,4,6-trimethyl-cyclohex-2-en-1-one (3-d$_3$). To a solution of 6-(trideuteriomethyl)-4,4,6-trimethyl-cyclohex-2-en-1-one (11, 501 mg, 3.23 mmol, 1 equiv) in pyridine (4 mL) and carbon tetrachloride (4 mL) was added iodine (2.46 g, 9.69 mmol, 3.0 equiv) and 4-(dimethylamino)pyridine (78.9 mg, 0.646 mmol, 0.2 equiv). The brown solution was heated to 49° C. for 2 h. The progress of the reaction was monitored by thin layer chromatography (20% ethyl acetate-hexanes, R$_f$=0.47, 0.37 2-iodo-6-(trideuteriomethyl)-4,4,6-trimethyl-cyclohex-2-en-1-one, 6-(trideuteriomethyl)-4,4,6-trimethyl-cyclohex-2-en-1-one, respectively; UV, ANIS). After allowing the flask to cool to room temperature, the solution was diluted with methylene chloride (50 mL) and washed successively with saturated aqueous sodium thiosulfate solution (2×25 mL), water (25 mL), and brine (25 mL). The combined aqueous layers were extracted with methylene chloride (2×50 mL). The combined organic layers were dried over sodium sulfate, filtered, and concentrated to furnish a red oil. Flash-column chromatography (5% tetrahydrofuran-hexanes) on a short (12-cm) column furnished 2-iodo-6-(trideuteriomethyl)-4,4,6-trimethyl-cyclohex-2-en-1-one (3-d$_3$, 846 mg, 93%) as a clear oil which solidified upon standing (mp 39-40° C.).

$^1$H NMR (400 MHz, CDCl$_3$), δ 7.35 (s, 1H, CH), 1.83 (s, 2H, CH$_2$), 1.21 (s, 9H, CH$_3$). $^{13}$C NMR (100 MHz, CDCl$_3$), δ 197.6, 165.9, 101.1, 48.9, 41.7, 38.3, 30.4, 28.0 (CD$_3$ not observed). IR (NaCl, thin film), cm$^{-1}$ 2964 (m), 1687 (s). HRMS (EI) m/z calcd for C$_{10}$H$_{12}$D$_3$IO [M]$^+$ 281.0353, found 281.0346.

6-(Trideuteriomethyl)-4,6,6-trimethyl-2-(o-nitrophenyl)-cyclohex-2-en-1-one (4-d$_3$). A 100-mL Schlenk-type flask was charged with 2-iodo-6-(trideuteriomethyl)-4,4,6-trimethyl-cyclohex-2-en-1-one (3-d$_3$, 720 mg, 2.56 mmol, 1 equiv), 2-(nitrophenyl)boronic acid (565 mg, 3.38 mmol, 1.3 equiv), Pd$_2$dba$_3$ (117 mg, 0.128 mmol, 0.05 equiv), 2-(di-t-butylphosphino)-biphenyl (157 mg, 0.512 mmol, 0.2 equiv), barium hydroxide octahydrate (2.42 g, 7.68 mmol, 3.0 equiv), tetrahydrofuran (40 mL), and distilled water (7.5 mL). The solution was heated to 35° C. for 5 h, then was allowed to cool to room temperature. Saturated aqueous ammonium chloride solution (15 mL) was added slowly to the flask. The solution was then extracted with four 30-mL portions of ethyl acetate. The combined organic layers were washed once with brine (20 mL), then were dried over sodium sulfate, filtered, and concentrated. Flash-column chromatography (6% tetrahydrofuran-hexanes) furnished 6-(trideuteriomethyl)-4,6,6-trimethyl-2-(o-nitrophenyl)-cyclohex-2-en-1-one (4-d$_3$, 660 mg, 93%).

$^1$H NMR (400 MHz, CDCl$_3$), δ 9.00 (dd, 1H, J=8, 1.2 Hz, ArH), 7.58 (td, 1H, J=7.6, 1.2 Hz, ArH), 7.46 (td, 1H, J=7.6, 1.2 Hz, ArH), 7.24 (dd, obs., 1H, J=7.6, 1.2 Hz, ArH), 6.62 (s, 1H, CH), 1.90 (s, 2H, CH$_2$), 1.30 (s, 6H, CH$_3$), 1.25 (s, 3H, CH$_3$). $^{13}$C NMR (100 MHz, CDCl$_3$), δ 201.6, 154.5, 149.0, 135.0, 133.3, 132.8, 132.5, 128.9, 124.4, 49.3, 41.2, 33.5, 30.9, 27.3 (CD$_3$ not observed). IR (NaCl, thin film), cm$^{-1}$ 2953 (w), 1692 (s), 1523 (vs), 1348 (s). HRMS (CI) m/z calcd for C$_{16}$H$_{17}$D$_3$NO$_3$ [M+H]$^+$ 277.1631, found 277.1627.

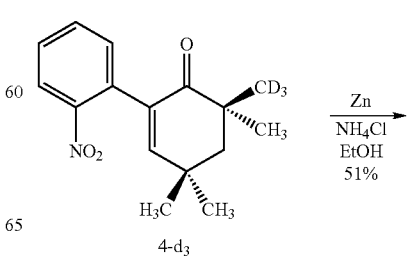

-continued

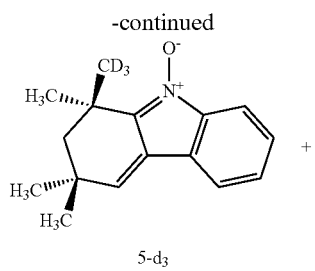

5-d₃

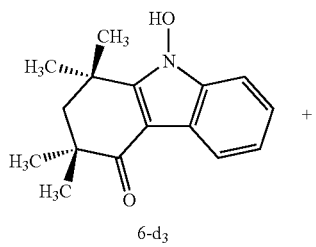

6-d₃

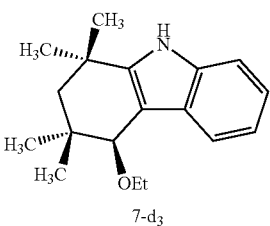

7-d₃

Reductive Condensation of 6-(Trideuteriomethyl)-4,6,6-trimethyl-2-(o-nitrophenyl)-cyclohex-2-en-1-one (4-d₃). A suspension of zinc powder (62.0 mg, 0.949 mmol, 2.7 equiv) and 1,2-dibromoethane (6 μL, 0.06 mmol, 0.067 equiv based on zinc) in tetrahydrofuran (2 mL) was heated to a vigorous boil (70° C.), then was allowed to cool to room temperature (23° C.). After repeating the process three additional times, trimethylsilyl chloride (5 μL, 0.04 mmol, 0.05 equiv based on zinc) was injected and the grey suspension was vigorously stirred at 23° C. 10 m. A separate 25-mL flask was charged sequentially with 6-(trideuteriomethyl)-4,6,6-trimethyl-2-(o-nitrophenyl)-cyclohex-2-en-1-one (4-d₃, 149.0 mg, 0.542 mmol, 1 equiv), absolute ethanol (5.4 mL), and aqueous ammonium chloride solution (1 M, 1.19 mL, 1.19 mmol, 2.2 equiv). The resulting yellow solution was heated to 50° C. in an oil bath. Using a cannula, the zinc suspension was transferred dropwise to the reaction vessel. After 4 h, the reaction vessel was allowed to cool to 23° C. and ethyl acetate (18 mL) was added. The solution was filtered through a Celite plug and the filtrate was concentrated in vacuo to provide a yellow oil which was purified by flash-column chromatography (6% ethyl acetate-hexanes initially, grading to 40% ethyl acetate-hexanes), to yield separately trideuterated 3-alkylidene-3H-indole 1-oxide 5-d₃ (43.7 mg, 33%, brown solid), trideuterated N-hydroxy indole 6-d₃ (15.6 mg, 11%, clear oil), and trideuterated indole 7-d₃ (11.1 mg, 7%, clear oil, inseparable mixture of diastereomers).

3-Alkylidene-3H-indole 1-Oxide 5-d₃: ¹H NMR (500 MHz, CD₂Cl₂) δ 7.66 (d, 1H, J=8 Hz, ArH), 7.63 (d, 1H, J=7 Hz, ArH), 7.47 (t, 1H, J=7 Hz, ArH), 7.42 (t, 1H, J=8 Hz, ArH), 6.78 (s, 1H, CH), 1.76 (s, 2H, CH₂), 1.58 (s, 3H, H₃CCCD₃), 1.28 (s, 6H, CH₃). ¹³C NMR (100 MHz, CD₂Cl₂), δ 146.7, 144.7, 141.5, 128.6, 128.0, 127.8, 125.5, 119.5, 113.4, 52.1, 35.5, 32.6, 30.7, 25.7 (CD₃ not observed). IR (NaCl, thin film), cm⁻¹ 3326 (m), 2945 (s), 2917 (s), 1639 (w), 1453 (m), 1315 (m). HRMS (CI) m/z calcd for C₁₆H₁₇D₃NO [M+H]⁺ 245.1725, found 245.1732.

The location of the trideuteriomethyl group (see below) was established using an HMBC experiment. Critical HMBC couplings are shown.

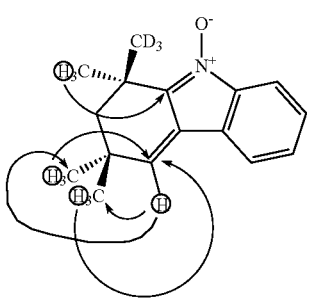

5-d₃

N-Hydroxy Indole 6-d₃: ¹H NMR (400 MHz, d₆-DMSO) δ 11.7 (br, 1H, OH), 8.06 (d, 1H, J=7 Hz, ArH), 7.42 (d, 1H, J=7.5 Hz, ArH), 7.24 (t, 1H, J=7.5 Hz, ArH), 7.17 (t, 1H, J=7 Hz, ArH), 1.95 (s, 2H, CH₂), 1.55 (s, 6H, CH₃), 1.15 (s, 3H, H₃CCCD₃). ¹³C NMR (100 MHz, d₆-DMSO), δ 198.2, 152.1, 135.7, 123.4, 122.8, 121.4, 121.2, 109.5, 103.8, 52.9, 42.2, 32.7, 29.1, 27.8 (CD₃ not observed). IR (NaCl, thin film), cm⁻¹ 2933 (m), 1605 (s), 1405 (s). HRMS (CI) m/z calcd for C₁₆H₁₇D₃NO₂ [M+H]⁺ 261.1679, found 261.1680.

The location of the trideuteriomethyl group (see below) was established using an HMBC experiment. Critical HMBC couplings are shown.

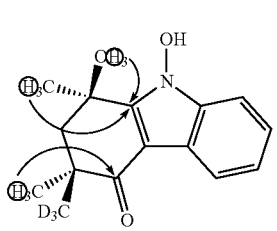

6-d₃

Indole 7-d₃: ¹H NMR (500 MHz, CD₂Cl₂) δ 8.02 (br, 1H, NH), 7.59 (d, 1H, J=7.5 Hz, ArH), 7.33 (d, 1H, J=7.5 Hz, ArH), 7.12 (t, 1H, J=7.5 Hz, ArH), 7.08 (t, 1H, J=7.5 Hz), 4.17 (s, 1H, OCH), 3.66 (m, 2H, OCH₂CH₃), 2.07 (d, 1H, J=13.5 Hz, CH₂), 1.41 (d, 1H, J=14 Hz, CH₂), 1.35 (s, 1.5H, H₃CCCD₃), 1.34 (s, 1.5H, H₃CCCD₃), 1.15 (m, 6H, OCH₂CH₃, CH₃), 0.94 (s, 3H, CH₃). ¹³C (detected indirectly using HSQC and HMBC experiments, CDCl₃) 142.4, 136.0, 128.4, 121.0, 119.4, 118.5, 110.6, 110.2, 78.0, 65.6, 47.0, 36.5, 32.6, 31.0, 29.6, 27.4, 27.0, 15.6 (CD₃ not observed). IR (NaCl, thin film), cm⁻¹ 3341 (m), 3319 (m), 2951 (s), 1462 (s). HRMS (EI) m/z calcd for C₁₆H₂₂D₃NO [M]⁺ 274.2121, found 274.2121.

The location of the trideuteriomethyl group (see below) was established using an HMBC experiment. Critical HMBC couplings are shown.

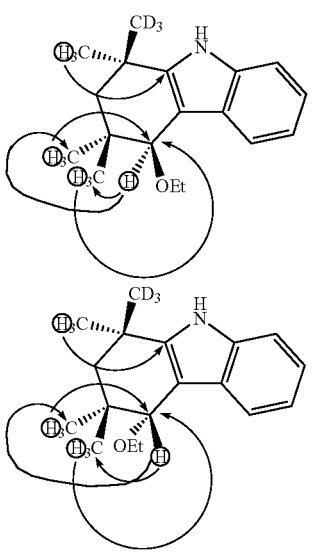

Preparation of Acyclic Nitrones.

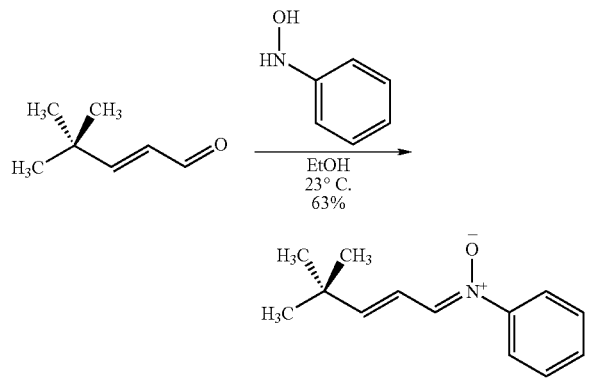

α-(trans-3,3-dimethyl-1-butenyl)-N-phenylnitrone. To a solution of (E)-4,4-dimethyl-2-pentenal (Lau et al. *J. Org. Chem.* 1978, 43, 1595; incorporated herein by reference) (42.3 mg, 0.381 mmol, 1 equiv) in ethanol (0.10 mL, absolute) at 23° C. was added N-phenyl-hydroxylamine (Bordwell et al. *J. Am. Chem. Soc.* 1996, 118, 8777; incorporated herein by reference) (41.6 mg, 0.381 mmol, 1.0 equiv) in one portion. The resulting yellow solution was stirred at 23° C. in the dark. The progress of the reaction was monitored by thin-layer chromatography (20% ethyl acetate-hexanes, $R_f$=0.13, 0.21, 0.67 for α-(trans-3,3-dimethyl-1-butenyl)-N-phenylnitrone, N-phenyl-hydroxylamine, and (E)-4,4-dimethyl-2-pentenal, respectively). After 55 min, the solution was diluted with dichloromethane (10 mL) and, without concentration, loaded onto a silica gel column, and purified by flash-column chromatography (65% ether-hexanes) to furnish α-(trans-3,3-dimethyl-1-butenyl)-N-phenylnitrone (49.1 mg, 63%, clear oil). When protected from light, the nitrone was found to be stable for at least 7 h at 23° C. as a 37 mM solution in methylene-$d_2$-chloride; however, upon concentration to dryness, the nitrone decomposed within two hours ($^1$H NMR analysis).

$^1$H NMR (600 MHz, CD$_2$Cl$_2$), δ 7.70 (m, 2H, Ph), 7.62 (dd, 1H, J=9.0, 1.2 Hz, PhN(O)CHCHCHC(CH$_3$)$_3$), 7.46 (m, 3H, Ph), 6.83 (dd, 1H, J=17, 9.6 Hz, PhN(O)CHCHCHC(CH$_3$)$_3$), 6.44 (dd, 1H, J=16.2, 1.2 Hz, PhN(O)CHCHCHC(CH$_3$)$_3$), 1.13 (s, 9H, C(CH$_3$)$_3$). $^{13}$C NMR (100 MHz, CD$_2$Cl$_2$), δ 115.6, 147.8, 136.6, 129.9, 129.2, 121.6, 117.3, 34.7, 29.0. IR (NaCl, thin film), cm$^{-1}$ 2953 (s), 2861 (m), 1533 (m), 1379 (m). HRMS (ESI) m/z calcd for C$_{13}$H$_{18}$NO [M+H]$^+$ 204.1388, found 204.1381.

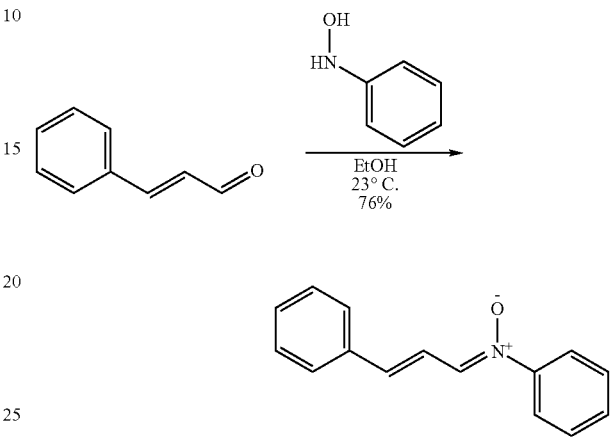

α-(trans-2-phenyl-ethenyl)-N-phenylnitrone. According to the literature procedure (Utzinger et al. *Helv. Chim. Acta* 1954, 37, 1892; incorporated herein by reference) N-phenyl-hydroxylamine (188.7 mg, 1.7 mmol, 1.0 equiv) was added to a solution of (E)-cinnamaldehyde (218 μL, 1.73 mmol, 1 equiv) in ethanol (1.5 mL, absolute). The bright yellow solution was stirred for 9 h at 23° C. in the dark, and then was cooled in an ice bath. The cooled, heterogeneous solution was filtered and the filter cake was washed once with hexanes (10 mL). The filter cake was dried in vacuo overnight, furnishing α-(trans-2-phenyl-ethenyl)-N-phenylnitrone (293 mg, 76%, yellow solid) mp=150-152° C. (lit. 150-151° C.). $^1$H NMR data were in accord with that previously reported.

Example 2

Synthesis of Avrainvillamide

The complex alkaloid stephacidin B (1) was recently isolated from a fungal culture by a multi-step process (Qian-Cutrone et al. Stephacidin Antitumor Antibiotics. U.S. Pat. No. 6,291,461, 2001; Qian-Cutrone et al. *J. Am. Chem. Soc.* 2002, 124, 14556; each of which is incorporated herein by reference; for reviews of prenylated indole alkaloids from fungi, see: Williams, R. M.; Cox, R. J. *Acc. Chem. Res.* 2003, 36, 127; Stocking, E. M.; Williams, R. M. Angew. *Chem., Int. Ed. Engl.* 2003, 42, 3078; each of which is incorporated herein by reference). It was recognized that 1 is potentially formed by dimerization of 2. A mechanism for the putative dimerization reaction was advanced that involved protonation of 2 followed by formation of bonds b and a (see structure 1), in that order, via cationic intermediates (Qian-Cutrone et al. *J. Am. Chem. Soc.* 2002, 124, 14556; incorporated herein by reference).

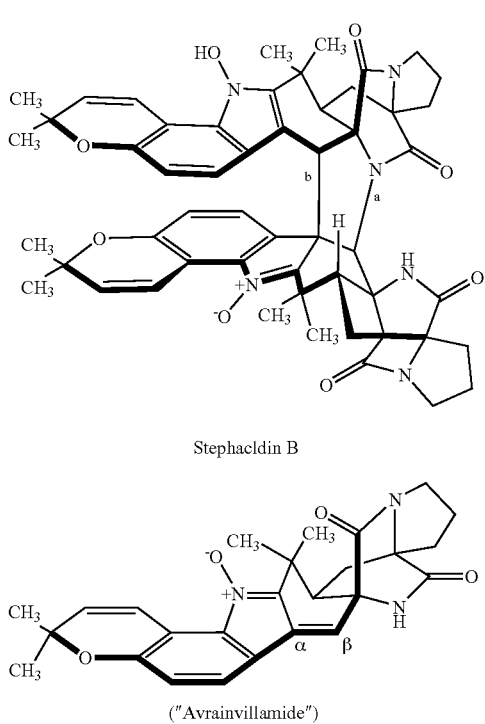

Stephacidin B (1)

("Avrainvillamide") 2

The structure 2 had previously appeared in the patent literature as the antiproliferative fungal isolate "avrainvillamide" (where it was depicted as ent-2; neither relative nor absolute stereochemical assignments were discussed) (Fenical et al. "Avrainvillamide, a Cytotoxic Marine Natural Product, and Derivatives thereof" U.S. Pat. No. 6,066,635, 2000; incorporated herein by reference) and was later described by Sugie and co-workers as "CJ-17,665", an isolate from a different fungal strain (neither relative nor absolute stereochemistry was defined) (Sugie et al. J. Antibiot. 2001, 54, 911; incorporated herein by reference). Both stephacidin B and avrainvillamide are reported to inhibit the growth of cultured human cancer cells ($IC_{50}$ values ~50-100 nM), but side-by-side comparisons of these compounds have not been made, so far as we are aware. We have previously described methodology to synthesize the substructure depicted in red within structure 2 and found that the unsaturated nitrone (3-alkylidene-3H-indole 1-oxide) function within the model compound we synthesized readily underwent reversible addition of oxygen- and sulfur-based nucleophiles to the carbon labeled β, which suggested that the putative dimerization of 2 to form 1 might be initiated by bond formation to carbon β (Myers, A. G.; Herzon, S. B. J. Am. Chem. Soc. 2003, 125, 12080; incorporated herein by reference) (see also, Nussbaum, F. Angew. Chem., Int. Ed. Engl. 2003, 42, 3068; incorporated herein by reference), and not carbon α as originally proposed (Qian-Cutrone et al. J. Am. Chem. Soc. 2002, 124, 14556; incorporated herein by reference). Here, we describe an enantioselective synthesis of structure 2 (levorotatory, vide infra) and observe that (−)-2 undergoes spontaneous dimerization to form (+)-stephacidin B (1) in the presence of triethylamine (for syntheses of alkaloids structurally related to 2, see: (a) (−)-Brevianamide B: Williams et al. J. Am. Chem. Soc. 1990, 112, 808. (b) (+)-Paraherquamide B: Cushing et al. J. Am. Chem. Soc. 1996, 118, 557. (c) (±)-VM55599: Stocking et al. J. Am. Chem. Soc. 2000, 122, 1675. (d) (−)-VM55599: Sanz-Cervera, J. F.; Williams, R. M. J. Am. Chem. Soc. 2002, 124, 2556. (e) Paraherquamide A: Williams et al. J. Am. Chem. Soc. 2003, 125, 12172. (f) Stephacidin A: Bran et al. Angew. Chem., Int. Ed. Engl. 2004, 44, 606; each of which is incorporated herein by reference).

Our synthetic route to 2 and stephacidin B (1) begins with the known, achiral cyclohexanone derivative 3 (Nelson et al. Tetrahedron 1991, 47, 3259; incorporated herein by reference), which was transformed via its trimethylsilyl enol ether into the corresponding α,β-unsaturated ketone in small-scale reactions by palladium-mediated oxidation (98% yield, 1.3-g scale, Scheme 1) (Ito et al. J. Org. Chem. 1978, 43, 1011; incorporated herein by reference). In larger scale preparations, 3 was oxidized directly with 2-iodoxybenzoic acid in the presence of 4-methoxypyridine N-oxide (70% yield, 10.4-g scale) (Nicolaou et al. Angew. Chem., Int. Ed. Engl. 2002, 41, 993; incorporated herein by reference). Enantioselective reduction of the α,β-unsaturated ketone produced by either method was achieved using the Corey-Bakshi-Shibata (CBS) catalytic protocol (Corey et al. J. Am. Chem. Soc. 1987, 109, 5551; Corey, E. J.; Helal, C. J. Angew. Chem., Int. Ed. Engl. 1998, 37, 1986; each of which is incorporated herein by reference).

Scheme 2-1

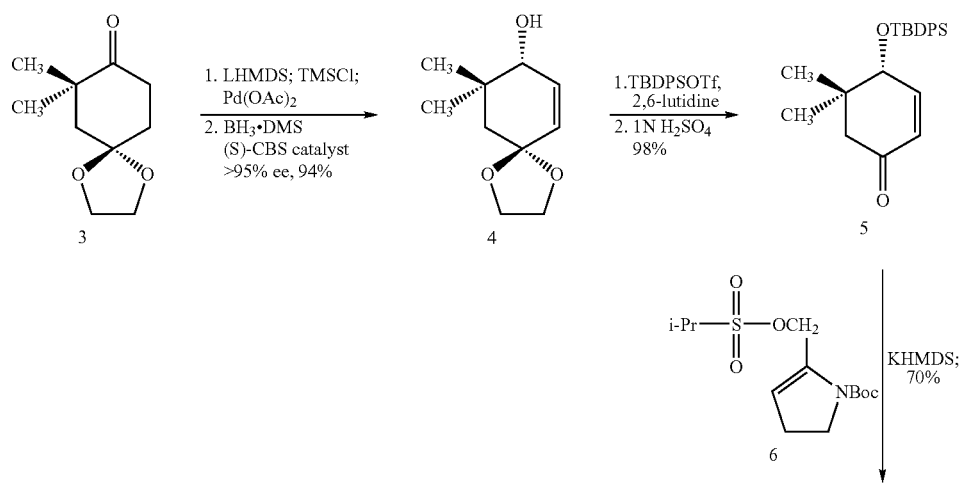

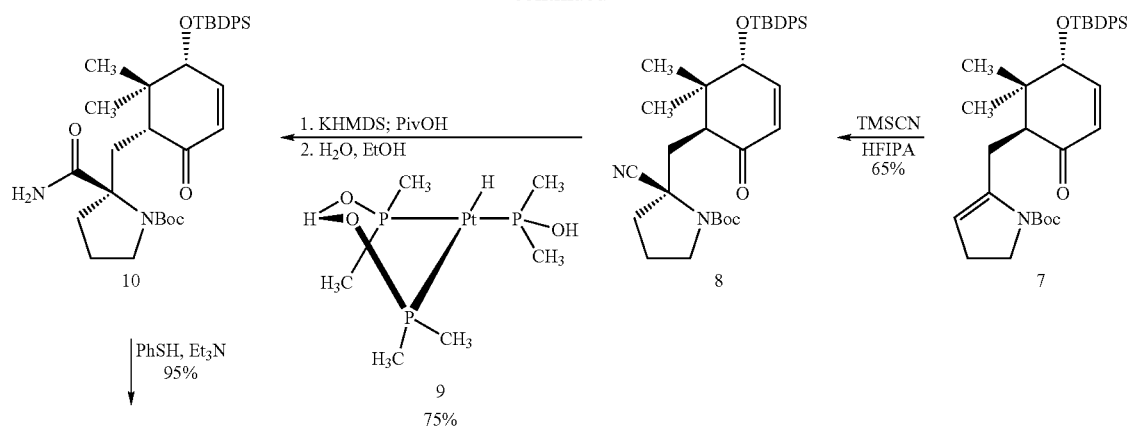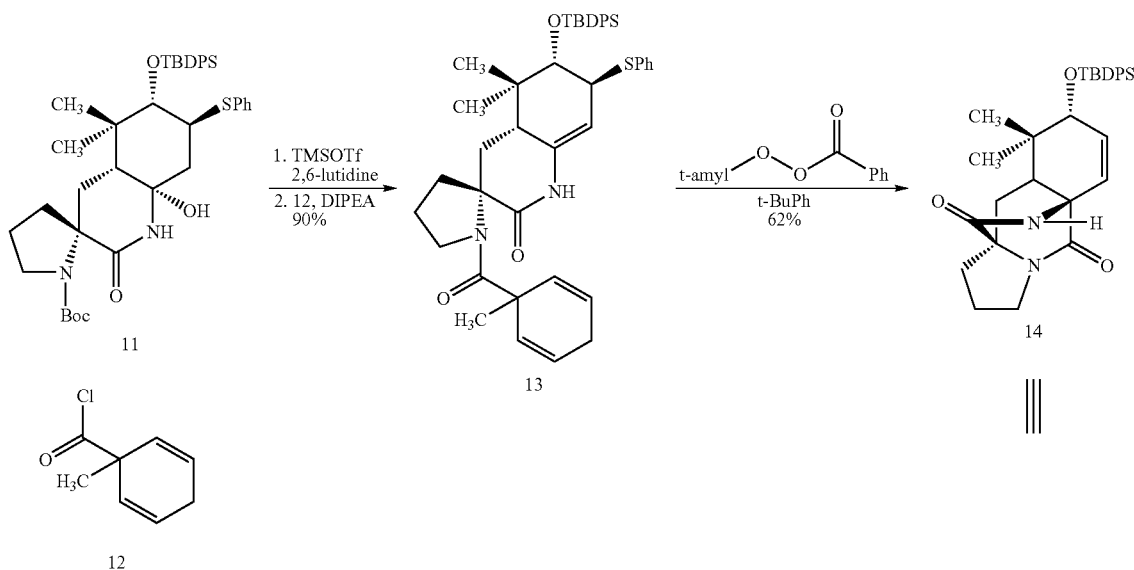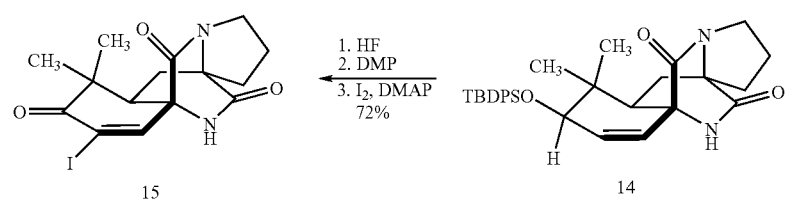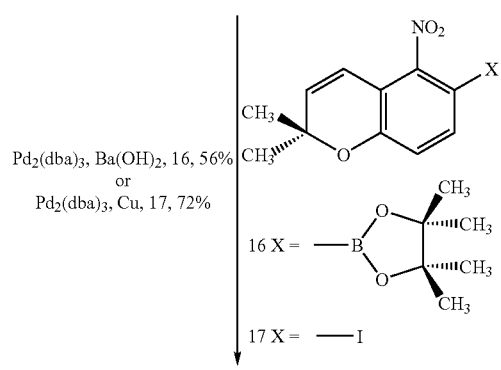

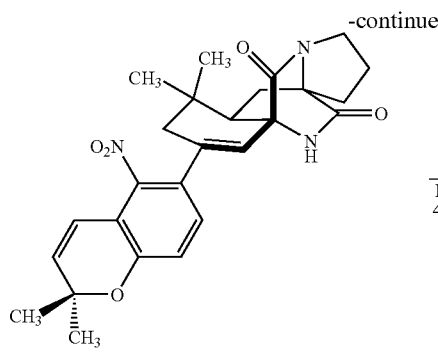

18

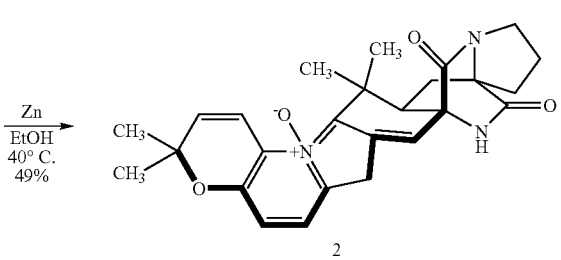

2

Zn
EtOH
40° C.
49%

The stereochemistry of the single stereogenic center introduced in the CBS reduction step was subsequently relayed to all others within stephacidin B (1). Because neither the chirality of 1 nor 2 was known, we randomly selected the (S)-CBS catalyst to illustrate our enantioselective route to stephacidin B (1), forming the (R)-allylic alcohol 4 in >95% ee (96% yield) (The absolute stereochemistry of 4 was determined by the modified Mosher method and is consistent with the established transition-state model for the oxazaborolidine reduction. (a) Dale et al. *J. Am. Chem. Soc.* 1973, 95, 512; Ohtani et al. *J. Am. Chem. Soc.* 1991, 113, 4092; each of which is incorporated herein by reference). Silyl ether formation and ketal hydrolysis then gave the α,β-unsaturated ketone 5 (98% yield, two steps).

In a key carbon-carbon bond-forming reaction, the ketone 5 was deprotonated with potassium hexamethyldisilazide (KHMDS) and the resulting enolate was trapped with the novel electrophile 6 [synthesized from N-(tert-butoxycarbonyl)-2,3-dihydropyrrole by a sequence involving α-lithiation (Tae et al. *Can. J. Chem.* 2000, 78, 689; incorporated herein by reference), formylation, reduction (borohydride), and isopropylsulfonylation], producing the trans-coupling product 7 as a single diastereomer (70%, 4.4-g scale). Use of the methanesulfonate ester corresponding to 6 in the alkylation gave 7 in lower yield (50%), presumably due to competitive proton-transfer from the methanesulfonate group. In a second critical transformation, the alkylation product 7 was found to undergo Strecker-like addition of hydrogen cyanide, but only in the solvent hexafluoroisopropanol (HFIPA, 0° C., 4 days), forming the N-Boc amino nitrile 8 (65%) and 16% of the diastereomeric amino nitrile (not shown, yields of pure diastereomers, separated by flash-column chromatography). We know of no close precedence for Strecker-like additions to N-Boc enamine substrates such as 7. To establish the stereo-relationships required for synthesis of stephacidin B, the α-carbon of the ketone 8 was epimerized by deprotonation with KHMDS followed by quenching of the resultant enolate with pivalic acid (88%, 487-mg scale). The platinum catalyst 9 of Ghaffar and Parkins (Ghaffar et al. *Tetrahedron Lett.* 1995, 36, 8657. (b) Ghaffar et al. *J. Mol. Catal. A* 2000, 160, 249; each of which is incorporated herein by reference) then served to transform the nitrile group of the epimerized product into the corresponding primary amide (10, 85%). The latter transformation was conducted under essentially neutral conditions; its success within a complex substrate suggests that the method may be of value in extension to the hydrolysis of other Strecker-derived addition products (typically conducted at the extremes of pH) (Schaefew, F. C. In *The Chemistry of the Cyano Group*; Rappoport, Z., Ed.; The Chemistry of Functional Groups; Wiley and Sons: New York, 1970; p 239; incorporated herein by reference). Treatment of the primary amide 10 with thiophenol and triethylamine led to conjugate addition of thiophenol as well as cyclic hemiaminal formation, giving the tricyclic product 11 (95%). A strictly analogous transformation occurred when p-methoxythiophenol was used as nucleophile, giving a crystalline product, whose structure (including all relative stereochemical assignments) was solved by X-ray analysis (see Experimentals below). Dehydration of the cyclic hemiaminal 11 in the presence of trimethylsilyl triflate and 2,6-lutidine was accompanied by cleavage of the N-Boc protective group; acylation of the pyrrolidinyl amine group that was liberated with 1-methyl-2,5-cyclohexadiene-1-carbonyl chloride, an acyl radical precursor developed by Jackson and Walton (Jackson et al. *Chem. Commun.* 2000, 2327; Bella et al. *Org. Biomol. Chem.* 2004, 2, 421; each of which is incorporated herein by refemce), then formed the amide 13 (90% yield, two steps). Heating of rigorously deoxygenated solutions of 13 and t-amyl peroxybenzoate in t-butyl benzene as solvent at 119° C. produced the bridged diketopiperazine core of stephacidin B in the form of the tetracyclic product 14 (62% yield, 144-mg scale). This key transformation (13→14), is believed to involve the formation of an aminoacyl radical intermediate, as would be expected based on precedent (Jackson et al. *Chem. Commun.* 2000, 2327; Bella et al. *Org. Biomol. Chem.* 2004, 2, 421; each of which is incorporated herein by reference), followed by attack of that aminoacyl radical upon the more substituted carbon of the enamide C—C double bond and expulsion of phenylthiyl radical, events that were less predictable. All efforts to prepare 14 using cyanide as the source of the final (bridging) carbon atom and intermediates such as 10, 11, or their derivatives as starting materials, were unsuccessful.

With the development of an efficient synthetic sequence to the tetracyclic product 14, completion of the synthesis of 2 and 1 was straightforward. First, 14 was transformed into the α-iodoenone 15 in a three-step sequence (72% yield, Scheme 2-1). Next, the α-iodoenone 15 was coupled in a Suzuki reaction with the arylboronic acid derivative 16 (Prepared from the aryl iodide 17 by the method of Sapountzis and Knochel: *Angew. Chem., Int. Ed. Engl.* 2002, 41, 1610; incorporated herein by reference. See Experimentals below for details) (56% yield) or, more efficiently, by an Ullmann-like coupling (Banwell et al. *Org. Lett.*, 2003, 5, 2497; incorporated herein by reference) with the aryl iodide 17 (Iodide 17 was prepared in two steps following a route previously developed by others for the synthesis of similarly substituted chromene derivatives. (a) Elomri, A.; Michel, S.; Tillequin, F.; Koch, M. *Heterocycles* 1992, 34, 799. (b) Cox, R. J.; Williams, R. M. *Tetrahedron Lett.* 2002, 43, 2149. (c) See also Baran et al. *Angew. Chem., Int. Ed. Engl.* 2004, 44, 606. An alternative preparation of 17 has been reported: (d) Sun, H.; Qing, F.; Chen, X. *Synthesis* 1997, 1249; each of which is incorporated herein by reference) (10 mol % Pd$_2$dba$_3$, Cu powder, 72% yield). Finally, the nitroarene coupling product (18) was reduced in the presence of activated zinc powder (Myers, A. G.; Herzon, S. B. *J. Am. Chem. Soc.* 2003, 125, 12080; Knochel, P.; Rao, C. J. *Tetrahedron* 1993, 49, 29; each of which is incorporated herein by reference), forming the heptacyclic unsaturated nitrone 2 as a yellow solid in 49% yield (scale: 5-10 mg, 17 steps, 4.2% yield from 3) after purification by flash-column chromatography.

Figure 2:
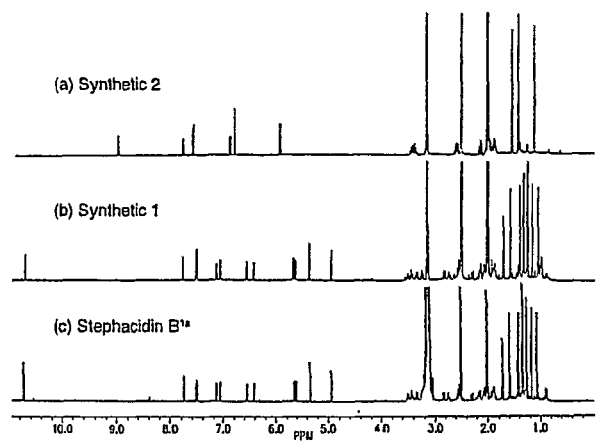
FIG. 2 is a series of $^1$H NMR spectra obtained at 23° C. (500 MHz, 1:1 DMSO-$d_6$-CD$_3$CN) of (a) synthetic avrainvillamide, (b) synthetic stephacidin B, (c) stephacidin B from a fungal source (Qian-Cutrone et al., U.S. Pat. No. 6,291,2001; Qian-Cutrone et al. J. Am. Chem. Soc. 124:14556, 2002; each of which is incorporated herein by reference).

An unequivocal link between synthetic and natural materials was established when we observed that pure synthetic (−)-2 was transformed into stephacidin B (1) in the presence of triethylamine at 23° C. (eq 1). Stirring a solution of (−)-2 and a large excess of triethylamine (15% by volume, 22 mM in 2) in acetonitrile at 23° C. led to gradual bleaching of the initially bright yellow solution with concomitant formation of a new, more polar material (TLC analysis). Concentration of the reaction mixture after 3.5 h and dissolution of the white solid residue obtained in a 1:1 mixture of DMSO-d$_6$-CD$_3$CN provided a nearly pure solution of stephacidin B (1, $^1$H NMR analysis, est. >95%, FIG. 2b).

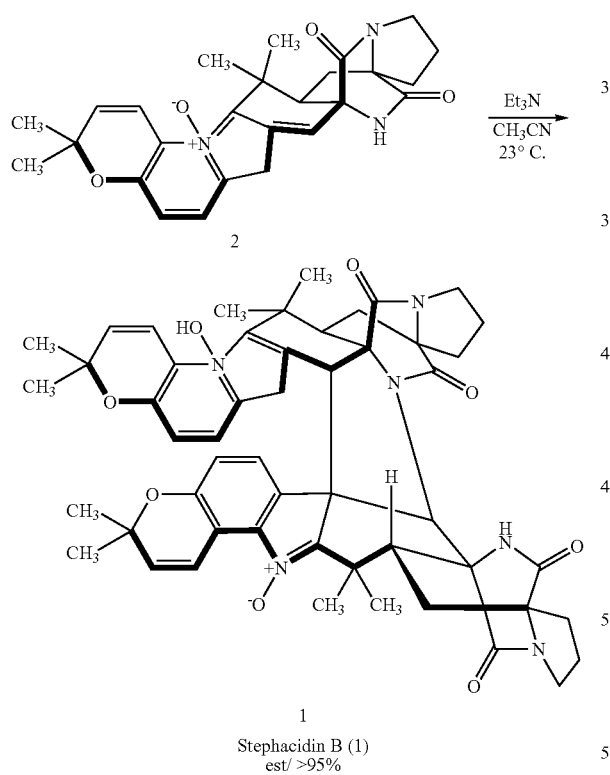

$^1$H NMR spectra of synthetic and natural stephacidin B (the latter from published data, Qian-Cutrone et al. Stephacidin Antitumor Antibiotics. U.S. Pat. No. 6,291,461, 2001; incorporated herein by reference) corresponded exactly (cf., FIG. 2b, c). Synthetic stephacidin B was found to be dextrorotatory ([α]$_D^{24}$=+91.0°, c 0.25, CH$_3$CN).

Our preliminary studies leave little doubt that 1 and 2 are readily interconverted in solution. For example, concentration of an acetonitrile-water solution of pure synthetic stephacidin B (1) at 38° C. afforded a 2:1 mixture of 2 and 1, as well as unidentified decomposition products. Also, whereas solutions of pure 1 in 50% DMSO-d$_6$-CD$_3$CN appeared to be stable for at least 48 h at 23° C. (The merits of the DMSO-d$_6$-CD$_3$CN solvent system in stabilizing stephacidin B were discussed in Qian-Cutrone et al. *J. Am. Chem. Soc.* 2002, 124, 14556; incorporated herein by reference.), addition of powdered 3-Å molecular sieves led to partial retro-dimerization, giving a 2:1 mixture of 1 and 2 within 1 h at 23° C. We also observed partial transformation of 1 to form 2 upon exposure to silica gel (2D-TLC analysis). From the data thus far it is clear that (−)-2 and (+)-1 readily interconvert under mild conditions. This suggests that it is possible that the observed biological activity of stephacidin B may be attributable to 2 formed from 1 in vivo. In theory, the converse may be true, though this seems less likely, simply upon consideration of concentration effects. Our results also leave open the possibility that stephacidin B is an artifact of the isolation of 2; the converse may be true instead, though this would appear to be less likely.

Finally, we have observed that solutions of 2 in pure methanol-d$_4$ rapidly (<10 min, 23° C.) form the diastereomeric products of 1,5-addition of methanol-d$_4$ (eq 2). The ratio of diastereomeric methanol-d$_4$ adducts was ~15:1 (stereochemistry not assigned). The ratio of these diastereomeric adducts combined to 2 remaining in solution suggests an equilibrium constant of 7.7 at 23° C., although this value must be regarded as tentative for we have not yet conducted the experiments to establish that a true equilibrium exists (the solution decomposed upon concentration). The value 7.7 is somewhat larger than the equilibrium constant we had measured for the model unsaturated nitrone previously prepared (K=2, 23° C.; the rate of methanol-d$_4$ addition was also faster: t$_{1/2}$<<10 min at 23° C. for 2 vs. t$_{1/2}$=5 h at 23° C. in the model system) (Myers et al. *J. Am. Chem. Soc.* 2003, 125, 12080; incorporated herein by reference), but these differences are not surprising given the structural differences between the two systems.

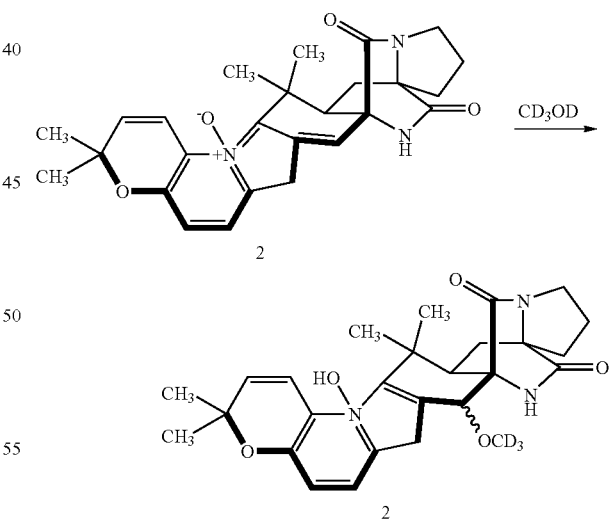

Experimentals:

General Experimental Procedures. All reactions were performed in single-neck, flame-dried, round-bottom flasks fitted with rubber septa under a positive pressure of argon, unless otherwise noted. Air- and moisture-sensitive liquids were transferred via syringe or stainless steel cannula. Where necessary (so noted), solutions were deoxygenated by successive freeze-pump-thaw cycles (≧3 iterations). Organic solutions were concentrated by rotary evaporation below 35° C. at 40 Torr (house vacuum). Analytical and preparative thin-layer chromatography (TLC) was performed using glass plates pre-coated with a 0.25-mm layer of silica gel impregnated with a fluorescent indicator (254 nm). TLC plates were visualized by exposure to ultraviolet light and/or submersion in aqueous ceric ammonium molybdate solution (CAM), acidic ethanolic p-anisaldehyde solution (anis), ethanolic phosphomolybdic acid (PMA), or solutions of ninhydrin in n-butanol, followed by brief heating on a hot plate (215° C., 10-15 s). Flash-column chromatography was performed as described by Still et al. (*J. Org. Chem.* 1978, 43, 2923; incorporated herein by reference), employing silica gel (60 Å, standard grade) purchased from Sorbent Technologies.

Materials. Commercial solvents and reagents were used as received with the following exceptions. Dichloromethane, tetrahydrofuran, methanol, and pyridine were purified by the method of Pangborn et al. (*Organometallics* 1996, 15, 1518; incorporated herein by reference) tert-Butyl benzene was distilled from calcium hydride at 760 Torr and was stored under argon. 1,1,1,3,3,3-Hexafluoro-2-propanol was purified by fractional distillation from 3-Å molecular sieves at 760 Torr and was stored under argon. Trimethylsilyl cyanide was distilled at 760 Torr and was stored under argon at −20° C. Trimethylsilyl chloride, triethylamine, N,N-diisopropylethylamine, and hexamethyldisilazane were distilled from calcium hydride at 760 Torr under an atmosphere of dinitrogen immediately prior to use. Isopropylsulfonyl chloride was distilled from phosphorous pentoxide at 40 Torr and was stored under argon at −20° C. Methanol-$d_4$ was distilled from calcium hydride at 760 Torr and was stored over 3-Å molecular sieves under argon. The molarity of n-butyllithium solutions was determined by titration against a standard solution of diphenylacetic acid in tetrahydrofuran (average of three determinations) (Kofron et al. *J. Org. Chem.* 1976, 41, 1879; incorporated herein by reference).

Instrumentation. Proton nuclear magnetic resonance spectra ($^1$H NMR) were recorded at 400, 500, or 600 MHz at 23° C., unless otherwise noted. Chemical shifts are expressed in parts per million (ppm, δ scale) downfield from tetramethylsilane and are referenced to residual protium in the NMR solvent (CHCl$_3$, δ 7.26; C$_6$HD$_5$, δ 7.15; CHD$_2$OD, δ 3.30; CHDCl$_2$, δ 5.33; (CHD$_2$)S(O)CD$_3$, δ 2.49, (CHD$_2$)C(O)CD$_3$, δ 2.05). Data are represented as follows: chemical shift, multiplicity (s=singlet, d=doublet, t=triplet, m=multiplet and/or multiple resonances, br=broad, app=apparent), integration, coupling constant in Hertz, and assignment. Carbon nuclear magnetic resonance spectra ($^{13}$C NMR) were recorded at 100 or 125 MHz at 23° C., unless otherwise noted. Chemical shifts are reported in parts per million downfield from tetramethylsilane and are referenced to the carbon resonances of the solvent (CDCl$_3$, δ 77.0; C$_6$D$_6$, δ 128.0; CD$_3$OD, δ 49.0; CD$_2$Cl$_2$, δ 52.5; (CD$_3$)S(O)CD$_3$, δ 39.5). Infrared (IR) spectra were obtained using a Perkin-Elmer FT-IR spectrometer referenced to a polystyrene standard. Data are represented as follows: frequency of absorption (cm$^{-1}$), intensity of absorption (vs=very strong, s=strong, m=medium, w=weak, br=broad). Optical rotations were determined using a JASCO DIP-370 digital polarimeter equipped with a sodium lamp source (589 nm). Reported readings are the average of seven measurements for each sample. High-resolution mass spectra were obtained at the Harvard University Mass Spectrometry Facility. Crystallographic analysis was performed at the Harvard University x-ray Crystallography Laboratory.

Synthetic Procedures.

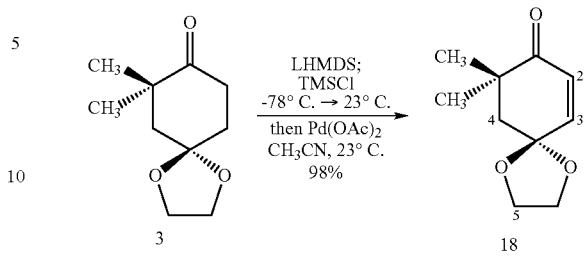

Small-Scale Oxidation of Ketone 3 (Enone 18)

A solution of n-butyllithium in hexanes (2.51 M, 3.05 mL, 7.65 mmol, 1.1 equiv) was added rapidly via syringe to a solution of hexamethyldisilazane (1.61 mL, 7.65 mmol, 1.1 equiv) in tetrahydrofuran (40 mL) at 0° C. After stirring at 0° C. for 15 min the reaction solution was cooled to −78° C. The cold solution was transferred via cannula to a stirring solution of 4,4-ethylenedioxy-2,2-dimethylcyclohexanone (Nelson et al. *Tetrahedron* 1991, 47, 3259; incorporated herein by reference) 3 (1.31 g, 6.95 mmol, 1 equiv) in tetrahydrofuran (20 mL) at −78° C. After 30 min, trimethylsilyl chloride (1.16 mL, 9.17 mmol, 1.32 equiv) was added rapidly to the cold reaction solution via syringe. Upon completion of the addition, the cooling bath was removed and the mixture was allowed to warm to 23° C. (~45 min). The product solution was then partitioned between ethyl acetate (50 mL) and saturated aqueous sodium bicarbonate solution (40 mL), the layers that formed were separated, and the aqueous layer was further extracted with two 50-mL portions of ethyl acetate. The combined organic layers were washed with saturated aqueous sodium chloride solution (10 mL) and the washed solution was dried over sodium sulfate. The dried solution was filtered and the filtrate was concentrated. The residue obtained was dissolved in acetonitrile (70 mL, 200-mL round-bottom flask containing a Teflon-coated stir bar) and the resulting solution was deoxygenated by alternately evacuating (5-10 s) and flushing the reaction flask with argon (3 iterations). Palladium acetate (1.87 g, 8.34 mmol, 1.2 equiv) was added in one portion, forming a red solution. The mixture was stirred for 2 days at 23° C. After this time, the reaction mixture was filtered through a pad of Celite eluting with ethyl acetate (125 mL). The filtrate was concentrated and the residue obtained was purified by flash-column chromatography (15% ethyl acetate-hexanes) to furnish the enone 18 as a clear, colorless oil (1.28 g, 98%).

R$_f$=0.18 (30% ethyl ether-hexanes). $^1$H NMR (400 MHz, C$_6$D$_6$), δ 6.06 (dd, 1H, J=10.4, 1.2 Hz, H$_3$), 5.83 (d, 1H, J=10.0 Hz, H$_2$), 3.39-3.30 (m, 4H, H$_5$), 1.93 (s, 2H, H$_4$), 1.20 (s, 6H, CH$_3$). $^{13}$C NMR (100 MHz, C$_6$D$_6$), δ 202.5, 143.8, 128.8, 103.9, 64.2, 46.1, 42.0, 26.3. IR (NaCl, thin film), cm$^{-1}$ 2966 (m), 2886 (m), 1683 (vs). HRMS-CI (m/z): [M+NH$_4$]$^+$ calcd for C$_{10}$H$_{18}$NO$_3$, 200.1287; found, 200.1279.

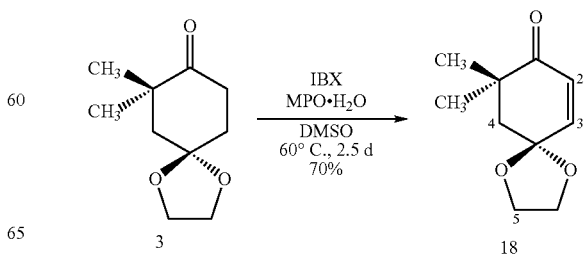

Large-Scale Oxidation of Ketone 3 (Enone 18)

4-Methoxypyridine N-oxide hydrate (34.8 g, 278 mmol, 3.5 equiv) was added in one portion to a suspension of 2-iodoxybenzoic acid (Frigerio et al. *J. Org. Chem.* 1999, 64, 4537; incorporated herein by reference) (IBX, 77.8 g, 278 mmol, 3.5 equiv) in dimethyl sulfoxide (278 mL) at 23° C. The resulting solution was stirred vigorously until it became homogeneous (~1 h), at which point 4,4-ethylenedioxy-2,2-dimethylcyclohexanone (Frigerio et al. *J. Org. Chem.* 1999, 64, 4537; incorporated herein by reference) 3 (15.0 g, 79.4 mmol, 1 equiv) was added via syringe. The reaction flask was placed in an oil bath preheated to 60° C. and the mixture was stirred at this temperature for 2.5 days. The reaction mixture was then allowed to cool to 23° C. and the cooled solution was diluted with 50% ethyl ether-hexanes (500 mL). The resulting suspension was filtered through a plug of Celite, eluting first with distilled water (1.5 L), then 50% ethyl ether-hexanes (1.0 L). The filtrate was transferred to a separatory funnel and the layers were separated. The aqueous layer was treated with saturated aqueous sodium carbonate solution (~50 mL) until all solids had dissolved. The homogeneous aqueous layer was then extracted with 50% ethyl ether-hexanes (1.5 L), and the combined organic layers were washed sequentially with saturated aqueous sodium bicarbonate solution (500 mL) and saturated aqueous sodium chloride solution (500 mL). The washed solution was dried over magnesium sulfate and the solids were filtered. The filtrate was concentrated and the residue obtained was purified by flash-column chromatography (10% ethyl acetate-hexanes) to furnish the enone 18 as a clear, colorless oil (10.4 g, 70%).

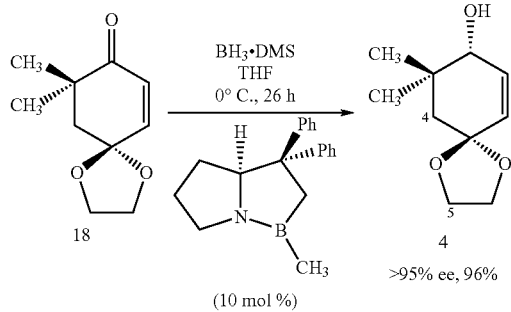

Enantioselective Reduction of Enone 18 (Alcohol 4)

A solution of (S)-1-methyl-3,3-diphenyl-hexahydropyrrolo[1,2-c][1,3,2]oxazaborole (Corey et al. *J. Am. Chem. Soc.* 1987, 109, 7925; incorporated herein by reference) in toluene (0.2 M, 12.3 mL, 2.46 mmol, 0.1 equiv) was added to a stirring solution of the enone 18 (4.60 g, 24.6 mmol, 1 equiv) in tetrahydrofuran (246 mL) at 23° C. The reaction solution was cooled to 0° C. and the cooled solution was treated with a solution of borane-methyl sulfide complex in tetrahydrofuran (2.0 M, 7.4 mL, 14.8 mmol, 0.60 equiv). After stirring at 0° C. for 26 h, the reaction solution was diluted with aqueous potassium phosphate buffer solution (pH 7.0, 0.05 M, 200 mL). The biphasic mixture produced was concentrated by rotary evaporation to ~300 mL total volume, and the concentrated biphasic mixture was then extracted with three 200-mL portions of ethyl acetate. The organic layers were combined and the resulting solution was washed with saturated aqueous sodium chloride solution (150 mL), then was dried over sodium sulfate. The dried solution was filtered and the filtrate was concentrated. The residue obtained was purified by flash-column chromatography (30% ethyl acetate-hexanes initially, grading to 40% ethyl acetate-hexanes) to give the alcohol 4, as a clear, colorless oil (4.47 g, >95% ee, 1-(R)-isomer (Dale et al. *J. Am. Chem. Soc.* 1983, 95, 512; Ohtani et al. *J. Am. Chem. Soc.* 1991, 113, 4092; each of which is incorporated herein by reference), 96%).

$R_f$=0.26 (40% ethyl acetate-hexanes). $^1$H NMR (500 MHz, CDCl$_3$), δ 5.81 (dd, 1H, J=10.0, 2.5 Hz, H$_3$), 5.58 (d×d, 1H, J=10.0, 1.5 Hz, H$_2$), 4.01-3.86 (m, 5H, H$_1$, H$_5$), 1.80 (dd, 1H, J=14.0, 1.5 Hz, H$_4$), 1.69 (d, 1H, J=14.0 Hz, H$_4$), 1.64 (d, 1H, J=8.0 Hz, OH), 1.03 (s, 3H, CH$_3$), 0.99 (s, 3H, CH$_3$). $^{13}$C NMR (100 MHz, CDCl$_3$), δ 133.8, 127.9, 105.2, 74.5, 64.9, 64.3, 44.8, 36.3, 27.8, 20.9. IR (NaCl, thin film), cm$^{-1}$ 3425 (br), 2952 (m), 2880 (m). HRMS-CI (m/z): [M+NH$_4$]$^+$ calcd for C$_{10}$H$_{20}$NO$_3$, 202.1443; found, 202.1447.

The enantiomeric excess and absolute configuration of 4 were determined by the modified Mosher method. The stereochemical outcome also conforms to that predicted by the Corey model for such reductions (Corey, E. J.; Helal, C. J. *Angew. Chem., Int. Ed. Engl.* 1998, 37, 1986; incorporated herein by reference).

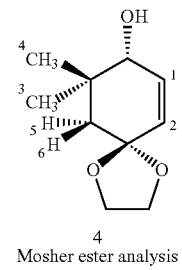

4
Mosher ester analysis

| H | Δδ (CDCl$_3$) |
|---|---|
| 1 | 0.0945 |
| 2 | 0.051 |
| 3 | −0.076 |
| 4 | −0.058 |
| 5 | −0.024 |
| 6 | 0.011 |

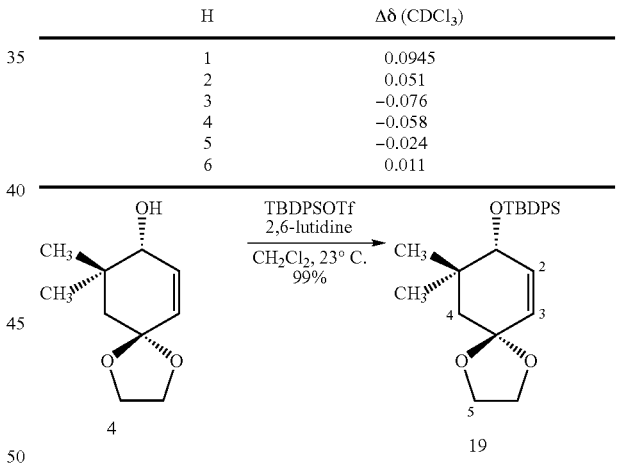

Silyl Ether 19

2,6-Lutidine (4.15 mL, 35.5 mmol, 1.5 equiv) and tert-butyldiphenylsilyl trifluoromethanesulfonate (Bassindale et al. *J. Organomet. Chem.* 1984, 271, C1; incorporated herein by reference) (10.6 g, 27.3 mmol, 1.15 equiv) were added in sequence to a stirring solution of the (R)-allylic alcohol 4 (4.47 g, 23.6 mmol, 1 equiv) in dichloromethane (14.7 mL) at 23° C. The mixture was stirred at 23° C. for 17 h, then was diluted with ethyl acetate (200 mL). The resulting solution was then washed sequentially with saturated aqueous sodium bicarbonate solution (20 mL) and saturated aqueous sodium chloride solution (20 mL). The washed solution was dried over sodium sulfate and the solids were filtered. The filtrate was then concentrated and the residue obtained was purified by flash-column chromatography (4% acetone-hexanes initially, grading to 8% acetone-hexanes) to give the silyl ether 19 as a viscous, colorless oil (9.88 g, 99%).

$R_f$=0.61 (20% ethyl acetate-hexanes). $^1$H NMR (500 MHz, CDCl$_3$), δ 7.71-7.67 (m, 4H, ArH), 7.44-7.36 (m, 6H, ArH), 5.56 (dd, 1H, J=10.0, 2.0 Hz, H$_3$), 5.37 (d, 1H, J=10.0 Hz, H$_2$), 3.99-3.84 (m, 5H, H$_1$, H$_5$), 1.81 (d, 1H, J=14.0, H$_4$), 1.60 (d, 1H, J=14.0 Hz, H$_4$), 1.21 (s, 3H, CH$_3$), 1.07 (s, 9H, SiC(CH$_3$)$_3$), 0.96 (s, 3H, CH$_3$). $^{13}$C NMR (100 MHz, CDCl$_3$), δ 136.3, 136.2, 134.8, 134.6, 133.6, 130.0, 129.7, 127.9, 127.7, 126.5, 105.3, 76.2, 64.9, 64.1, 45.1, 37.3, 28.3, 27.2, 21.4, 19.9. IR (NaCl, thin film), cm$^{-1}$ 2942 (m), 2860 (m). HRMS-CI (m/z): [M+H]$^+$ calcd for C$_{26}$H$_{35}$O$_3$Si, 423.2355; found, 423.2361.

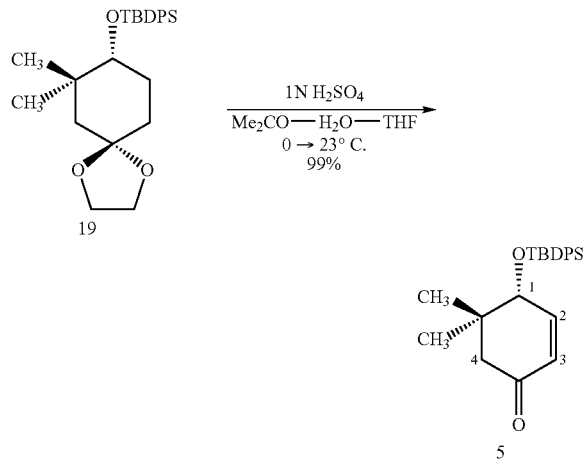

Deprotection of 19 (Enone 5)

Acetone (80 mL) and 1 N aqueous sulfuric acid solution (80 mL) were added in sequence to a stirring solution of the acetal 19 (9.88 g, 23.4 mmol, 1 equiv) in tetrahydrofuran (80 mL) at 0° C. Upon completion of the addition, the cooling bath was removed and the reaction solution was allowed to warm to 23° C. After 3.5 h, saturated aqueous sodium bicarbonate solution (100 mL) was added and the layers that formed were separated. The aqueous layer was then extracted with two 200-mL portions of ethyl acetate. The combined organic layers were washed with saturated aqueous sodium chloride solution (100 mL), then dried over sodium sulfate. The solids were filtered and the filtrate was concentrated to afford the enone 5 as a clear, colorless oil (8.91 g, 99%).

$R_f$=0.42 (10% acetone-hexanes). $^1$H NMR (400 MHz, C$_6$D$_6$), δ 7.70-7.67 (m, 2H, ArH), 7.66-7.63 (m, 2H, ArH), 7.18-7.14 (m, 6H, ArH), 6.28 (dd, 1H, J=10.4, 2.8 Hz, H$_2$), 5.63 (d, 1H, J=10.4 Hz, H$_3$), 4.09 (app t, 1H, J=2.0 Hz, H$_1$), 2.15 (d, 1H, J=15.0 Hz, H$_4$), 1.64 (d, 1H, J=15.0 Hz, H$_4$), 1.07 (s, 9H, SiC(CH$_3$)$_3$), 0.97 (s, 3H, CH$_3$), 0.72 (s, 3H, CH$_3$). $^{13}$C NMR (125 MHz, C$_6$D$_6$), δ 196.7, 149.3, 136.2, 136.1, 134.3, 133.1, 130.2, 130.1, 128.7, 128.1, 127.8, 76.2, 50.1, 40.0, 27.6, 27.0, 20.5, 19.6. IR (NaCl, thin film), cm$^{-1}$ 2943 (m), 2861 (m), 1682 (s). HRMS-CI (m/z): [M+H]$^+$ calcd for C$_{24}$H$_{31}$O$_2$Si, 379.2093; found, 379.2094.

Synthesis of Electrophile 6 (Step 1)

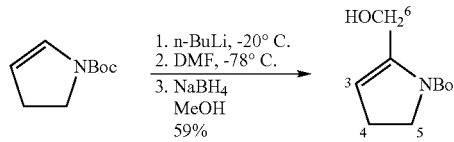

N-(tert-Butoxycarbonyl)-2-Hydroxymethyl-4,5-Dihydropyrrole

A solution of n-butyllithium in hexanes (2.43 M, 27.6 mL, 67.0 mmol, 1.10 equiv) was added dropwise via syringe to a stirred solution of N-(tert-butoxycarbonyl)-2,3-dihydropyrrole (Oliveira et al. *J. Org. Chem.* 1999, 64, 6646; incorporated herein by reference) (10.3 g, 60.9 mmol, 1 equiv) in tetrahydrofuran (300 mL) at −20° C. The reaction mixture was stirred at −20° C. for 3 h, then was cooled to −78° C. The cold solution was then transferred via cannula over 25 min to a separate flask containing a stirred solution of N,N-dimethylformamide (DMF, 7.10 mL, 91.4 mmol, 1.5 equiv) in tetrahydrofuran (30 mL) at −78° C. The reaction mixture was stirred at −78° C. for 30 min, then was transferred rapidly via cannula to a vigorously stirred solution of saturated aqueous ammonium chloride (500 mL) at 23° C. Upon completion of the addition the layers that formed were separated. The aqueous layer was then extracted with two 750-mL portions of ethyl acetate. The combined organic layers were washed sequentially with saturated aqueous sodium bicarbonate solution (300 mL) and saturated aqueous sodium chloride solution (300 mL). The washed solution was dried over sodium sulfate and the solids were filtered. The filtrate was concentrated. The residue obtained was dissolved in methanol (300 mL, 1-L round-bottom flask containing a Teflon-coated stir bar). The resulting solution was cooled to 0° C. and sodium borohydride (2.53 g, 67.0 mmol, 1.1 equiv) was added in one portion (gas evolution was observed). The mixture was stirred for 35 min at 0° C. The product solution was then slowly poured into a solution of saturated aqueous ammonium chloride (200 mL), and the biphasic mixture was diluted with water (50 mL). The layers were separated and the aqueous layer was extracted with two 500-mL portions of ethyl acetate. The combined organic layers were washed with saturated aqueous sodium bicarbonate solution (120 mL) and hexanes (500 mL) was added. The product solution was washed with saturated aqueous sodium chloride solution (200 mL) and the washed solution was dried over sodium sulfate. The dried solution was filtered and the filtrate was concentrated. The residue obtained was purified by flash-column chromatography (20% ethyl acetate-hexanes initially, grading to 30% ethyl acetate-hexanes) to furnish N-(tert-butoxycarbonyl)-2-hydroxymethyl-4,5-dihydropyrrole as a pale yellow oil (6.75 g, 59%).

$R_f$=0.36 (25% ethyl acetate-hexanes). $^1$H NMR (400 MHz, C$_6$D$_6$), δ 4.78 (br t, 1H, J=6.4 Hz, OH), 4.59 (s, 1H, H$_3$), 4.34 (d, 2H, J=7.6 Hz, H$_6$), 3.29 (t, 2H, J=8.8 Hz, H$_5$), 1.93 (t, 2H, J=8.4 Hz, H$_4$), 1.33 (s, 9H, C(CH$_3$)$_3$). $^{13}$C NMR (100 MHz, C$_6$D$_6$), δ 153.2, 143.9, 108.8, 80.2, 58.1, 47.7, 28.1, 26.9. IR (NaCl, thin film), cm$^{-1}$ 3446 (m, br), 2964 (m), 2923 (m), 2851 (m), 1682 (s), 1451 (s). HRMS-CI (m/z): [M+H]$^+$ calcd for C$_{10}$H$_{18}$NO$_3$, 200.1286; found, 200.1280.

Synthesis of Electrophile 6 (Step 2)

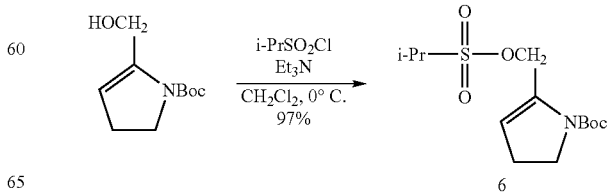

Sulfonate Ester 6

Isopropylsulfonyl chloride (2.07 mL, 18.5 mmol, 1.1 equiv) was added dropwise via syringe to a stirred solution of N-(tert-butoxycarbonyl)-2-hydroxymethyl-4,5-dihydropyrrole (3.34 g, 16.8 mmol, 1 equiv) and triethylamine (2.58 mL, 18.5 mmol, 1.1 equiv) in dichloromethane (42.0 mL) at 0° C. The reaction mixture was stirred at 0° C. for 35 min, then was diluted with hexanes (50 mL). The cooling bath was removed and the product solution was allowed to warm to 23° C. The product solution was then filtered through a 1.5-cm pad of silica gel, eluting with 10% acetone-hexanes (300 mL). The filtrate was concentrated, furnishing the crude isopropylsulfonate 6 as a clear, colorless oil (4.99 g, 97%). The sulfonate ester 6 was found to be unstable towards storage or purification (significant decomposition within one week at −20° C.; decomposition upon exposure to silica gel), and therefore was used directly in the following reaction.

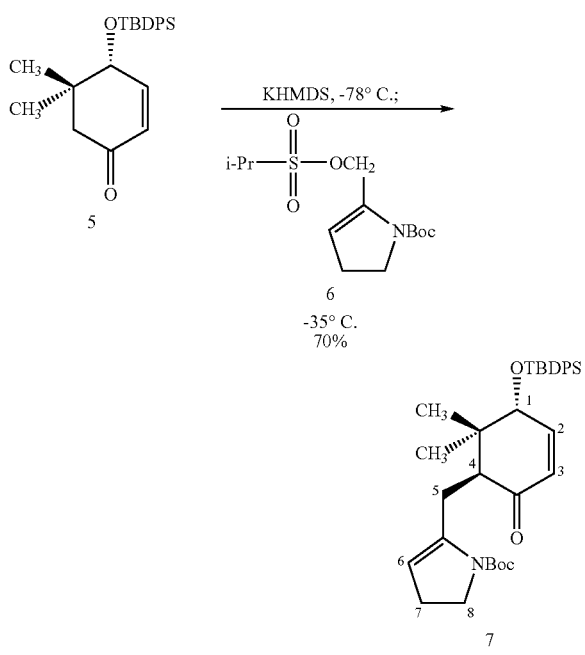

Alkylation of Ketone 5 (Alkylation Product 7)

A solution of potassium N,N-bis(trimethylsilyl)amide in toluene (0.50 M, 24.7 mL, 12.3 mmol, 1.1 equiv) was added dropwise via syringe to a stirred solution of the enone 5 (4.24 g, 11.2 mmol, 1 equiv, dried by azeotropic distillation with toluene, 3 mL) in tetrahydrofuran (31.3 mL) at −78° C. and the reaction solution was stirred at −78° C. for 30 min. A solution of the isopropyl sulfonate ester 6 (4.99 g, 16.2 mmol, 1.45 equiv, prepared immediately prior to use, dried by azeotropic distillation with toluene, 3 mL) in tetrahydrofuran (3.0 mL) was then added dropwise via cannula to the cold reaction solution. The flask containing the sulfonate ester 6 was rinsed with two 3.0-mL portions of tetrahydrofuran, which were transferred to the reaction flask via cannula. Upon completion of the addition, the reaction flask was immersed in a −35° C. bath and the reaction solution was stirred at this temperature 30 h. The product solution was then partitioned between saturated aqueous sodium bicarbonate solution (100 mL) and ethyl acetate (200 mL). The layers were separated, and the organic layer was washed with saturated aqueous sodium chloride solution (100 ml). The washed solution was dried over sodium sulfate. The dried solution was filtered and the filtrate was concentrated. The residue obtained was purified by flash-column chromatography on silica gel (deactivated with 10% triethylamine-ethyl acetate, eluting with 10% ethyl ether-hexanes initially, grading to 20% ethyl ether-hexanes, 5%-steps) to furnish the alkylation product 7 as a white foam (4.37 g, 70%).

$R_f$=0.31 (10% ethyl acetate-hexanes). $^1$H NMR (400 MHz, 60° C., $C_6D_6$), δ 7.77-7.71 (m, 4H, ArH), 7.25-7.18 (m, 6H, ArH), 6.28 (dd, 1H, J=10.2, 3.0 Hz, $H_2$), 5.68 (d, 1H, J=10.4 Hz, $H_3$), 4.58 (s, 1H, $H_6$), 4.09 (s, 1H, $H_1$), 3.66-3.53 (m, 2H, $H_8$), 3.18 (d, 1H, J=14 Hz, $H_5$), 3.00 (dd, 1H, J=10.4, 3.6 Hz, $H_4$), 2.61 (t, 1H, J=8.8 Hz, $H_5$), 2.03 (t, 2H, J=8.8 Hz, $H_7$), 1.41 (s, 9H, $NCO_2C(CH_3)_3$), 1.23 (s, 3H, $CH_3$), 1.35 (s, 9H, $SiC(CH_3)_3$), 1.07 (s, 3H, $CH_3$). $^{13}$C NMR (100 MHz, 60° C., $C_6D_6$), δ 199.7, 152.4, 146.3, 143.0, 136.4, 136.3, 134.7, 133.5, 130.3, 130.1, 128.2, 127.9, 127.7, 108.2, 79.2, 75.1, 56.6, 48.7, 42.8, 28.6, 27.3, 26.9, 25.9, 24.0, 23.4, 19.8. IR (NaCl, thin film), cm$^{-1}$ 2933 (m), 1692 (vs), 1400 (s). HRMS-CI (m/z): [M+H]$^+$ calcd for $C_{34}H_{46}NO_4Si$, 560.3196; found, 560.3193.

Note: That the alkylation product 7 possesses the 4-(S)-stereochemistry is supported by the observation of an NOE (500 MHz, 60° C., $C_6D_6$, mixing time=1.0 s) between proton HI and the protons of the $C_5$ methylene group (5.93, 0.99%).

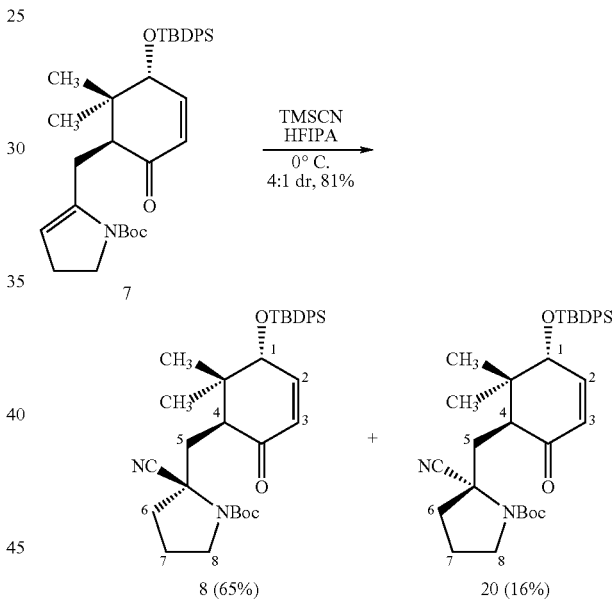

Addition of Hydrogen Cyanide to Alkylation Product 7 (Nitrile 8)

Trimethylsilyl cyanide (409 μL, 3.89 mmol, 3.0 equiv) was added dropwise via syringe to a stirred solution of the alkylation product 7 (725 mg, 1.29 mmol, 1 equiv, dried by two successive azeotropic distillations with toluene, 3 mL, 1 mL) in 1,1,1,3,3,3-hexafluoro-2-propanol (2.58 mL) at 0° C. The bright yellow mixture was stirred at 0° C. for 4 days. Hexanes (50 mL) and aqueous potassium hydroxide solution (2.2 M, 14 mL) were added to the product solution. The layers were separated and the organic layer was washed with water (20 mL), then brine (67% saturated, 18 mL). The washed solution was dried over sodium sulfate. The solids were filtered and the filtrate was concentrated. The residue obtained was purified by flash-column chromatography on silica gel (5% acetone-hexanes) to furnish separately the pure nitrile diastereomers 8 (higher $R_f$ diastereomer, a clear, colorless oil, 487 mg, 65%), and 20, (lower $R_f$ diastereomer, a clear, colorless oil, 116 mg, 16%).

Major Diastereomer (8).

$R_f$=0.34 (20% acetone-hexanes). $^1$H NMR (400 MHz, 70° C., $C_6D_6$), δ 7.80-7.76 (m, 2H, ArH), 7.75-7.73 (m, 2H, ArH), 7.26-7.21 (m, 6H, ArH), 6.19 (dd, 1H, J=10.6, 4.6 Hz, $H_2$), 5.71 (d, 1H, J=10.4 Hz, $H_3$), 4.00 (d, 1H, J=4.8 Hz, $H_1$), 3.28 (br m, 1H, $H_8$), 3.12 (m, 1H, $H_8$), 3.04 (d, 1H, J=7.2 Hz, $H_4$), 2.62 (br s, 1H, $H_5$), 2.20-2.10 (m, 2H, $H_5$, $H_6$), 2.03 (m, 1H, $H_6$), 1.58-1.41 (m, 14H, $NCO_2C(CH_3)_3$, 2×$H_7$, $CH_3$), 1.17 (s, 9H, $SiC(CH_3)_3$), 0.68 (s, 3H, $CH_3$). $^{13}$C NMR (100 MHz, $C_6D_6$, ~1:1 mixture of carbamate rotamers, * denotes second rotamer), δ 200.1, 199.7*, 153.3, 153.0*, 145.8, 145.6*, 136.4, 136.4*. 136.3, 136.3*, 134.5, 134.4*, 133.3, 133.3*, 130.4, 130.4*, 130.1, 130.1*, 128.6, 128.6*, 128.1, 127.9*, 127.7, 127.7*, 121.1, 120.7*, 81.1, 80.1*, 74.2, 74.2*, 61.6, 60.5*, 50.6, 50.6*, 47.9, 47.9*, 42.8, 42.8*, 37.9, 37.9*, 30.4, 29.3*, 28.6, 28.4*, 27.3, 27.3*, 24.8, 22.9*, 22.3, 22.2, 22.0*, 21.9*, 19.8, 19.8*. IR (NaCl, thin film), cm$^{-1}$ 2967 (m), 2279 (w), 1699 (vs), 1384 (s). HRMS-CI (m/z): [M+H]$^+$ calcd for $C_{35}H_{47}N_2O_4Si$, 587.3305; found, 587.3301.

Minor Diastereomer (20).

$R_f$=0.30 (20% acetone-hexanes). $^1$H NMR (500 MHz, 75° C., $C_6D_6$), δ 7.76-7.74 (m, 2H, ArH), 7.70-7.67 (m, 2H, ArH), 7.26-7.18 (m, 6H, ArH), 6.19 (dd, 1H, J=9.8, 4.0 Hz, $H_2$), 5.72 (d, 1H, J=9.5 Hz, $H_3$), 3.94 (br, 1H, $H_1$), 3.46 (br, 1H, $H_8$), 3.22 (m, 1H, $H_8$), 2.92 (br, 1H, J=7.2 Hz, $H_4$), 2.54 (br, 1H, $H_5$), 2.34 (br, 1H, $H_5$), 2.16 (m, 1H, $H_6$), 2.01 (m, 1H, $H_6$), 1.54-1.50 (m, 10H, $NCO_2C(CH_3)_3$, $H_7$), 1.32 (br, 1H, $H_7$), 1.71 (s, 3H, $CH_3$), 1.13 (s, 9H, $SiC(CH_3)_3$), 0.59 (s, 3H, $CH_3$). $^{13}$C NMR (100 MHz, $C_6D_6$, ~2:1 mixture of carbamate rotamers, * denotes second rotamer), δ 200.2, 199.6*, 153.5, 153.5*, 145.0, 145.0*, 136.4, 136.4*, 136.3, 136.3*, 134.4, 134.3*, 133.2, 133.2*, 130.4, 130.4*, 130.2, 130.2*, 128.9, 128.9*, 128.1, 128.1*, 127.9, 127.9*, 121.1, 121.1*, 81.5, 80.1*, 74.5, 74.5*, 60.1, 59.6*, 50.2, 48.9*, 48.7, 48.7*, 42.8, 42.8*, 38.5, 37.7*, 31.3*, 29.9, 28.4, 28.4*, 27.2, 27.2*, 25.1, 23.2*, 22.7, 22.2*, 21.6, 21.6*, 19.8, 19.8*. IR (NaCl, thin film), cm$^{-1}$ 2967 (m), 2279 (w), 1702 (vs), 1376 (s). HRMS-CI (m/z): [M+H]$^+$ calcd for $C_{35}H_{47}N_2O_4Si$, 587.3305; found, 587.3304.

Epimerization of Nitrile 8 (Nitrile 21)

A solution of potassium N,N-bis(trimethylsilyl)amide in toluene (0.5 M, 6.0 mL, 3.0 mmol, 3.6 equiv) was added dropwise via syringe to a stirred solution of the nitrile 8 (487 mg, 831 μmol, 1 equiv, dried by azeotropic distillation with toluene, 2×2 mL) in tetrahydrofuran (648 μL) at −78° C. Upon completion of the addition, the cooling bath was removed and the reaction flask was placed in a 23° C. water bath (the temperature of the bath was maintained by adding warm water). The mixture was stirred at 23° C. for 17 min and then was cooled to −78° C. A solution of pivalic acid in tetrahydrofuran (1.0 M, 3.32 mL, 3.32 mmol, 4.0 equiv) was added to the cold reaction solution dropwise via syringe. Upon completion of the addition, the reaction solution was stirred at −78° C. for 5 min and then the reaction flask was removed from the cooling bath. The reaction solution was allowed to warm to 23° C. over 10 min. The product solution was then diluted with ethyl acetate (100 mL) and the diluted solution was washed sequentially with saturated aqueous sodium bicarbonate solution (20 mL) and saturated aqueous sodium chloride solution (20 mL). The washed solution was dried over sodium sulfate and the solids were filtered. The filtrate was concentrated. The residue obtained was purified by flash-column chromatography on silica gel (5% acetone-hexanes initially, grading to 10% acetone-hexanes) to furnish the nitrile 21 as a clear, colorless oil (425 mg, 88%).

$R_f$=0.21 (15% acetone-hexanes). $^1$H NMR (400 MHz, 70° C., $C_6D_6$), δ 7.74-7.69 (m, 4H, ArH), 7.23-7.20 (m, 6H, ArH), 6.39 (d, 1H, J=10.4 Hz, $H_2$), 5.69 (d, 1H, J=10.0 Hz, $H_3$), 4.50 (s, 1H, $H_1$), 3.33 (br, 1H, $H_8$), 3.02 (m, 1H, $H_8$), 2.76 (dd, 1H, J=13.8, 7.0 Hz, $H_5$), 2.41 (br, 1H, $H_4$), 2.04-1.98 (m, 2H, $H_5$, $H_6$), 1.68 (m, 1H, $H_6$), 1.44 (s, 9H, $NCO_2C(CH_3)_3$), 1.33 (m, 1H, $H_7$), 1.23 (m, 1H, $H_7$), 1.19 (s, 3H, $CH_3$), 1.12 (s, 9H, $SiC(CH_3)_3$), 0.88 (s, 3H, $CH_3$). $^{13}$C NMR (100 MHz, $C_6D_6$, ~1:1 mixture of carbamate rotamers, * denotes second rotamer), δ 198.7, 197.5*, 153.4, 153.4*, 148.7, 148.7*, 136.3, 136.3*, 136.2, 136.2*, 134.3, 134.3*, 132.7, 132.7*, 130.5, 130.5*, 130.2, 130.2*, 128.6, 128.6*, 128.1, 128.1*, 127.9, 127.9*, 120.9, 120.9*, 81.6, 80.0*, 78.0, 78.0*, 60.1, 59.6*, 52.9, 52.9*, 48.3, 48.3*, 46.0, 46.0*, 39.1, 38.7*, 31.0, 31.0*, 28.3, 28.3*, 27.1, 27.1*, 25.8, 25.8*, 22.8, 22.2*, 19.8, 19.8*, 15.4, 15.4*. IR (NaCl, thin film), cm$^{-1}$ 2960 (m), 2277 (w), 1698 (vs), 1382 (s). HRMS-CI (m/z): [M+H]$^+$ calcd for $C_{35}H_{47}N_2O_4Si$, 587.3305; found, 587.3306.

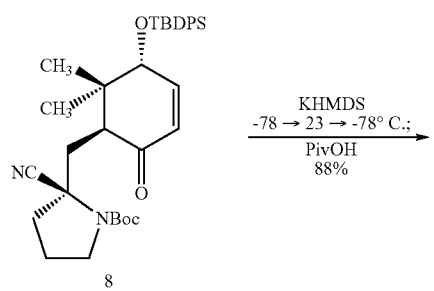

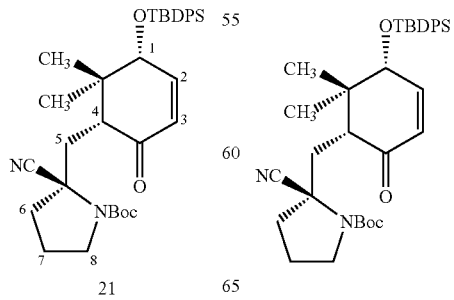

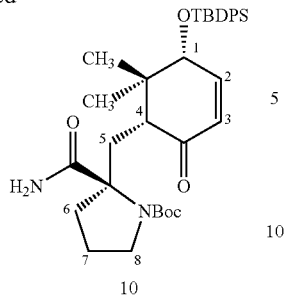

10

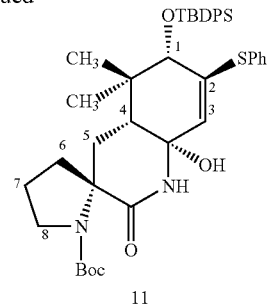

11

Hydrolysis of Nitrile 21 (Amide 10)

Platinum catalyst 9 (Ghaffar et al. *Tetrahedron Lett.* 1995, 36, 8657; Ghaffar et al. *J. Mol. Catal. A* 2000, 160, 249; each of which is incorporated herein by reference) (62.2 mg, 145 μmol, 0.2 equiv) was added in one portion to a stirred solution of the nitrile 21 (425 mg, 725 μmol, 1 equiv) in a mixture of ethanol (1.16 mL) and water (290 μL) at 23° C. The reaction flask was placed in an oil bath preheated to 70° C. The reaction solution was stirred at 70° C. for 1 h, then was allowed to cool to 23° C. The product solution was then filtered through a short column containing a layer of sodium sulfate on top of a layer of silica gel (each 2.5 cm deep), eluting with ethyl acetate (300 mL). The eluent was concentrated. The residue obtained was purified by flash-column chromatography on silica gel (20% acetone-hexanes initially, grading to 30% acetone-hexanes), furnishing the amide 10 as a white foam (374 mg, 85%).

$R_f$=0.20 (30% acetone-hexanes). $^1$H NMR (500 MHz, 75° C., $C_6D_6$), δ 7.77-7.74 (m, 2H, ArH), 7.72-7.70 (m, 2H, ArH), 7.23-7.20 (m, 6H, ArH), 6.36 (dd, 1H, J=10.3, 1.0 Hz, $H_2$), 5.73 (dd, 1H, J=10.3, 2.3 Hz, $H_3$), 5.60 (br, 2H, $NH_2$), 4.54 (app t, 1H, J=2.3 Hz, $H_1$), 3.39 (br, 1H, $H_8$), 3.27 (m, 1H, $H_8$), 2.98 (br, 1H, $H_5$), 2.51 (d, 1H, J=7.0 Hz, $H_4$), 2.32 (br, 1H, $H_6$), 2.25 (d, 1H, J=14.0 Hz, $H_5$), 1.72 (m, 1H, $H_6$), 1.50 (m, 1H, $H_7$), 1.40 (m, 10H, $NCO_2C(CH_3)_3$, $H_7$), 1.28 (s, 3H, $CH_3$), 1.13 (s, 9H, $SiC(CH_3)_3$), 0.98 (s, 3H, $CH_3$). $^{13}$C NMR (100 MHz, $C_6D_6$, ~3:1 mixture of carbamate rotamers, * denotes minor rotamer), δ 200.1*, 199.7, 177.3*, 176.5, 155.1, 154.0*, 148.4*, 147.7, 136.3, 136.3*, 136.2, 136.2*, 134.5, 135.4*, 133.1, 132.8*, 130.3, 130.3*, 130.1, 130.1*, 128.9, 128.9*, 128.1, 128.1*, 127.9, 127.9*, 80.2*, 79.4, 79.4*, 78.3, 70.7, 69.3*, 53.7, 53.7*, 49.4, 49.4*, 46.6*, 46.5, 38.9*, 37.4, 28.5, 28.5*, 28.3, 27.1, 27.1*, 27.0*, 26.2, 26.2*, 22.6, 22.6*, 19.8, 19.8*, 15.7, 15.7*. IR (NaCl, thin film), cm$^{-1}$ 3347 (br), 2969 (m), 1685 (vs), 1387 (s). HRMS-CI (m/z): $[M+H]^+$ calcd for $C_{35}H_{49}N_2O_5Si$, 605.3411; found, 605.3416.

Cyclization of Amide 10 (Hemiaminal 11)

Triethylamine (863 μL, 6.19 mmol, 10.0 equiv) and thiophenol (318 μL, 3.10 mmol, 5.0 equiv) were added in sequence to a stirred solution of the amide 10 (374 mg, 619 μmol, 1 equiv) in tetrahydrofuran (3.10 mL) at 23° C. The flask was fitted with an air condenser and the reaction mixture was heated to 70° C. for 3.5 h. The solution was allowed to cool to 23° C. and ethyl acetate (50 mL) and aqueous sulfuric acid solution (1N, 6.2 mL) were added. The layers were separated and the organic layer was washed sequentially with 10% aqueous sodium hydroxide solution (2×5 mL), aqueous potassium phosphate buffer (pH 7.0, 0.05 M, 20 mL), and saturated aqueous sodium chloride solution (10 mL). The washed solution was dried over sodium sulfate. The solids were filtered and the filtrate was concentrated. The residue obtained was purified by flash-column chromatography on silica gel (15% acetone-hexanes initially, grading to 20% acetone-hexanes) to furnish the hemiaminal 11 as a white foam (421 mg, 95%).

$R_f$=0.41 (30% acetone-hexanes). $^1$H NMR (400 MHz, $C_6D_6$), δ 8.04-8.01 (m, 2H, ArH), 7.96-7.92 (m, 2H, ArH), 7.33-7.15 (m, 6H, ArH), 7.07 (dd, 2H, J=8.4, 1.0 Hz, SPh), 6.97 (t, 2H, J=7.6 Hz, SPh), 6.88 (t, 1H, J=7.6 Hz, SPh), 5.44 (s, 1H, NH), 5.43 (s, 1H, OH), 3.89 (app td, 1H, J=11.5, 3.8 Hz, $H_2$), 3.63 (d, 1H, J=11.2 Hz, $H_1$), 3.40 (m, 1H, $H_8$), 3.31 (m, 1H, $H_8$), 2.53 (app t, 1H, J=13.6 Hz, $H_5$), 2.07 (m, 1H, $H_6$), 1.90 (dd, 1H, J=13.4, 3.8 Hz, $H_3$), 1.51 (m, 1H, $H_7$), 1.43-1.23 (m, 24H, $CH_3$, $H_5$, $NCO_2C(CH_3)_3$, $H_7$, $H_6$, SiC$(CH_3)_3$), 1.16 (dd, 1H, J=13, 2.6 Hz, $H_3$), 1.09 (dd, 1H, J=13.6, 3.2 Hz, $H_4$), 1.02 (s, 3H, $CH_3$). $^{13}$C NMR (100 MHz, $C_6D_6$), δ 172.9, 155.2, 136.8, 136.4, 136.1, 135.3, 135.2, 129.7, 129.6, 129.2, 128.9, 127.9, 127.4, 125.8, 82.3, 80.6, 80.1, 64.8, 48.5, 46.4, 45.8, 45.0, 40.8, 38.7, 31.1, 28.4, 28.0, 27.9, 23.8, 20.8, 15.5. IR (NaCl, thin film), cm$^{-1}$ 2360 (w), 2279 (w), 1666 (vs), 1404 (s). HRMS-CI (m/z): $[M-OH]^+$ calcd for $C_{41}H_{53}N_2O_4SSi$, 697.3495; found, 697.3501.

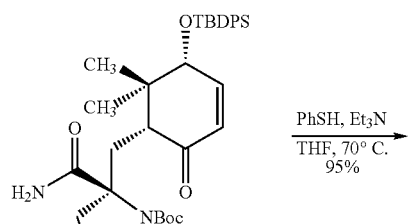

10

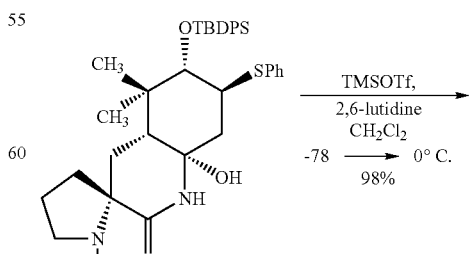

11

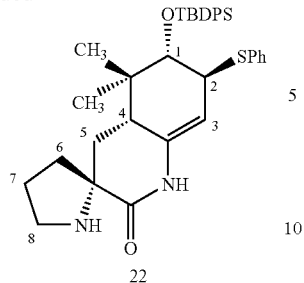

Dehydration and Deprotection of 11 (Enamide 22)

2,6-Lutidine (502 µL, 3.40 mmol, 10.0 equiv) and trimethylsilyl trifluoromethanesulfonate (308 µL, 1.70 mmol, 5.0 equiv) were added in sequence to a stirred solution of the hemiaminal 11 (243 mg, 340 µmol, 1 equiv, dried by azeotropic distillation with toluene, 1 mL) in dichloromethane (8.5 mL) at −78° C. The mixture was stirred at −78° C. for 20 min, then the reaction flask was immersed in an ice bath and the cooled solution was stirred vigorously for 20 min. The product solution was then diluted with saturated aqueous sodium bicarbonate solution (10 mL), ethyl acetate (50 mL), and hexanes (5 mL). The cooling bath was removed and the biphasic mixture was allowed to warm to 23° C. The layers were separated and the organic layer was washed with water (10 mL) and saturated aqueous sodium chloride solution (10 mL). The washed solution was dried over sodium sulfate and the solids were filtered. The filtrate was concentrated. The residue obtained was purified by flash-column chromatography on silica gel (3% methanol-dichloromethane initially, grading to 4% methanol-dichloromethane) to furnish the enamide 22 as a white solid (199 mg, 98%).

$R_f$=0.35 (10% methanol-dichloromethane). $^1$H NMR (500 MHz, 23° C., $C_6D_6$), δ 7.98-7.95 (m, 2H, ArH), 7.93-7.90 (m, 2H, ArH), 7.80 (br, 1H, CONH), 7.30-7.18 (m, 8H, ArH, SPh), 6.93 (m, 2H, SPh), 6.86 (m, 1H, SPh), 4.72 (br, 1H, H-3), 3.83 (m, 1H, $H_2$), 3.74 (d, 1H, J=8.0 Hz, $H_1$), 3.20 (m, 1H, $H_8$), 2.77 (m, 1H, $H_8$), 1.81-1.29 (m, 6H, $H_4$, 2×$H_5$, 2×$H_6$, $H_7$), 1.22 (s, 9H, SiC($CH_3$)$_3$), 1.02 (m, 7H, 2×$CH_3$, $H_7$). $^{13}$C NMR (100 MHz, $C_6D_6$), δ 173.6, 136.8, 136.5, 134.8, 134.7, 134.5, 134.4, 133.0, 129.8, 129.6, 128.6, 128.1, 127.9, 127.0, 103.7, 80.5, 64.8, 51.1, 47.5, 40.3, 40.1, 37.1, 33.5, 27.8, 26.4, 25.4, 20.4, 14.4. IR (NaCl, thin film), cm$^{-1}$ 3057 (w), 2931 (m), 2856 (m), 1676 (vs). HRMS-CI (m/z): [M+H]$^+$ calcd for $C_{36}H_{45}N_2O_2SSi$, 597.2971; found, 597.2979.

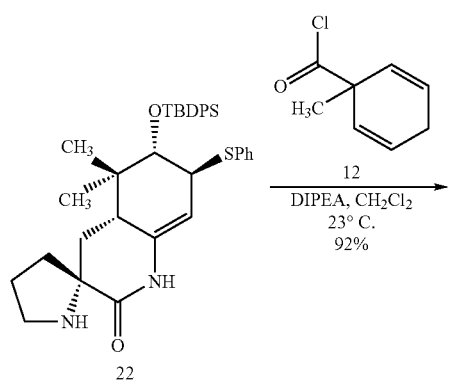

Acylation of 22 (Amide 13)

A solution of 1-methyl-2,5-cyclohexadienecarbonyl chloride (Jackson et al. *Chem. Commun.* 2000, 2327; Bella et al. *Org. Biomol. Chem.* 2004, 2, 421; each of which is incorporated herein by reference) 12 in dichloromethane (2.0 M, 751 µL, 1.5 mmol, 4.5 equiv) was added dropwise via syringe to a stirred solution of the enamide 22 (199 mg, 334 µmol, 1 equiv, dried by azeotropic distillation with toluene, 1 mL) and N,N-diisopropylethylamine (350 µL, 2.0 mmol, 6.0 equiv) in dichloromethane (835 µL) at 23° C. The mixture was stirred at 23° C. for 24 h, then was diluted with ethyl acetate (50 mL). The product solution was washed sequentially with aqueous sulfuric acid solution (1N, 5 mL), saturated aqueous sodium bicarbonate solution (10 mL) and saturated aqueous sodium chloride solution (10 mL). The washed solution was dried over sodium sulfate, the solids were filtered, and the filtrate was concentrated. The residue obtained was purified by flash-column chromatography on silica gel (15% acetone-hexanes initially, grading to 20% acetone-hexanes) to give the amide 13 as a white foam (220 mg, 92%).

$R_f$=0.57 (10% methanol-dichloromethane). $^1$H NMR (500 MHz, $C_6D_6$), δ 7.98-7.96 (m, 2H, ArH), 7.91-7.89 (m, 2H, ArH), 7.56 (s, 1H, NH), 7.29-7.16 (m, 6H, ArH), 6.97-6.90 (m, 3H, SPh), 6.84 (dd, 2H, J=8.2, 1.7 Hz, SPh), 5.86 (dd, 1H, J=9.7, 2.0 Hz, Hg), 5.59 (dd, H J=10.5, 2.0 Hz, Hs), 5.46 (m, 2H, $H_{10}$), 4.56 (app t, 1H, J=2.5 Hz, $H_3$), 3.89 (dt, J=8.5, 2.5 Hz, $H_2$), 3.77-3.73 (m, 2H, $H_1$, $H_8$), 3.45 (m, 1H, $H_8$), 2.99 (app t, 1H, J=13.5 Hz, Hs), 2.34 (br d, 1H, J=23.0 Hz, $H_{11}$), 2.20 (br d, 1H, J=23.0 Hz, $H_{11}$), 1.70-1.60 (m, 3H, $H_4$, $H_6$, $H_7$), 1.52 (s, 3H, $CH_3$), 1.32-1.26 (m, 2H, $H_5$, $H_6$), 1.83 (s, 9H, SiC($CH_3$)$_3$), 1.29 (s, 3H, $CH_3$), 1.07-1.03 (m, 4H, $CH_3$, $H_7$). $^{13}$C NMR (100 MHz, $C_6D_6$), δ 171.2, 170.4, 136.8, 136.4, 135.4, 134.9, 134.8, 134.6, 131.5, 130.1, 129.8, 129.4, 128.7, 128.1, 127.9, 127.6, 126.3, 123.8, 123.5, 102.4, 80.3, 67.0, 50.6, 48.5, 45.6, 40.4, 39.9, 36.4, 30.3, 28.4, 27.8, 26.1, 25.6, 24.5, 20.5, 14.7. IR (NaCl, thin film), cm$^{-1}$ 3253 (w), 2966 (m), 2859 (m), 1682 (vs), 1629 (s), 1384 (s). HRMS-CI (m/z): [M+H]$^+$ calcd for $C_{44}H_{53}N_2O_3SSi$, 717.3546; found, 717.3545.

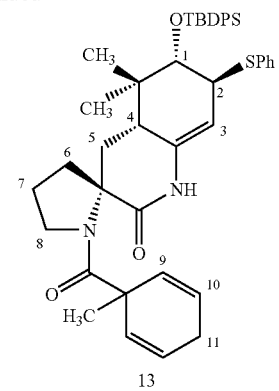

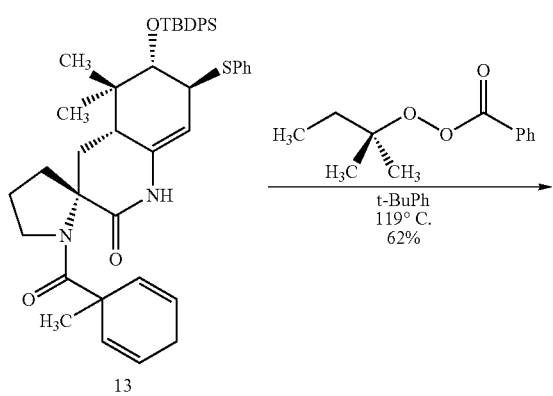

13

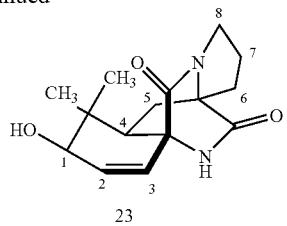

14

Cyclization of Amide 13 (Tetracyclic Diketopiperazine 14)

A solution of the amide 13 (144 mg, 201 μmol, 1 equiv) and tert-amylperoxy benzoate (165 μL, 804 μmol, 4.0 equiv) in tert-butyl benzene (40.2 mL) was degassed by four freeze-pump-thaw cycles and the degassed solution was warmed in a preheated oil bath (119° C.). The mixture was stirred at 119° C. for 75 min, then was rapidly cooled by immersing the flask in a 23° C. water bath (with stirring). The cooled solution was then loaded onto a column of silica gel. tert-Butyl benzene was eluted with hexanes, then the tetracyclic diketopiperazine product 14 was eluted using 20% acetone-hexanes. The product 14 was obtained as a clear, colorless oil (63.6 mg, 62%). The column fractions eluting between tert-butyl benzene and the product 14 contained peroxides and were pooled and stirred with saturated aqueous sodium thiosulfate solution before disposal.

$R_f$=0.16 (30% acetone-hexanes). $^1$H NMR (500 MHz, $C_6D_6$), δ 7.82-7.77 (m, 4H, ArH), 7.25-7.21 (m, 6H, ArH), 5.89 (dd, 1H, J=10.5, 1.5 Hz, $H_2$), 5.50 (dd, 1H, J=10.5, 2.4 Hz, $H_3$), 5.02 (s, 1H, NH), 3.97 (app t, 1H, J=2.0 Hz, $H_1$), 3.28 (m, 1H, $H_8$), 2.91 (m, 1H, $H_8$), 2.61 (m, 1H, $H_6$), 1.50-1.05 (m, 18H, $H_4$, 2×$H_5$, $H_6$, 2×$H_7$, $CH_3$, $SiC(CH_3)_3$), 0.74 (s, 3H, $CH_3$). $^{13}$C NMR (100 MHz, $C_6D_6$), δ 172.7, 167.9, 136.6, 136.5, 136.4, 134.6, 133.5, 130.2, 130.1, 128.1, 127.9, 123.2, 78.5, 67.1, 60.9, 50.7, 43.8, 39.4, 32.7, 29.4, 27.2, 24.9, 24.5, 19.8, 14.1. IR (NaCl, thin film), cm$^{-1}$ 3231 (w), 2958 (m), 2858 (m), 1694 (vs). HRMS-CI (m/z): [M+H]$^+$ calcd for $C_{31}H_{39}N_2O_3Si$, 515.2730; found, 515.2730.

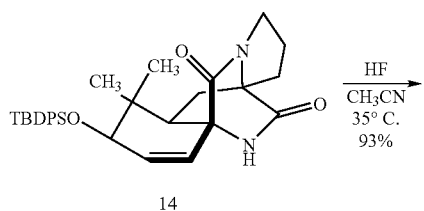

14

Deprotection of Tetracyclic Diketopiperazine 14 (Alcohol 23)

Aqueous hydrogen fluoride solution (48%, 500 μL) was added to a polypropylene reaction flask containing a stirred solution of the silyl ether 14 (53.2 mg, 103 μmol, 1 equiv) in acetonitrile (500 μL). The mixture was warmed to 35° C. for 33 h, then was allowed to cool to 23° C. The product solution was then treated with saturated aqueous dipotassiunm hydrogenphosphate solution (2 mL), solid dipotassium hydrogenphosphate (2 g), and distilled water (5 mL), forming a turbid solution. The aqueous solution was extracted with four 20-mL portions of 50% ethyl acetate-hexanes. The combined organic layers were dried over sodium sulfate and the solids were filtered. The filtrate was concentrated. The residue obtained was purified by flash-column chromatography (5% methanol-dichloromethane initially, grading to 7.5% methanol-dichloromethane) providing the alcohol 23 as a white foam (26.4 mg, 93%).

$R_f$=0.24 (70% acetone-hexanes). $^1$H NMR (500 MHz, CDCl$_3$), δ 6.35 (s, 1H, NH) 6.06 (dd, 1H, J=10.5, 2.0 Hz, $H_2$), 5.84 (dd, 1H, J=10.5, 2.5 Hz, $H_3$), 4.05 (br, 1H, $H_1$), 3.59 (m, 1H, $H_8$), 3.43 (m, 1H, $H_8$), 2.77 (m, 1H, $H_6$), 2.23 (dd, 1H, J=10.0, 7.5 Hz, $H_4$), 2.15 (dd, 1H, J=13.0, 10.0 Hz, Hs), 2.04 (m, 1H, $H_7$), 1.96 (m, 1H, $H_7$), 1.83-1.72 (m, 2H, Hs, $H_6$), 1.00 (s, 3H, $CH_3$), 0.79 (s, 3H, $CH_3$). $^{13}$C NMR (100 MHz, CDCl$_3$), δ 173.1, 168.6, 138.1, 122.8, 76.7, 67.7, 61.3, 51.5, 42.3, 38.8, 32.6, 30.0, 24.9, 24.8, 13.3. IR (NaCl, thin film), cm$^{-1}$ 3409 (br), 3230 (br), 2956 (w), 1687 (vs). HRMS-CI (mt/z): [M+H]$^+$ calcd for $C_{15}H_{21}N_2O_3$, 277.1552; found, 277.1556.

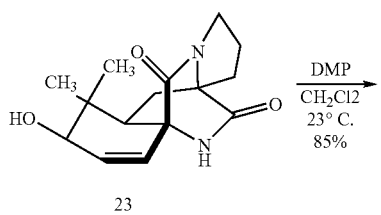

23

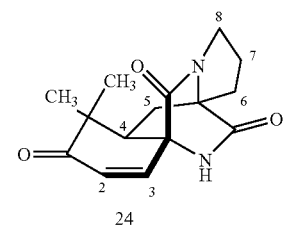

24

Oxidation of Alcohol 23 (Enone 24)

1,1,1-Triacetoxy-1,1-dihydro-1,2-benziodoxol-3(1H)-one (Dess et al. *J. Am. Chem. Soc.* 1991, 113, 7277; Meyer et al. *J. Org. Chem.* 1994, 59, 7549; each of which is incorporated herein by reference) (DMP, 63.5 mg, 150 μmol, 2.14 equiv) was added in one portion to a stirred solution of the alcohol 23 (19.3 mg, 69.9 μmol, 1 equiv) in dichloromethane (3.50 mL) at 23° C. The reaction solution was stirred at 23° C. for 40 min, then was diluted with ethyl acetate (10 mL), water (2.8 mL), saturated aqueous sodium thiosulfate solution (2.8 mL), and saturated aqueous sodium bicarbonate solution (1.4 mL). The resulting biphasic mixture was stirred vigorously until both layers were clear and colorless (~5 min). The layers were separated and the aqueous layer was extracted with two 20-mL portions of ethyl acetate. The combined organic layers were dried over sodium sulfate and filtered. The filtrate was concentrated. The residue obtained was purified by flash-column chromatography on silica gel (3→5% methanol/dichloromethane) to give the enone 24 as a clear, colorless oil (16.2 mg, 85%).

$R_f$=0.41 (7.5% methanol-dichloromethane). $^1$H NMR (500 MHz, CDCl$_3$), δ 7.34 (br, 1H, NH), 6.84 (d, 1H, J=10.5 Hz, H$_3$), 6.28 (d, 1H, J=10.5 Hz, H$_2$), 3.61 (m, 1H, H$_8$), 3.45 (m, 1H, H$_8$), 2.78 (m, 1H, H$_6$), 2.65 (dd, 1H, J=10.3, 7.5 Hz, H$_4$), 2.19 (dd, 1H, J=13.3, 10.3 Hz, H$_5$), 2.09-1.99 (m, 2H, H$_7$), 1.89-1.81 (m, 2H, H$_5$, H$_6$), 1.09 (s, 3H, CH$_3$), 1.02 (s, 3H, CH$_3$). $^{13}$C NMR (100 MHz, CDCl$_3$), δ 201.8, 173.2, 167.4, 140.5, 132.4, 67.7, 61.2, 51.6, 45.2, 44.6, 32.4, 29.5, 24.9, 22.8, 18.6. IR (NaCl, thin film), cm$^{-1}$ 3229 (br), 2974 (w), 2882 (w), 1683 (s), 1407 (m). HRMS-CI (Qni/z): [M+H]$^+$ calcd for C$_{15}$H$_{19}$N$_2$O$_3$, 275.1395; found, 275.1401.

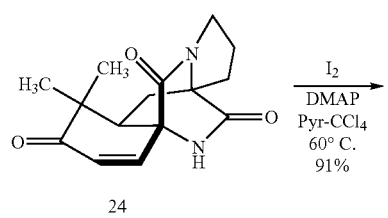

Iodination of Enone 24 (α-Iodoenone 15)

Iodine (41.4 mg, 163 μmol, 3.0 equiv) and 4-(dimethylamino)pyridine (19.9 mg, 163 μmol, 3.0 equiv) were added to a stirred solution of the enone 24 (14.9 mg, 54.3 μmol, 1 equiv) in a mixture of carbon tetrachloride (68 μL) and pyridine (68 μL). The dark reaction solution was heated to 60° C. for 10 h with protection from exposure to light. After cooling to 23° C., the product solution was partitioned between 50% ethyl acetate-hexanes (10 mL) and saturated aqueous sodium thiosulfate solution (5 mL). The layers were separated and the aqueous layer was extracted with three 10-mL portions of 50% ethyl acetate-hexanes. The combined organic layers were dried over sodium sulfate, the solids were filtered, and the filtrate was concentrated. The residue obtained was purified by flash-column chromatography (2% methanol-dichloromethane) to give the α-iodoenone 15 as a white amorphous solid (20.0 mg, 91%).

$R_f$=0.37 (5% methanol-dichloromethane). $^1$H NMR (500 MHz, CDCl$_3$), δ 7.65 (s, 1H, H$_3$), 6.85 (br, 1H, NH), 3.62 (m, 1H, H$_8$), 3.46 (m, 1H, H$_8$), 2.80 (m, 1H, H$_6$), 2.71 (dd, 1H, J=12.7, 8.0 Hz, H$_4$), 2.21 (dd, 1H, J=16.5, 13.0 Hz, H$_5$), 2.13-1.95 (m, 2H, H$_7$), 1.89-1.78 (m, 2H, H$_5$, H$_6$), 1.16 (s, 3H, CH$_3$), 1.05 (s, 3H, CH$_3$). $^{13}$C NMR (100 MHz, CDCl$_3$), δ 195.3, 172.3, 166.5, 149.0, 109.8, 67.8, 63.5, 51.5, 45.0, 44.6, 32.5, 29.5, 24.9, 23.9, 18.9. IR (NaCl, thin film), cm$^{-1}$ 3216 (br), 2975 (w), 1686 (s). HRMS-CI (m/z): [M+H]$^+$ calcd for C$_{15}$H$_{18}$IN$_2$O$_3$, 401.0362; found, 401.0365.

Synthesis of the Iodoarene Coupling Partner 17 (Step 1)

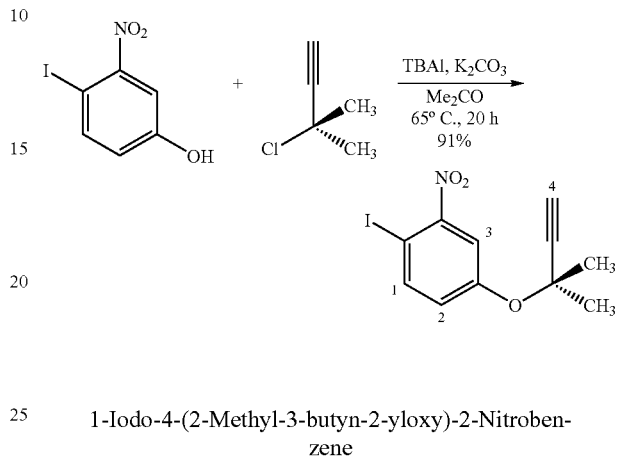

1-Iodo-4-(2-Methyl-3-butyn-2-yloxy)-2-Nitrobenzene

3-Chloro-3-methyl-1-butyne (640 μL, 5.7 mmol, 3.0 equiv) was added to a stirred solution of 4-iodo-3-nitrophenol (500 mg, 1.89 mmol, 1 equiv), tetrabutylammonium iodide (2.10 g, 5.7 mmol, 3.0 equiv), and potassium carbonate (522 mg, 3.8 mmol, 2.0 equiv) in acetone (5.2 mL) at 23° C. The reaction mixture was warmed to 65° C. and was heated at this temperature for 18 h. The product solution was allowed to cool to 23° C., then was diluted with ethyl acetate (50 mL). The diluted product solution was washed with saturated aqueous sodium bicarbonate solution (5 mL) and saturated aqueous sodium chloride solution (5 mL). After washing, the organic layer was dried over sodium sulfate and the solids were filtered. The filtrate was concentrated. The residue obtained was dissolved in ethyl acetate (10 mL) and the resulting solution was filtered through a pad of Celite, eluting with ethyl acetate (50 mL). The eluent was concentrated and the residue obtained was purified by flash-column chromatography (4% acetone-hexanes) to furnish 1-iodo-4-(2-methyl-3-butyn-2-yloxy)-2-nitrobenzene as a pale yellow oil (569 mg, 91%).

$R_f$=0.55 (20% ethyl acetate-hexanes). $^1$H NMR (400 MHz, CDCl$_3$), δ 7.88 (d, 1H, J=8.8 Hz, H$_1$), 7.78 (d, 1H, J=2.8 Hz, H$_3$), 7.14 (dd, 1H, J=8.8, 2.8 Hz, H$_2$), 2.67 (s, 1H, H$_4$), 1.68 (s, 6H, CH$_3$). $^{13}$C NMR (100 MHz, CDCl$_3$), δ156.6, 153.3, 142.0, 126.1, 117.8, 84.6, 77.1, 75.9, 73.7, 29.6. IR (NaCl, thin film), cm$^{-1}$ 3290 (m), 2991 (w), 1532 (s). HRMS-EI (m/z): [M]$^+$ calcd for C$_{11}$H$_{10}$INO$_3$, 330.9706; found, 330.9706.

Synthesis of the Iodoarene Coupling Partner 17 (Step 2)

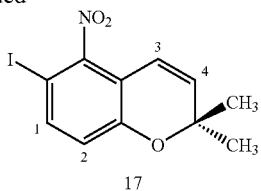

Iodoarene 17

A solution of 1-iodo-4-(2-methyl-3-butyn-2-yloxy)-2-nitrobenzene (526 mg, 1.59 mmol, 1 equiv) and 2,6-di-tert-butyl-4-methylphenol (BHT, 17.6 mg, 79.4 µmol, 0.05 equiv) in m-xylene (15.8 mL) was heated to 140° C. for 15 h, then was allowed to cool to 23° C. The cooled product solution was loaded onto a pad of silica gel (5-cm), eluting with hexanes (discarded), then 20% ethyl acetate-hexanes. The eluent was concentrated and the residue obtained was purified by flash-column chromatography (2% ethyl acetate-hexanes) to furnish the iodoarene 17 (409 mg, 78%) as a pale yellow oil. Note: $^1$H NMR data were in agreement with those reported from a preparation of 17 by a longer sequence (Sun et al. *Synthesis* 1997, 1249; incorporated herein by reference).

$R_f$=0.44 (10% ethyl acetate-hexanes). $^1$H NMR (500 MHz, CDCl$_3$), δ 7.54 (d, 1H, J=9.0 Hz, H$_1$), 6.67 (d, 1H, J=9.0 Hz, H$_2$), 6.18 (d, 1H, J=9.5 Hz, H$_4$), 5.79 (d, 1H, J=10.0 Hz, H$_3$), 1.45 (s, 6H, CH$_3$). $^{13}$C NMR (100 MHz, CDCl$_3$), δ 154.0, 145.1, 139.5, 134.9, 120.4, 116.0, 115.6, 77.5, 73.3, 28.1. IR (NaCl, thin film), cm$^{-1}$ 2976 (m), 1533 (s), 1456 (m), 1355 (m). HRMS-EI (m/z): [M]$^+$ calcd for C$_{11}$H$_{10}$INO$_3$, 330.9706; found, 330.9706.

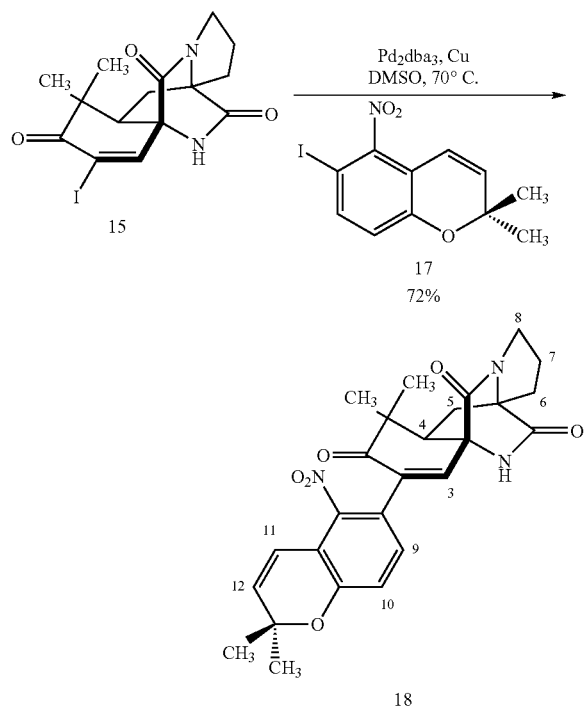

Palladium-Mediated Coupling of 15 and 10 (α-2-nitroarylenone 18)

Iodoarene 17 (11.8 mg, 35.6 µmol, 2.50 equiv), copper powder (40 mesh, 4.6 mg, 71 µmol, 5.0 equiv), and tris(dibenzylideneacetone)dipalladium (1.3 mg, 1.4 µmol, 0.10 equiv) were added in sequence to a solution of the α-iodoenone 15 (5.7 mg, 14.2 µmol, 1 equiv) in dimethyl sulfoxide (71 µL). The reaction solution was heated at 70° C. for 2 h. The product solution was allowed to cool to 23° C., then was partitioned between dichloromethane (20 mL) and aqueous ammonium hydroxide solution (30%, 10 mL). The mixture was shaken vigorously until the organic layer became clear. The layers were then separated and the aqueous layer was extracted with five 20-mL portions of dichloromethane. The combined organic layers were dried over sodium sulfate. The solution was filtered and the filtrate was concentrated. The residue obtained was purified by flash-column chromatography (2% methanol-dichloromethane), to afford the α-2-nitroarylenone 18 as a pale yellow oil (4.9 mg, 72%).

$R_f$=0.17 (40% acetone-hexanes). $^1$H NMR (500 MHz, CDCl$_3$), δ 7.13 (d, 1H, J=8.5 Hz, H$_9$), 6.97 (d, 1H, J=8.5 Hz, H$_{10}$), 6.82 (s, 1H, H$_3$), 6.49 (d, 1H, J=10.5 Hz, H$_{12}$), 6.33 (br, 1H, NH), 5.84 (d, 1H, J=10.0 Hz, H$_{11}$), 3.64 (m, 1H, H$_8$), 3.48 (m, 1H, H$_8$), 2.85-2.77 (m, 2H, H$_4$, H$_6$), 2.25 (dd, 1H, J=13.3, 10.0 Hz, H$_5$), 2.11-1.97 (m, 2H, 2×H$_7$), 1.91-1.84 (m, 2H, H$_5$, H$_6$) 1.48 (s, 3H, CH$_3$), 1.47 (s, 3H, CH$_3$), 1.12 (s, 3H, CH$_3$), 1.08 (s, 3H, CH$_3$). $^{13}$C NMR (100 MHz, CDCl$_3$), δ 199.1, 172.5, 167.3, 154.6, 146.7, 140.6, 137.6, 134.6, 131.3, 122.4, 119.8, 117.1, 115.1, 77.3, 67.8, 61.1, 51.1, 45.2, 44.6, 32.5, 29.6, 28.1, 28.0, 24.8, 23.3, 18.6. IR (NaCl, thin film), cm$^{-1}$ 3199 (w), 2974 (w), 1688 (s), 1530 (s). HRMS-CI (m/z): [M+H]$^+$ calcd for C$_{26}$H$_{28}$N$_3$O$_6$, 478.1978; found, 478.1981.

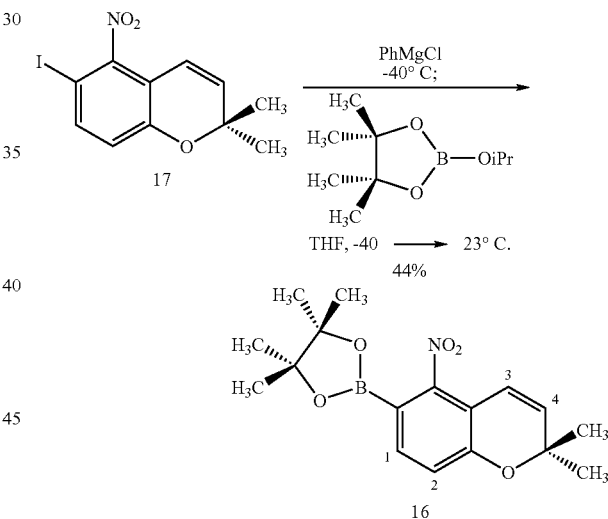

Pinacol Boronic Ester 16

Phenyl magnesium chloride (2.0 M in THF, 605 µL, 1.21 mmol, 1.10 equiv) was added dropwise to a stirred solution of the iodoarene 17 (365 mg, 1.10 mmol, 1 equiv) in tetrahydrofuran (11.0 mL) at −40° C. The solution was stirred at −40° C. for 10 min, then was treated with 2-isopropoxy-4,4,5,5-tetramethyl-1,3,2-dioxaborolane (370 µL, 1.81 mmol, 1.65 equiv) via syringe. Upon completion of the addition, the cooling bath was removed and the reaction solution was allowed to warm to 23° C. over 30 min. The product solution was poured into 50% ether-hexanes (50 mL) and the layers that formed were separated. The organic layer was washed with water (20 mL) and saturated aqueous sodium chloride solution (20 mL). The washed solution was dried over sodium sulfate. The solids were filtered and the filtrate was concentrated. The residue obtained was purified by flash-column chromatography (5% ethyl acetate-hexanes initially, grading to 10% ethyl acetate-hexanes) to give the boronic ester 16 as a viscous brown oil (160 mg, 44%).

$R_f$=0.55 (20% ethyl acetate-hexanes). $^1$H NMR (400 MHz, CDCl$_3$), δ 7.44 (d, 1H, J=8.0 Hz, H$_1$), 6.93 (d, 1H, J=8.0 Hz, H$_2$), 6.49 (d, 1H, J=10.0 Hz, H$_4$), 5.81 (d, 1H, J=10.0 Hz, H$_3$), 1.45 (s, 6H, CH$_3$), 1.32 (s, 12H, CH$_3$). $^{13}$C NMR (100 MHz, CDCl$_3$), δ 156.0, 151.8, 135.1, 134.2, 119.4, 116.8, 114.2, 84.6, 77.0, 28.0, 24.8. IR (NaCl, thin film), cm$^{-1}$ 2977 (m), 1606 (m), 1534 (s). HRMS-CI (m/z): [M+NH$_4$]$^+$ calcd for C$_{17}$H$_{26}$BN$_2$O$_5$, 349.1935; found, 349.1938.

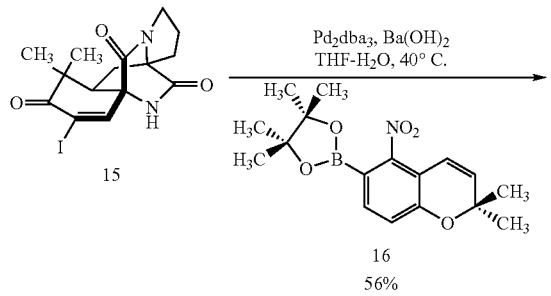

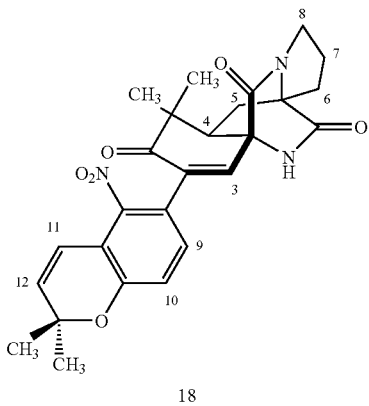

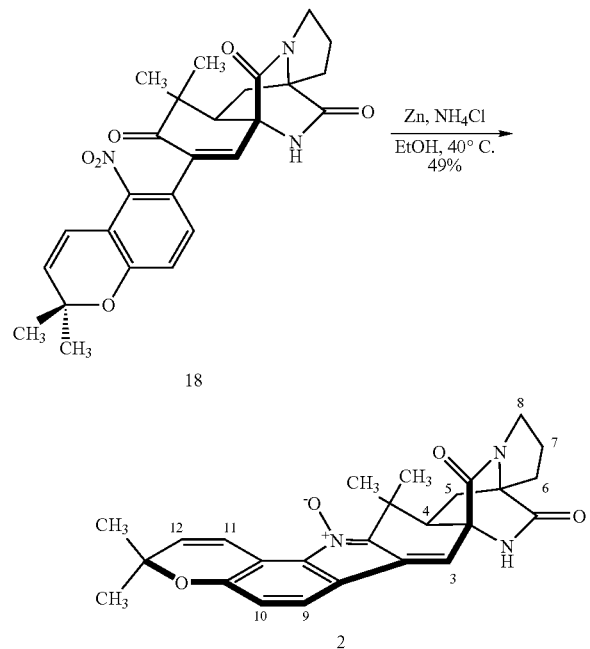

Palladium-Mediated Coupling of 15 and 16 (α-2-nitroarylenone 18)

Barium hydroxide (10.9 mg, 34.5 μmol, 3.0 equiv), 2-(di-t-butylphosphino)-biphenyl (3.2 mg, 10.7 μmol, 0.93 equiv), tris(dibenzylideneacetone)dipalladium (4.2 mg, 4.6 μmol, 0.40 equiv), and the pinacol boronate ester 16 (7.6 mg, 23.0 μmol, 2.0 equiv) were added in sequence to a solution of the α-iodoenone 15 (4.6 mg, 11.5 μmol, 1 equiv) in tetrahydrofuran (1.2 mL) and water (300 μL) at 23° C. The mixture was warmed to 40° C. for 3 h, then was allowed to cool to 23° C. The product solution was filtered through a pad of Celite, eluting with ethyl acetate (20 mL). The eluent was washed with water (5 mL), then brine (5 mL). The washed solution was dried over sodium sulfate and the solids were filtered. The filtrate was concentrated and the residue obtained was purified by flash-column chromatography (30% acetone-hexanes initially, grading to 40% acetone-hexanes) to afford the α-2-nitroarylenone 18 as a pale yellow oil (3.1 mg, 56%).

Unsaturated Nitrone 2

A stock suspension of activated zinc powder was prepared according to the procedure of Knochel and Rao (Knochel et al. Tetrahedron 1993, 49, 29; incorporated herein by reference) by heating a mixture of commercial zinc powder (100 mesh, 330 mg, 4.56 mmol) and 1,2-dibromoethane (85.6 μL, 456 μmol, 0.10 equiv based on zinc) in tetrahydrofuran (3.0 mL) to a vigorous boil, then cooling to 23° C. The boiling-cooling cycle was repeated three times,[15] then chlorotrimethylsilane (23.2 μL, 183 μmol, 0.04 equiv based on zinc) was injected into the cooled (23° C.) suspension. In a separate flask, a mixture of α-2-nitroarylenone 18 (3.8 mg, 7.9 μmol, 1 equiv), aqueous ammonium chloride solution (1.0 M, 17.5 μL, 17.5 μmol, 2.2 equiv), and ethanol (395 μL) was heated to 40° C. and the warmed solution was treated with a 10-μL aliquot of the stock solution of activated zinc powder (prepared <20 min prior to use). The reaction mixture was stirred at 40° C. Two additional 10-μL aliquots of the zinc suspension were added at 15-min intervals. The product solution was then cooled to 23° C. and filtered through a pad of silica gel, eluting with 5% methanol-dichloromethane. The eluent was concentrated and the residue obtained was purified by flash-column chromatography (2% methanol-dichloromethane) to afford the unsaturated nitrone 2 as a yellow solid (1.7 mg, 49%).

Figure 3:
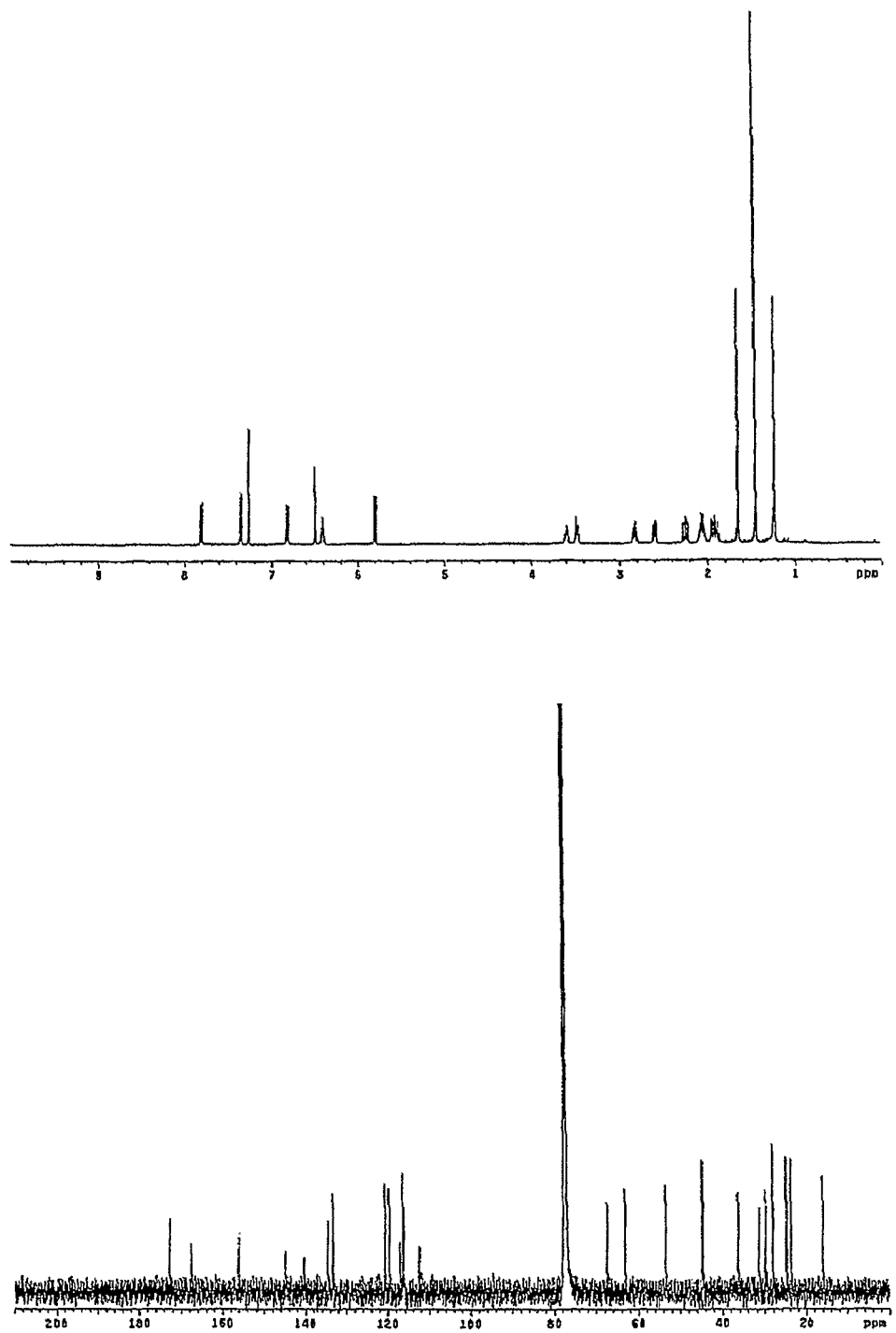
FIG. 3 includes $^1$H (500 MHz) and $^{13}$C (100 MHz) NMR of synthetic avrainvillamide (2) in CDCl$_3$.

$R_f$=0.21 (5% methanol-dichloromethane). $^1$H NMR (500 MHz, CDCl$_3$), δ 7.81 (d, 1H, J=10.0 Hz, H$_{11}$), 7.36 (d, 1H, J=8.0 Hz, H$_9$), 6.82 (d, 1H, J=8.0 Hz, H$_{10}$), 6.49 (s, 1H, H$_3$), 6.41 (br, 1H, NH), 5.80 (d, 1H, J=10.0 Hz, H$_{12}$), 3.58 (m, 1H, H$_8$), 3.47 (m, 1H, H$_8$), 2.81 (m, 1H, H$_6$), 2.60 (dd, 1H, J=10.2, 6.7 Hz, H$_4$), 2.25 (dd, 1H, J=13.5, 10.2 Hz, H$_5$), 2.10-1.99 (m, 2H, H$_7$), 1.96-1.86 (m, 2H, Hs, H$_6$), 1.66, (s, 3H, CH$_3$), 1.46 (s, 6H, CH$_3$), 1.24 (s, 3H, CH$_3$). $^{13}$C NMR (100 MHz, CDCl$_3$), δ 172.6, 167.4, 155.9, 144.7, 140.2, 134.5, 133.2, 120.5, 119.6, 117.0, 116.3, 116.2, 112.3, 77.1, 67.3, 63.1, 53.4, 44.7, 36.3, 31.3, 29.6, 28.1, 28.0, 24.8, 23.7, 15.9. IR (NaCl, thin film), cm$^{-1}$ 3208 (w), 2922 (w), 1707 (s), 1692 (s) HRMS-CI (m/z): [M+H]$^+$ calcd for C$_{26}$H$_{28}$N$_3$O$_4$, 446.2080; found, 446.2076. [α]$_D^{25}$: −35.1 (c 0.1, CHCl$_3$). See FIG. 3 for the actual NMR spectra of avrainvillamide (2).

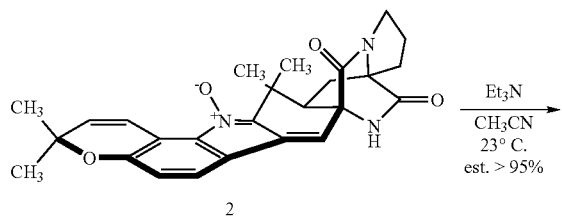

Figure 4A:
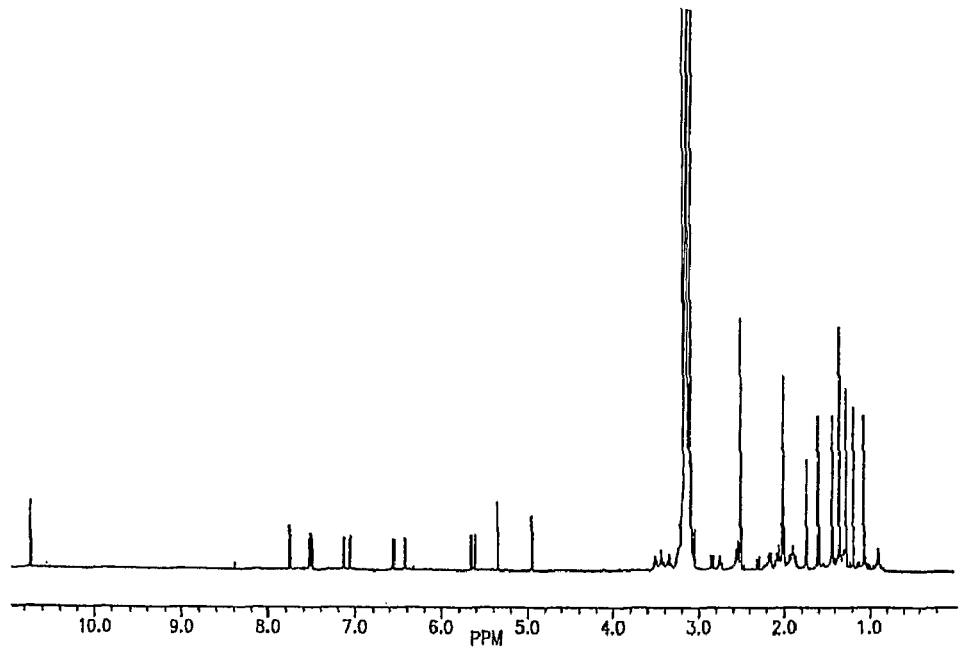
FIG. 4 includes a $^1$H NMR spectra of authentic stephacidin B (500 MHz, 50% $d_6$-DMSO-CD$_3$CN) from Qian-Cutrone et al., U.S. Pat. No. 6,291,461, issued Sep. 18, 2001, incorporated herein by reference) (FIG. 4A), of synthetic stephacidin B (500 MHz, 50% $d_6$-DMSO-CD$_3$CN) (FIG. 4B), and of synthetic stephacidin B (500 MHz, 50% $d_6$-DMSO-CD$_3$CN) with an expansion of the peaks at approximately 7.5 ppm (FIG. 4C). The chemical shifts at approximately 7.5 ppm vary slightly between synthetic samples.
Figure 4B:
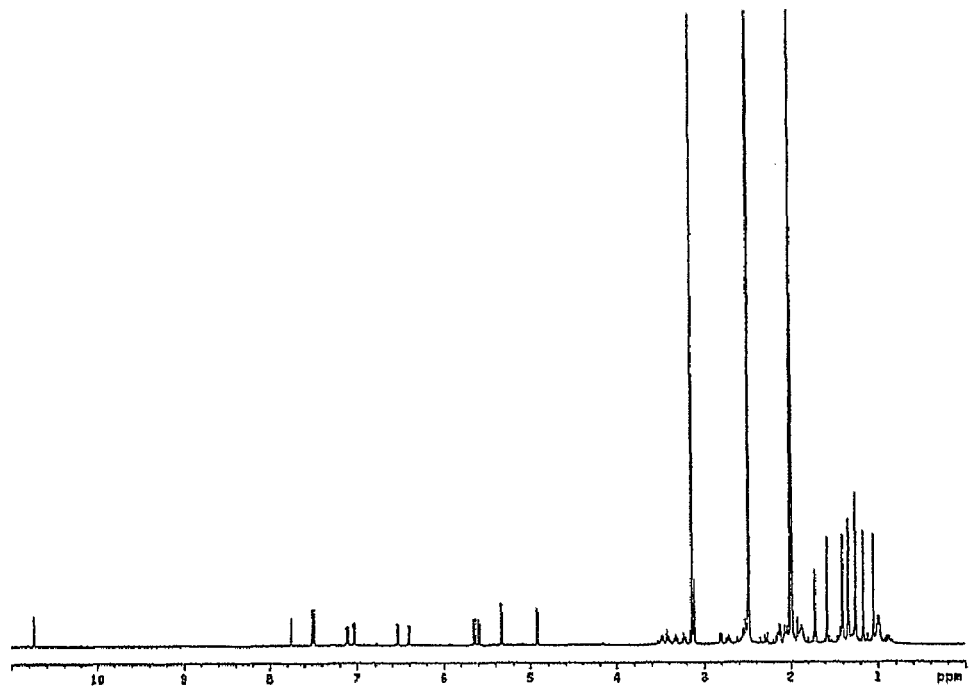
Figure 4C:
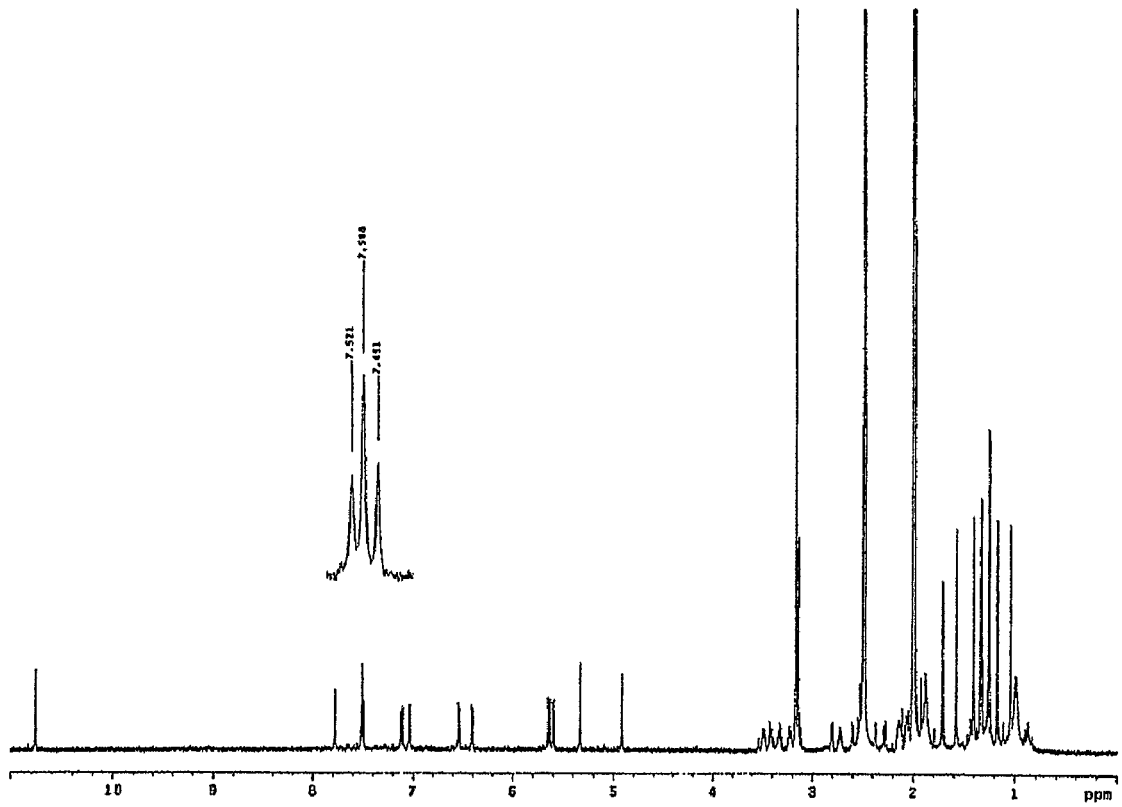
Figure 6:
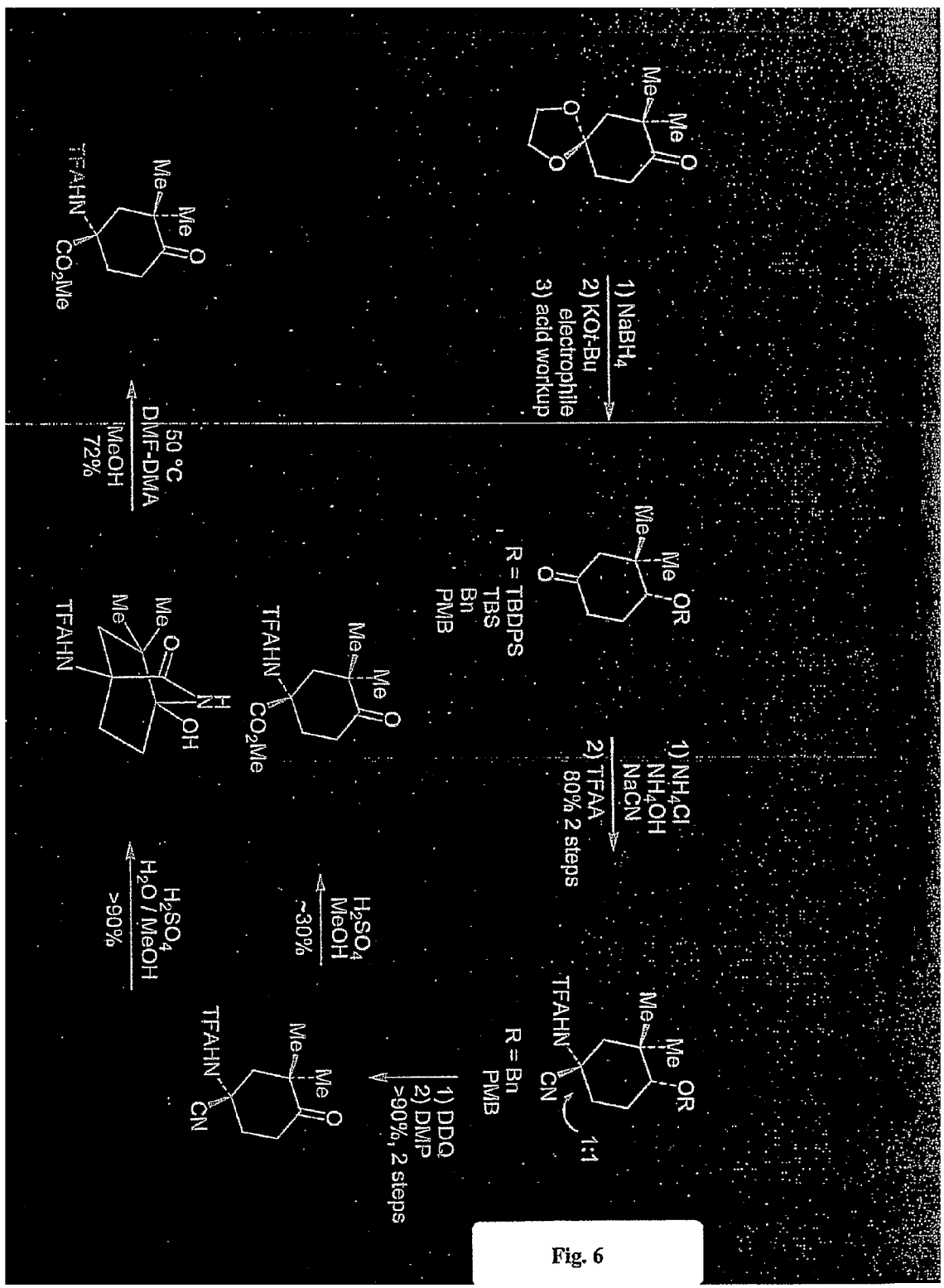
FIG. 6 shows a synthetic route to intermediates useful in the synthesis of amino ester substituted nitrones.
Figure 7A:
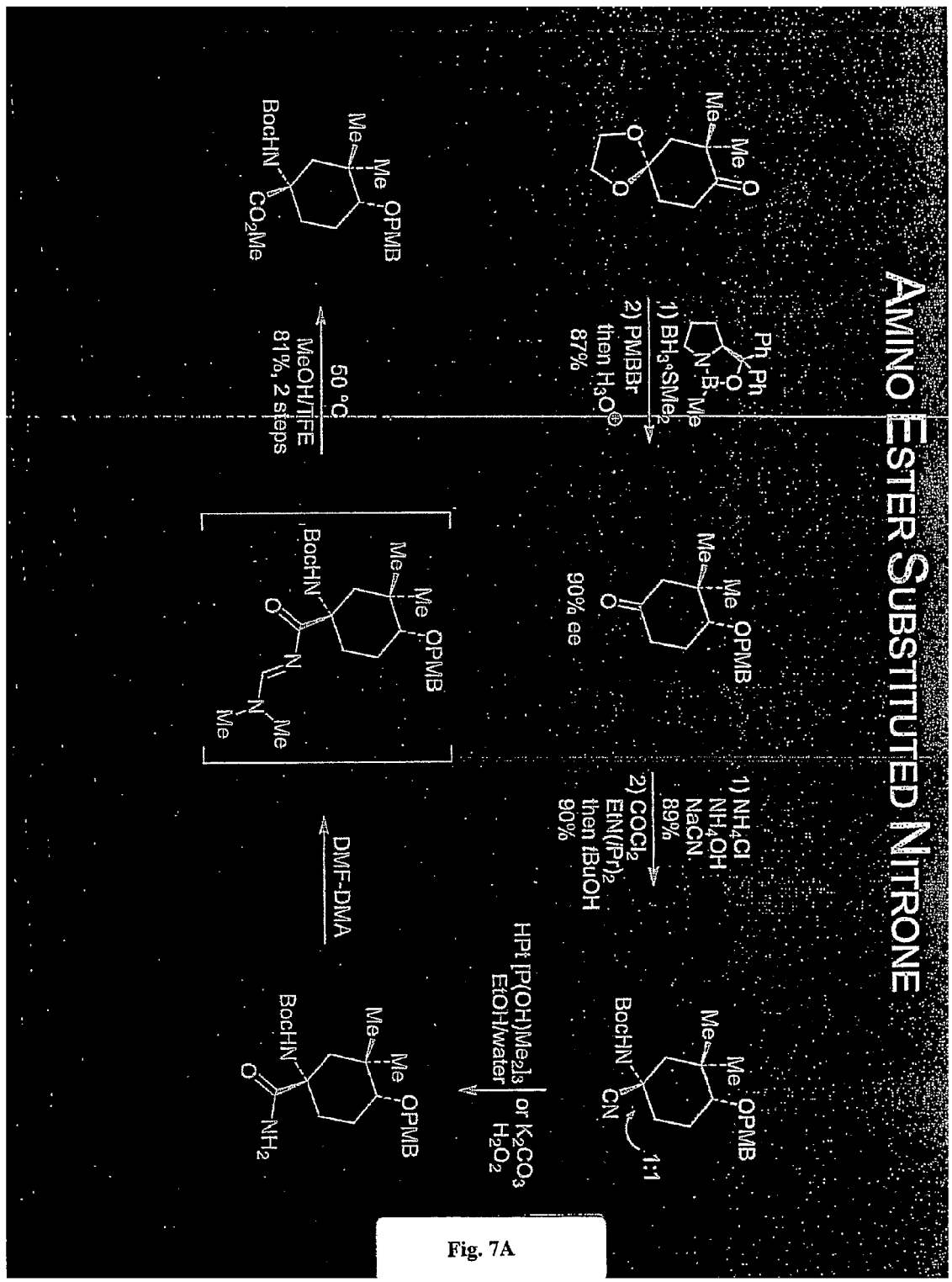
FIG. 7 shows a second synthetic route to intermediates useful in the synthetis of amino ester substituted nitrones.
Figure 7B:
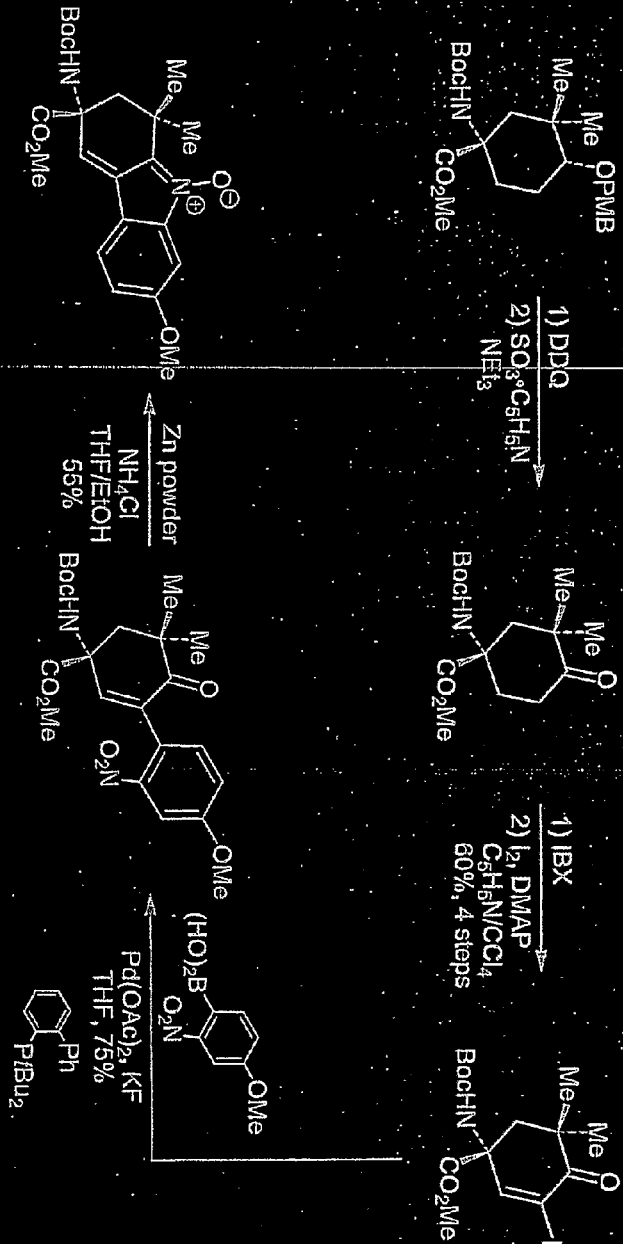
Figure 8:
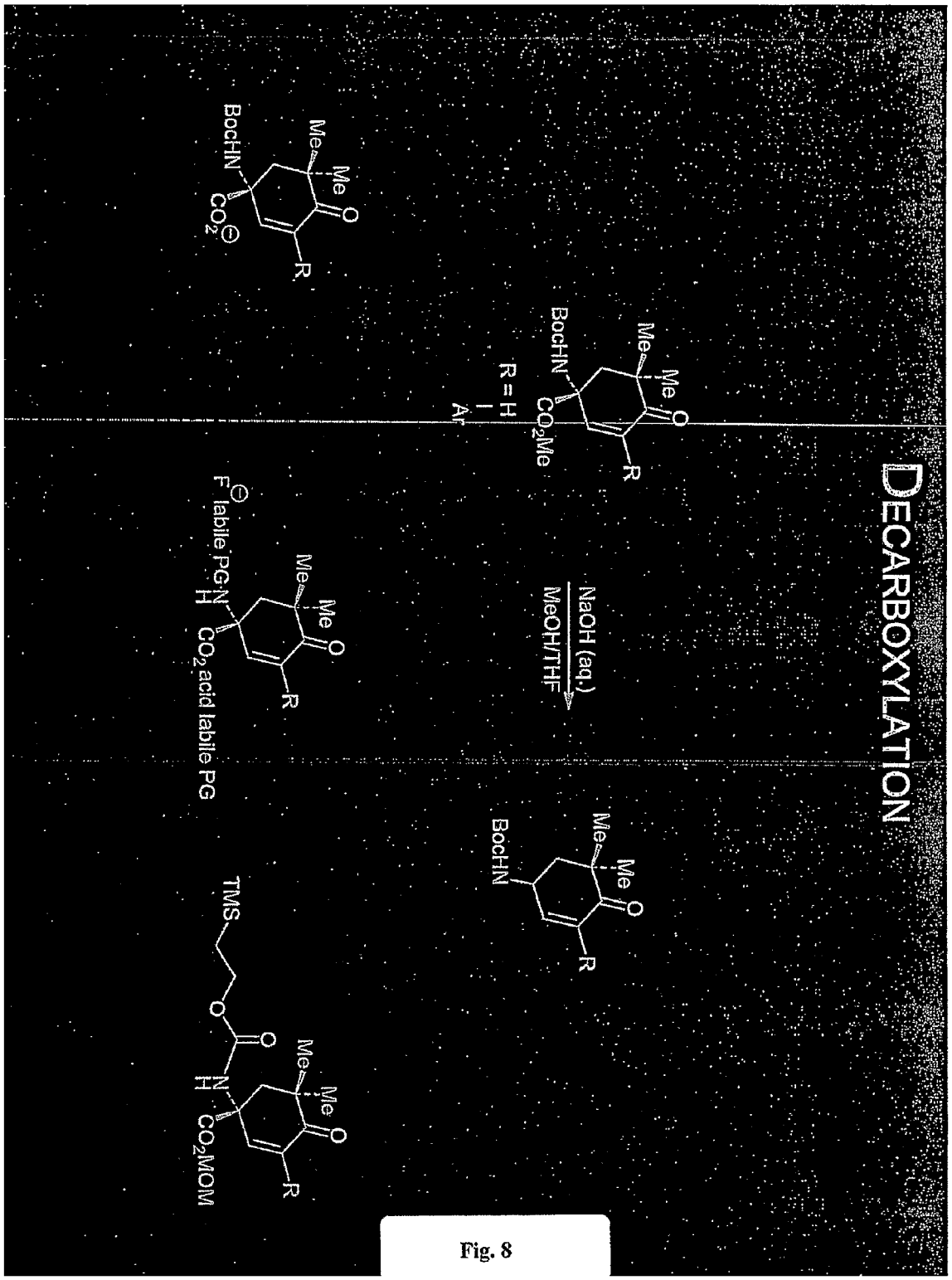
FIG. 8 shows the decarboxylation of the amino ester substituted intermediate.
Figure 9:
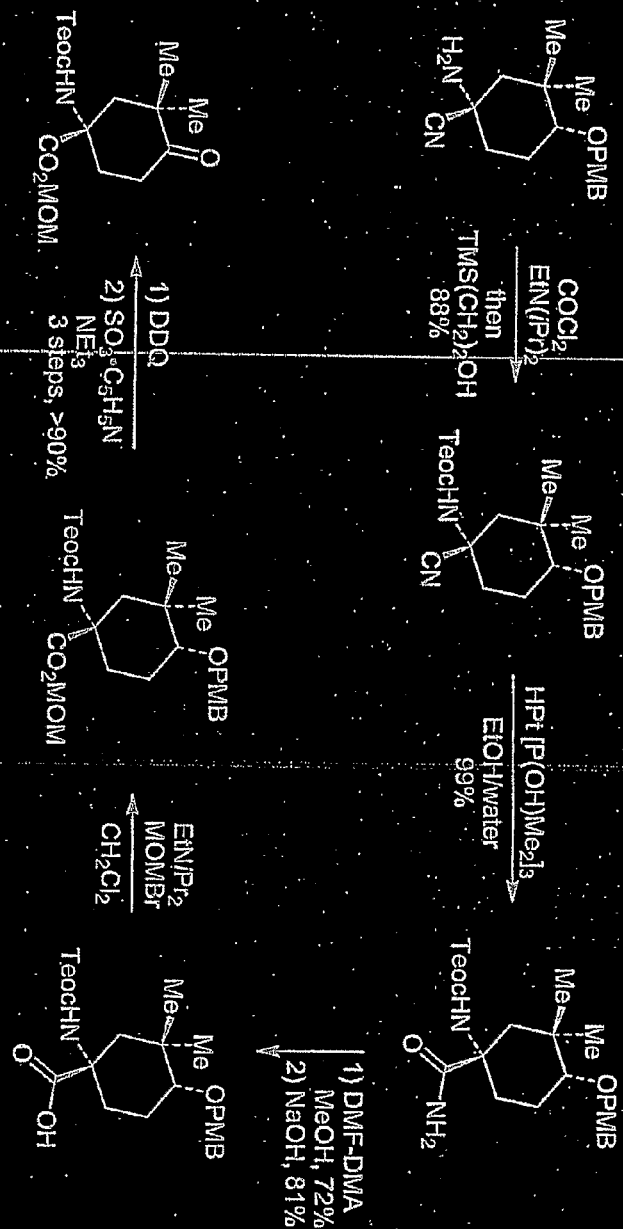
FIG. 9 shows another synthetic route to intermediates useful in the synthetis of amino ester substituted nitrones.
Figure 10:
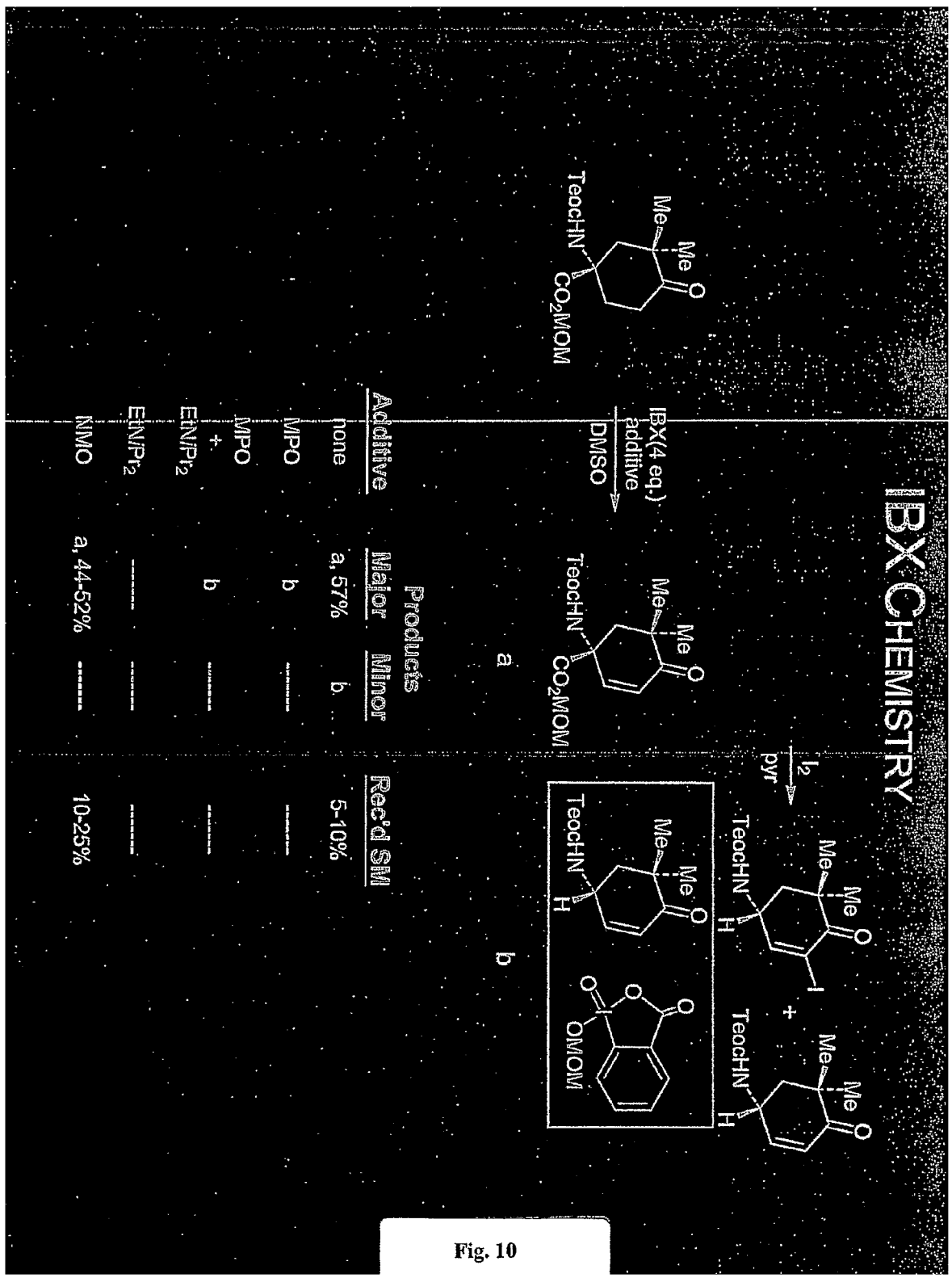
FIG. 10 shows the IBX chemistry useful in the preparation of compounds of the invention containing the α,β-unsaturated nitrone funationality of avrainvillamide.
Figure 11:
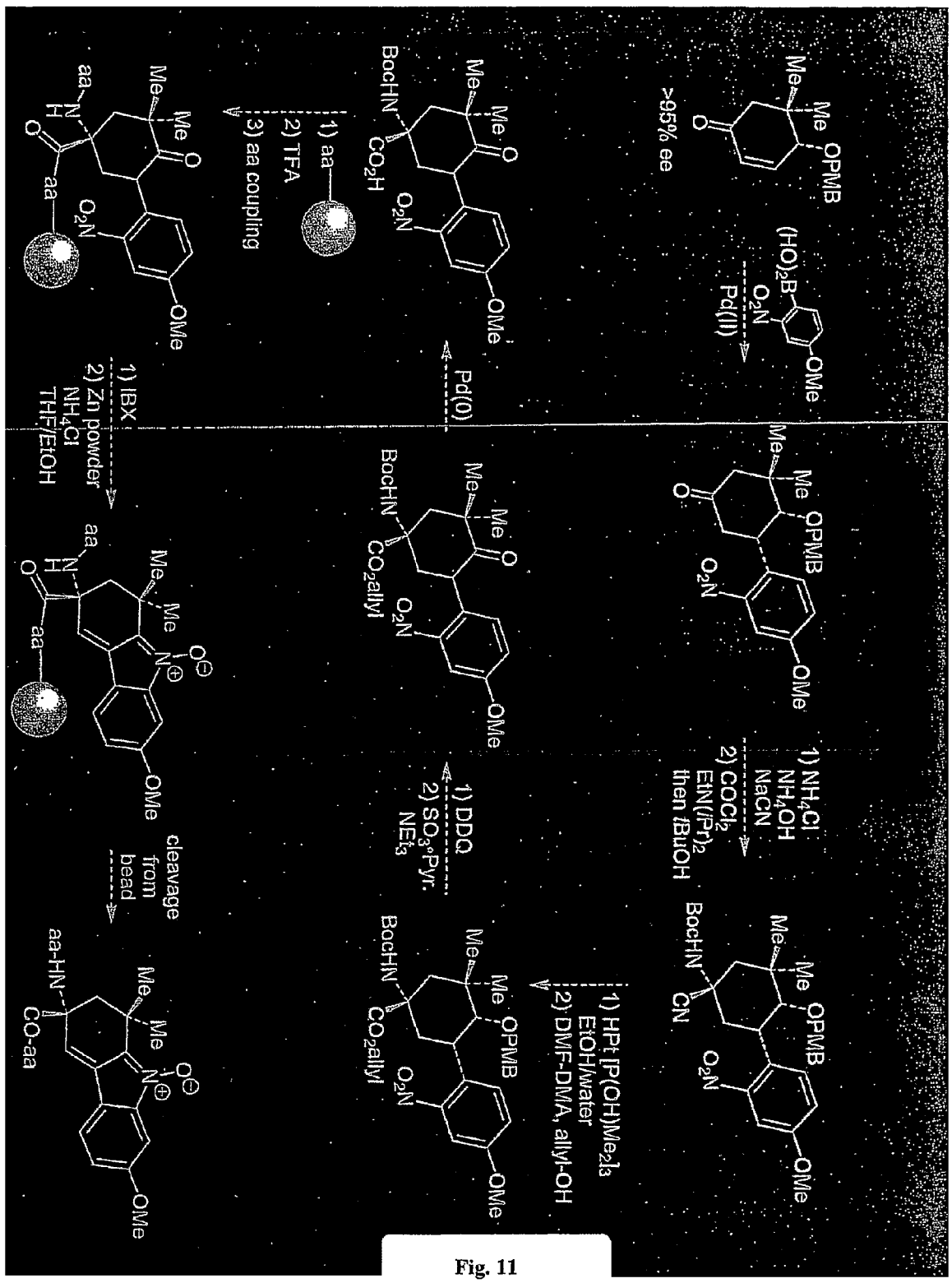
FIG. 11 shows a synthetic scheme for preparing amino acid derivatized compounds of the invention.
Figure 13B:
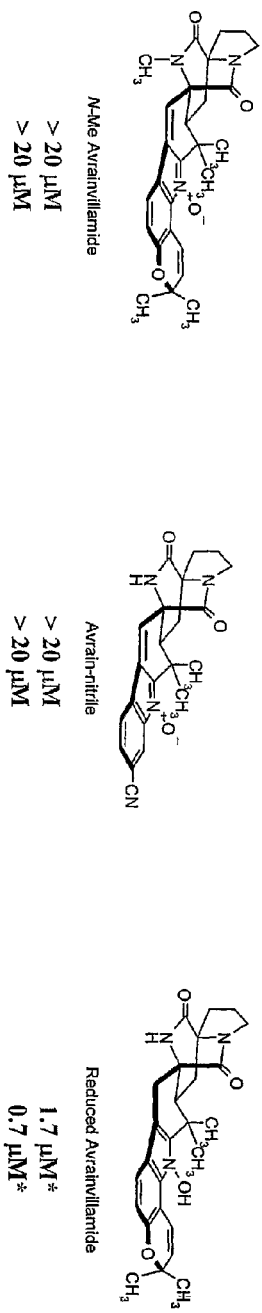
FIG. 13 shows GI50 data for several avrainvillamide analogues.
Figure 14:
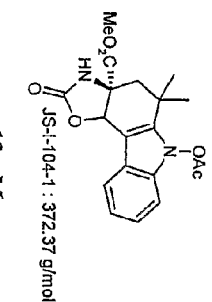
FIG. 14 shows GI50 data for several amino-ester analogues of avrainvillamide.
Figure 15:
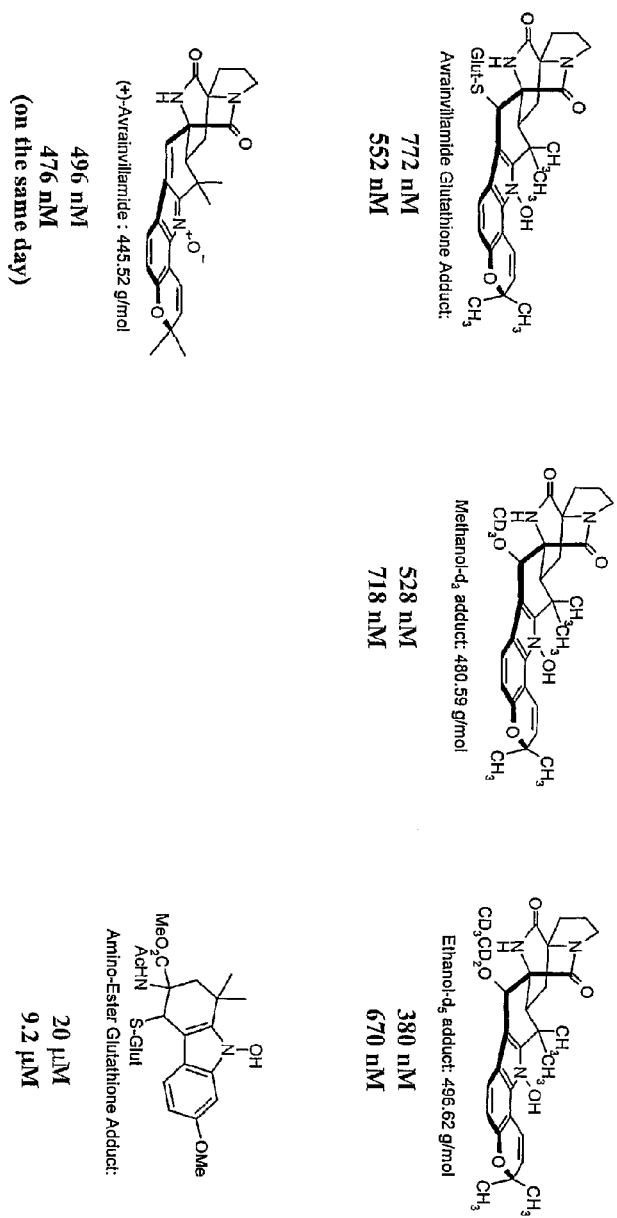
FIG. 15 shows GI50 data for several nucleophile adducts of analogues of avrainvillamide.
Figure 18:
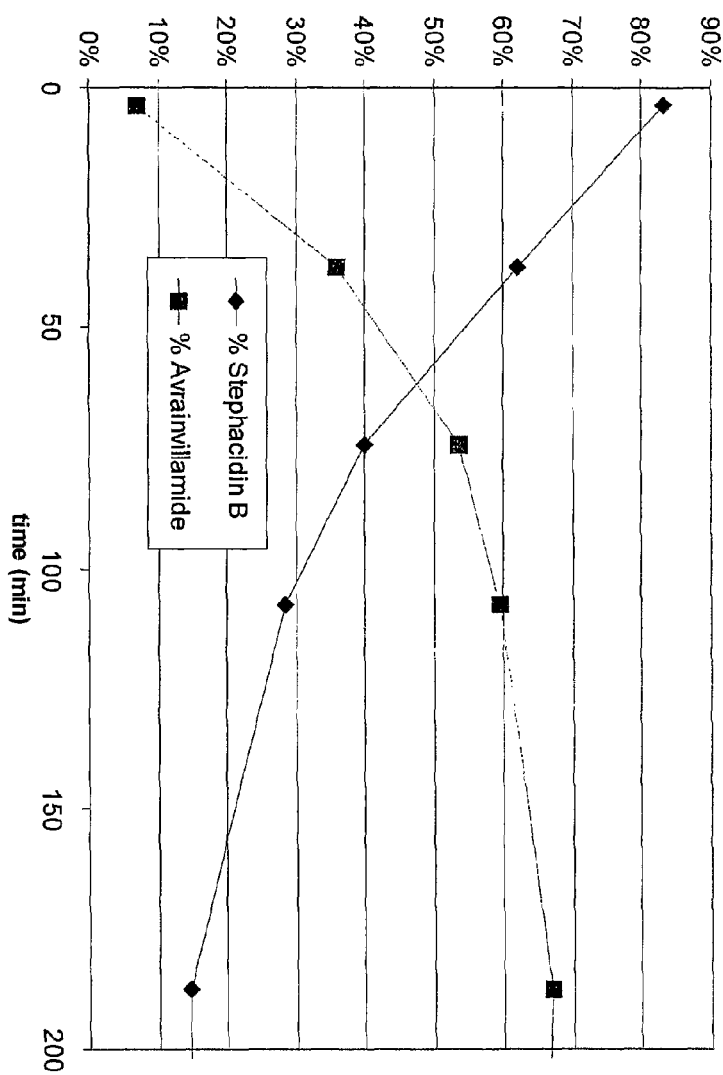
FIG. 18 shows the decomposition of stephacidin B into 1.7 equiv. of avrainvillamide. Avrainvillamide is the major species present under physiological conditions.
Figure 19:
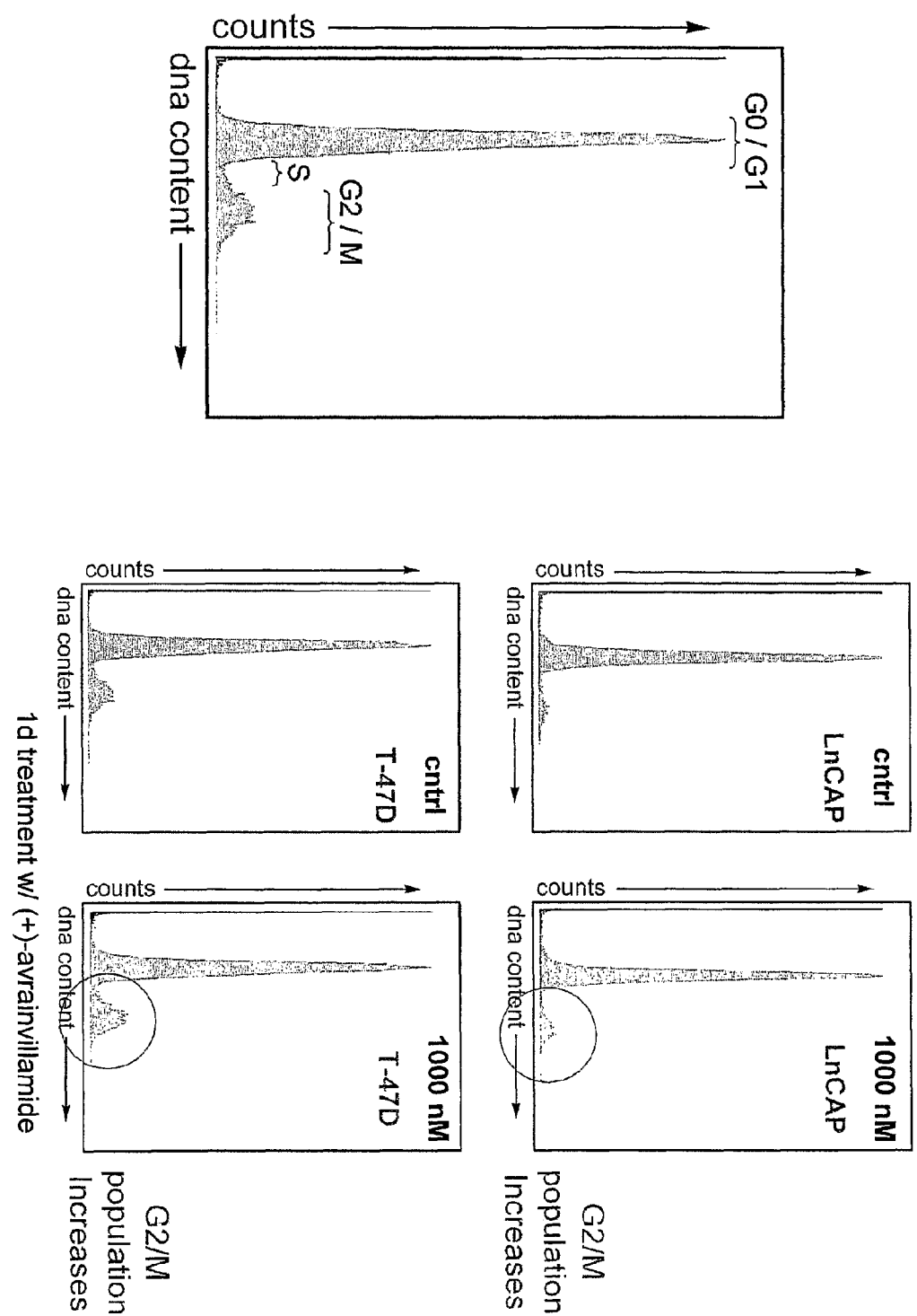
FIG. 19 shows the effect of avrainvillamide on the cell cycle. Avrainvillamide induces arrest in G2/M.

5.64 (d, 1H, J=10.5 Hz), 5.59 (d, 1H, J=10.5 Hz), 5.33 (s, 1H), 4.93 (s, 1H), 3.49 (m, 1H), 3.45 (m, 1H), 3.40 (m, 1H), 3.18-3.14 (m, 2H), 2.81 (m, 1H), 2.72 (m, 1H), 2.52 (m, 2H), 2.28 (m, 1H), 2.15 (m, 2H), 2.10-2.00 (m, 2H), 1.93-1.85 (m, 4H), 1.72 (s, 3H), 1.58 (s, 3H), 1.41 (s, 3H), 1.34 (s, 3H), 1.33 (s, 3H), 1.26 (s, 3H), 1.17 (s, 3H), 1.05 (s, 3H). IR (NaCl, thin film), cm$^{-1}$ 3232 (w), 2975 (m), 1681 (br vs), 1522, 1461, 1385, 1337, 1277, 1214, 1191, 1162, 1115. HRMS-FAB (m/z): [M+Na]$^{+}$ calcd for $C_{52}H_{54}N_{6}NaO_{8}$, 913.3901; found, 913.3902. $[\alpha]_D^{24}$: +91.0 (c 0.25, $CH_3CN$). See FIGS. 4A and 4B for the actual NMR spectra of stephacidin B (1).

| Comparative $^1$H NMR Data for Stephacidin B (500 MHz, 50% $d_6$-DMSO-CD$_3$CN). | | | |
|---|---|---|---|
| Authentic Stephacidin B$^1$ | Synthetic Stephacidin B$^2$ | Authentic Stephacidin B | Synthetic Stephacidin B |
| n/r$^3$ | 10.74 (s, 1H) | 3.22-3.10 (m, 2H) | 3.18-3.14 (m, 2H) |
| 7.73 (s, 1H) | 7.76 (s, 1H) | 2.82 (m, 1H) | 2.81 (m, 1H) |
| 7.50 (d, 1H, J = 10.2 Hz) | 7.50 (app d, 2H, J = 9.5 Hz)$^4$ | 2.72 (m, 1H) | 2.72 (m, 1H) |
| 7.48 (d, 1H, J = 8.3 Hz) | 7.50 (app d, 2H, J = 9.5 Hz)$^4$ | 2.52 (m, 2H) | 2.52 (m, 2H) |
| 7.11 (d, 1H, J = 10.0 Hz) | 7.11 (d, 1H, J = 9.5 Hz) | 2.30 (m, 1H) | 2.28 (m, 1H) |
| 7.04 (d, 1H, J = 8.6 Hz) | 7.04 (d, 1H, J = 9.0 Hz) | 2.15 (m, 2H) | 2.15 (m, 2H) |
| 6.54 (d, 1H, J = 8.2 Hz) | 6.54 (d, 1H, J = 8.5 Hz) | 2.10-2.00 (m, 2H) | 2.10-2.00 (m, 2H) |
| 6.41 (d, 1H, J = 8.6 Hz) | 6.41 (d, 1H, J = 9.0 Hz) | 1.95-1.85 (m, 4H) | 1.93-1.85 (m, 4H) |
| 5.64 (d, 1H, J = 10.2 Hz) | 5.64 (d, 1H, J = 10.5 Hz) | 1.72 (s, 3H) | 1.72 (s, 3H) |
| 5.59 (d, 1H, J = 10.0 Hz) | 5.59 (d, 1H, J = 10.5 Hz) | 1.58 (s, 3H) | 1.58 (s, 3H) |
| 5.34 (s, 1H) | 5.33 (s, 1H) | 1.41 (s, 3H) | 1.41 (s, 3H) |
| 4.93 (s, 1H) | 4.93 (s, 1H) | 1.35 (s, 6H) | 1.34 (s, 3H); 1.33 (s, 3H) |
| 3.49 (m, 1H) | 3.49 (m, 1H) | 1.26 (s, 3H) | 1.26 (s, 3H) |
| 3.45 (m, 1H) | 3.45 (m, 1H) | 1.17 (s, 3H) | 1.17 (s, 3H) |
| 3.40 (m, 1H) | 3.40 (m, 1H) | 1.05 (s, 3H) | 1.05 (s, 3H) |

$^1$Data taken from: Qian-Cutrone, J.; Huang, S.; Shu, Y.; Vyas, D.; Fairchild, C.; Menendez, A.; Krampitz, K.; Dalterio, R.; Klohr, S.; Gao, Q. J. Am. Chem. Soc. 2002, 124, 14556; 500 MHz, 50% $d_6$-DMSO-CD$_3$CN.
$^2$500 MHz, 50% $d_6$-DMSO-CD$_3$CN, sample referenced to CD$_2$HSOCD$_3$ = 2.49 ppm.
$^3$The chemical shift of this resonance was not tabulated; the resonance is observed in the published spectrum.
$^4$The chemical shifts of these signals appeared to vary slightly between synthetic samples (compare synthetic spectra above).

Determination of Relative Stereochemistry by X-Ray Analysis:

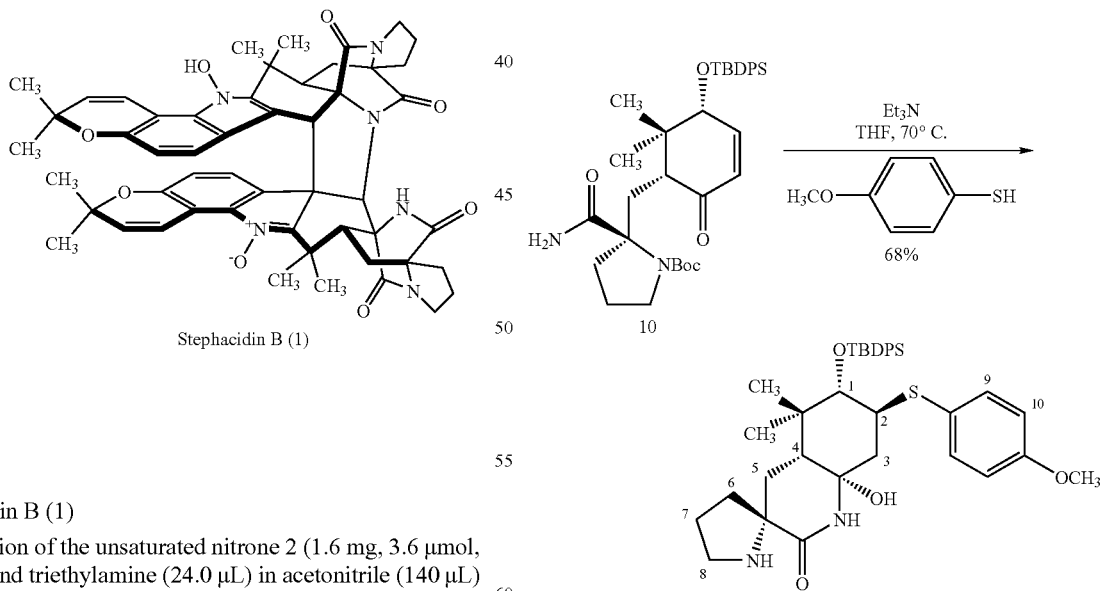

Stephacidin B (1)

Stephacidin B (1)

A solution of the unsaturated nitrone 2 (1.6 mg, 3.6 μmol, 1 equiv) and triethylamine (24.0 μL) in acetonitrile (140 μL) was allowed to stand at 23° C. for 3.5 h, then was concentrated to dryness to give stephacidin B (1) as a white solid (est. >95%, $^1$H NMR analysis).

R$_f$=0.14 (3% methanol-dichloromethane). $^1$H NMR (500 MHz, 50% $d_6$-DMSO-CD$_3$CN), δ 10.74 (s, 1H), 7.76 (s, 1H), 7.50 (app d, 2H, J=9.5 Hz), 7.11 (d, 1H, J=9.5 Hz), 7.04 (d, 1H, J=9.0 Hz), 6.54 (d, 1H, J=8.5 Hz), 6.41 (d, 1H, J=9.0 Hz), Triethylamine (58.5 μL, 420 μmol, 10.0 equiv) and p-methoxybenzenethiol (25.8 μL, 210 μmol, 5.0 equiv) were added sequentially to a stirred solution of the amide (10, 25.4 mg, 42.0 μmol, 1 equiv) in tetrahydrofuran (210 μL) at 23° C. The flask was fitted with an air condenser and the mixture was warmed to 70° C. for 3.5 h. The product solution was allowed to cool to 23° C., then was concentrated, and the residue was purified by flash-column chromatography (20% acetone-hexanes) to furnish the hemiaminal depicted as a white solid (21.0 mg, 68%). Crystals suitable for X-ray analysis were obtained by recrystallization from ethanol.

$R_f$=0.39 (30% acetone-hexanes). $^1$H NMR (500 MHz, $C_6D_6$), δ 8.04 (m, 4H, ArH), 7.31 (m, 6H, ArH), 6.98 (d, 2H, J=9.0 Hz, $H_9$), 6.61 (d, 2H, J=9.0 Hz, $H_{10}$), 5.73 (s, 1H, OH), 5.41 (d, 1H, J=2.5 Hz, NH), 3.79 (td, 1H, J=11.0, 4.0 Hz, $H_2$), 3.68 (d, 1H, J=10.5 Hz, $H_1$), 3.41 (m, 1H, $H_8$), 3.31 (m, 1H, $H_8$), 3.22 (s, 3H, $OCH_3$), 2.53 (t, 1H, J=14.0 Hz, $H_5$), 2.04 (m, 1H, $H_6$), 1.93 (dd, J=13.0, 4.0 Hz, $H_3$), 1.51-1.10 (m, 27H, $H_3$, $H_4$, $H_5$, 2×$H_7$, $H_8$, $CH_3$, $SiC(CH_3)_3$, $NCO_2C(CH_3)_3$), 1.04 (s, 3H, $CH_3$). $^{13}$C NMR (100 MHz, $C_6D_6$), δ 172.9, 159.4, 155.1, 136.7, 136.4, 135.4, 135.3, 134.2, 129.5, 129.2, 127.5, 127.2, 125.1, 114.6, 82.9, 80.4, 80.2, 64.9, 54.6, 48.4, 47.1, 46.4, 44.6, 40.7, 38.5, 31.0, 28.3, 28.0, 27.8, 23.7, 20.8, 15.5. IR (NaCl, thin film), $cm^{-1}$ 3377 (br), 2956 (s), 1679 (s), 1405 (s). HRMS-CI (m/z): $[M-OH]^+$ calcd for $C_{42}H_{55}N_2O_5SSi$, 727.3601; found, 727.3613.

X-Ray Analysis (Hydrogen Atoms Omitted for Clarity).

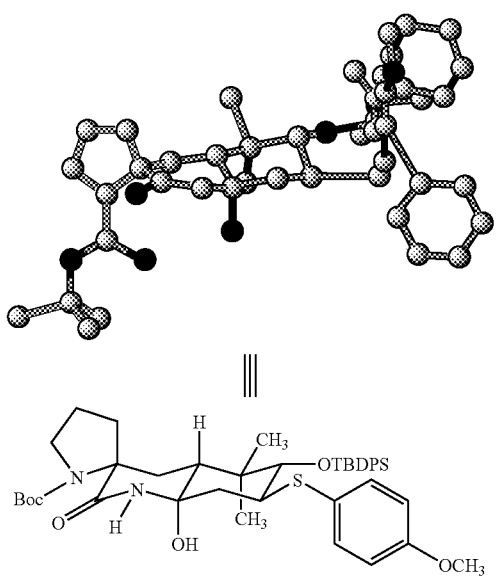

Example 3

Biological Data for Avrainvillamide Analogs

General

LNCaP (human prostate cancer), T-47D (human breast ductal carcinoma), BT-549 (human breast carcinoma), and MALME-3M (human melanoma) cells were purchased from the American Type Culture Collection (ATCC), and grown in a mixture of RPMI 1640 media (Mediatech, Inc. (Herndon, Va.), 90%), fetal bovine serum (Mediatech, Inc. (Herdon, Va.), 10%), L-glutamine (Mediatech, Inc. (Herdon, Va.), 2 mM), and HEPES (Mediatech, Inc. (Herdon, Va.), 10 mM). All cell-culture work was conducted in a class II biological safety cabinet. Antiproliferative assays and other operations requiring the handling of nitrone species were conducted in the dark to prevent the occurrence of unwanted rearrangement reactions.

Antiproliferative Assays: "Method C"

LNCaP and T-47D cells grown to approximately 80% confluence were trypsinized, collected, and pelleted by centrifugation (10 minutes at 183×g). The supernatant was discarded, and the cell pellet was resuspended in enough fresh media to achieve a cell concentration of approximately 1.0 to $1.5×10^6$ cells/mL. A sample was diluted 1 to 10 with media, and the actual concentration of cells was counted using a hemacytometer.

The cell suspension was diluted to $1.0×10^5$ cells/mL. A multichannel pipette was used to charge the wells of a 96-well plate (BD Falcon) with 100 μL per well of the diluted cell suspension. The plates were incubated for 24 hours at 37° C., under an atmosphere of 5% $CO_2$.

The following day, nitrone analogues were removed from the −80° C. freezer. The samples were thawed and dissolved in enough filter-sterilized DMSO to achieve a concentration of 5 mM. Aliquots of 6.5 μL of the resulting nitrone solution were dissolved in 643.5 μL of media to achieve a final concentration of 50 μM. Serial dilutions were employed to generate a range of different concentrations for analysis. Finally, 100 μL aliquots of this diluted nitrone solution were added to the wells containing adhered cells, resulting in final assay concentrations of up to 25 μM.

The treated cell samples were incubated for 72 hours at 37° C. (5% $CO_2$). To each well was added 20 μL of CellTiter-Blue Cell Viability Assay Reagent (Promega). The samples were returned to the incubator. Fluorescence (560 nm excitation/590 nm emission) was recorded on a fluorescence plate reader following 2.5 hours and 4.0 hours incubation (37° C., 5% $CO_2$).

Percent viability inhibition and percent growth inhibition was calculated for each well, based upon the following formulae:

Percent viability inhibition=$100×(B_t−S)/(B_t)$

Percent growth inhibition=$100×(S−B_0)/(B_t−B_0)$ where S is the sample reading, $B_t$ is the average reading for a vehicle-treated population of cells at the completion of the assay, and $B_0$ is the average reading for an untreated population of cells at the beginning of the assay.

Each analogue was run a minimum of eight times, over a period of at least two weeks. The average inhibition at each concentration was plotted against concentration, and a curve fit was generated with the XLfit4 plugin (IDBS software) running in Excel (Microsoft). To eliminate positional effects (i.e., cell samples in the center of the plate grow more slowly than those near the edge), the data was automatically scaled to ensure that the curves show no inhibition at negligible concentrations of added compound. Such a precaution was found to generate more consistent data from week to week, without affecting the final results. Final IC50 and GI50 values reflect the concentrations at which the resulting curves pass through 50 percent inhibition.

Antiproliferative Assays: "Method A"

As for method "C" but with the following changes: (1) The cell suspensions were diluted to $6×10^4$ cells/mL prior to use; (2) only 50 μL per well of cell suspension was used, followed by 50 μL of drug-treated media after one day of incubation; (3) the cells were incubated for 48 hours with the compounds, rather than 72 hours; and (4) the final viability analysis was conducted with the MTS-based Celltiter 96 AQueous Non-Radioactive Cell Proliferation Assay Kit (Promega).

Results

GI50 data for (+)-avrainvillamide, (−)-avrainvillamide, (−)-stephacidin B, and (+)-stephacidin on BT-549, T-47D, MALME-3M, and LNCaP cells based on Method A are shown in FIG. 12 with reported literature values. As expected, the natural enantiomers are more potent than the unnatural enantiomers.

GI50 data for various avrainvillamide analogues on LNCaP and T-47D cells based on Method C are shown in FIGS. 13-16.

Example 4

Identification of a Biological Target of Avrainvillamide

In-Cellulo Activity Based Probe (Pulldown) Experiments

LNCaP and T-47D cells grown to approximately 80% confluence were trypsinized, collected, and pelleted by centrifugation (10 minutes at 183×g). The supernatant was discarded, and the cell pellet was resuspended in enough fresh media to achieve a concentration of approximately 1.0 to 1.5×10$^6$ cells/mL. A sample was diluted 1 to 10 with media, and the actual concentration of cells was counted using a hemacytometer.

The cell suspension was diluted to 5.0×10$^5$ cells/mL. The wells of a 12-well plate (BD Falcon) were charged with 3 mL per well of the diluted cell suspension. The plates were incubated for 24 hours at 37° C., under an atmosphere of 5% $CO_2$.

The following day, a sample of the biotinylated nitrone probe (see FIG. 24 for the synthesis of the probe) was dissolved in filter-sterilized DMSO to provide a stock solution of 5 mM. Aliquots of this probe were dissolved in cell culture media to afford concentrations of 0 to 63 µM probe. DMSO was added to the samples as required to maintain a constant loading.

To the various wells of adhered cells was added 500 µL of probe solution, resulting in a final concentration of 0, 3, 6, or 9 µM probe, with a constant DMSO loading of 0.24%. Various control samples were prepared in a similar manner, all containing identical DMSO concentrations.

The drugged cells were incubated for 2 days (37° C., 5% $CO_2$). The media was then removed from the cells and collected in centrifuge tubes. The adherent cells were washed twice with 1×PBS (1 mL per well for each wash). The washes were combined with the collected supernatant. Any detached cells were collected by centrifugation (10 minutes at 1643×g) and washed with PBS.

A solution of RIPA buffer (50 mM Tris.HCl, 150 mM NaCl, 1 mM EDTA, 1% Triton X-100, 1% sodium deoxycholate, 0.1% SDS, pH 7.35) was charged with protease inhibitors (1 mM PMSF, 5 µg/mL aprotinin, 5 µg/mL leupeptin, 200 µM $Na_3VO_4$, 50 mM NaF, 10 mM iodoacetamide). All the cells (adhered and detached) were lysed at 4° C. for 1 hour with 300 µL per well of the complete RIPA buffer. The resulting lysates were transferred into 1.5 mL centrifuge tubes. The samples were then centrifuged at 10000×g (4° C.). Insoluble nuclear material was removed with a pipette tip, and the remaining clarified lysates were transferred to clean 1.5 mL centrifuge tubes. A small aliquot (25 µL) from each tube was set aside for use as a positive control, and for determination of total protein by Bradford analysis.

Meanwhile, a 1 mL sample of suspended Sepharose 6B (Sigma) was transferred to a 1.5 mL centrifuge tube. The resin was collected by centrifugation at 10000×g, and washed twice with 1 mL of 50 mM Tris.HCl, pH 7.8. For each wash, the resin was thoroughly suspended in the buffer, then collected by centrifugation at 10000×g. Finally, the resin was resuspended in 1 mL of 50 mM Tris.HCl, pH 7.8.

To each of the cell lysates was added 15 µL of the Sepharose 6B suspension. The samples were rotated end-over-end at 4° C. for 2 hours, then centrifuged for 10 minutes at 10000×g (4° C.). A 225 µL aliquot of each stripped, clarified lysate was transferred to a clean 1.5 mL centrifuge tube, and diluted with 225 µL of 50 mM Tris.HCl, pH 7.8 buffer. To each sample was added 15 µL of well-suspended streptavidin-agarose resin (Sigma). The samples were rotated end-over-end at 4° C. for 15 hours, then centrifuged 10 minutes at 10000×g (4° C.). The supernatants were discarded, and the resin was washed at room temperature, once with 500 µL RIPA buffer (without additives) and twice with 500 µL 50 mM Tris.HCl buffer. Each wash consisted of 10 minutes of mixing, followed by a 10 minute centrifugation at 10000×g (r.t.).

Each sample of washed resin was suspended in 50 µL of 2× Laemmli loading buffer (Sigma), and heated to 95° C. for 6 minutes to liberate bound proteins. After centrifugation to precipitate the spent resin, aliquots of the protein solutions were loaded onto a 1.0 mm Novex 10% tris-glycine gel (Invitrogen), in accordance with the Bradford analysis results from above (5 µL to 7.6 µL per lane). After elution (1 hour at 150 V), the gel was stained for total protein with the Silver Stain Plus kit (Bio-Rad). This revealed, in addition to various non-specific bands, an apparently selective protein binder with a mass of approximately 66 kDa.

A 1.5 mm Novex 10% tris-glycine gel (Invitrogen) was then charged with 24.4 to 37.0 µL per lane (in accordance with the Bradford analysis from above) of the protein samples. After elution (as above) the gel was stained for total protein with the Novex Colloidal Blue staining kit (Invitrogen). The 66 kda band was excised from the gel and submitted to the Taplin Biological Mass Spectrometry Facility (Harvard Medical School, Boston, Mass.) for MS/MS analysis. Results of the analysis are given below:

TABLE 4-1

MS/MS Analysis of the 66 kDa Band

| Observed Protein | MW | Coverage | Assignment |
|---|---|---|---|
| bovine serum albumin (BSA) | 69293 | 26% | known media contaminant - confirmed as nonspecific |
| cytoskeletal linking membrane protein-63 (CLIMP-63)‡ | 66022 | 22% | most likely corresponds to the observed specific 66 kda band. |
| propionyl-coa carboxylase alpha chain (PCCA) | 77354 (M.P.)* | 19% | almost certainly corresponds to the nonspecific double band observed at 77/74 kda (apparent) |
| propionyl-coa carboxylase beta chain (PCCB) | 58206 (M.P.)* | 8% | almost certainly corresponds to the nonspecific double band observed at 57/55 kda (apparent) |
| heat shock 70 kDa protein 1-like (HS70L) | 70375 | 10% | these isoforms of HSP70 are most likely to be ubiquitous, nonspecific binders. |
| heat shock 70 kDa protein 1 (HSP71) | 70052 | 7% | |
| heat shock cognate 71 kDa protein (HSP7C) | 70898 | 2% | |

*M.P. = Mass of the mitochondrial precursor. Typically these proteins show two bands, separated by ~2 kDa in molecular weight.
‡The peptide fragments observed for CLIMP-63 all originate in the lumenal tail, which raises the possibility that the observed protein may correspond to a previously unobserved isoform of CLIMP-63. However, the Western blot results (vide infra) suggest that this is not the case.

Figure 24:
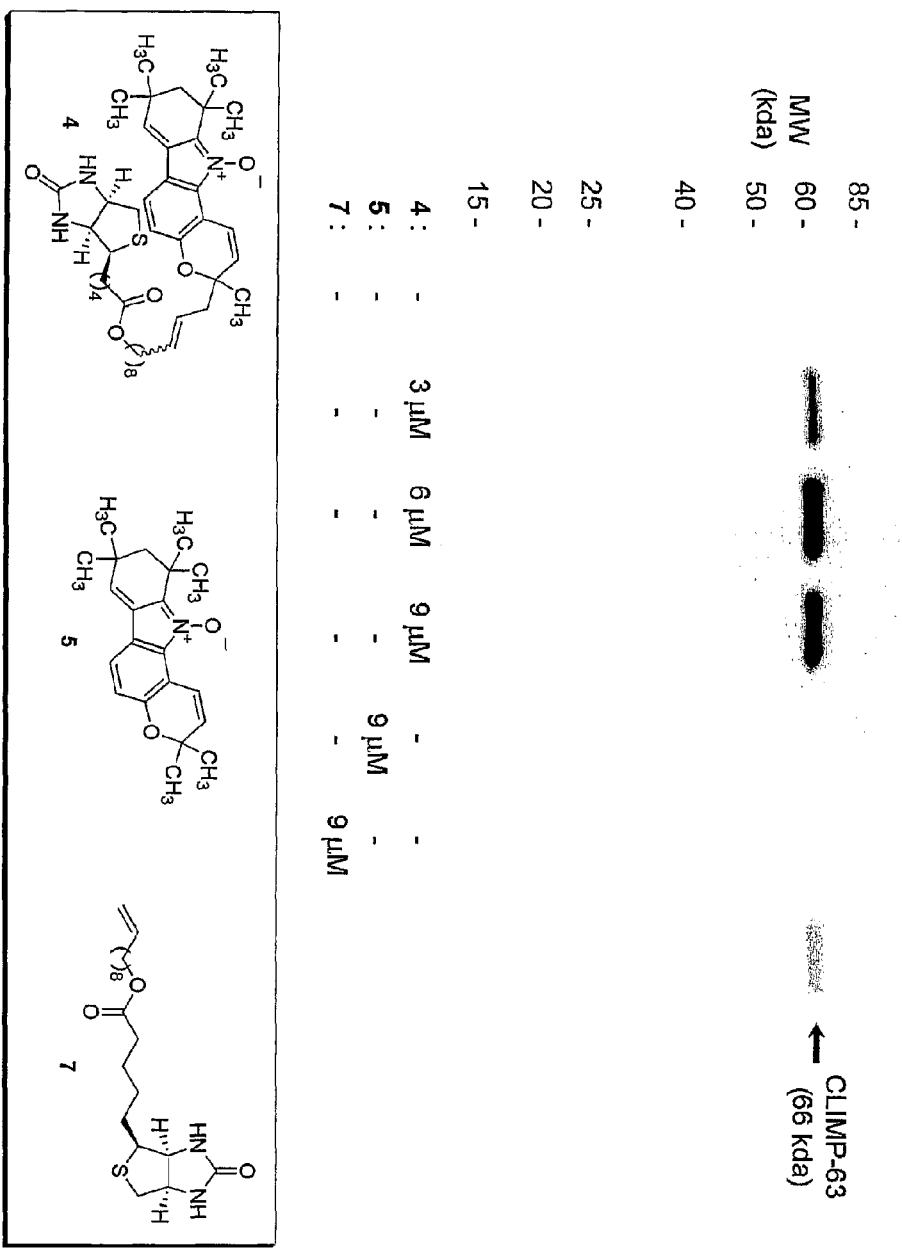
FIG. 24 shows the confirmation of CLIMP-63 as a biological target of avrainvillamide by Western blotting.
Figure 26A:
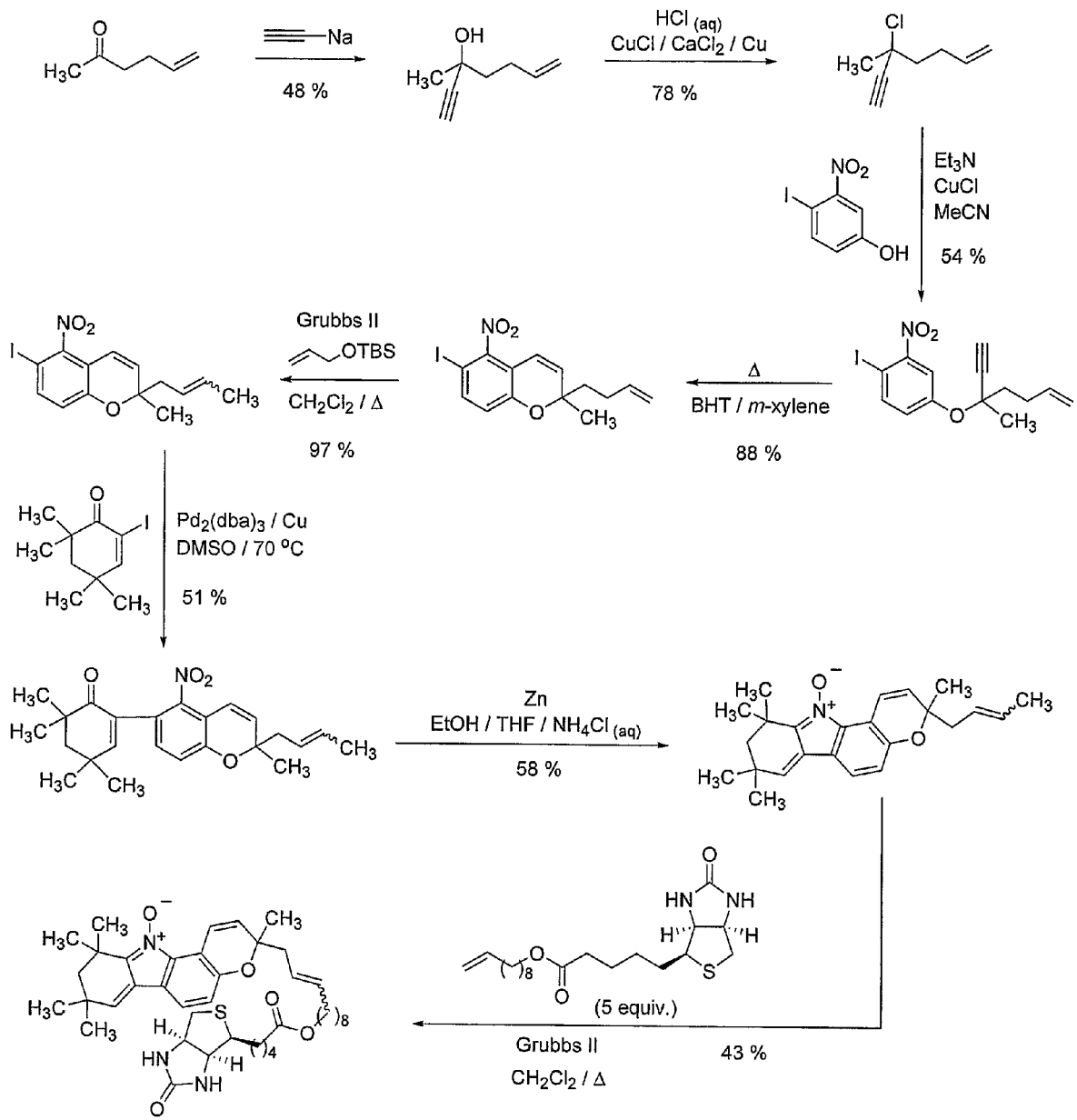
FIG. 26 shows the synthesis of the biotin-labelled probe.
Figure 27:
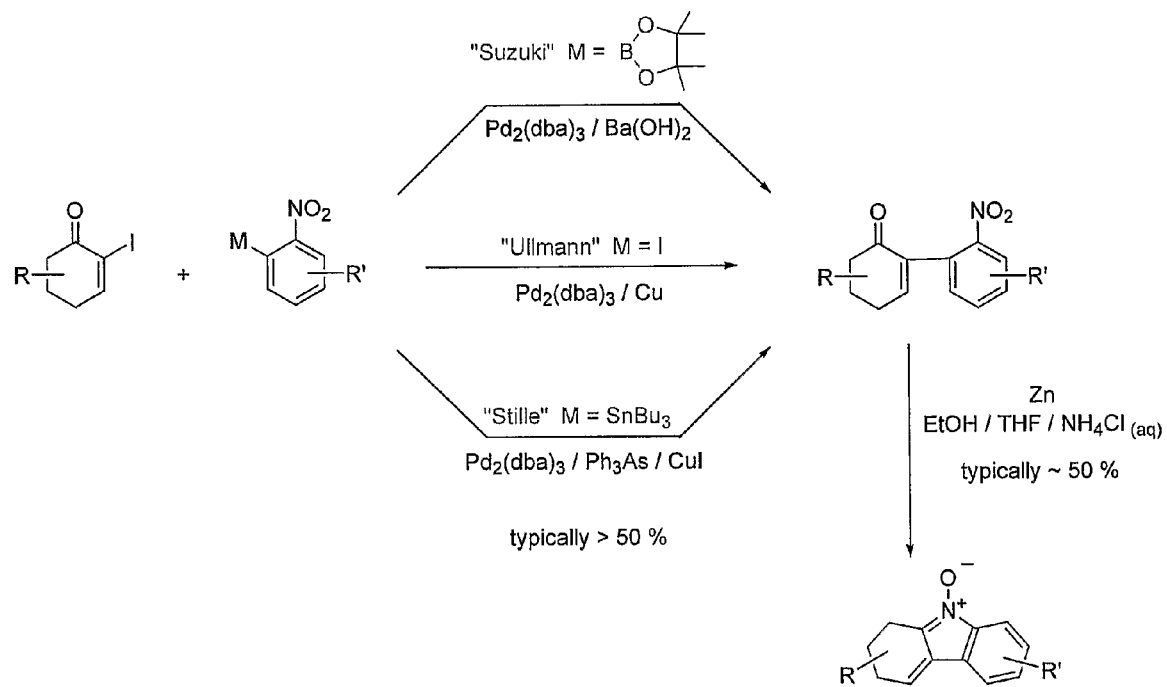
FIG. 27 shows three ways of coupling (Suzuki coupling, Ullmann coupling, Stille coupling) the left and right halves of avrainvillamide analogs.

Confirmation of CLIMP-63 by Western Blot (FIG. 24)

A protein pulldown similar to that detailed above was performed on T-47D cells. The final sample lysates, dissolved in 2× Laemmli loading buffer, were loaded onto a 1.0 mm Novex 4-20% tris-glycine gel (Invitrogen). After elution (150

V, 1 hour), the separated proteins were transferred to a nitrocellulose membrane (100 mA, 14 hours).

The membrane was treated with blocking solution (3% nonfat milk in 40 mL TBS, containing 1% tween-20) for 1 hour at room temperature. After washing (two 10 minute washes with 40 mL TBS, containing 1% tween-20), the membrane was treated with an antibody to CLIMP-63 (Axxora, mouse monoclonal antibody, 10 μg in 20 mL of TBS, containing 1% tween-20 and 1% nonfat milk) for 1 hour at room temperature. After washing (two 10 minute washes with 40 mL TBS, containing 1% tween-20), the membrane was treated with goat anti-mouse Ig HRP conjugate (Imgenex, 10 μL in 20 mL of TBS, containing 1% Tween-20 and 1% nonfat milk) for 1 hour at room temperature. After washing (three 10 minute washes with 40 mL TBS, containing 1% tween-20), the membrane was treated with 3 mL each of a stabilized peroxide solution and a luminol/enhancer solution (Supersignal West Pico, Pierce) for 3 minutes. Emitted light was visualized using an Alpha Imager in chemiluminescent detection mode.

By Western blot, CLIMP-63 (the amino acid sequence of CLIMP-63 is shown in FIG. 25) appeared to be selectively harvested with the biotinylated probe. By contrast, Western blotting results for bovine serum albumin, glutathione reductase, and glyceraldehyde phosphate dehydrogenase show these proteins to be present nonspecifically, if at all.

Other Embodiments

The foregoing has been a description of certain non-limiting preferred embodiments of the invention. Those of ordinary skill in the art will appreciate that various changes and modifications to this description may be made without departing from the spirit or scope of the present invention, as defined in the following claims.

What is claimed is:
1. A compound of the formula:

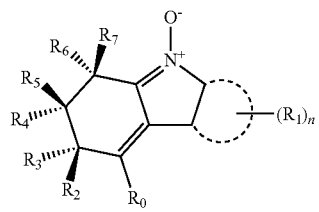

wherein $R_0$, $R_1$, $R_2$, $R_3$, $R_4$, $R_5$, $R_6$, and $R_7$ are independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_G$; —C(=O)$R_G$; —CO$_2R_G$; —CN; —SCN; —$SR_G$; —$SOR_G$; —$SO_2R_G$; —$NO_2$; —$N_3$; —N($R_G$)$_2$; —NHC(=O)$R_G$; —$NR_G$C(=O)N($R_G$)$_2$; —OC(=O)$OR_G$; —OC(=O)$R_G$; —OC(=O)N($R_G$)$_2$; —$NR_G$C(=O)$OR_G$; or —C($R_G$)$_3$; wherein each occurrence of $R_G$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

wherein two or more substituents may form substituted or unsubstituted, cyclic, heterocyclic, aryl, or heteroaryl structures;

wherein $R_2$ and $R_3$, $R_4$ and $R_5$, or $R_6$ and $R_7$ may form together =O, =$NR_G$, or =C($R_G$)$_2$, wherein each occurrence of $R_G$ is defined as above;

represents a substituted or unsubstituted, cyclic, heterocyclic, aryl, or heteroaryl ring system; and n is an integer between 0 and 4, with the proviso that the compound is not (+)-avrainvillamide or

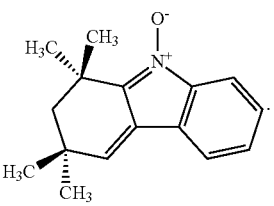

2. The compound of claim 1, wherein

is a substituted or unsubstituted 5- or 6-membered monocyclic ring.

3. The compound of claim 1, wherein

is a substituted or unsubstituted 8-, 9-, 10-, 11-, or 12-membered bicyclic ring system.

4. The compound of claim 1 of formula:

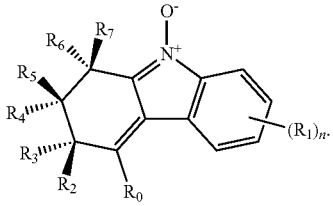

5. The compound of claim 1, wherein $R_0$ is hydrogen as in the formula:

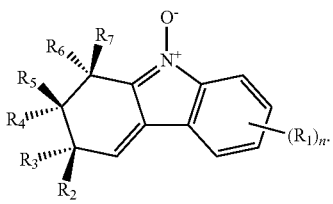

6. The compound of claim 1, wherein $R_0$, $R_4$, and $R_5$ are each hydrogen as in the formula:

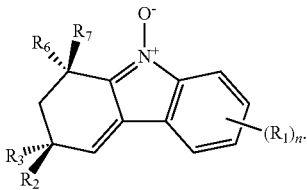

7. The compound of claim 1 of formula:

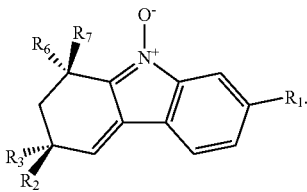

8. The compound of claim 1 of formula:

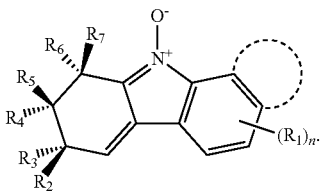

9. The compound of claim 1, wherein $R_2$ and $R_3$ are each independently selected from the group consisting of hydrogen, methyl, ethyl, n-propyl, iso-propyl, n-butyl, iso-butyl, tert-butyl, pentyl, or hexyl.

10. The compound of claim 1, wherein $R_4$ and $R_5$ are both hydrogen.

11. The compound of claim 1, wherein $R_6$ and $R_7$ are each independently selected from the group consisting of hydrogen, methyl, ethyl, n-propyl, iso-propyl, n-butyl, iso-butyl, or tert-butyl.

12. The compound of claim 1, wherein $R_1$ is hydrogen, halogen, substituted or unsubstituted aliphatic, alkoxy, alkylthioxy, acyl, cyano, nitro, amino, alkylamino, or dialkylamino.

13. The compound of claim 1, wherein n is 0.

14. The compound of claim 1, wherein n is 1.

15. The compound of claim 1 of formula:

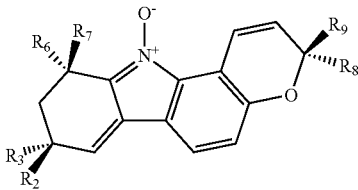

wherein each of $R_2$, $R_3$, $R_6$, $R_7$, $R_8$ and $R_9$ are independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_G$; —C(=O)$R_G$; —$CO_2R_G$; —CN; —SCN; —$SR_G$; —$SOR_G$; —$SO_2R_G$; —$NO_2$; —$N_3$; —N($R_G$)$_2$; —NHC(=O)$R_G$; —$NR_G$C(=O)N($R_G$)$_2$; —OC(=O)$OR_G$; —OC(=O)$R_G$; —OC(=O)N($R_G$)$_2$; —$NR_G$C(=O)$OR_G$; or —C($R_G$)$_3$; wherein each occurrence of $R_G$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety.

16. The compound of claim 1 of formula:

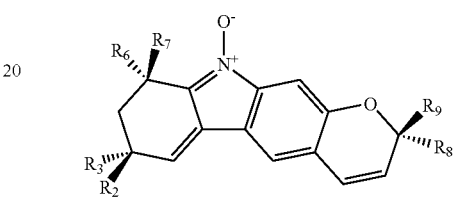

wherein each of $R_2$, $R_3$, $R_6$, $R_7$, $R_8$ and $R_9$ are independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_G$; —C(=O)$R_G$; —$CO_2R_G$; —CN; —SCN; —$SR_G$; —$SOR_G$; —$SO_2R_G$; —$NO_2$; —$N_3$; —N($R_G$)$_2$; —NHC(=O)$R_G$; —$NR_G$C(=O)N($R_G$)$_2$; —OC(=O)$OR_G$; —OC(=O)$R_G$; —OC(=O)N($R_G$)$_2$; —$NR_G$C(=O)$OR_G$; or —C($R_G$)$_3$; wherein each occurrence of $R_G$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety.

17. The compound of claim 1 of the formula:

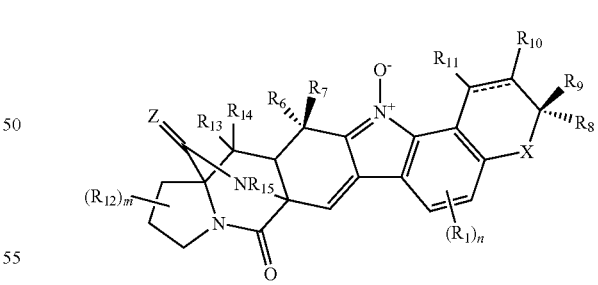

wherein each occurrence of $R_1$ is independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_A$; —C(=O)$R_A$; —$CO_2R_A$; —CN; —SCN; —$SR_A$; —$SOR_A$; —$SO_2R_A$; —$NO_2$; —$N_3$; —N($R_A$)$_2$; —NHC(=O) $R_A$;

—NR$_A$C(=O)N(R$_A$)$_2$; —OC(=O)OR$_A$; —OC(=O)R$_A$; —OC(=O)N(R$_A$)$_2$; —NR$_A$C(=O)OR$_A$; or —C(R$_A$)$_3$; wherein each occurrence of R$_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

R$_6$ is selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_F$; —C(=O)R$_F$; —CO$_2$R$_F$; —CN; —SCN; —SR$_F$; —SOR$_F$; —SO$_2$R$_F$; —NO$_2$; —N$_3$; —N(R$_F$)$_2$; —NHC(=O)R$_F$; —NR$_F$C(=O)N(R$_F$)$_2$; —OC(=O)OR$_F$; —OC(=O)R$_F$; —OC(=O)N(R$_F$)$_2$; —NR$_F$C(=O)OR$_F$; or —C(R$_F$)$_3$; wherein each occurrence of R$_F$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

R$_7$ is selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_G$; —C(=O)R$_G$; —CO$_2$R$_G$; —CN; —SCN; —SR$_G$; —SOR$_G$; —SO$_2$R$_G$; —NO$_2$; —N$_3$; —N(R$_G$)$_2$; —NHC(=O)R$_G$; —NR$_G$C(=O)N(R$_G$)$_2$; —OC(=O)OR$_G$; —OC(=O)R$_G$; —OC(=O)N(R$_G$)$_2$; —NR$_G$C(=O)OR$_G$; or —C(R$_G$)$_3$; wherein each occurrence of R$_G$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

R$_8$ and R$_9$ are independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_H$; —C(=O)R$_H$; —CO$_2$R$_H$; —CN; —SCN; —SR$_H$; —SOR$_H$; —SO$_2$R$_H$; —NO$_2$; —N$_3$; —N(R$_H$)$_2$; —NHC(=O)R$_H$; —NR$_H$C(=O)N(R$_H$)$_2$; —OC(=O)OR$_H$; —OC(=O)R$_H$; —OC(=O)N(R$_H$)$_2$; —NR$_H$C(=O)OR$_H$; or —C(R$_H$)$_3$; wherein each occurrence of R$_H$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

R$_{10}$ and R$_{11}$ are independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_J$; —C(=O)R$_J$; —CO$_2$R$_J$; —CN; —SCN; —SR$_J$; —SOR$_J$; —SO$_2$R$_J$; —NO$_2$; —N$_3$; —N(R$_J$)$_2$; —NHC(=O)R$_J$; —NR$_J$C(=O)N(R$_J$)$_2$; —OC(=O)OR$_J$; —OC(=O)R$_J$; —OC(=O)N(R$_J$)$_2$; —NR$_J$C(=O)OR$_J$; or —C(R$_J$)$_3$; wherein each occurrence of R$_J$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

R$_{12}$ is selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_L$; —C(=O)R$_L$; —CO$_2$R$_L$; —CN; —SCN; —SR$_L$; —SOR$_L$; —SO$_2$R$_L$; —NO$_2$; —N$_3$; —N(R$_L$)$_2$; —NHC(=O)R$_L$; —NR$_L$C(=O)N(R$_L$)$_2$; —OC(=O)OR$_L$; —OC(=O)R$_L$; —OC(=O)N(R$_L$)$_2$; —NR$_L$C(=O)OR$_L$; or —C(R$_L$)$_3$; wherein each occurrence of R$_L$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

R$_{13}$ and R$_{14}$ are independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_M$; —C(=O)R$_M$; —CO$_2$R$_M$; —CN; —SCN; —SR$_M$; —SOR$_M$; —SO$_2$R$_M$; —NO$_2$; —N$_3$; —N(R$_M$)$_2$; —NHC(=O)R$_M$; —NR$_M$C(=O)N(R$_M$)$_2$; —OC(=O)OR$_M$; —OC(=O)R$_M$; —OC(=O)N(R$_M$)$_2$; —NR$_M$C(=O)OR$_M$; or —C(R$_M$)$_3$; wherein each occurrence of R$_M$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

R$_{15}$ is selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_P$; —C(=O)R$_P$; —CO$_2$R$_P$; —CN; —SCN; —SR$_P$; —SOR$_P$; —SO$_2$R$_P$; —NO$_2$; —N$_3$; —N(R$_P$)$_2$; —NHC(=O)R$_P$; —NR$_P$C(=O)N(R$_P$)$_2$; —OC(=O)OR$_P$; —OC(=O)R$_P$; —OC(=O)N(R$_P$)$_2$; —NR$_P$C(=O)OR$_P$; or —C(R$_P$)$_3$; wherein each occurrence of R$_P$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

wherein two or more substituents may form substituted or unsubstituted, cyclic, heterocyclic, aryl, or heteroaryl structures;

wherein $R_6$ and $R_7$, $R_8$ and $R_9$, $R_{13}$ and $R_{14}$, and one $R_{12}$ and another $R_{12}$ may form together =O, =NR$_G$, or =C(R$_G$)$_2$, wherein each occurrence of R$_G$ is defined as above;

X is O, S, C(R$_X$)$_2$, or NR$_X$, wherein R$_X$ is hydrogen, a protecting group, an aliphatic, heteroaliphatic, aryl, heteroaryl, alkylaryl, or alkylheteroaryl moiety, Z is O, S, or NR$_Z$, wherein R$_Z$ is hydrogen, a protecting group, an aliphatic, heteroaliphatic, aryl, heteroaryl, alkylaryl, or alkylheteroaryl moiety, or OR$_Z$, wherein R$_Z$ is hydrogen, a protecting group, an aliphatic, heteroaliphatic, aryl, heteroaryl, alkylaryl, or alkylheteroaryl moiety;

the dashed line represents the presence or absence of a bond;

m is an integer between 0 and 6, inclusive; and n is an integer between 0 and 2, inclusive;

with the proviso that when $R_{10}$, $R_{11}$, $R_{12}$, $R_{13}$, and $R_{14}$ are hydrogen, X is O, Z is O, and the dashed line represent a bond, then $R_6$, $R_7$, $R_8$, $R_9$, and $R_{15}$ are not hydrogen, alkyl, aminoalkyl, or perfluoroalkyl.

18. The compound of claim 17 with the stereochemistry as defined in the formula:

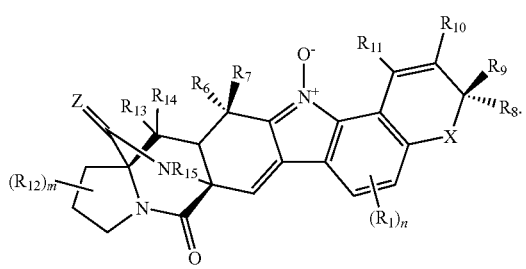

19. A method of preparing a nitrone of formula:

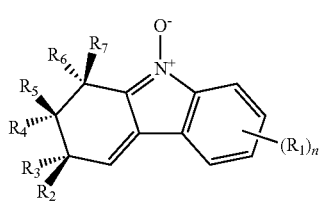

wherein $R_1$, $R_2$, $R_3$, $R_4$, $R_5$, $R_6$, and $R_7$ are independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_G$; —C(=O)R$_G$; —CO$_2$R$_G$; —CN; —SCN; —SR$_G$; —SOR$_G$; —SO$_2$R$_G$; —NO$_2$; —N$_3$; —N(R$_G$)$_2$; —NHC(=O)R$_G$; —NR$_G$C(=O)N(R$_G$)$_2$; —OC(=O)OR$_G$; —OC(=O)R$_G$; —OC(=O)N(R$_G$)$_2$; —NR$_G$C(=O)OR$_G$; or —C(R$_G$)$_3$; wherein each occurrence of R$_G$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

wherein two or more substituents may form substituted or unsubstituted, cyclic, heterocyclic, aryl, or heteroaryl structures;

wherein $R_2$ and $R_3$, $R_4$ and $R_5$, or $R_6$ and $R_7$ may form together =O, =NR$_G$, or =C(R$_G$)$_2$, wherein each occurrence of R$_G$ is defined as above; and n is an integer between 0 and 4;

with the proviso that if n is 0, and $R_4$ and $R_5$ are both hydrogen, then $R_2$, $R_3$, $R_6$ and $R_7$ can not all be methyl;

the method comprising steps of:

reacting a compound of formula:

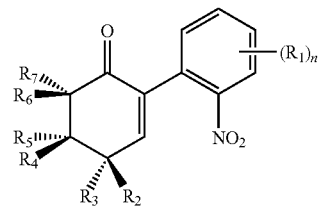

wherein $R_1$, $R_2$, $R_3$, $R_4$, $R_5$, $R_6$, $R_7$, and n are as defined above; with zinc powder to form the nitrone.

20. The compound of claim 1 of one of the formulae:

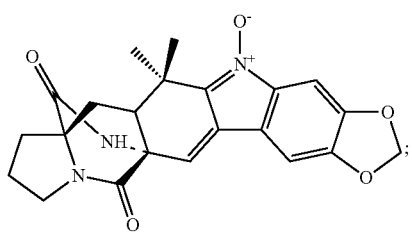

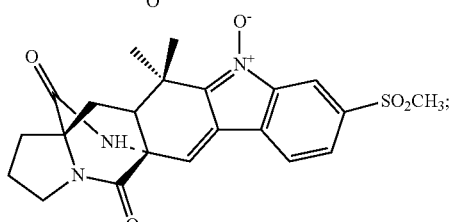

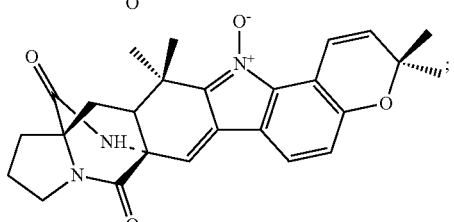

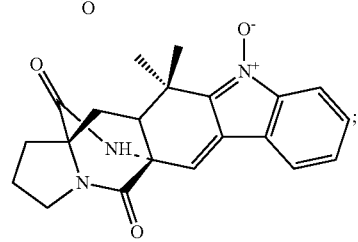

143
-continued
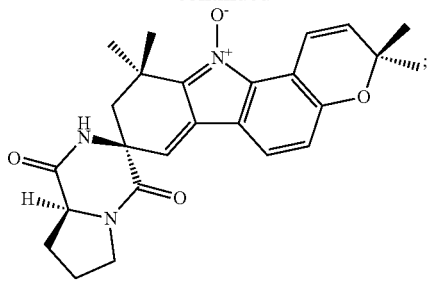
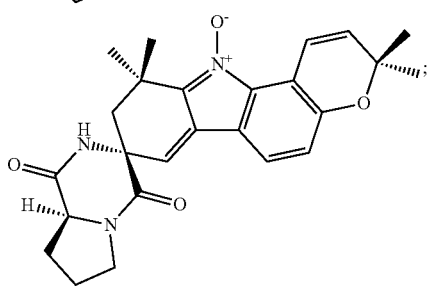
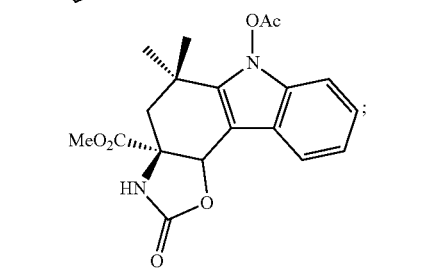
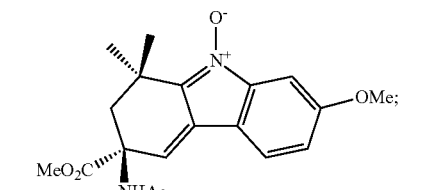
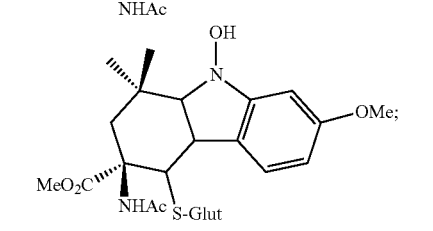
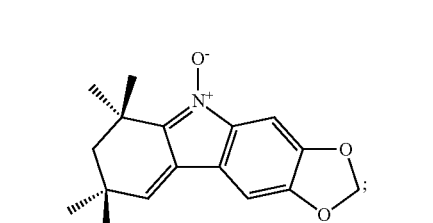
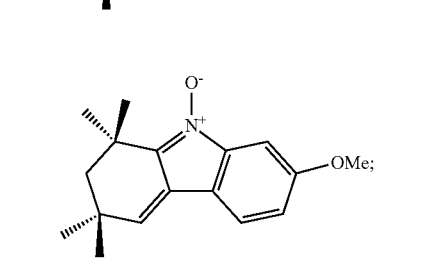
144
-continued
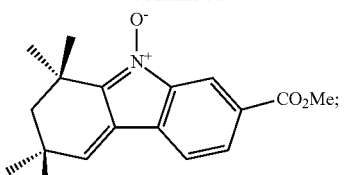
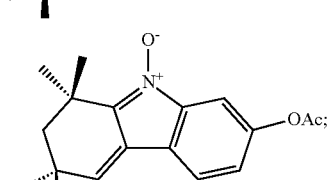
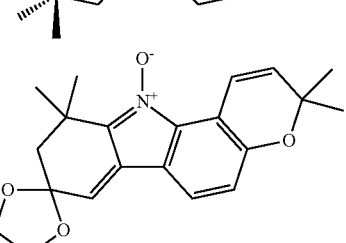
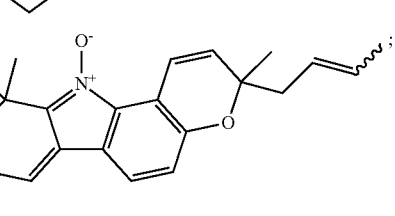
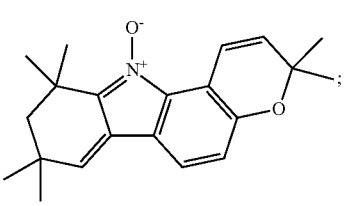
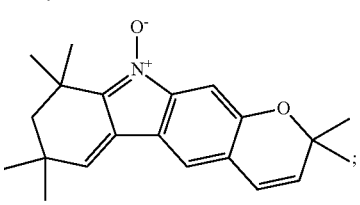
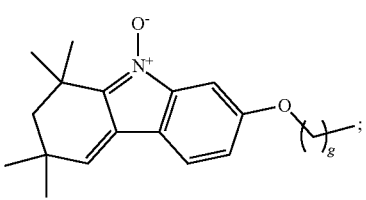
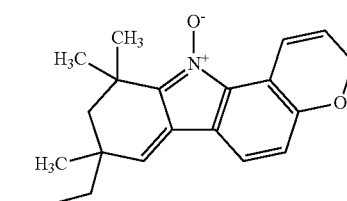

-continued

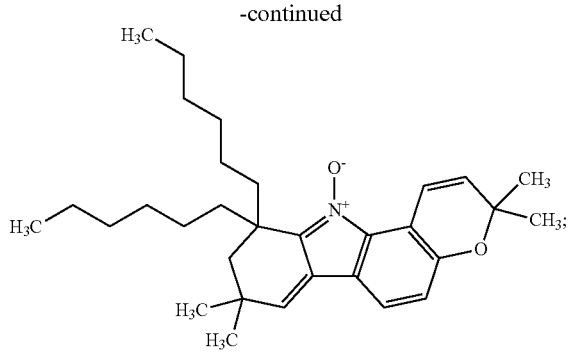

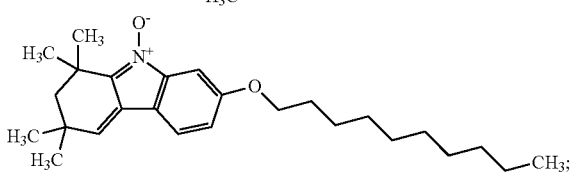

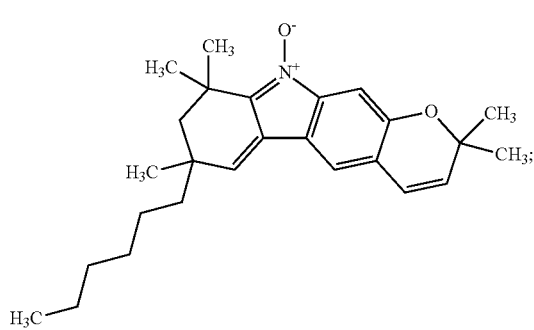

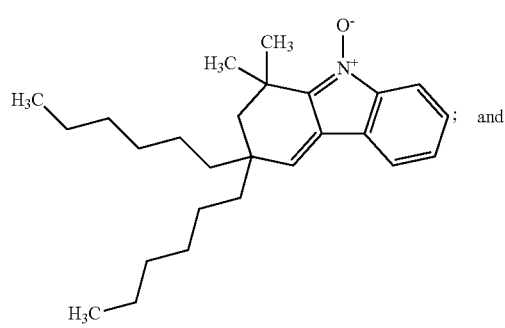

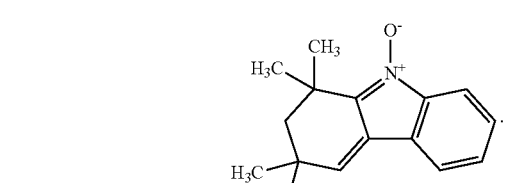

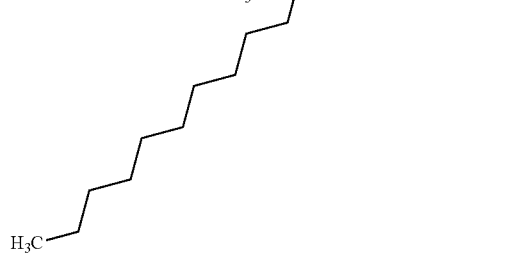

21. The compound of claim 1, wherein

represents a substituted or unsubstituted, aryl or heteroaryl ring system.

22. The compound of claim 1, wherein

is a monocyclic ring system.

23. The compound of claim 1, wherein

is a bicyclic ring system.

24. The compound of claim 1, wherein

is a tricyclic ring system.

25. The compound of claim 1, wherein one of $R_1$, $R_2$, $R_3$, $R_4$, $R_5$, $R_6$, and $R_7$ comprises a radiolabel, peptide, protein, epitope, biotin, phosphorescent tag, chemiluminescent tag, colored tag, or a fluorescent tag.

26. The compound of claim 1 of the formula:

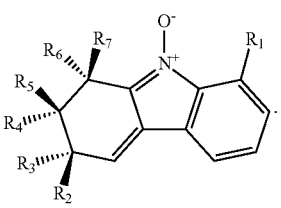

27. The compound of claim 1 of the formula:

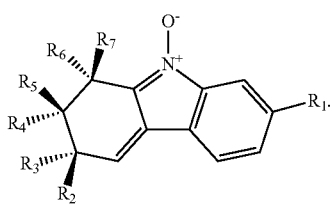

28. The compound of claim 1 of the formula:

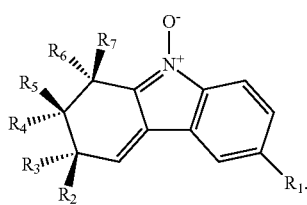

29. The compound of claim 1 of the formula:

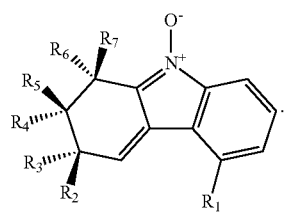

30. The compound of claim 1 of the formula:

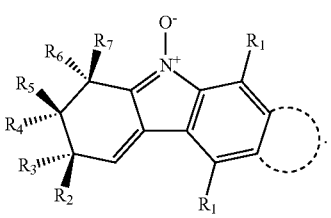

31. The compound of claim 1 of the formula:

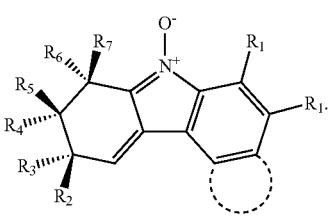

32. The compound of claim 1, wherein $R_2$ and $R_3$ are each hydrogen or aliphatic.

33. The compound of claim 1, wherein $R_2$ and $R_3$ are each methyl.

34. The compound of claim 1, wherein at least one of $R_2$, $R_3$, $R_4$, and $R_5$ is not methyl.

35. The compound of claim 1, wherein $R_2$ is —(C=O)-AA or —NH-AA, wherein AA is an amino acid or oligomer of amino acids.

36. The compound of claim 1, wherein $R_2$ is —(C=O)-AA, wherein AA is an amino acid or oligomer of amino acids.

37. The compound of claim 1, wherein $R_3$ is —(C=O)-AA or —NH-AA, wherein AA is an amino acid or oligomer of amino acids.

38. The compound of claim 1, wherein $R_3$ is —NH-AA, wherein AA is an amino acid or oligomer of amino acids.

39. The compound of claim 1, wherein $R_6$ and $R_7$ are each hydrogen or $C_{1-6}$ aliphatic.

40. The compound of claim 1, wherein $R_6$ and $R_7$ are each methyl.

41. The compound of claim 1, wherein $R_6$ and $R_7$ are not methyl.

42. The compound of claim 1, wherein $R_1$ is hydrogen, alkoxy, acetoxy, or tosyloxy.

43. The compound of claim 1, wherein n is 2.

44. The compound of claim 1, wherein n is 3.

45. The compound of claim 1, wherein n is 4.

46. The compound of claim 1, wherein $R_1$, $R_2$, $R_3$, $R_4$, $R_5$, $R_6$, or $R_7$ is substituted with biotin.

47. The compound of claim of formula:

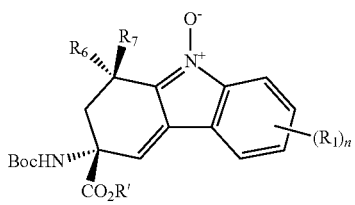

wherein R' is hydrogen, $C_{1-20}$ aliphatic, or an oxygen protecting group; $R_6$ is hydrogen or $C_{1-20}$ aliphatic; and $R_7$ is hydrogen or $C_{1-20}$ aliphatic.

48. The compound of claim 15, wherein at least two of $R_2$, $R_3$, $R_6$, $R_7$, $R_8$, and $R_9$ are methyl.

49. The compound of claim 15, wherein at least four of $R_2$, $R_3$, $R_6$, $R_7$, $R_8$, and $R_9$ are methyl.

50. The compound of claim 15, wherein all of $R_2$, $R_3$, $R_6$, $R_7$, $R_8$, and $R_9$ are methyl.

51. The compound of claim 15, wherein at least one of $R_2$, $R_3$, $R_6$, $R_7$, $R_8$, and $R_9$ is a $C_1$-$C_{20}$ aliphatic moiety.

52. The compound of claim 15, wherein at least one of $R_2$, $R_3$, $R_6$, $R_7$, $R_8$, and $R_9$ is a $C_3$-$C_{20}$ aliphatic moiety.

53. The compound of claim 15, wherein at least one of $R_2$, $R_3$, $R_6$, $R_7$, $R_8$, and $R_9$ is an acyl moiety.

54. The compound of claim 15, wherein at least one of $R_2$, $R_3$, $R_6$, $R_7$, $R_8$, and $R_9$ is $OR_G$.

55. The compound of claim 16, wherein at least two of $R_2$, $R_3$, $R_6$, $R_7$, $R_8$, and $R_9$ are methyl.

56. The compound of claim 16, wherein at least four of $R_2$, $R_3$, $R_6$, $R_7$, $R_8$, and $R_9$ are methyl.

57. The compound of claim 16, wherein all of $R_2$, $R_3$, $R_6$, $R_7$, $R_8$, and $R_9$ are methyl.

58. The compound of claim 16, wherein at least one of $R_2$, $R_3$, $R_6$, $R_7$, $R_8$, and $R_9$ is a $C_1$-$C_{20}$ aliphatic moiety.

59. The compound of claim 16, wherein at least one of $R_2$, $R_3$, $R_6$, $R_7$, $R_8$, and $R_9$ is a $C_3$-$C_{20}$ aliphatic moiety.

60. The compound of claim 16, wherein at least one of $R_2$, $R_3$, $R_6$, $R_7$, $R_8$, and $R_9$ is an acyl moiety.

61. The compound of claim 16, wherein at least one of $R_2$, $R_3$, $R_6$, $R_7$, $R_8$, and $R_9$ is $OR_G$.

62. The compound of claim 17, with the proviso that when $R_{10}$, $R_{11}$, $R_{12}$, $R_{13}$, and $R_{14}$ are hydrogen; X is O; Z is O; and the dashed line represents a bond, then all of $R_6$, $R_7$, $R_8$, and $R_9$ are not methyl, or $R_{15}$ is not hydrogen.

63. The compound of claim 17 of the formula:

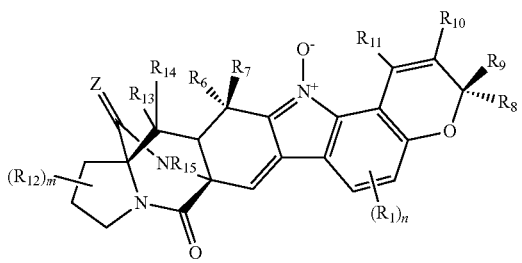

wherein X is oxygen.

64. The compound of claim 17 of the formula:

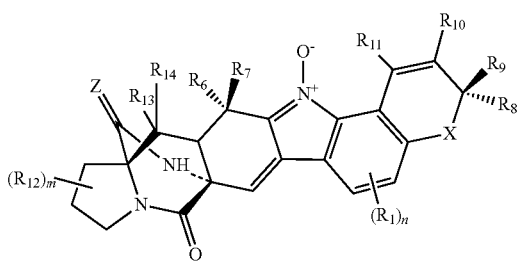

wherein $R_{15}$ is hydrogen.

65. The compound of claim 17 of the formula:

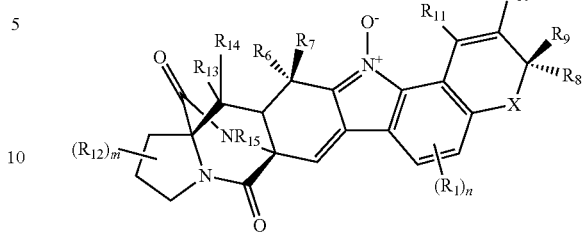

wherein Z is oxygen.

66. The method of claim 19, wherein the step of reacting is performed in a polar solvent.

67. The method of claim 66, wherein the solvent is an alcohol.

68. The method of claim 67, wherein the solvent is ethanol.

69. The method of claim 19, wherein the step of reacting is performed in the presence of $NH_4Cl$.

* * * * *

UNITED STATES PATENT AND TRADEMARK OFFICE
CERTIFICATE OF CORRECTION

PATENT NO. : 7,902,196 B2
APPLICATION NO. : 11/908901
DATED : March 8, 2011
INVENTOR(S) : Andrew G. Myers et al.

It is certified that error appears in the above-identified patent and that said Letters Patent is hereby corrected as shown below:

On the first page of the U.S. Patent, section (54) and in the specification at column 1, lines 1-3, please replace the following title:
"SYNTHESIS OF AVRAINVILLAMIDE, STREPHACIDIN B, AND ANALOGUES THEREOF"
with the following amended title:
"SYNTHESIS OF AVRAINVILLAMIDE, STEPHACIDIN B, AND ANALOGUES THEREOF".

At column 3, lines 34-44, please replace the following formula:

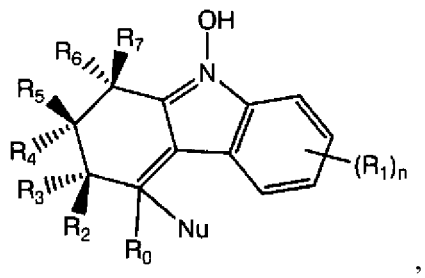

with the following amended formula:

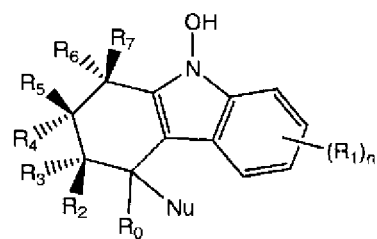

At column 3, lines 54-67, please replace the following formula:

Signed and Sealed this
Eighteenth Day of October, 2011

David J. Kappos
*Director of the United States Patent and Trademark Office*

CERTIFICATE OF CORRECTION (continued)
U.S. Pat. No. 7,902,196 B2

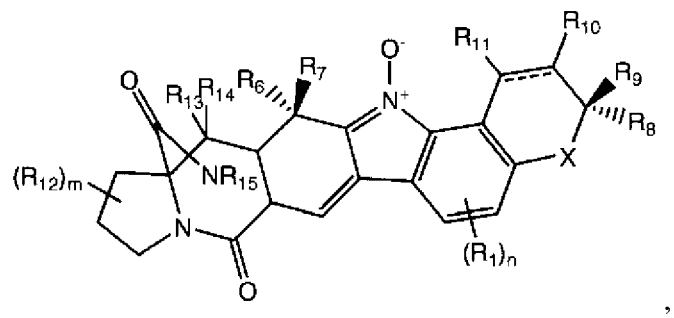

with the following amended formula:

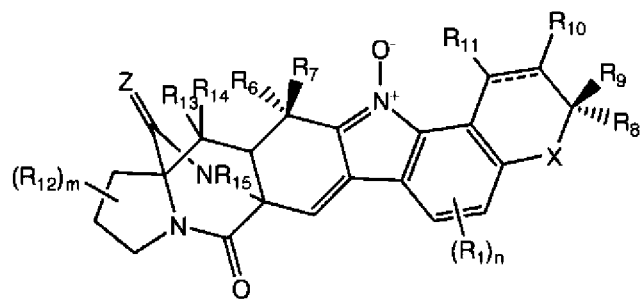

At column 4, lines 2-14, please replace the following formula:

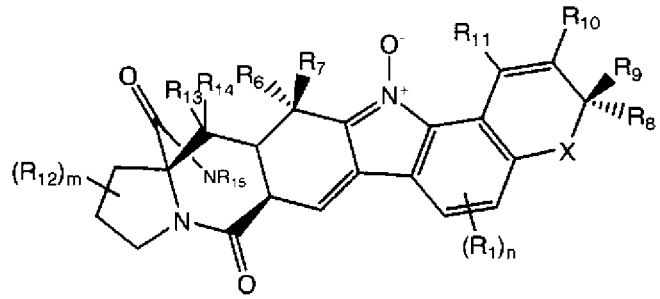

with the following amended formula:

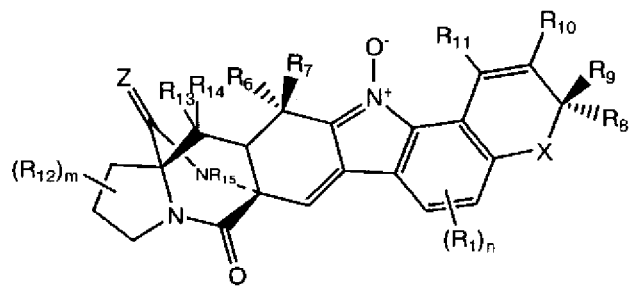

At column 4, lines 18-30, please replace the following formula:

CERTIFICATE OF CORRECTION (continued)
U.S. Pat. No. 7,902,196 B2

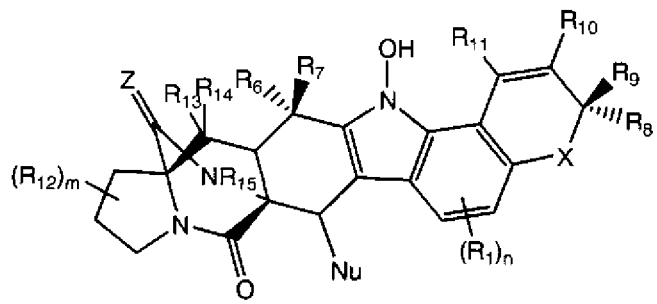

with the following amended formula:

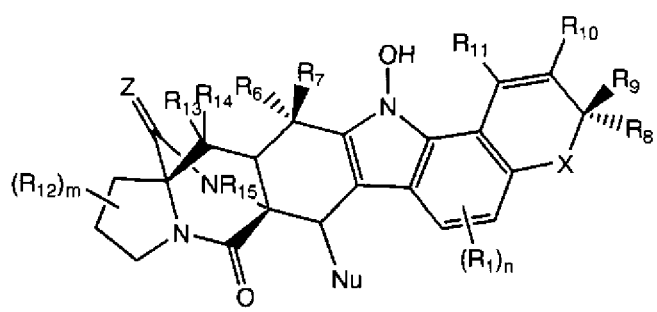

At column 36, lines 27-38, please replace the following formula:

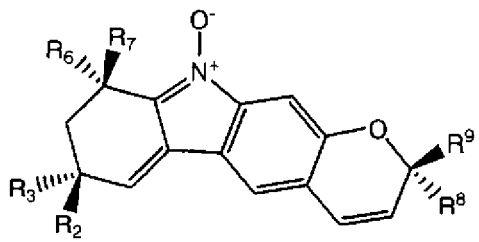

with the following amended formula:

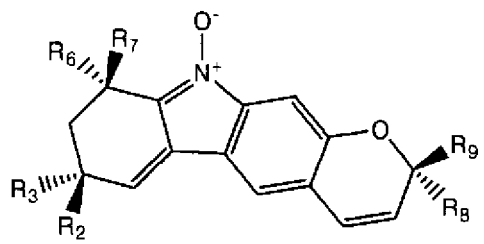

At column 46, lines 55-70, please replace the following formula:

CERTIFICATE OF CORRECTION (continued)
U.S. Pat. No. 7,902,196 B2

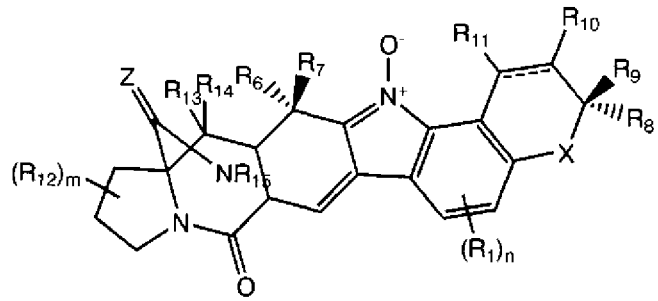

with the following amended formula:

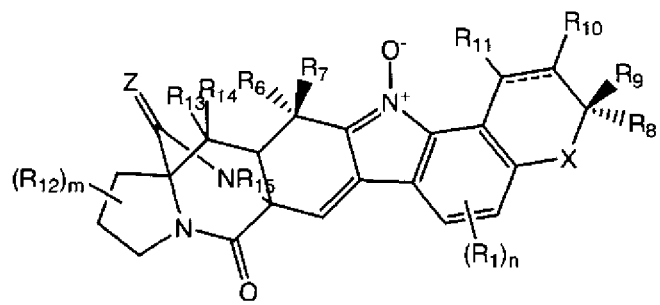

At column 49, lines 40-52, please replace the following formula:

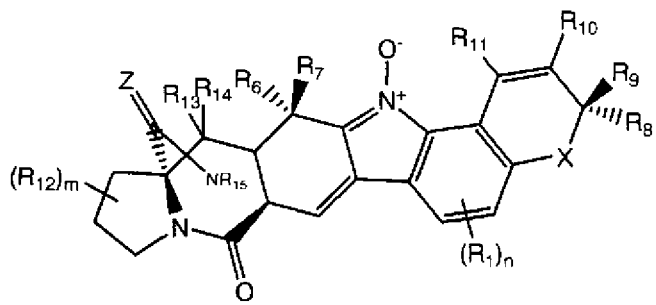

with the following amended formula:

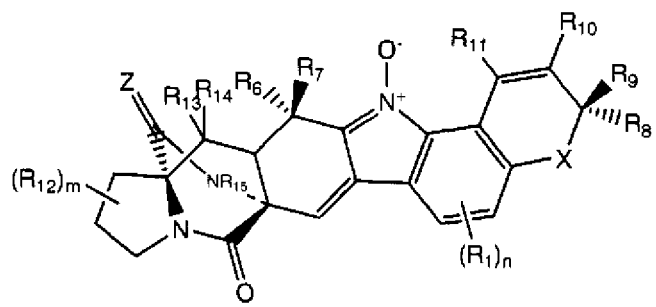

At column 51, lines 7-18, please replace the following formula:

CERTIFICATE OF CORRECTION (continued)
U.S. Pat. No. 7,902,196 B2

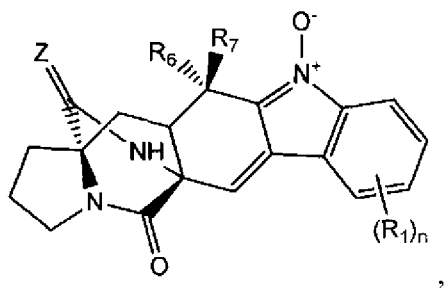

with the following amended formula:

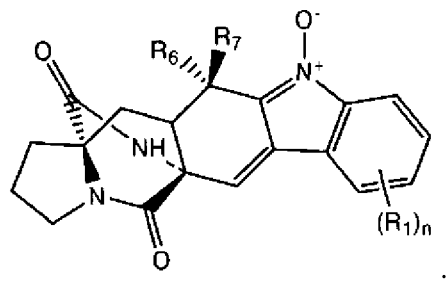

At column 51, lines 35-47, please replace the following formula:

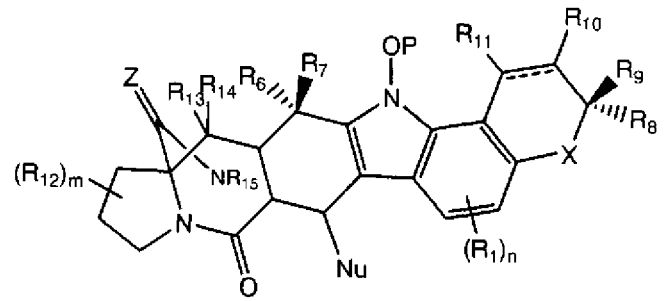

with the following amended formula:

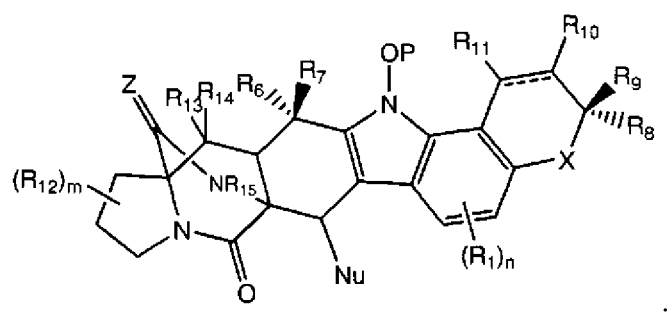

At column 63, lines 23-32, please replace the following formula:

CERTIFICATE OF CORRECTION (continued)
U.S. Pat. No. 7,902,196 B2

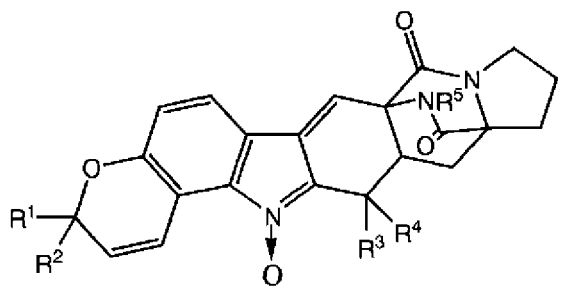

with the following amended formula:

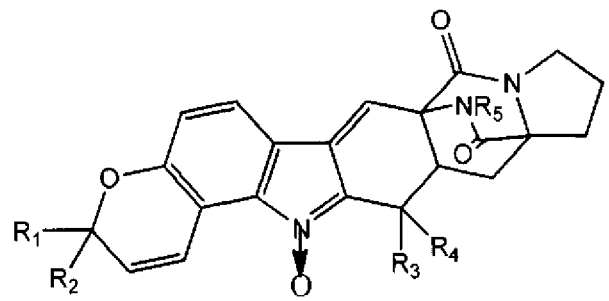

At column 64, lines 1-12, please replace the following formula:

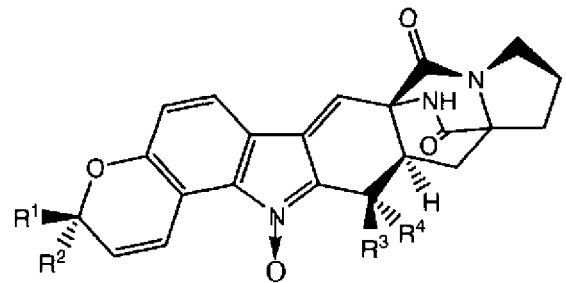

with the following amended formula:

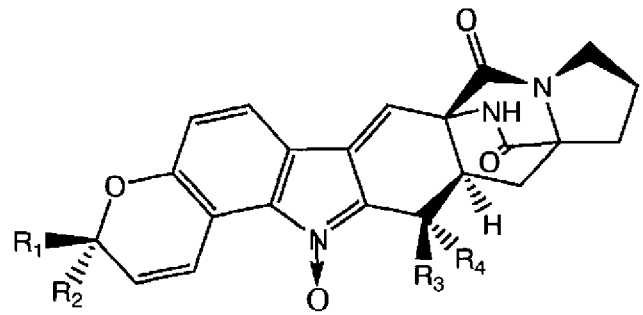

At column 71, lines 1-12, please replace the following formula:

CERTIFICATE OF CORRECTION (continued)
U.S. Pat. No. 7,902,196 B2

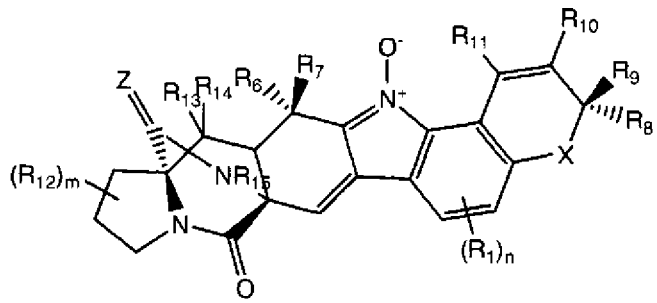

with the following amended formula:

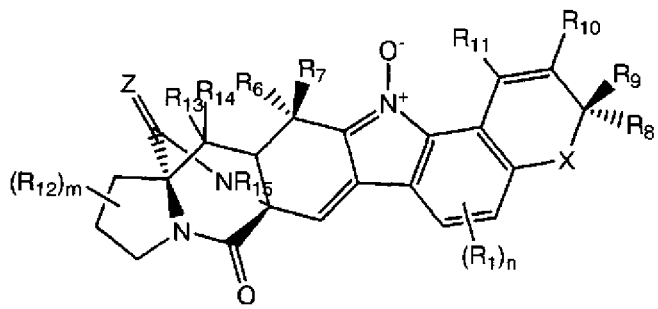

At column 81, line 10, please replace the following label:
"Avrainvillamide",
with the following amended label:
"Avrainvillamide (1)".

At column 81, line 27, please replace the following label:
"Stephacldin B",
with the following amended label:
"Stephacidin B (2)".

At column 82, line 42, please replace the following label:
"6 (48%)",
with the following amended label:
"5 (48%)".

At column 82, line 51, please replace the following label:
"(9%)",
with the following amended label:
"6 (9%)".

At column 82, line 61, please replace the following label:
"(7%)",
with the following amended label:
"7 (7%)".

At column 83, line 51, please replace the following label:

with the following amended label:
"6",
"5".
At column 87, lines 22-32, please replace the following scheme:
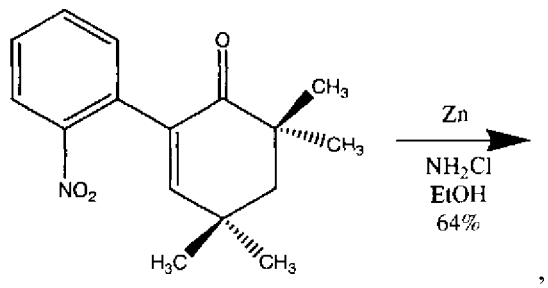
,
with the following amended scheme:
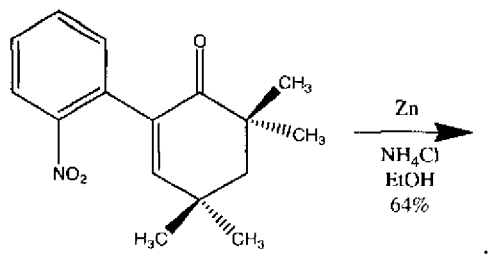
At column 89, lines 19-29, please replace the following scheme:
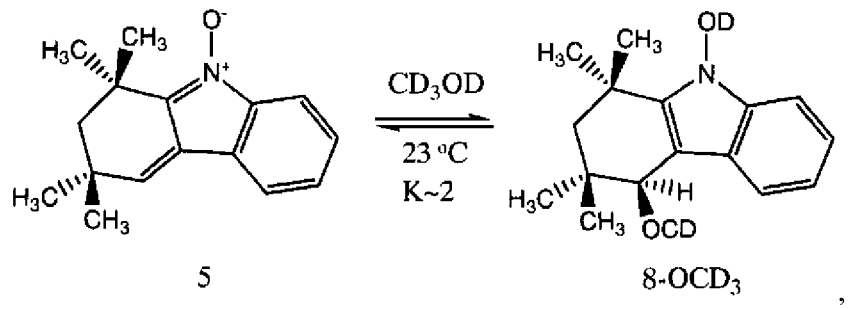
,
with the following amended scheme:
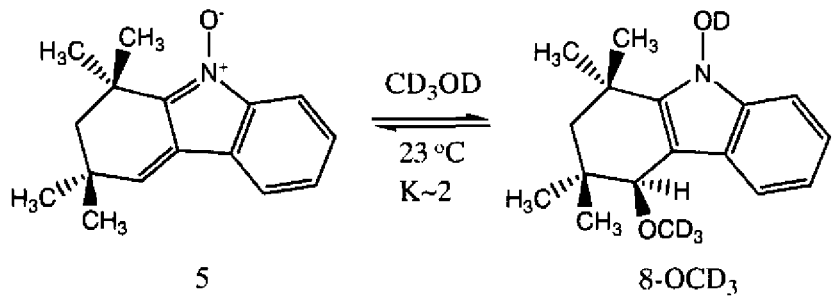
At column 99, line 19, please replace the following label:

CERTIFICATE OF CORRECTION (continued)
U.S. Pat. No. 7,902,196 B2

"Stephacldin B", with the following amended label:

"Stephacidin B (1)".

At column 99, line 28, please replace the following label:

"("Avrainvillamide")", with the following amended label:

"2 ("Avrainvillamide")".

At columns 103 and 104, lines 1-17, please replace the following scheme:

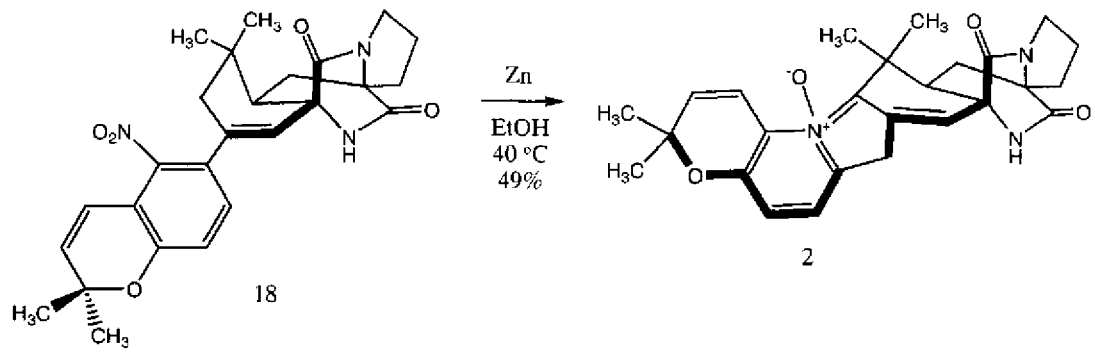

with the following amended scheme:

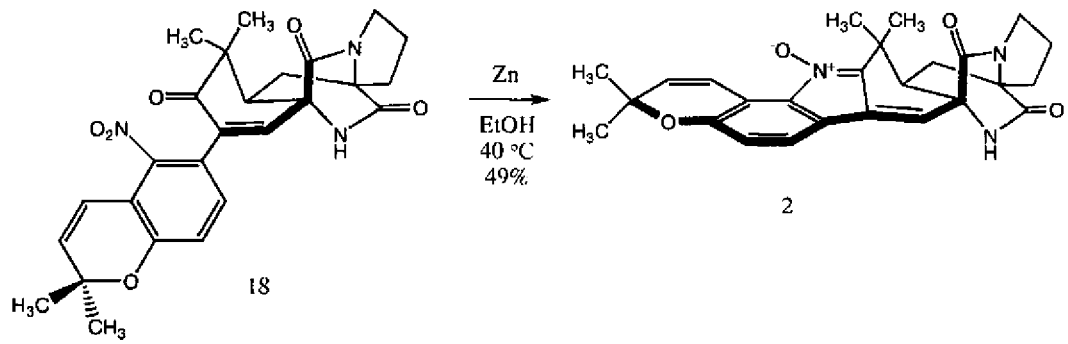

,

.

At column 105, lines 26-57, please replace the following scheme:

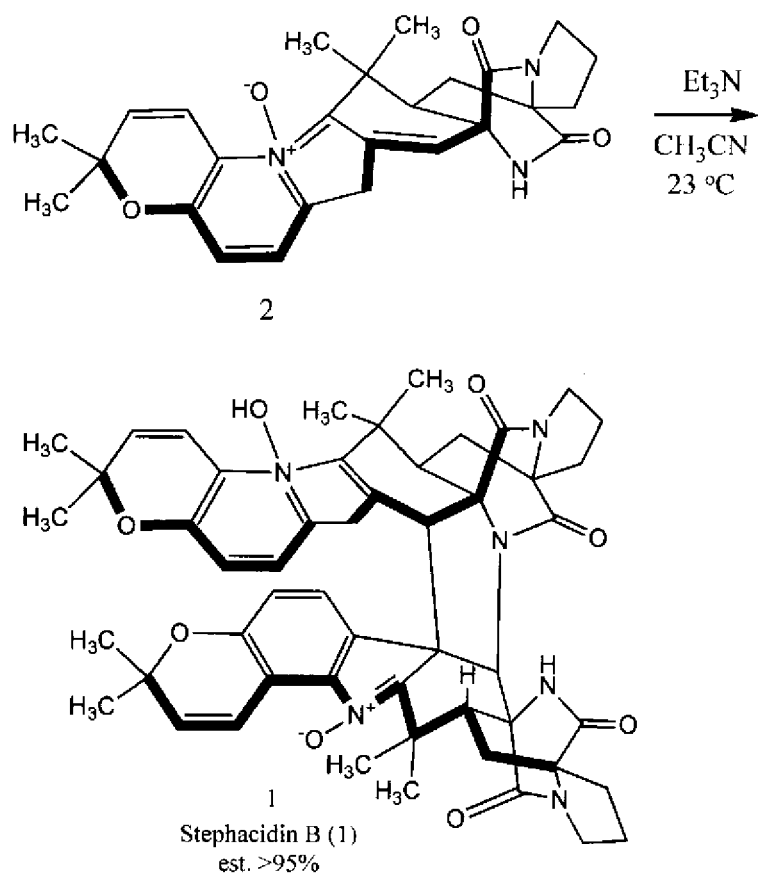
with the following amended scheme:

CERTIFICATE OF CORRECTION (continued)
U.S. Pat. No. 7,902,196 B2

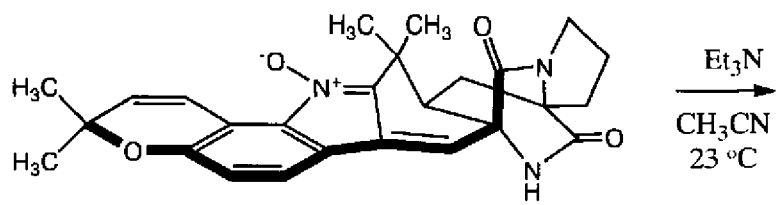

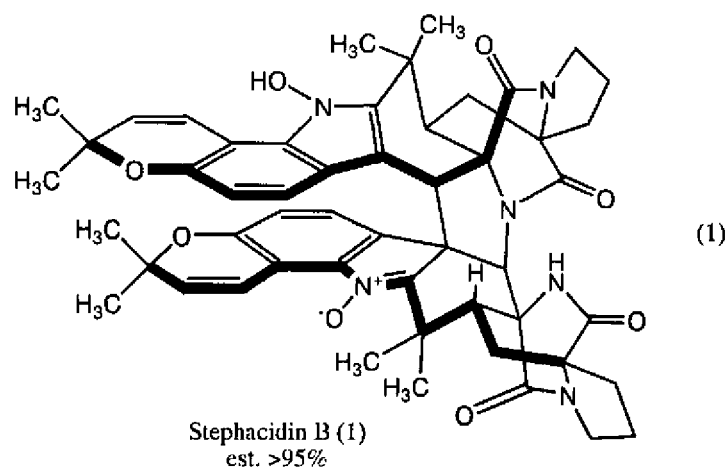

At column 106, lines 37-59, please replace the following scheme:

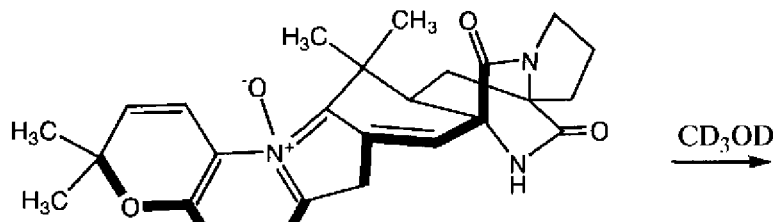

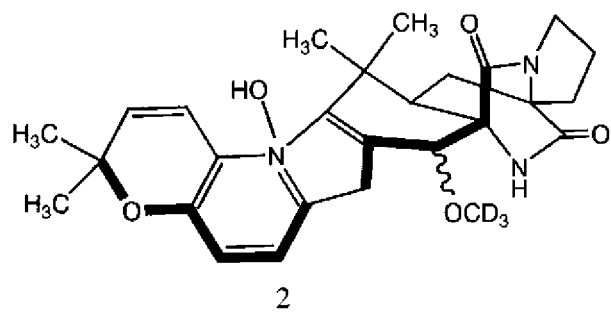

with the following amended scheme:

CERTIFICATE OF CORRECTION (continued)
U.S. Pat. No. 7,902,196 B2

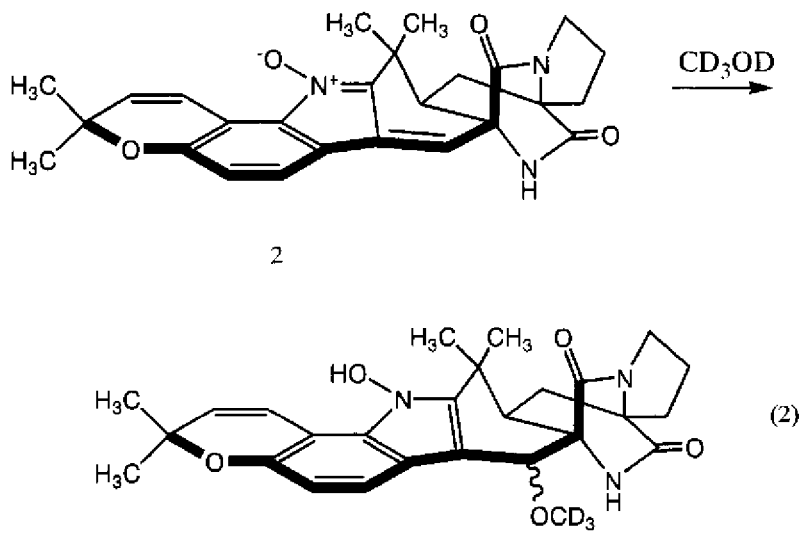

At column 118, lines 0-14, please replace the following formula:

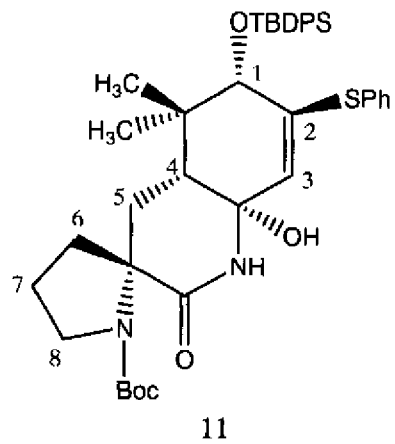

with the following amended formula:

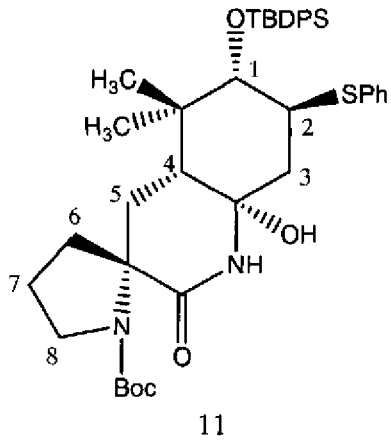

In claim 17, at column 138, lines 45-57, please replace the following formula:

CERTIFICATE OF CORRECTION (continued)
U.S. Pat. No. 7,902,196 B2

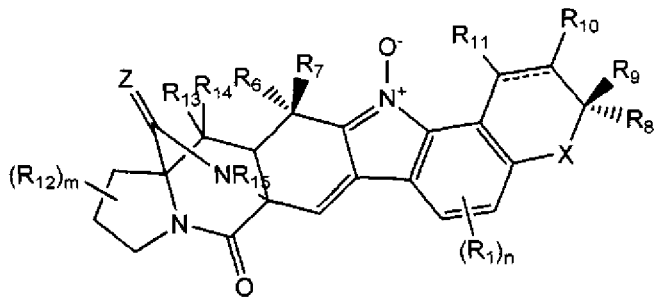

with the following amended formula:

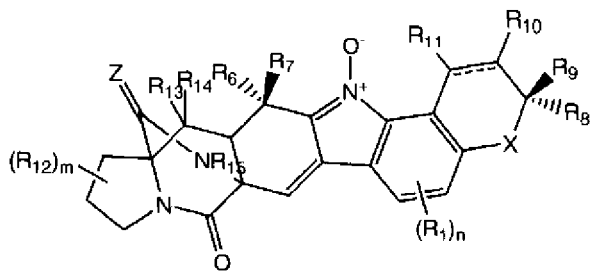

In claim 17 at column 140, line 40, please replace the following:
...—C (=0)R$_M$; ...

with the following:
...—C (=O)R$_M$; ....

In claim 17 at column 140, line 61, please replace the following:
... (=0)R$_P$; ...

with the following:
... (=O)R$_P$; ....

In claim 17 at column 141, line 13, please replace the following:
... OR$_Z$, wherein R$_Z$ ...

with the following:
... OR$_{Z'}$, wherein R$_{Z'}$ ...

In claim 18 at column 141, lines 28-40, please replace the following formula:

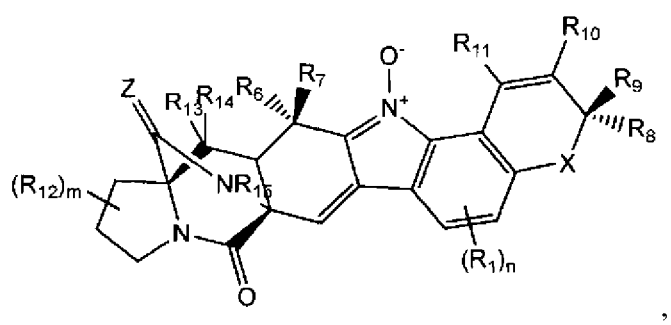

with the following amended formula:

CERTIFICATE OF CORRECTION (continued)
U.S. Pat. No. 7,902,196 B2

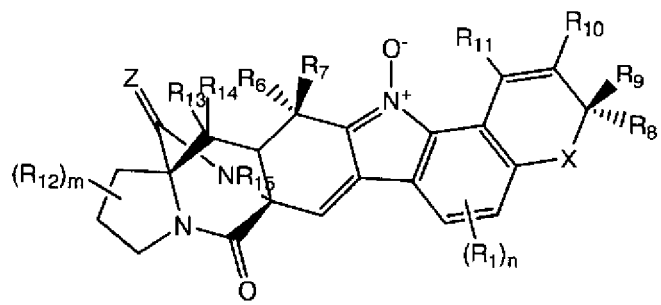

In claim 19 at column 141, line 64, please replace the following:

... —OC(=0)N(R_G)₂ ...

with the following:

... —OC(=O)N(R_G)₂ ....

In claim 20 at column 144, lines 48-54, please replace the following formula:

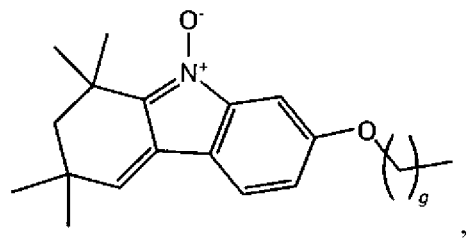

, with the following amended formula:

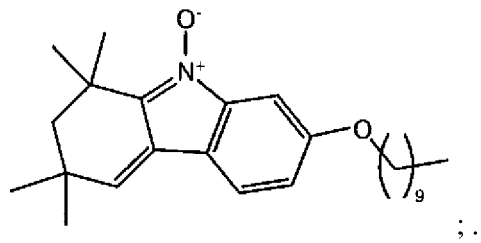

; .